United States Patent
Bayer et al.

(10) Patent No.: US 6,509,379 B1
(45) Date of Patent: Jan. 21, 2003

(54) PHENYLACETIC ACID DERIVATIVES, PROCESS AND INTERMEDIATE PRODUCTS FOR THEIR PREPARATION, AND THEIR USE AS FUNGICIDES AND PESTICIDES

(75) Inventors: Herbert Bayer, Mannheim (DE); Hubert Sauter, Mannheim (DE); Klaus Oberdorf, Heidelberg (DE); Wassilios Grammenos, Ludwigshafen (DE); Thomas Grote, Schifferstadt (DE); Reinhard Kirstgen, Neustadt (DE); Bernd Müller, Frankenthal (DE); Ruth Müller, Friedelsheim (DE); Franz Röhl, Schifferstadt (DE); Eberhard Ammermann, Heppenheim (DE); Volker Harries, Frankenthal (DE); Gisela Lorenz, Hambach (DE); Siegfried Strathmann, Limburgerhof (DE); Norbert Götz, Worms (DE); Albrecht Harreus, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/051,996
(22) PCT Filed: Oct. 24, 1996
(86) PCT No.: PCT/EP96/04621
  § 371 (c)(1),
  (2), (4) Date: Apr. 23, 1998
(87) PCT Pub. No.: WO97/16412
  PCT Pub. Date: May 9, 1997

(30) Foreign Application Priority Data

Oct. 30, 1995 (DE) .......................................... 195 40 361

(51) Int. Cl.$^7$ ...................... A01N 37/34; A01N 31/38; A01N 43/06; A01N 43/40; A01N 37/18
(52) U.S. Cl. .......................... 514/620; 558/405; 564/74; 564/162; 564/163; 564/164; 564/165; 564/166; 564/167; 564/256; 514/347; 514/348; 514/351; 514/365; 514/374; 514/376; 514/423; 514/448; 514/466; 514/539; 514/523; 514/599; 514/621; 546/296; 546/298; 548/200; 548/236; 548/561; 549/72; 549/441; 560/35
(58) Field of Search ................................ 514/640, 466, 514/618, 619, 620, 347, 348, 351, 365, 374, 376, 423, 448, 539, 523, 599, 621; 564/256, 163, 164, 165, 166, 167; 549/441, 72; 546/296, 298; 548/200, 236, 561; 560/35; 558/405

(56) References Cited

U.S. PATENT DOCUMENTS

| | | | |
|---|---|---|---|
| 3,996,374 A | 12/1976 | Jaunin | 424/274 |
| 4,077,978 A | 3/1978 | Jaunin | 260/326.1 |
| 4,616,015 A | 10/1986 | Teraji et al. | 514/242 |
| 4,762,921 A | 8/1988 | Reed, III | 540/310 |
| 4,956,387 A | 9/1990 | Wenderoth et al. | 514/522 |
| 4,966,855 A | 10/1990 | Deneke et al. | 436/66 |
| 5,856,560 A | 1/1999 | Bayer et al. | 560/35 |

FOREIGN PATENT DOCUMENTS

| | | | |
|---|---|---|---|
| DE | 25 53 595 | | 8/1976 |
| DE | 34 25 118 | | 8/1986 |
| EP | 122 627 | | 10/1984 |
| EP | 201 221 | | 12/1986 |
| EP | 331 061 | | 9/1989 |
| WO | 95/18789 | * | 7/1995 |
| WO | 95/21153 | | 8/1995 |
| WO | 95/21154 | | 8/1995 |
| WO | 95/34526 | | 12/1995 |
| WO | 96/32373 | | 10/1996 |

OTHER PUBLICATIONS

Murahashi et al. An attempt to prepare linear chelate polymers, Bull. Chem. Soc. JP 35(9), 1465–71 (1962).
Domagala et al. Synthesis of (Z)-4-(acylamino)-and 4-(alkylamino)-a-oximinophenylacetic acids, J. Org. Chem. 46(1), 134–40 (1981).
Marais et al. Sodium dichloroisocyanurate oxidation of a sterically hindered tetrahydro-9(10H)-acridinone, J. Org. Chem. 55(6), 1669–72 (1990).

* cited by examiner

Primary Examiner—Peter O'Sullivan
(74) Attorney, Agent, or Firm—Keil & Weinkauf

(57) ABSTRACT

Phenylacetic acid derivatives of the formula I

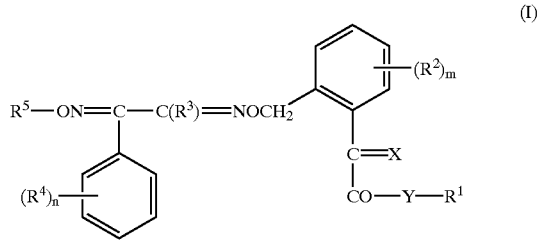

where the variables are as disclosed herein, their salts, processes and intermediates for their preparation, and their use for controlling harmful fungi and animal pests.

18 Claims, No Drawings

PHENYLACETIC ACID DERIVATIVES, PROCESS AND INTERMEDIATE PRODUCTS FOR THEIR PREPARATION, AND THEIR USE AS FUNGICIDES AND PESTICIDES

This application is a 371 of PCT/EP90/04621, filed Oct. 24, 1996.

The present invention relates to phenylacetic acid derivatives of the formula I

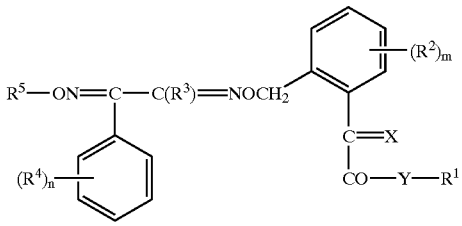

where the variables have the following meanings:
X is $NOCH_3$, $CHOCH_3$ or $CHCH_3$;
Y is O or NZ, Z being hydrogen or $C_1$–$C_4$-alkyl;
$R^1$ is hydrogen or $C_1$–$C_4$-alkyl;
$R^2$ is cyano, nitro, trifluoromethyl, halogen, $C_1$–$C_4$-alkyl or $C_1$–$C_4$-alkoxy;
m is 0, 1 or 2, it being possible for the radicals $R^2$ to be different if m is 2;
$R^3$ is hydrogen, cyano, $C_1$–$C_4$-alkyl, $C_1$–$C_4$-haloalkyl, $C_1$–$C_4$-alkoxy or cyclopropyl;
$R^4$ is $C_1$–$C_4$-alkylenedioxy, the alkylene groups being partially or fully halogenated, or is one of the radicals:
—(C=O)—$R^a$,
—C(=$NOR^a$)—$A_p$—$R^b$,
—$NR^c$—(C=O)—$A_p$—$R^a$,
—O—(C=O)—$NR^aR^b$ or
—N($R^c$)—$OR^d$, where
$R^a$, $R^b$ independently of one another are hydrogen or in each case unsubstituted or substituted alkyl, alkenyl, alkynyl, cycloalkyl, cycloalkenyl, heterocyclyl, aryl or hetaryl,
$R^c$, $R^d$ independently of one another are hydrogen or in each case unsubstituted or substituted alkyl, alkenyl, alkynyl, alkylcarbonyl, alkenylcarbonyl, alkynylcarbonyl, alkoxycarbonyl, alkenyloxycarbonyl, alkynyloxycarbonyl, cycloalkyl, cycloalkylcarbonyl, cycloalkyloxycarbonyl, arylcarbonyl or hetarylcarbonyl,
p is 0 or 1 and
A is oxygen, sulfur or nitrogen, the nitrogen having attached to it hydrogen or $C_1$–$C_6$-alkyl;
n is 1 or 2, it being possible for the radicals $R^4$ to be different if n is 2;
$R^5$ is hydrogen,
$C_1$–$C_6$-alkylsulfonyl, $C_1$–$C_6$-alkyl, $C_3$–$C_6$-alkenyl, $C_3$–$C_6$-alkynyl, it being possible for these radicals to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, arylthio, hetaryl, hetaryloxy, hetarylthio, it being possible for the cyclic groups, in turn, to be partially or fully halogenated and/or to have attached to them one to three of the following substituents: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C_3$–$C_6$-alkynyloxy;
$C_3$–$C_6$-cycloalkyl, which can be partially or fully halogenated and/or, independently of each other, can have attached to it one to three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio, and to salts thereof.

Moreover, the invention relates to processes and intermediates for the preparation of these compounds and to their use for controlling animal pests and harmful fungi.

Phenylacetic acid derivatives for pest control have been disclosed in the literature (cf. WO-A 95/18789, WO-A 95/21153, WO-A 95/21154), but they are not yet satisfactory with a view to their activity.

It is an object of the present invention to provide novel compounds of this type which have an improved activity.

We have found that this object is achieved by the phenylacetic acid derivatives I defined at the outset. Moreover, we have found processes and intermediates for their preparation, compositions comprising them for controlling animal pests and harmful fungi, and their use for these purposes.

The compounds I are accessible via various routes by processes known per se.

When synthesizing the compounds I, it is, in principle, irrelevant whether the group —C(X)—CO—Y—$R^1$ or the group

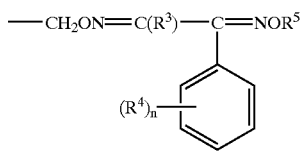

is first synthesized.

The synthesis of the group —C(X)—CO—Y—$R^1$ is disclosed, for example, in the publications cited at the outset and in the following: EP-A 242 070, EP-A 254 426, EP-A 370 629, EP-A 398 692, EP-A 422 597, EP-A 463 488, EP-A 472 300, EP-A 513 580, EP-A 656 352, German Application P 44 20 416.7.

When synthesizing the group

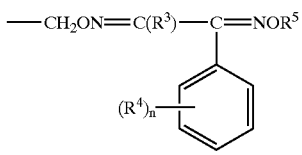

a procedure is generally followed in which a benzyl derivative of the formula II is reacted with a hydroxyimine of the formula III.

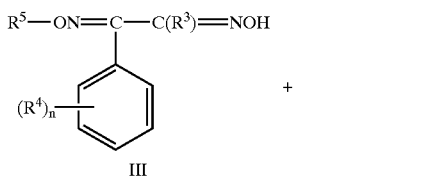

+

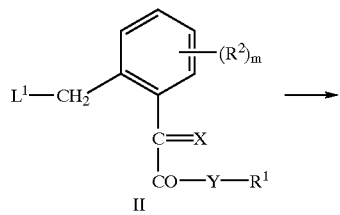

→

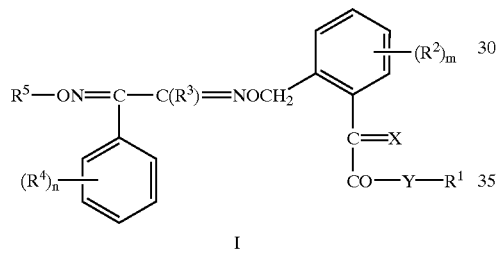

I $L^1$ in formula II is a nucleophilically exchangeable leaving group, eg. halogen or sulfonate groups, preferably chlorine, bromine, iodine, mesylate, tosylate or triflate.

The reaction is carried out in a manner known per se in an inert organic solvent in the presence of a base, eg. sodium hydride, potassium hydroxide, potassium carbonate or triethylamine, following the methods described in Houben-Weyl, 4th Edition, Vol. E 14b, p. 370 et seq. and ibd. Vol. 10/1, p. 1189 et seq.

The hydroxyimine III which is required is obtained, for example, by reacting a corresponding dihydroxyimine IV with the compound of the formula VI

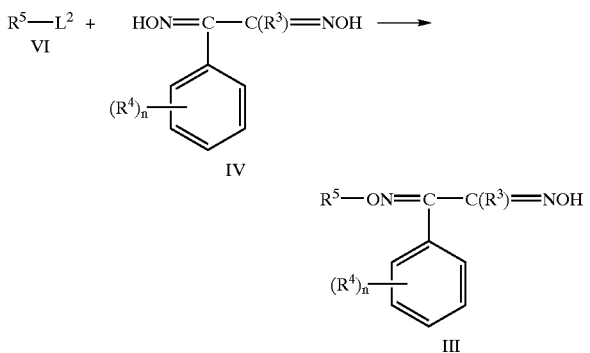

$L^2$ in formula VI is a nucleophilically exchangeable leaving group, eg. halogen or sulfonate groups, preferably chlorine, bromine, iodine, mesylate, tosylate or triflate.

The reaction is carried out in a manner known per se in an inert organic solvent in the presence of a base, eg. potassium carbonate, potassium hydroxide, sodium hydride, pyridine or triethylamine as described in: Houben-Weyl, 4th Edition, Vol. E 14b, p. 307 et seq., p. 370 et seq. and p. 385 et seq.; ibid., 4th Edition, Vol. 10/4, p. 55 et seq., p. 180 et seq. and p. 217 et seq.; ibid., 4th Edition, Vol. E 5, p. 780 et seq.

Those compounds of the formula IV which are not already known can be prepared by methods known per se (cf. Gazz. Chim. Ital. 59 (1929), 719; Collect. Bull. Soc. Chim. Fr. 17 (1897), 71).

Alternatively, the compounds I can also be obtained by reacting the benzyl derivative II first with the dihydroxyimino derivative IV to give a corresponding benzyl oxime of the formula V, V subsequently being reacted with a compound of a [sic] formula VI to give I.

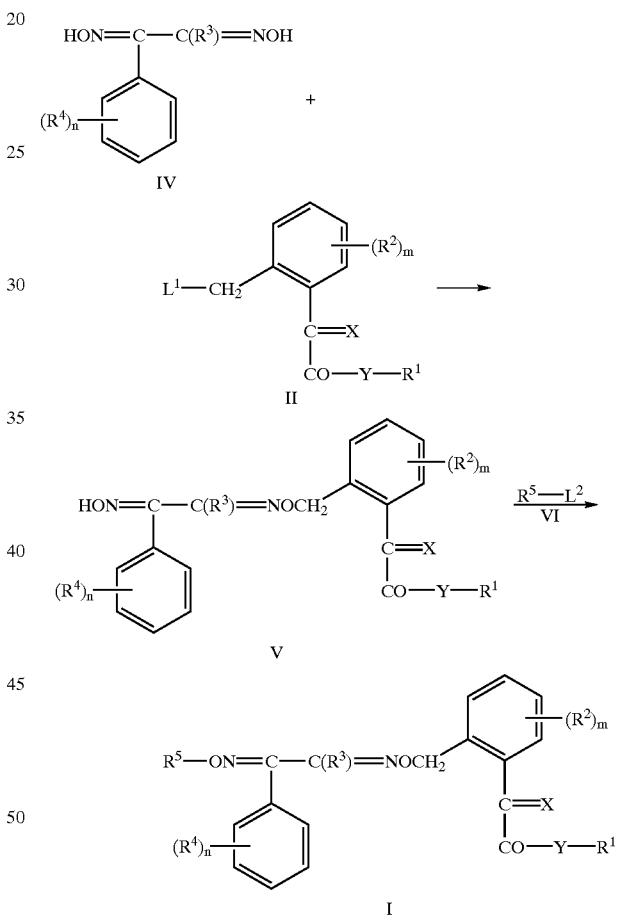

The reaction is carried out in a manner known per se in an inert organic solvent in the presence of a base, eg. potassium carbonate, potassium hydroxide, sodium hydride, pyridine or triethylamine following the methods described in Houben-weyl, 4th Edition, Vol. 10/1, p. 1189 et seq., Vol. E 14b, p. 307 et seq., p. 370 et seq. and p. 385 et seq., Vol. 10/4, p. 55 et seq., p. 180 et seq. and p. 217 et seq., Vol. E 5, p. 780 et seq.

Similarly, it is also possible to prepare the hydroxyimine [sic] of the formula III which is required from a carbonyl-hydroxyimine VII by reacting the latter with a hydroxylamine IXa or a salt thereof IXb.

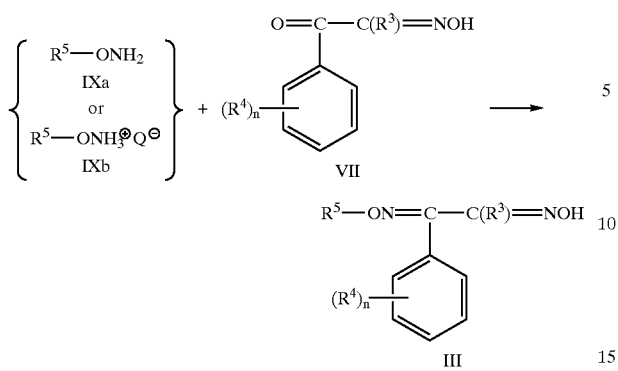

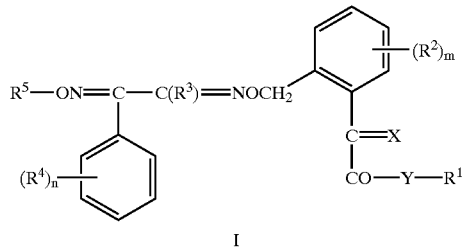

I

The reaction is carried out in a manner known per se in an inert organic solvent following the methods described in Houben-Weyl, 4th Edition, Vol. E 14b, p. 369 et seq., Vol. 10/1, p. 1189 et seq. and Vol. 10/4, p. 73 et seq. or EP-A 513 580.

$Q^{\ominus}$ in formula IXb is the anion of an acid, in particular of an inorganic acid, eg. halide, such as chloride.

The reaction is carried out in a manner known per se in an inert organic solvent following the methods described in EP-A 513 580; Houben-Weyl, 4th Edition, Vol. 10/4, p. 73 et seq., Vol. E 14b, p. 369 et seq. and p. 385 et seq.

Those compounds of the formula VII which are not already known can be prepared by methods known per se (J. Am. Pharm. Assoc. 35 (1946), 15).

Alternatively, the compounds I can also be obtained by reacting the benzyl derivative II first with the carbonylhydroxyimino derivative VII to give a corresponding benzyloxyimine of the formula VIII, VIII subsequently being reacted with the hydroxylamine IXa or the salt thereof IXb to give I.

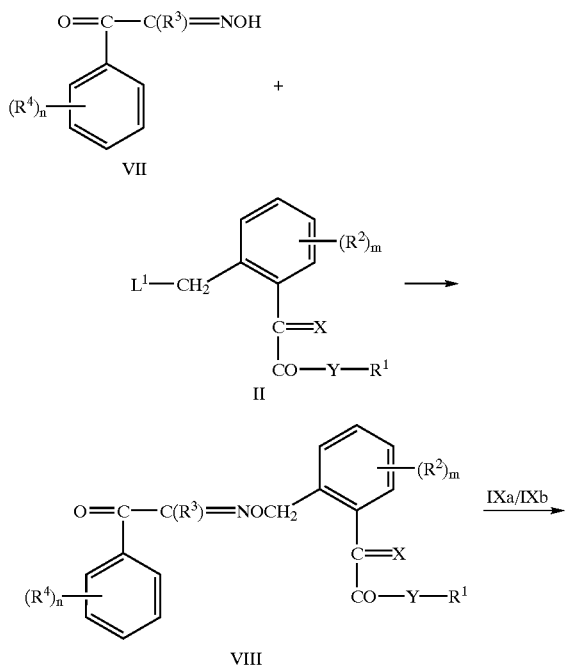

A further possibility of preparing the compounds I where $R^3$ is not $C_1$–$C_4$-alkoxy is to react the benzyl derivative II with N-hydroxyphthalimide, subsequently subjecting the product to hydrazinolysis to give the benzylhydroxylamine IIa and further reacting IIa with a carbonyl compound X.

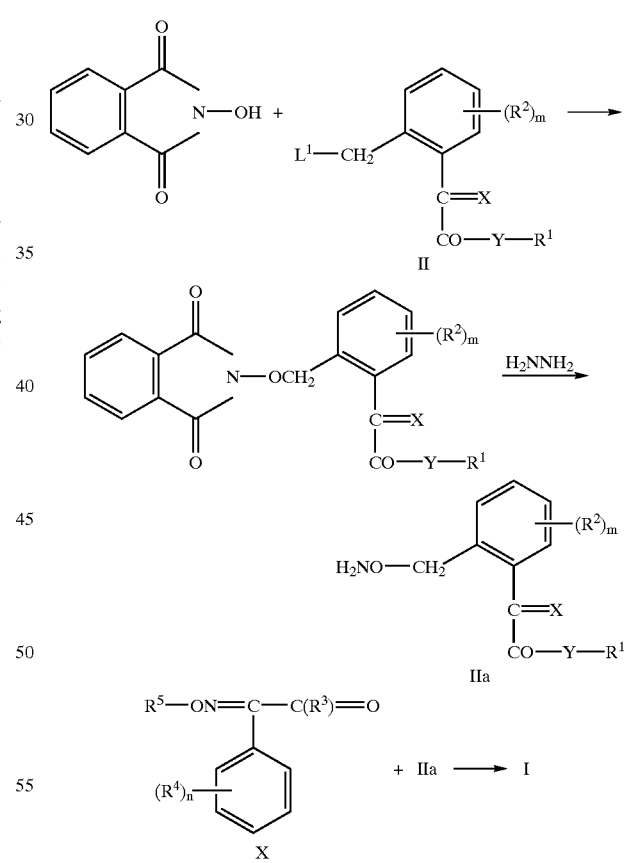

The reaction is carried out in a manner known per se in an inert organic solvent following the methods described in EP-A 463 488 and EP-A 585 751.

The carbonyl compound X which is required is obtained, for example, by reacting a corresponding hydroxyiminocarbonyl compound VIIa with a compound of the formula VI

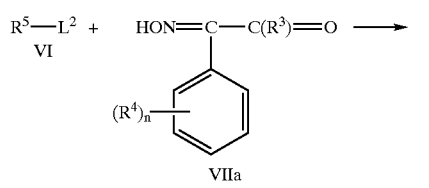

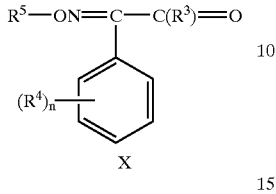

or by reacting a corresponding dicarbonyl compound XI with a hydroxylamine IXa or a salt thereof IXb

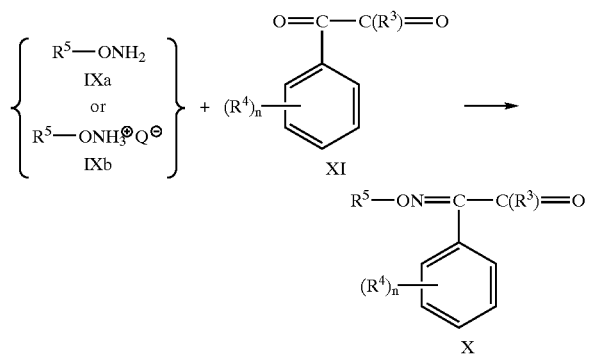

The reactions are carried out in a manner known per se in an inert organic solvent following the methods described in EP-A 513 580, Houben-Weyl, 4th Edition, Vol. 10/4, p. 55 et seq., p. 73 et seq., p. 180 et seq. and p. 217 et seq., Vol. E 14b, p. 307 ff and 369 et seq., Vol. E 5, p. 780 et seq.

Those compounds of the formula VIIa or XI which are not already known can be prepared by methods known per se (J. Chem. Soc., 3094 (1955); Bull. Soc. Chim. Fr., 2894 (1969); Tetrahedron 40 (1984), 2035).

Similarly, the compounds I can also be obtained by first reacting the benzylhydroxylamine IIa with the hydroxy-imino derivative VIIa to give the corresponding benzyloxy-imino derivative of the formula V, V subsequently being reacted with a compound of the formula VI as described above to give I.

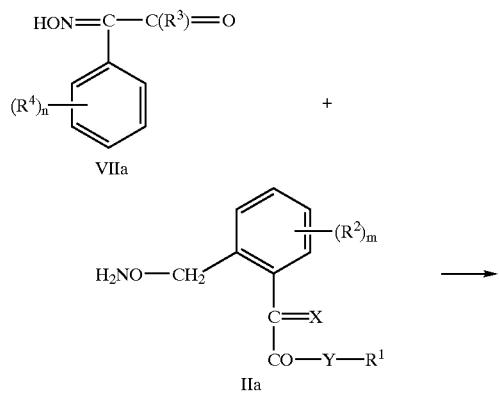

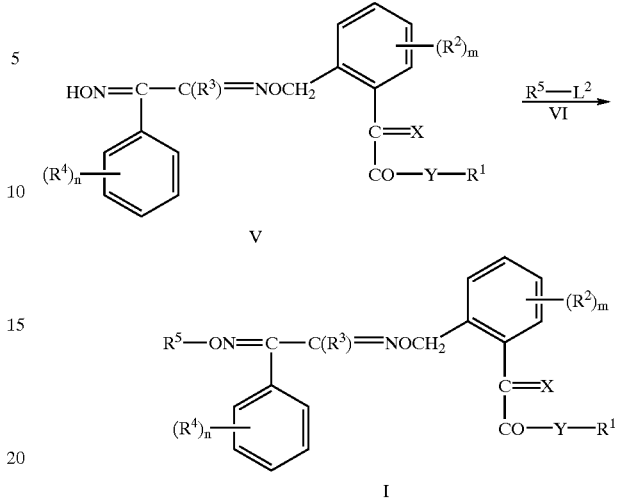

Similarly, the compounds I can also be prepared by first converting the benzylhydroxylamine IIa with the dicarbonyl derivative of the formula XI to give the benzyloxyimino derivative of the formula VIII and subsequently reacting VIII with the hydroxylamine IXa or a salt thereof IXb as described above to give I.

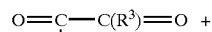

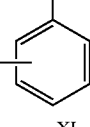

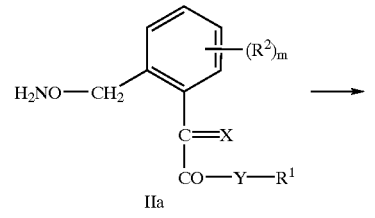

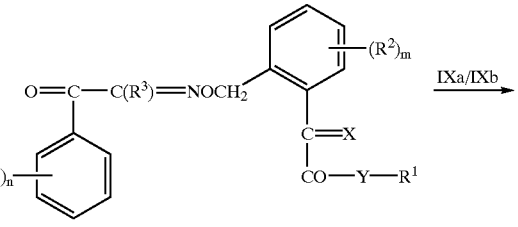

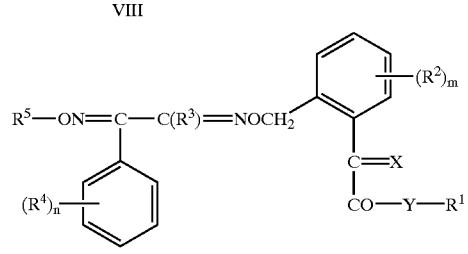

Furthermore, the compounds I are also obtained by first converting a compound III with a lactone XII following the methods described in EP-A 493 711 to give the corresponding benzoic acid XIII and converting XIII into the cyanocarboxylic acids XIV via the corresponding halides, and the cyanocarboxylic acids XIV are converted into the α-ketoesters XV via a Pinner reaction (Angew. Chem. 94 (1982), 1) and, if desired, the α-ketoesters XV are reacted further to give the α-ketoamides XVI (cf. EP-A 348 766, DE-A 37 05 389, EP-A 178 826, DE-A 36 23 921, Houben-Weyl, 4th dition, Vol. E5, p. 941 et seq.).

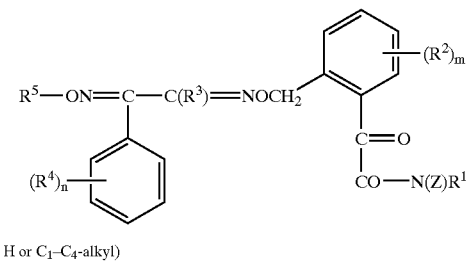

(Z = H or C$_1$–C$_4$-alkyl)

The α-ketoesters XV and the α-ketoamides XVI can be converted into the compounds I following customary methods (cf. EP-A 178 826, EP-A 513 580, DE-A 36 23 921, EP-A 398 692).

Compounds I where R$^1$ is hydrogen are obtained by this process by means of hydrolyzing the esters XV and subsequent reaction to give I.

The compounds I where R$^4$ is —C(=NOR$^a$)—R$^b$, —NR$^c$—(C=O)—A$_p$—R$^a$, —O—(C=O)—NR$^a$R$^b$ or —N(R$^c$)—OR$^d$ are preferably synthesized by generally known methods starting from the compounds XVII, XVIII, XIX or XX.

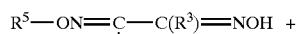
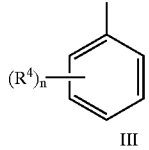
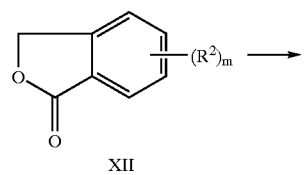
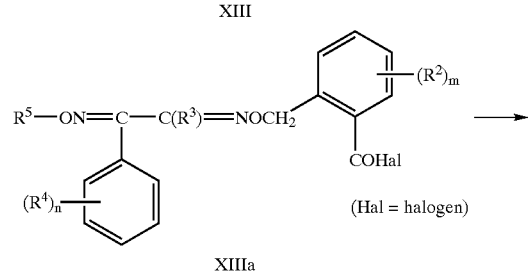
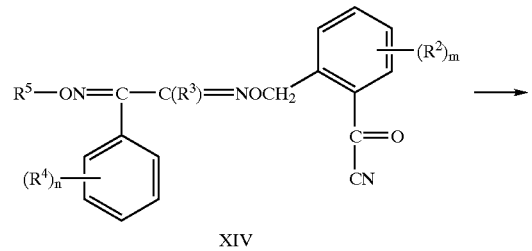

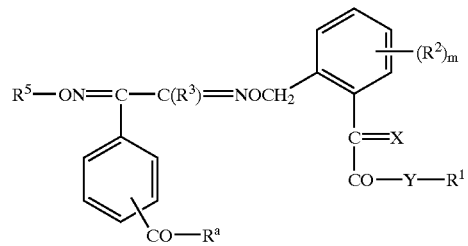
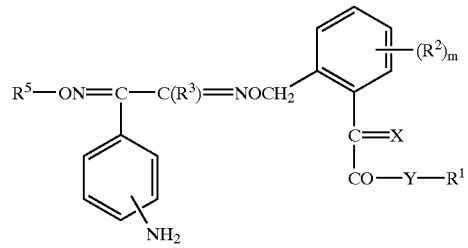
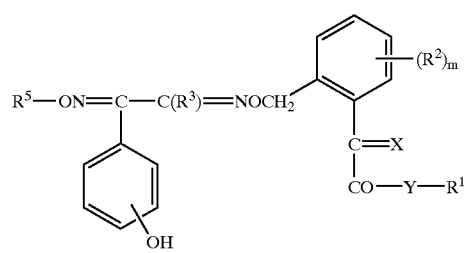

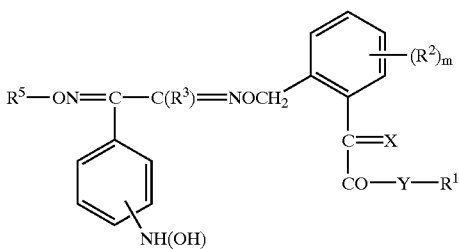

The compounds I where Y is NH can also be obtained from the corresponding esters (Y=O) by reacting the latter with amines of the formula R¹NH₂.

Those compounds II which are not already known (EP-A 513 580, EP-A 477 631, EP-A 463 488, EP-A 251 082, EP-A 400 417, EP-A 585 751) can be prepared following the methods described in these publications.

Owing to their C=C and C=N double bonds, the compounds I can be obtained from their preparation as E/Z isomer mixtures, which can be separated into the individual compounds in the customary manner, for example by crystallization or chromatography.

If isomer mixtures are obtained from the synthesis, however, a separation is generally not absolutely necessary since in some cases the individual isomers can be converted into each other during formulation for use or upon use (eg. when exposed to light, acids or bases). Similar conversions can also take place after use, for example in the case of the treatment of plants in the treated plants or in the harmful fungus or animal pest to be controlled.

As regards the C=X double bond, the E isomers of the compounds I are preferred with a view to their activity (configuration based on the —OCH₃ or the —CH₃ group relative to the —CO—Y—R¹ group).

As regards the —C(R³)=NOCH₂— double bond, the cis isomers of the compounds I are preferred with a view to their activity (configuration based on the radical R³ relative to the —OCH₂ group).

In the definitions of the compounds I given at the outset, collective terms were used which generally represent the following groups:

Halogen: fluorine, chlorine, bromine and iodine;

Alkyl: straight-chain or branched alkyl groups having 1 to 4, 6 or 10 carbon atoms, eg. C₁–C₆-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl and 1-ethyl-2-methylpropyl;

Alkylamino: an amino group which has attached to it a straight-chain or branched alkyl group having 1 to 6 carbon atoms as mentioned above;

Dialkylamino: an amino group which has attached to it two straight-chain or branched alkyl groups which are independent of each other and have in each case 1 to 6 carbon atoms as mentioned above;

Alkylcarbonyl: straight-chain or branched alkyl groups having 1 to 10 carbon atoms which are linked to the skeleton via a carbonyl group (—CO—);

Alkylsulfonyl: straight-chain or branched alkyl groups having 1 to 6 or 10 carbon atoms which are linked to the skeleton via a sulfonyl group (—SO₂—);

Alkylsulfoxyl: straight-chain or branched alkyl groups having 1 to 6 carbon atoms which are linked to the skeleton via a sulfoxyl group (—S(=O)—);

Alkylaminocarbonyl: alkylamino groups having 1 to 6 carbon atoms as mentioned above which are linked to the skeleton via a carbonyl group (—CO—);

Dialkylaminocarbonyl: dialkylamino groups having in each case 1 to 6 carbon atoms per alkyl radical as mentioned above which are linked to the skeleton via a carbonyl group (—CO—);

Alkylaminothiocarbonyl: alkylamino groups having 1 to 6 carbon atoms as mentioned above which are linked to the skeleton via a thiocarbonyl group (—CS—);

Dialkylaminothiocarbonyl: dialkylamino groups having in each case 1 to 6 carbon atoms per alkyl radical as mentioned above which are linked to the skeleton via a thiocarbonyl group (—CS—);

Haloalkyl: straight-chain or branched alkyl groups having 1 to 6 carbon atoms, it being possible for some or all of the hydrogen atoms in these groups to be replaced by halogen atoms as mentioned above, eg. C₁–C₂-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 4 or 6 carbon atoms as mentioned above which are linked to the skeleton via an oxygen atom (—O—), eg. C₁–C₆-alkoxy, such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethyl-butyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy;

Alkoxycarbonyl: straight-chain or branched alkyl groups having 1 to 6 carbon atoms which are linked to the skeleton via an oxycarbonyl group (—OC(=O)—);

Haloalkoxy: straight-chain or branched alkyl groups having 1 to 6 carbon atoms, it being possible for some or all of the hydrogen atoms in these groups to be replaced by halogen atoms as mentioned above, and these groups being linked to the skeleton via an oxygen atom;

Alkylthio: straight-chain or branched alkyl groups having 1 to 4 or 6 carbon atoms as mentioned above which are linked to the skeleton via a sulfur atom (—S—), eg. C₁–C₆-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

Alkylenedioxy: divalent branched or unbranched chains of 1–4 $CH_2$ groups which may be partially or fully halogenated, and both valencies are linked to the skeleton via an oxygen atom, eg. $OCH_2$—O, O—$CH_2CH_2$—O, O—CHCl—CHCl—O— or O—$(CH_2)_3$—O;

Cycloalkyl: monocyclic alkyl groups having 3 to 6 carbon ring members, eg. cyclopropyl, cyclobutyl, cyclopentyl and cyclohexyl;

Alkenyl: straight-chain or branched alkenyl groups having 2 to 6 or 10 carbon atoms and a double bond in any position, eg. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-di-methyl-3-butenyl, 1,2-dimethyl-1-butenyl, 1,2-dimethyl-2-butenyl, 1,2-dimethyl-3-butenyl, 1,3-dimethyl-2-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenyloxy: straight-chain or branched alkenyl groups having 2 to 6 carbon atoms and a double bond in any position which are linked to the skeleton via an oxygen atom (—O—);

Alkenylthio and alkenylamino: straight-chain or branched alkenyl groups having 2 to 6 carbon atoms and a double bond in any position which are linked to the skeleton via a sulfur atom (alkenylthio) or a nitrogen atom (alkenylamino);

Alkenylcarbonyl: straight-chain or branched alkenyl groups having 2 to 10 carbon atoms and a double bond in any position which are linked to the skeleton via a carbonyl-group (—CO—);

Alkynyl: straight-chain or branched alkynyl groups having 2 to 10 carbon atoms and a triple bond in any position, eg. $C_2$–$C_6$-alkynyl, such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

Alkynyloy, or alkynylthio and alkynylamino: straight-chain or branched alkynyl groups having 2 to 6 carbon atoms and a triple bond in any position which are linked to the skeleton via an oxygen atom (alkynyloxy), via a sulfur atom (alkynylthio) or via a nitrogen atom (alkynylamino).

Alkynylcarbonyl: straight-chain or branched alkynyl groups having 3 to 10 carbon atoms and a triple bond in any position which are linked to the skeleton via a carbonyl group (—CO—);

Cycloalkenyl, or cycloalkenyloxy, cycloalkenylthio and cycloalkenylamino: monocyclic alkenyl groups having 3 to 6 carbon ring members which are linked to the skeleton directly or via an oxygen atom (cycloalkenyloxy) or a sulfur atom (cycloalkenylthio) or via a nitrogen atom (cycloalkenylamino), eg. cyclopropenyl, cyclobutenyl, cyclopentenyl or cyclohexenyl;

Cycloalkyloxy, or cycloalkylthio and cycloalkylamino: monocyclic alkyl groups having 3 to 6 carbon ring members which are linked to the skeleton via an oxygen atom (cycloalkyloxy) or a sulfur atom (cycloalkylthio) or via a nitrogen atom (cycloalkylamino), eg. cyclopropyl, cyclobutyl, cyclopentyl or cyclohexyl;

Cycloalkylcarbonyl: cycloalkyl groups as defined above which are linked to the skeleton via a carbonyl group (—CO—);

Cycloalkyloxycarbonyl: cycloalkyloxy groups as defined above which are linked to the skeleton via a carbonyl group (—CO—);

Alkenyloxycarbonyl: alkenyloxy groups as defined above which are linked to the skeleton via a carbonyl group (—CO—);

Alkynyloxycarbonyl: alkynyloxy groups as defined above which are linked to the skeleton via a carbonyl group (—CO—);

Heterocyclyl, or Heterocyclyl, heterocyclylthio and heterocyclylamino: three- to six-membered saturated or partially unsaturated mono- or polycyclic heterocycles which contain one to three hetero atoms selected from a group consisting of oxygen, nitrogen and sulfur and which are linked to the skeleton directly, or via an oxygen atom (heterocyclyloxy) or via a sulfur atom (heterocyclylthio) or via a nitrogen atom (heterocyclylamino), eg. 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazoldinyl [sic], 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydro-fur-4-yl, 2,3-dihydro-fur-5-yl, 2,5-dihydro-fur-2-yl, 2,5-dihydro-fur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, Aryl, or aryloxy, arylthio, arylcarbonyl and arylsulfonyl: aromatic mono- or polycyclic hydrocarbon radicals which are linked to the skeleton directly, or (aryloxy) via an oxygen atom (—O—), (arylthio) via a sulfur atom (—S—), or (arylcarbonyl) via a carbonyl group (—CO—) or (arylsulfonyl) via a sulfonyl group (—SO$_2$—), eg. phenyl, naphthyl and phenanthrenyl, or phenyloxy, naphthyloxy and phenanthrenyloxy and the corresponding carbonyl and sulfonyl radicals;

Arylamino: aromatic mono- or polycyclic hydrocarbon radicals which are linked to the skeleton via a nitrogen atom;

Hetaryl, or hetaryloxy, hetarylthio, hetarylcarbonyl and hetarylsulfonyl: aromatic mono- or polycyclic radicals which, besides carbon ring members, can additionally contain one to four nitrogen atoms or one to three nitrogen atoms and one oxygen or one sulfur atom or one oxygen or one sulfur atom and which are linked to the skeleton directly, or (hetaryloxy) via an oxygen atom (—O—) or (hetarylthio) via a sulfur atom (—S—), (hetarylcarbonyl) via a carbonyl group (—CO—) or (hetarylsulfonyl) via a sulfonyl group (—SO$_2$—), eg.

5-membered hetaryl containing one to three nitrogen atoms: 5-membered hetaryl ring groups which, besides carbon atoms, can contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl containing one to four nitrogen atoms or one to three nitrogen atoms and one sulfur or oxygen atom or one oxygen or one sulfur atom: 5-membered hetaryl ring groups which, besides carbon atoms, can contain one to four nitrogen atoms or one to three nitrogen atoms and one sulfur or oxygen atom or one oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered hetaryl containing one to three nitrogen atoms or one nitrogen atom and/or one oxygen or sulfur atom: 5-membered hetaryl ring groups which, besides carbon atoms, can contain one to four nitrogen atoms or one to three nitrogen atoms and one sulfur or oxygen atom or one oxygen or one sulfur atom as ring members, and in which two adjacent carbon ring members or one nitrogen and an adjacent carbon ring member can be bridged by a buta-1,3-diene-1,4-diyl group;

5-membered hetaryl, linked via nitrogen and containing one to 4 nitrogen atoms, or benzo-fused 5-membered hetaryl linked via nitrogen and containing one to three nitrogen atoms: 5-membered hetaryl ring groups which, besides carbon atoms, can contain one to four nitrogen atoms, or one to three nitrogen atoms, respectively, as ring members and in which two adjacent carbon ring members or one nitrogen and an adjacent carbon ring member can be bridged by a buta-1,3-diene-1,4-diyl group, these rings being linked to the skeleton via one of the nitrogen ring members;

6-membered hetaryl containing one to three, or one to four, nitrogen atoms: 6-membered hetaryl ring groups which, besides carbon ring members, can contain one to three, or one to four, nitrogen atoms, respectively, as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl containing one to four nitrogen atoms: 6-membered hetaryl ring groups in which two adjacent carbon ring members can be bridged by a buta-1,3-diene-1,4-diyl group, eg. quinoline, isoquinoline, quinazoline and quinoxaline, and the corresponding oxy, thio, carbonyl or sulfonyl groups.

Netarylamino: aromatic mono- or polycyclic radicals which, besides carbon ring members, can additionally contain one to four nitrogen atoms or one to three nitrogen atoms and one oxygen or one sulfur atom and which are linked to the skeleton via a nitrogen atom.

The term "partially or fully halogenated" is intended to express that some or all of the hydrogen atoms in thus characterized groups can be replaced by identical or different halogen atoms as mentioned above.

Compounds I which are preferred for their biological activity are those where $R^a$ and $R^b$ independently of one another are:

hydrogen;

$C_1$–$C_6$-alkyl, $C_2$–$C_6$-alkenyl, $C_2$–$C_6$-alkynyl, it being possible for these radicals to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, arylthio, hetaryl, hetaryloxy, hetarylthio, it being possible for the cyclic groups, in turn, to be partially or fully halogenated and/or to have attached to them one to three of the following substituents: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C_3$–$C_6$-alkynyloxy;

$C_3$–$C_6$-cycloalkyl, $C_3$–$C_6$-cycloalkenyl, heterocyclyl, it being possible for these radicals to be partially or fully halogenated and/or to have attached to them one to three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio; aryl or hetaryl, it being possible for these radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, Di-$C_1$–$C_6$-alkylamino, $C_1$–$C_6$-alkylaminocarbonyl, Di-$C_1$–$C_6$-alkylaminocarbonyl, $C_1$–$C_6$-alkylaminothiocarbonyl, Di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio, $C_3$–$C_6$-alkynyloxy and $C_1$–$C_4$-alkylenedioxy or halogenated $C_1$–$C_4$-alkylenedioxy.

Other preferred compounds I are those where $R^c$ and $R^d$ independently of one another are:

hydrogen;

$C_1$–$C_6$-alkyl, $C_2$–$C_6$-alkenyl, $C_2$–$C_6$-alkynyl, $C_1$–$C_6$-alkylcarbonyl, $C_2$–$C_6$-alkenylcarbonyl, $C_2$–$C_6$-alkynylcarbonyl, $C_1$–$C_6$-alkoxycarbonyl, $C_2$–$C_6$-alkenyloxycarbonyl, $C_2$–$C_6$-alkynyloxycarbonyl, it being possible for these radicals to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, arylthio, hetaryl, hetaryloxy, hetarylthio, it being possible for the cyclic groups, in turn, to be partially or fully halogenated and/or to have attached to them one to three of the following substituents: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C_3$–$C_6$-alkynyloxy;

$C_3$–$C_6$-cycloalkyl, cycloalkylcarbonyl, cycloalkyloxycarbonyl, it being possible for these radicals to be partially or fully halogenated and/or to have attached to them one to three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio;

arylcarbonyl or hetarylcarbonyl, it being possible for these radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio, $C_3$–$C_6$-alkynyloxy and $C_1$–$C_4$-alkylenedioxy or halogenated $C_1$–$C_4$-alkylenedioxy.

Moreover, preferred compounds I are those where $R^5$ is:

hydrogen;

$C_1$–$C_6$-alkyl, $C_2$–$C_6$-alkenyl, $C_2$–$C_6$-alkynyl, it being possible for these radicals to be partially or fully halogenated or to have attached to them one to three of the following groups: cyano, hydroxyl, $C_1$–$C_6$-alkoxy, $C_1$–$C_6$-alkoxycarbonyl, $C_1$–$C_6$-alkylthio, $C_3$–$C_6$- cycloalkyl or oxiranyl, it being possible for the cyclic groups, in turn, to have attached to them one to five of the following substituents: halogen and $C_1$–$C_4$-alkyl.

Especially preferred compounds I are those where $R^a$ and $R^b$ independently of one another are:

hydrogen;

$C_1$–$C_6$-alkyl, $C_2$–$C_6$-alkenyl, $C_2$–$C_6$-alkynyl, it being possible for these radicals to be partially or fully halogenated and/or to have attached to them one to three of the following groups: cyano, nitro, hydroxyl, $C_1$–$C_6$-alkoxy, $C_1$–$C_6$-haloalkoxy, $C_1$–$C_6$-alkoxycarbonyl, $C_1$–$C_6$-alkylthio, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, hetaryl, hetaryloxy, it being possible for the cyclic groups, in turn, to be partially or fully halogenated and/or to have attached to them one to three of the following substituents: cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy and $C_3$–$C_6$-alkynyloxy;

$C_3$–$C_6$-cycloalkyl, $C_3$–$C_6$-cycloalkenyl, heterocyclyl, it being possible for these radicals to be partially or fully halogenated and/or to have attached to them one to three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio;

aryl or hetaryl, it being possible for these radicals, in turn, to be partially or fully halogenated and/or to have attached to them one to three of the following groups: cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy or halogenated $C_1$–$C_4$-alkylenedioxy.

Furthermore, especially preferred compounds I are those where $R^c$ and $R^d$ independently of one another are:

hydrogen;

$C_1$–$C_6$-alkyl, $C_2$–$C_6$-alkenyl, $C_2$–$C_6$-alkynyl, $C_1$–$C_6$-alkylcarbonyl, $C_2$–$C_6$-alkenylcarbonyl, $C_2$–$C_6$-alkynylcarbonyl, $C_1$–$C_6$-alkoxycarbonyl, $C_2$–$C_6$-alkenyloxycarbonyl, $C_2$–$C_6$-alkynyloxycarbonyl, it being possible for these radicals to be partially or fully halogenated and/or to have attached to them one to three of the following groups: cyano, nitro, hydroxyl, $C_1$–$C_6$-alkoxy, $C_1$–$C_6$-haloalkoxy, $C_1$–$C_6$-alkoxycarbonyl, $C_1$–$C_6$-alkylthio, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, hetaryl, hetaryloxy, it being possible for the cyclic groups, in turn, to be partially or fully halogenated and/or to have attached to them one to three of the following substituents: cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy and $C_3$–$C_6$-alkynyloxy;

$C_3$–$C_6$-cycloalkyl, cycloalkylcarbonyl, cycloalkyloxycarbonyl, it being possible for these radicals to be partially or fully halogenated and/or to have attached to them one to three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio;

arylcarbonyl or hetarylcarbonyl, it being possible for these radicals, in turn, to be partially or fully halogenated and/or to have attached to them one to three of the following groups: cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy or halogenated $C_1$–$C_4$-alkylenedioxy.

Furthermore, preferred compounds of the formula I are those where m is 0.

Equally, preferred compounds of the formula I are those where $R^1$ is methyl.

Other preferred compounds I are those where $R^1$ is hydrogen.

Besides, preferred compounds I are those where $R^3$ is hydrogen, cyclopropyl, methyl, ethyl, 1-methylethyl, methoxy, cyano or trifluoromethyl.

Especially preferred compounds I are those where $R^3$ is methyl.

Furthermore, preferred compounds I are those where $R^3$ is methoxy.

Moreover, preferred compounds I are those where $R^3$ is cyano.

Furthermore, preferred compounds I are those where $R^3$ is trifluoromethyl.

Furthermore, preferred compounds I are those where n is 1.

Moreover, preferred compounds I are those where $R^4$ is —(C=O)—$R^a$.

Furthermore, preferred compounds I are those where $R^4$ is $C_1$–$C_4$-alkylcarbonyl.

Moreover, preferred compounds I are those where $R^4$ is —C(=NOR$^a$)—A$_p$—R$^b$.

Furthermore, preferred compounds I are those where $R^4$ is —C(=NOR$^a$)—R$^b$.

Moreover, preferred compounds I are those where $R^4$ is NR$^c$—(C=O)—A$_p$—R$^a$.

Moreover, preferred compounds I are those where $R^4$ is —O—(C=O)—NR$^a$R$^b$.

Furthermore, preferred compounds I are those where $R^4$ is N(R$^c$)—OR$^d$.

Furthermore, preferred compounds I are those where $R^a$ or $R^b$ is $C_1$–$C_6$-alkyl or $C_2$–$C_6$-alkenyl.

Furthermore, preferred compounds I are those where $R^4$ is $C_1$–$C_4$-alkylenedioxy, the alkylene groups being partially or fully halogenated, preferably fluorinated.

Especially preferred compounds I are those where $R^4$ is difluoromethylenedioxy.

Moreover, preferred compounds I are those where $R^5$ is hydrogen, $C_3$–$C_6$-cycloalkyl, arylalkyl, hetarylalkyl, aryloxyalkyl, hetaryloxyalkyl.

Especially preferred compounds I are those where $R^5$ is $C_1$–$C_6$-alkyl.

Very especially preferred compounds I are those where $R^5$ is methyl or ethyl.

Furthermore, preferred compounds I are those where $R^5$ is $C_1$–$C_6$-alkylsulfonyl.

Besides, preferred compounds of the formula I are those where X is NOCH$_3$.

Besides, preferred compounds of the formula I are those where X is CHOCH$_3$ and Y is O.

Besides, preferred compounds of the formula I are those where X is CHCH$_3$ and Y is O.

Moreover, preferred compounds of the formula I are those where Y is O.

Furthermore, preferred compounds of the formula I are those where Y is NH or N—CH$_3$.

Especially preferred compounds of the formula I are those where Y is NH and R$^1$ is methyl.

Especially preferred compounds of the formula I are those where Y is O and R$^1$ is methyl.

Compounds I which are particularly preferred with a view to their use are those compiled in the tables which follow.

The tables which follow (1 to 596) are based on the formulae I.1, I.2, I.3 and I.4, the double bonds marked "E" having the E configuration:

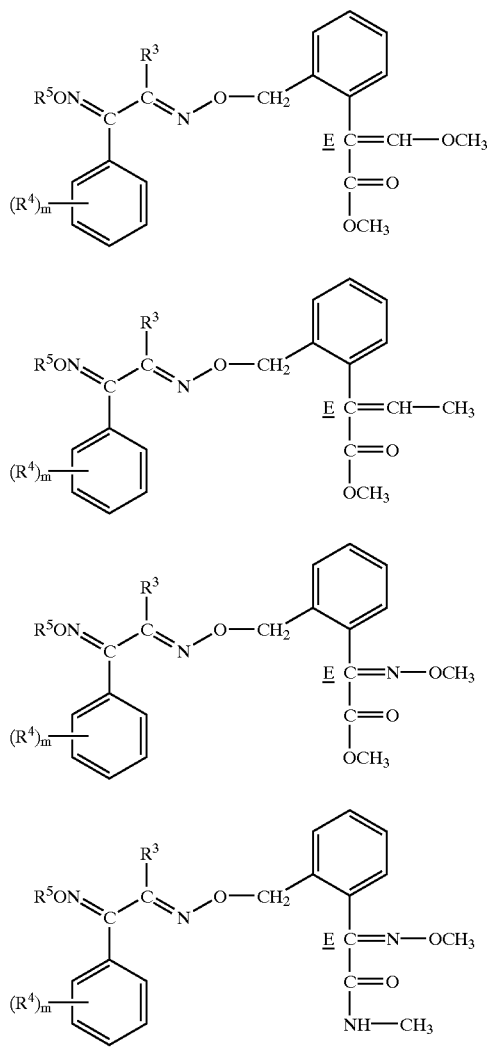

TABLE 1

Compounds of the formula I.1 where

R$^3$ = hydrogen;
R$^5$ = hydrogen;
R$^4$ = in each case one line of Table A.

TABLE 2

Compounds of the formula I.2 where

R$^3$ = hydrogen;
R$^5$ = hydrogen;
R$^4$ = in each case one line of Table A.

TABLE 3

Compounds of the formula I.3 where

R$^3$ = hydrogen;
R$^5$ = hydrogen;
R$^4$ = in each case one line of Table A.

TABLE 4

Compounds of the formula I.4 where

R$^3$ = hydrogen;
R$^5$ = hydrogen;
R$^4$ = in each case one line of Table A.

TABLE 5

Compounds of the formula I.1 where

R$^3$ = hydrogen;
R$^5$ = methyl;
R$^4$ = in each case one line of Table A.

TABLE 6

Compounds of the formula I.2 where

R$^3$ = hydrogen;
R$^5$ = methyl;
R$^4$ = in each case one line of Table A.

TABLE 7

Compounds of the formula I.3 where

R$^3$ = hydrogen;
R$^5$ = methyl;
R$^4$ = in each case one line of Table A.

TABLE 8

Compounds of the formula I.4 where

R$^3$ = hydrogen;
R$^5$ = methyl;
R$^4$ = in each case one line of Table A.

TABLE 9

Compounds of the formula I.1 where

R$^3$ = hydrogen;
R$^5$ = ethyl;
R$^4$ = in each case one line of Table A.

TABLE 10

Compounds of the formula I.2 where $R^3$ = hydrogen;
$R^5$ = ethyl;
$R^4$ = in each case one line of Table A.

TABLE 11

Compounds of the formula I.3 where $R^3$ = hydrogen;
$R^5$ = ethyl;
$R^4$ = in each case one line of Table A.

TABLE 12

Compounds of the formula I.4 where $R^3$ = hydrogen;
$R^5$ = ethyl;
$R^4$ = in each case one line of Table A.

TABLE 13

Compounds of the formula I.1 where $R^3$ = hydrogen;
$R^5$ = n-propyl;
$R^4$ = in each case one line of Table A.

TABLE 14

Compounds of the formula I.2 where $R^3$ = hydrogen;
$R^5$ = n-propyl;
$R^4$ = in each case one line of Table A.

TABLE 15

Compounds of the formula I.3 where $R^3$ = hydrogen;
$R^5$ = n-propyl;
$R^4$ = in each case one line of Table A.

TABLE 16

Compounds of the formula I.4 where $R^3$ = hydrogen;
$R^5$ = n-propyl;
$R^4$ = in each case one line of Table A.

TABLE 17

Compounds of the formula I.1 where $R^3$ = hydrogen;
$R^5$ = iso-propyl;
$R^4$ = in each case one line of Table A.

TABLE 18

Compounds of the formula I.2 where $R^3$ = hydrogen;
$R^5$ = iso-propyl;
$R^4$ = in each case one line of Table A.

TABLE 19

Compounds of the formula I.3 where $R^3$ = hydrogen;
$R^5$ = iso-propyl;
$R^4$ = in each case one line of Table A.

TABLE 20

Compounds of the formula I.4 where $R^3$ = hydrogen;
$R^5$ = iso-propyl;
$R^4$ = in each case one line of Table A.

TABLE 21

Compounds of the formula I.1 where $R^3$ = hydrogen;
$R^5$ = cyclopropyl;
$R^4$ = in each case one line of Table A.

TABLE 22

Compounds of the formula I.2 where $R^3$ = hydrogen;
$R^5$ = cyclopropyl;
$R^4$ = in each case one line of Table A.

TABLE 23

Compounds of the formula I.3 where $R^3$ = hydrogen;
$R^5$ = cyclopropyl;
$R^4$ = in each case one line of Table A.

TABLE 24

Compounds of the formula I.4 where $R^3$ = hydrogen;
$R^5$ = cyclopropyl;
$R^4$ = in each case one line of Table A.

TABLE 25

Compounds of the formula I.1 where $R^3$ = hydrogen;
$R^5$ = n-butyl;
$R^4$ = in each case one line of Table A.

TABLE 26

Compounds of the formula I.2 where $R^3$ = hydrogen;
$R^5$ = n-butyl;
$R^4$ = in each case one line of Table A.

TABLE 27

Compounds of the formula I.3 where $R^3$ = hydrogen;
$R^5$ = n-butyl;
$R^4$ = in each case one line of Table A.

TABLE 28

Compounds of the formula I.4 where $R^3$ = hydrogen;
$R^5$ = n-butyl;
$R^4$ = in each case one line of Table A.

TABLE 29

Compounds of the formula I.1 where $R^3$ = hydrogen;
$R^5$ = 2-methoxyeth-1-yl;
$R^4$ = in each case one line of Table A.

TABLE 30

Compounds of the formula I.2 where $R^3$ = hydrogen;
$R^5$ = 2-methoxyeth-1-yl;
$R^4$ = in each case one line of Table A.

TABLE 31

Compounds of the formula I.3 where $R^3$ = hydrogen;
$R^5$ = 2-methoxyeth-1-yl;
$R^4$ = in each case one line of Table A.

TABLE 32

Compounds of the formula I.4 where $R^3$ = hydrogen;
$R^5$ = 2-methoxyeth-1-yl;
$R^4$ = in each case one line of Table A.

TABLE 33

Compounds of the formula I.1 where $R^3$ = hydrogen;
$R^5$ = prop-2-en-1-yl;
$R^4$ = in each case one line of Table A.

TABLE 34

Compounds of the formula I.2 where $R^3$ = hydrogen;
$R^5$ = prop-2-en-1-yl;
$R^4$ = in each case one line of Table A.

TABLE 35

Compounds of the formula I.3 where $R^3$ = hydrogen;
$R^5$ = prop-2-en-1-yl;
$R^4$ = in each case one line of Table A.

TABLE 36

Compounds of the formula I.4 where $R^3$ = hydrogen;
$R^5$ = prop-2-en-1-yl;
$R^4$ = in each case one line of Table A.

TABLE 37

Compounds of the formula I.1 where $R^3$ = hydrogen;
$R^5$ = E-but-2-en-1-yl;
$R^4$ = in each case one line of Table A.

TABLE 38

Compounds of the formula I.2 where $R^3$ = hydrogen;
$R^5$ = E-but-2-en-1-yl;
$R^4$ = in each case one line of Table A.

TABLE 39

Compounds of the formula I.3 where $R^3$ = hydrogen;
$R^5$ = E-but-2-en-1-yl;
$R^4$ = in each case one line of Table A.

TABLE 40

Compounds of the formula I.4 where $R^3$ = hydrogen;
$R^5$ = E-but-2-en-1-yl;
$R^4$ = in each case one line of Table A.

TABLE 41

Compound of the formula I.1 where $R^3$ = hydrogen;
$R^5$ = Z-but-2-en-1-yl;
$R^4$ = in each case one line of Table A.

TABLE 42

Compounds of the formula I.2 where $R^3$ = hydrogen;
$R^5$ = Z-but-2-en-1-yl;
$R^4$ = in each case one line of Table A.

TABLE 43

Compounds of the formula I.3 where $R^3$ = hydrogen;
$R^5$ = Z-but-2-en-1-yl;
$R^4$ = in each case one line of Table A.

TABLE 44

Compounds of the formula I.4 where $R^3$ = hydrogen;
$R^5$ = Z-but-2-en-1-yl;
$R^4$ = in each case one line of Table A.

TABLE 45

Compounds of the formula I.1 where $R^3$ = hydrogen;
$R^5$ = E-3-chloroprop-2-en-1-yl;
$R^4$ = in each case one line of Table A.

TABLE 46

Compounds of the formula I.2 where $R^3$ = hydrogen;
$R^5$ = E-3-chloroprop-2-en-1-yl;
$R^4$ = in each case one line of Table A.

TABLE 47

Compounds of the formula I.3 where $R^3$ = hydrogen;
$R^5$ = E-3-chloroprop-2-en-1-yl;
$R^4$ = in each case one line of Table A.

TABLE 48

Compounds of the formula I.4 where $R^3$ = hydrogen;
$R^5$ = E-3-chloroprop-2-en-1-yl;
$R^4$ = in each case one line of Table A.

TABLE 49

Compounds of the formula I.1 where $R^3$ = hydrogen;
$R^5$ = Z-3-chloroprop-2-en-1-yl;
$R^4$ = in each case one line of Table A.

TABLE 50

Compounds of the formula I.2 where $R^3$ = hydrogen;
$R^5$ = Z-3-chloroprop-2-en-1-yl;
$R^4$ = in each case one line of Table A.

TABLE 51

Compounds of the formula I.3 where $R^3$ = hydrogen;
$R^5$ = Z-3-chloroprop-2-en-1-yl;
$R^4$ = in each case one line of Table A.

TABLE 52

Compounds of the formula I.4 where $R^3$ = hydrogen;
$R^5$ = Z-3-chloroprop-2-en-1-yl;
$R^4$ = in each case one line of Table A.

TABLE 53

Compounds of the formula I.1 where $R^3$ = hydrogen;
$R^5$ = prop-2-yn-1-yl;
$R^4$ = in each case one line of Table A.

TABLE 54

Compounds of the formula I.2 where $R^3$ = hydrogen;
$R^5$ = prop-2-yn-1-yl;
$R^4$ = in each case one line of Table A.

TABLE 55

Compounds of the formula I.3 where $R^3$ = hydrogen;
$R^5$ = prop-2-yn-1-yl;
$R^4$ = in each case one line of Table A.

TABLE 56

Compounds of the formula I.4 where $R^3$ = hydrogen;
$R^5$ = prop-2-yn-1-yl;
$R^4$ = in each case one line of Table A.

TABLE 57

Compounds of the formula I.1 where $R^3$ = cyclopropyl;
$R^5$ = hydrogen;
$R^4$ = in each case one line of Table A.

TABLE 58

Compounds of the formula I.2 where $R^3$ = cyclopropyl;
$R^5$ = hydrogen;
$R^4$ = in each case one line of Table A.

TABLE 59

Compounds of the formula I.3 where $R^3$ = cyclopropyl;
$R^5$ = hydrogen;
$R^4$ = in each case one line of Table A.

TABLE 60

Compounds of the formula I.4 where $R^3$ = cyclopropyl;
$R^5$ = hydrogen;
$R^4$ = in each case one line of Table A.

TABLE 61

Compounds of the formula I.1 where $R^3$ = cyclopropyl;
$R^5$ = methyl;
$R^4$ = in each case one line of Table A.

TABLE 62

Compounds of the formula I.2 where $R^3$ = cyclopropyl;
$R^5$ = methyl;
$R^4$ = in each case one line of Table A.

TABLE 63

Compounds of the formula I.3 where $R^3$ = cyclopropyl;
$R^5$ = methyl;
$R^4$ = in each case one line of Table A.

TABLE 64

Compounds of the formula I.4 where $R^3$ = cyclopropyl;
$R^5$ = methyl;
$R^4$ = in each case one line of Table A.

TABLE 65

Compounds of the formula I.1 where $R^3$ = cyclopropyl;
$R^5$ = ethyl;
$R^4$ = in each case one line of Table A.

TABLE 66

Compounds of the formula I.2 where $R^3$ = cyclopropyl;
$R^5$ = ethyl;
$R^4$ = in each case one line of Table A.

TABLE 67

Compounds of the formula I.3 where $R^3$ = cyclopropyl;
$R^5$ = ethyl;
$R^4$ = in each case one line of Table A.

TABLE 68

Compounds of the formula I.4 where $R^3$ = cyclopropyl;
$R^5$ = ethyl;
$R^4$ = in each case one line of Table A.

TABLE 69

Compounds of the formula I.1 where $R^3$ = cyclopropyl;
$R^5$ = n-propyl;
$R^4$ = in each case one line of Table A.

TABLE 70

Compounds of the formula I.2 where $R^3$ = cyclopropyl;
$R^5$ = n-propyl;
$R^4$ = in each case one line of Table A.

TABLE 71

Compounds of the formula I.3 where $R^3$ = cyclopropyl;
$R^5$ = n-propyl;
$R^4$ = in each case one line of Table A.

TABLE 72

Compounds of the formula I.4 where $R^3$ = cyclopropyl;
$R^5$ = n-propyl;
$R^4$ = in each case one line of Table A.

TABLE 73

Compounds of the formula I.1 where $R^3$ = cyclopropyl;
$R^5$ = iso-propyl;
$R^4$ = in each case one line of Table A.

TABLE 74

Compounds of the formula I.2 where $R^3$ = cyclopropyl;
$R^5$ = iso-propyl;
$R^4$ = in each case one line of Table A.

TABLE 75

Compounds of the formula I.3 where $R^3$ = cyclopropyl;
$R^5$ = iso-propyl;
$R^4$ = in each case one line of Table A.

TABLE 76

Compounds of the formula I.4 where $R^3$ = cyclopropyl;
$R^5$ = iso-propyl;
$R^4$ = in each case one line of Table A.

TABLE 77

Compounds of the formula I.1 where $R^3$ = cyclopropyl;
$R^5$ = cyclopropyl;
$R^4$ = in each case one line of Table A.

TABLE 78

Compounds of the formula I.2 where $R^3$ = cyclopropyl;
$R^5$ = cyclopropyl;
$R^4$ = in each case one line of Table A.

TABLE 79

Compounds of the formula I.3 where $R^3$ = cyclopropyl;
$R^5$ = cyclopropyl;
$R^4$ = in each case one line of Table A.

TABLE 80

Compounds of the formula I.4 where $R^3$ = cyclopropyl;
$R^5$ = cyclopropyl;
$R^4$ = in each case one line of Table A.

TABLE 81

Compounds of the formula I.1 where $R^3$ = cyclopropyl;
$R^5$ = n-butyl;
$R^4$ = in each case one line of Table A.

TABLE 82

Compounds of the formula I.2 where $R^3$ = cyclopropyl;
$R^5$ = n-butyl;
$R^4$ = in each case one line of Table A.

TABLE 83

Compounds of the formula I.3 where $R^3$ = cyclopropyl;
$R^5$ = n-butyl;
$R^4$ = in each case one line of Table A.

TABLE 84

Compounds of the formula I.4 where $R^3$ = cyclopropyl;
$R^5$ = n-butyl;
$R^4$ = in each case one line of Table A.

TABLE 85

Compounds of the formula I.1 where $R^3$ = cyclopropyl;
$R^5$ = 2-methoxyeth-1-yl;
$R^4$ = in each case one line of Table A.

TABLE 86

Compounds of the formula I.2 where $R^3$ = cyclopropyl;
$R^5$ = 2-methoxyeth-1-yl;
$R^4$ = in each case one line of Table A.

TABLE 87

Compounds of the formula I.3 where $R^3$ = cyclopropyl;
$R^5$ = 2-methoxyeth-1-yl;
$R^4$ = in each case one line of Table A.

TABLE 88

Compounds of the formula I.4 where $R^3$ = cyclopropyl;
$R^5$ = 2-methoxyeth-1-yl;
$R^4$ = in each case one line of Table A.

TABLE 89

Compounds of the formula I.1 where $R^3$ = cyclopropyl;
$R^5$ = prop-2-en-1-yl;
$R^4$ = in each case one line of Table A.

TABLE 90

Compounds of the formula I.2 where $R^3$ = cyclopropyl;
$R^5$ = prop-2-en-1-yl;
$R^4$ = in each case one line of Table A.

TABLE 91

Compounds of the formula I.3 where $R^3$ = cyclopropyl;
$R^5$ = prop-2-en-1-yl;
$R^4$ = in each case one line of Table A.

TABLE 92

Compounds of the formula I.4 where $R^3$ = cyclopropyl;
$R^5$ = prop-2-en-1-yl;
$R^4$ = in each case one line of Table A.

TABLE 93

Compounds of the formula I.1 where $R^3$ = cyclopropyl;
$R^5$ = E-but-2-en-1-yl;
$R^4$ = in each case one line of Table A.

TABLE 94

Compounds of the formula I.2 where $R^3$ = cyclopropyl;
$R^5$ = E-but-2-en-1-yl;
$R^4$ = in each case one line of Table A.

TABLE 95

Compounds of the formula I.3 where $R^3$ = cyclopropyl;
$R^5$ = E-but-2-en-1-yl;
$R^4$ = in each case one line of Table A.

TABLE 96

Compounds of the formula I.4 where $R^3$ = cyclopropyl;
$R^5$ = E-but-2-en-1-yl;
$R^4$ = in each case one line of Table A.

TABLE 97

Compounds of the formula I.1 where $R^3$ = cyclopropyl;
$R^5$ = Z-but-2-en-1-yl;
$R^4$ = in each case one line of Table A.

TABLE 98

Compounds of the formula I.2 where $R^3$ = cyclopropyl;
$R^5$ = Z-but-2-en-1-yl;
$R^4$ = in each case one line of Table A.

TABLE 99

Compounds of the formula I.3 where $R^3$ = cyclopropyl;
$R^5$ = Z-but-2-en-1-yl;
$R^4$ = in each case one line of Table A.

TABLE 100

Compounds of the formula I.4 where $R^3$ = cyclopropyl;
$R^5$ = Z-but-2-en-1-yl;
$R^4$ = in each case one line of Table A.

TABLE 101

Compounds of the formula I.1 where $R^3$ = cyclopropyl;
$R^5$ = E-3-chloroprop-2-en-1-yl;
$R^4$ = in each case one line of Table A.

TABLE 102

Compounds of the formula I.2 where $R^3$ = cyclopropyl;
$R^5$ = E-3-chloroprop-2-en-1-yl;
$R^4$ = in each case one line of Table A.

TABLE 103

Compounds of the formula I.3 where $R^3$ = cyclopropyl;
$R^5$ = E-3-chloroprop-2-en-1-yl;
$R^4$ = in each case one line of Table A.

TABLE 104

Compounds of the formula I.4 where $R^3$ = cyclopropyl;
$R^5$ = E-3-chloroprop-2-en-1-yl;
$R^4$ = in each case one line of Table A.

TABLE 105

Compounds of the formula I.1 where $R^3$ = cyclopropyl;
$R^5$ = Z-3-chloroprop-2-en-1-yl;
$R^4$ = in each case one line of Table A.

TABLE 106

Compounds of the formula I.2 where $R^3$ = cyclopropyl;
$R^5$ = Z-3-chloroprop-2-en-1-yl;
$R^4$ = in each case one line of Table A.

TABLE 107

Compounds of the formula I.3 where $R^3$ = cyclopropyl;
$R^5$ = Z-3-chloroprop-2-en-1-yl;
$R^4$ = in each case one line of Table A.

TABLE 108

Compounds of the formula I.4 where $R^3$ = cyclopropyl;
$R^5$ = Z-3-chloroprop-2-en-1-yl;
$R^4$ = in each case one line of Table A.

TABLE 109

Compounds of the formula I.1 where $R^3$ = cyclopropyl;
$R^5$ = prop-2-yn-1-yl;
$R^4$ = in each case one line of Table A.

TABLE 110

Compounds of the formula I.2 where $R^3$ = cyclopropyl;
$R^5$ = prop-2-yn-1-yl;
$R^4$ = in each case one line of Table A.

TABLE 111

Compounds of the formula I.3 where $R^3$ = cyclopropyl;
$R^5$ = prop-2-yn-1-yl;
$R^4$ = in each case one line of Table A.

TABLE 112

Compounds of the formula I.4 where $R^3$ = cyclopropyl;
$R^5$ = prop-2-yn-1-yl;
$R^4$ = in each case one line of Table A.

TABLE 113

Compounds of the formula I.1 where $R^3$ = ethyl;
$R^5$ = hydrogen;
$R^4$ = in each case one line of Table A.

TABLE 114

Compounds of the formula I.2 where $R^3$ = ethyl;
$R^5$ = hydrogen;
$R^4$ = in each case one line of Table A.

TABLE 115

Compounds of the formula I.3 where $R^3$ = ethyl;
$R^5$ = hydrogen;
$R^4$ = in each case one line of Table A.

TABLE 116

Compounds of the formula I.4 where $R^3$ = ethyl;
$R^5$ = hydrogen;
$R^4$ = in each case one line of Table A.

TABLE 117

Compounds of the formula I.1 where $R^3$ = ethyl;
$R^5$ = methyl;
$R^4$ = in each case one line of Table A.

TABLE 118

Compounds of the formula I.2 where $R^3$ = ethyl;
$R^5$ = methyl;
$R^4$ = in each case one line of Table A.

TABLE 119

Compounds of the formula I.3 where $R^3$ = ethyl;
$R^5$ = methyl;
$R^4$ = in each case one line of Table A.

TABLE 120

Compounds of the formula I.4 where $R^3$ = ethyl;
$R^5$ = methyl;
$R^4$ = in each case one line of Table A.

TABLE 121

Compounds of the formula I.1 where $R^3$ = ethyl;
$R^5$ = ethyl;
$R^4$ = in each case one line of Table A.

TABLE 122

Compounds of the formula I.2 where $R^3$ = ethyl;
$R^5$ = ethyl;
$R^4$ = in each case one line of Table A.

TABLE 123

Compounds of the formula I.3 where $R^3$ = ethyl;
$R^5$ = ethyl;
$R^4$ = in each case one line of Table A.

TABLE 124

Compounds of the formula I.4 where $R^3$ = ethyl;
$R^5$ = ethyl;
$R^4$ = in each case one line of Table A.

TABLE 125

Compounds of the formula I.1 where $R^3$ = ethyl;
$R^5$ = n-propyl;
$R^4$ = in each case one line of Table A.

TABLE 126

Compounds of the formula I.2 where $R^3$ = ethyl;
$R^5$ = n-propyl;
$R^4$ = in each case one line of Table A.

TABLE 127

Compounds of the formula I.3 where $R^3$ = ethyl;
$R^5$ = n-propyl;
$R^4$ = in each case one line of Table A.

TABLE 128

Compounds of the formula I.4 where $R^3$ = ethyl;
$R^5$ = n-propyl;
$R^4$ = in each case one line of Table A.

TABLE 129

Compounds of the formula I.1 where $R^3$ = ethyl;
$R^5$ = iso-propyl;
$R^4$ = in each case one line of Table A.

TABLE 130

Compounds of the formula I.2 where $R^3$ = ethyl;
$R^5$ = iso-propyl;
$R^4$ = in each case one line of Table A.

TABLE 131

Compounds of the formula I.3 where $R^3$ = ethyl;
$R^5$ = iso-propyl;
$R^4$ = in each case one line of Table A.

TABLE 132

Compounds of the formula I.4 where $R^3$ = ethyl;
$R^5$ = iso-propyl;
$R^4$ = in each case one line of Table A.

TABLE 133

Compounds of the formula I.1 where $R^3$ = ethyl;
$R^5$ = cyclopropyl;
$R^4$ = in each case one line of Table A.

TABLE 134

Compounds of the formula I.2 where $R^3$ = ethyl;
$R^5$ = cyclopropyl;
$R^4$ = in each case one line of Table A.

TABLE 135

Compounds of the formula I.3 where $R^3$ = ethyl;
$R^5$ = cyclopropyl;
$R^4$ = in each case one line of Table A.

TABLE 136

Compounds of the formula I.4 where $R^3$ = ethyl;
$R^5$ = cyclopropyl;
$R^4$ = in each case one line of Table A.

TABLE 137

Compounds of the formula I.1 where $R^3$ = ethyl;
$R^5$ = n-butyl;
$R^4$ = in each case one line of Table A.

TABLE 138

Compounds of the formula I.2 where $R^3$ = ethyl;
$R^5$ = n-butyl;
$R^4$ = in each case one line of Table A.

TABLE 139

Compounds of the formula I.3 where $R^3$ = ethyl;
$R^5$ = n-butyl;
$R^4$ = in each case one line of Table A.

TABLE 140

Compounds of the formula I.4 where $R^3$ = ethyl;
$R^5$ = n-butyl;
$R^4$ = in each case one line of Table A.

TABLE 141

Compounds of the formula I.1 where $R^3$ = ethyl;
$R^5$ = 2-methoxyeth-1-yl;
$R^4$ = in each case one line of Table A.

TABLE 142

Compoundss of the formula I.2 where $R^3$ = ethyl;
$R^5$ = 2-methoxyeth-1-yl;
$R^4$ = in each case one line of Table A.

TABLE 143

Compounds of the formula I.3 where $R^3$ = ethyl;
$R^5$ = 2-methoxyeth-1-yl;
$R^4$ = in each case one line of Table A.

TABLE 144

Compounds of the formula I.4 where $R^3$ = ethyl;
$R^5$ = 2-methoxyeth-1-yl;
$R^4$ = in each case one line of Table A.

TABLE 145

Compounds of the formula I.1 where $R^3$ = ethyl;
$R^5$ = prop-2-en-1-yl;
$R^4$ = in each case one line of Table A.

TABLE 146

Compounds of the formula I.2 where $R^3$ = ethyl;
$R^5$ = prop-2-en-1-yl;
$R^4$ = in each case one line of Table A.

TABLE 147

Compounds of the formula I.3 where $R^3$ = ethyl;
$R^5$ = prop-2-en-1-yl;
$R^4$ = in each case one line of Table A.

TABLE 148

Compounds of the formula I.4 where $R^3$ = ethyl;
$R^5$ = prop-2-en-1-yl;
$R^4$ = in each case one line of Table A.

TABLE 149

Compounds of the formula I.1 where $R^3$ = ethyl;
$R^5$ = E-but-2-en-1-yl;
$R^4$ = in each case one line of Table A.

TABLE 150

Compounds of the formula I.2 where $R^3$ = ethyl;
$R^5$ = E-but-2-en-1-yl;
$R^4$ = in each case one line of Table A.

TABLE 151

Compounds of the formula I.3 where $R^3$ = ethyl;
$R^5$ = E-but-2-en-1-yl;
$R^4$ = in each case one line of Table A.

TABLE 152

Compounds of the formula I.4 where $R^3$ = ethyl;
$R^5$ = E-but-2-en-1-yl;
$R^4$ = in each case one line of Table A.

TABLE 153

Compounds of the formula I.1 where $R^3$ = ethyl;
$R^5$ = Z-but-2-en-1-yl;
$R^4$ = in each case one line of Table A.

TABLE 154

Compounds of the formula I.2 where $R^3$ = ethyl;
$R^5$ = Z-but-2-en-1-yl;
$R^4$ = in each case one line of Table A.

TABLE 155

Compounds of the formula I.3 where $R^3$ = ethyl;
$R^5$ = Z-but-2-en-1-yl;
$R^4$ = in each case one line of Table A.

TABLE 156

Compounds of the formula I.4 where $R^3$ = ethyl;
$R^5$ = Z-but-2-en-1-yl;
$R^4$ = in each case one line of Table A.

TABLE 157

Compounds of the formula I.1 where $R^3$ = ethyl;
$R^5$ = E-3-chloroprop-2-en-1-yl;
$R^4$ = in each case one line of Table A.

TABLE 158

Compounds of the formula I.2 where $R^3$ = ethyl;
$R^5$ = E-3-chloroprop-2-en-1-yl;
$R^4$ = in each case one line of Table A.

TABLE 159

Compounds of the formula I.3 where $R^3$ = ethyl;
$R^5$ = E-3-chloroprop-2-en-1-yl;
$R^4$ = in each case one line of Table A.

TABLE 160

Compounds of the formula I.4 where $R^3$ = ethyl;
$R^5$ = E-3-chloroprop-2-en-1-yl;
$R^4$ = in each case one line of Table A.

TABLE 161

Compounds of the formula I.1 where $R^3$ = ethyl;
$R^5$ = Z-3-chloroprop-2-en-1-yl,
$R^4$ = in each case one line of Table A.

TABLE 162

Compounds of the formula I.2 where $R^3$ = ethyl;
$R^5$ = Z-3-chloroprop-2-en-1-yl;
$R^4$ = in each case one line of Table A.

TABLE 163

Compounds of the formula I.3 where $R^3$ = ethyl;
$R^5$ = Z-3-chloroprop-2-en-1-yl;
$R^4$ = in each case one line of Table A.

TABLE 164

Compounds of the formula I.4 where $R^3$ = ethyl;
$R^5$ = Z-3-chloroprop-2-en-1-yl;
$R^4$ = in each case one line of Table A.

TABLE 165

Compounds of the formula I.1 where $R^3$ = ethyl;
$R^5$ = prop-2-yn-1-yl;
$R^4$ = in each case one line of Table A.

TABLE 166

Compounds of the formula I.2 where $R^3$ = ethyl;
$R^5$ = prop-2-yn-1-yl;
$R^4$ = in each case one line of Table A.

TABLE 167

Compounds of the formula I.3 where $R^3$ = ethyl;
$R^5$ = prop-2-yn-1-yl;
$R^4$ = in each case one line of Table A.

TABLE 168

Compounds of the formula I.4 where $R^3$ = ethyl;
$R^5$ = prop-2-yn-1-yl;
$R^4$ = in each case one line of Table A.

TABLE 169

Compounds of the formula I.1 where $R^3$ = trifluoromethyl;
$R^5$ = hydrogen;
$R^4$ = in each case one line of Table A.

TABLE 170

Compounds of the formula I.2 where $R^3$ = trifluoromethyl;
$R^5$ = hydrogen;
$R^4$ = in each case one line of Table A.

TABLE 171

Compounds of the formula I.3 where $R^3$ = trifluoromethyl;
$R^5$ = hydrogen;
$R^4$ = in each case one line of Table A.

TABLE 172

Compounds of the formula I.4 where $R^3$ = trifluoromethyl;
$R^5$ = hydrogen;
$R^4$ = in each case one line of Table A.

TABLE 173

Compounds of the formula I.1 where $R^3$ = trifluoromethyl;
$R^5$ = methyl;
$R^4$ = in each case one line of Table A.

TABLE 174

Compounds of the formula I.2 where $R^3$ = trifluoromethyl;
$R^5$ = methyl;
$R^4$ = in each case one line of Table A.

TABLE 175

Compounds of the formula I.3 where $R^3$ = trifluoromethyl;
$R^5$ = methyl;
$R^4$ = in each case one line of Table A.

TABLE 176

Compounds of the formula I.4 where $R^3$ = trifluoromethyl;
$R^5$ = methyl;
$R^4$ = in each case one line of Table A.

TABLE 177

Compounds of the formula I.1 where $R^3$ = trifluoromethyl;
$R^5$ = ethyl;
$R^4$ = in each case one line of Table A.

TABLE 178

Compounds of the formula I.2 where $R^3$ = trifluoromethyl;
$R^5$ = ethyl;
$R^4$ = in each case one line of Table A.

TABLE 179

Compounds of the formula I.3 where $R^3$ = trifluoromethyl;
$R^5$ = ethyl;
$R^4$ = in each case one line of Table A.

TABLE 180

Compounds of the formula I.4 where $R^3$ = trifluoromethyl;
$R^5$ = ethyl;
$R^4$ = in each case one line of Table A.

TABLE 181

Compounds of the formula I.1 where $R^3$ = trifluoromethyl;
$R^5$ = n-propyl;
$R^4$ = in each case one line of Table A.

TABLE 182

Compounds of the formula I.2 where $R^3$ = trifluoromethyl;
$R^5$ = n-propyl;
$R^4$ = in each case one line of Table A.

TABLE 183

Compounds of the formula I.3 where $R^3$ = trifluoromethyl;
$R^5$ = n-propyl;
$R^4$ = in each case one line of Table A.

TABLE 184

Compounds of the formula I.4 where $R^3$ = trifluoromethyl;
$R^5$ = n-propyl;
$R^4$ = in each case one line of Table A.

TABLE 185

Compounds of the formula I.1 where $R^3$ = trifluoromethyl;
$R^5$ = iso-propyl;
$R^4$ = in each case one line of Table A.

TABLE 186

Compounds of the formula I.2 where $R^3$ = trifluoromethyl;
$R^5$ = iso-propyl;
$R^4$ = in each case one line of Table A.

TABLE 187

Compounds of the formula I.3 where $R^3$ = trifluoromethyl;
$R^5$ = iso-propyl;
$R^4$ = in each case one line of Table A.

TABLE 188

Compounds of the formula I.4 where $R^3$ = trifluoromethyl;
$R^5$ = iso-propyl;
$R^4$ = in each case one line of Table A.

TABLE 189

Compounds of the formula I.1 where $R^3$ = trifluoromethyl;
$R^5$ = cyclopropyl;
$R^4$ = in each case one line of Table A.

TABLE 190

Compounds of the formula I.2 where $R^3$ = trifluoromethyl;
$R^5$ = cyclopropyl;
$R^4$ = in each case one line of Table A.

TABLE 191

Compounds of the formula I.3 where $R^3$ = trifluoromethyl;
$R^5$ = cyclopropyl;
$R^4$ = in each case one line of Table A.

TABLE 192

Compounds of the formula I.4 where $R^3$ = trifluoromethyl;
$R^5$ = cyclopropyl;
$R^4$ = in each case one line of Table A.

TABLE 193

Compounds of the formula I.1 where $R^3$ = trifluoromethyl;
$R^5$ = n-butyl;
$R^4$ = in each case one line of Table A.

TABLE 194

Compounds of the formula I.2 where $R^3$ = trifluoromethyl;
$R^5$ = n-butyl;
$R^4$ = in each case one line of Table A.

TABLE 195

Compounds of the formula I.3 where $R^3$ = trifluoromethyl;
$R^5$ = n-butyl;
$R^4$ = in each case one line of Table A.

TABLE 196

Compounds of the formula I.4 where $R^3$ = trifluoromethyl;
$R^5$ = n-butyl;
$R^4$ = in each case one line of Table A.

TABLE 197

Compounds of the formula I.1 where $R^3$ = trifluoromethyl;
$R^5$ = 2-methoxyeth-1-yl;
$R^4$ = in each case one line of Table A.

TABLE 198

Compounds of the formula I.2 where $R^3$ = trifluoromethyl;
$R^5$ = 2-methoxyeth-1-yl;
$R^4$ = in each case one line of Table A.

TABLE 199

Compounds of the formula I.3 where $R^3$ = trifluoromethyl;
$R^5$ = 2-methoxyeth-1-yl;
$R^4$ = in each case one line of Table A.

TABLE 200

Compounds of the formula I.4 where $R^3$ = trifluoromethyl;
$R^5$ = 2-methoxyeth-1-yl;
$R^4$ = in each case one line of Table A.

TABLE 201

Compounds of the formula I.1 where $R^3$ = trifluoromethyl;
$R^5$ = prop-2-en-1-yl;
$R^4$ = in each case one line of Table A.

TABLE 202

Compounds of the formula I.2 where $R^3$ = trifluoromethyl;
$R^5$ = prop-2-en-1-yl;
$R^4$ = in each case one line of Table A.

TABLE 203

Compounds of the formula I.3 where $R^3$ = trifluoromethyl;
$R^5$ = prop-2-en-1-yl;
$R^4$ = in each case one line of Table A.

TABLE 204

Compounds of the formula I.4 where $R^3$ = trifluoromethyl;
$R^5$ = prop-2-en-1-yl;
$R^4$ = in each case one line of Table A.

TABLE 205

Compounds of the formula I.1 where $R^3$ = trifluoromethyl;
$R^5$ = E-but-2-en-1-yl;
$R^4$ = in each case one line of Table A.

TABLE 206

Compounds of the formula I.2 where $R^3$ = trifluoromethyl;
$R^5$ = E-but-2-en-1-yl;
$R^4$ = in each case one line of Table A.

TABLE 207

Compounds of the formula I.3 where $R^3$ = trifluoromethyl;
$R^5$ = E-but-2-en-1-yl;
$R^4$ = in each case one line of Table A.

TABLE 208

Compounds of the formula I.4 where $R^3$ = trifluoromethyl;
$R^5$ = E-but-2-en-1-yl;
$R^4$ = in each case one line of Table A.

TABLE 209

Compounds of the formula I.1 where $R^3$ = trifluoromethyl;
$R^5$ = Z-but-2-en-1-yl;
$R^4$ = in each case one line of Table A.

TABLE 210

Compounds of the formula I.2 where $R^3$ = trifluoromethyl;
$R^5$ = Z-but-2-en-1-yl;
$R^4$ = in each case one line of Table A.

TABLE 211

Compounds of the formula I.3 where $R^3$ = trifluoromethyl;
$R^5$ = Z-but-2-en-1-yl;
$R^4$ = in each case one line of Table A.

TABLE 212

Compounds of the formula I.4 where $R^3$ = trifluoromethyl;
$R^5$ = Z-but-2-en-1-yl;
$R^4$ = in each case one line of Table A.

TABLE 213

Compounds of the formula I.1 where $R^3$ = trifluoromethyl;
$R^5$ = E-3-chloroprop-2-en-1-yl;
$R^4$ = in each case one line of Table A.

TABLE 214

Compounds of the formula I.2 where $R^3$ = trifluoromethyl;
$R^5$ = E-3-chloroprop-2-en-1-yl;
$R^4$ = in each case one line of Table A.

TABLE 215

Compounds of the formula I.3 where $R^3$ = trifluoromethyl;
$R^5$ = E-3-chloroprop-2-en-1-yl;
$R^4$ = in each case one line of Table A.

TABLE 216

Compounds of the formula I.4 where $R^3$ = trifluoromethyl;
$R^5$ = E-3-chloroprop-2-en-1-yl;
$R^4$ = in each case one line of Table A.

TABLE 217

Compounds of the formula I.1 where $R^3$ = trifluoromethyl;
$R^5$ = Z-3-chloroprop-2-en-1-yl;
$R^4$ = in each case one line of Table A.

TABLE 218

Compounds of the formula I.2 where $R^3$ = trifluoromethyl;
$R^5$ = Z-3-chloroprop-2-en-1-yl;
$R^4$ = in each case one line of Table A.

TABLE 219

Compounds of the formula I.3 where $R^3$ = trifluoromethyl;
$R^5$ = Z-3-chloroprop-2-en-1-yl;
$R^4$ = in each case one line of Table A.

TABLE 220

Compounds of the formula I.4 where $R^3$ = trifluoromethyl;
$R^5$ = Z-3-chloroprop-2-en-1-yl;
$R^4$ = in each case one line of Table A.

TABLE 221

Compounds of the formula I.1 where $R^3$ = trifluoromethyl;
$R^5$ = prop-2-yn-1-yl;
$R^4$ = in each case one line of Table A.

TABLE 222

Compounds of the formula I.2 where $R^3$ = trifluoromethyl;
$R^5$ = prop-2-yn-1-yl;
$R^4$ = in each case one line of Table A.

TABLE 223

Compounds of the formula I.3 where $R^3$ = trifluoromethyl;
$R^5$ = prop-2-yn-1-yl;
$R^4$ = in each case one line of Table A.

TABLE 224

Compounds of the formula I.4 where $R^3$ = trifluoromethyl;
$R^5$ = prop-2-yn-1-yl;
$R^4$ = in each case one line of Table A.

TABLE 225

Compounds of the formula I.1 where $R^3$ = methyl;
$R^5$ = hydrogen;
$R^4$ = in each case one line of Table A.

TABLE 226

Compounds of the formula I.2 where $R^3$ = methyl;
$R^5$ = hydrogen;
$R^4$ = in each case one line of Table A.

TABLE 227

Compounds of the formula I.3 where $R^3$ = methyl;
$R^5$ = hydrogen;
$R^4$ = in each case one line of Table A.

TABLE 228

Compounds of the formula I.4 where $R^3$ = methyl;
$R^5$ = hydrogen;
$R^4$ = in each case one line of Table A.

TABLE 229

Compounds of the formula I.1 where $R^3$ = methyl;
$R^5$ = methyl;
$R^4$ = in each case one line of Table A.

TABLE 230

Compounds of the formula I.2 where $R^3$ = methyl;
$R^5$ = methyl;
$R^4$ = in each case one line of Table A.

TABLE 231

Compounds of the formula I.3 where $R^3$ = methyl;
$R^5$ = methyl;
$R^4$ = in each case one line of Table A.

TABLE 232

Compounds of the formula I.4 where $R^3$ = methyl;
$R^5$ = methyl;
$R^4$ = in each case one line of Table A.

TABLE 233

Compounds of the formula I.1 where $R^3$ = methyl;
$R^5$ = ethyl;
$R^4$ = in each case one line of Table A.

TABLE 234

Compounds of the formula I.2 where $R^3$ = methyl;
$R^5$ = ethyl;
$R^4$ = in each case one line of Table A.

TABLE 235

Compounds of the formula I.3 where $R^3$ = methyl;
$R^5$ = ethyl;
$R^4$ = in each case one line of Table A.

TABLE 236

Compounds of the formula I.4 where $R^3$ = methyl;
$R^5$ = ethyl;
$R^4$ = in each case one line of Table A.

TABLE 237

Compounds of the formula I.1 where $R^3$ = methyl;
$R^5$ = n-propyl;
$R^4$ = in each case one line of Table A.

TABLE 238

Compounds of the formula I.2 where $R^3$ = methyl;
$R^5$ = n-propyl;
$R^4$ = in each case one line of Table A.

TABLE 239

Compounds of the formula I.3 where $R^3$ = methyl;
$R^5$ = n-propyl;
$R^4$ = in each case one line of Table A.

TABLE 240

Compounds of the formula I.4 where $R^3$ = methyl;
$R^5$ = n-propyl;
$R^4$ = in each case one line of Table A.

TABLE 241

Compounds of the formula I.1 where $R^3$ = methyl;
$R^5$ = iso-propyl;
$R^4$ = in each case one line of Table A.

TABLE 242

Compounds of the formula I.2 where $R^3$ = methyl;
$R^5$ = iso-propyl;
$R^4$ = in each case one line of Table A.

TABLE 243

Compounds of the formula I.3 where $R^3$ = methyl;
$R^5$ = iso-propyl;
$R^4$ = in each case one line of Table A.

TABLE 244

Compounds of the formula I.4 where $R^3$ = methyl;
$R^5$ = iso-propyl;
$R^4$ = in each case one line of Table A.

TABLE 245

Compounds of the formula I.1 where $R^3$ = methyl;
$R^5$ = cyclopropyl;
$R^4$ = in each case one line of Table A.

TABLE 246

Compounds of the formula I.2 where $R^3$ = methyl;
$R^5$ = cyclopropyl;
$R^4$ = in each case one line of Table A.

TABLE 247

Compounds of the formula I.3 where $R^3$ = methyl;
$R^5$ = cyclopropyl;
$R^4$ = in each case one line of Table A.

TABLE 248

Compounds of the formula I.4 where $R^3$ = methyl;
$R^5$ = cyclopropyl;
$R^4$ = in each case one line of Table A.

TABLE 249

Compounds of the formula I.1 where $R^3$ = methyl;
$R^5$ = n-butyl;
$R^4$ = in each case one line of Table A.

TABLE 250

Compounds of the formula I.2 where $R^3$ = methyl;
$R^5$ = n-butyl;
$R^4$ = in each case one line of Table A.

TABLE 251

Compounds of the formula I.3 where $R^3$ = methyl;
$R^5$ = n-butyl;
$R^4$ = in each case one line of Table A.

TABLE 252

Compounds of the formula I.4 where $R^3$ = methyl;
$R^5$ = n-butyl;
$R^4$ = in each case one line of Table A.

TABLE 253

Compounds of the formula I.1 where $R^3$ = methyl;
$R^5$ = 2-methoxyeth-1-yl;
$R^4$ = in each case one line of Table A.

TABLE 254

Compounds of the formula I.2 where $R^3$ = methyl;
$R^5$ = 2-methoxyeth-1-yl;
$R^4$ = in each case one line of Table A.

TABLE 255

Compounds of the formula I.3 where $R^3$ = methyl;
$R^5$ = 2-methoxyeth-1-yl;
$R^4$ = in each case one line of Table A.

TABLE 256

Compounds of the formula I.4 where $R^3$ = methyl;
$R^5$ = 2-methoxyeth-1-yl;
$R^4$ = in each case one line of Table A.

TABLE 257

Compounds of the formula I.1 where $R^3$ = methyl;
$R^5$ = prop-2-en-1-yl;
$R^4$ = in each case one line of Table A.

TABLE 258

Compounds of the formula I.2 where $R^3$ = methyl;
$R^5$ = prop-2-en-1-yl;
$R^4$ = in each case one line of Table A.

TABLE 259

Compounds of the formula I.3 where $R^3$ = methyl;
$R^5$ = prop-2-en-1-yl;
$R^4$ = in each case one line of Table A.

TABLE 260

Compounds of the formula I.4 where $R^3$ = methyl;
$R^5$ = prop-2-en-1-yl;
$R^4$ = in each case one line of Table A.

TABLE 261

Compounds of the formula I.1 where $R^3$ = methyl;
$R^5$ = E-but-2-en-1-yl;
$R^4$ = in each case one line of Table A.

TABLE 262

Compounds of the formula I.2 where $R^3$ = methyl;
$R^5$ = E-but-2-en-1-yl;
$R^4$ = in each case one line of Table A.

TABLE 263

Compounds of the formula I.3 where $R^3$ = methyl;
$R^5$ = E-but-2-en-1-yl;
$R^4$ = in each case one line of Table A.

TABLE 264

Compounds of the formula I.4 where $R^3$ = methyl;
$R^5$ = E-but-2-en-1-yl;
$R^4$ = in each case one line of Table A.

TABLE 265

Compounds of the formula I.1 where $R^3$ = methyl;
$R^5$ = Z-but-2-en-1-yl;
$R^4$ = in each case one line of Table A.

TABLE 266

Compounds of the formula I.2 where $R^3$ = methyl;
$R^5$ = Z-but-2-en-1-yl;
$R^4$ = in each case one line of Table A.

TABLE 267

Compounds of the formula I.3 where $R^3$ = methyl;
$R^5$ = Z-but-2-en-1-yl;
$R^4$ = in each case one line of Table A.

TABLE 268

Compounds of the formula I.4 where $R^3$ = methyl;
$R^5$ = Z-but-2-en-1-yl;
$R^4$ = in each case one line of Table A.

TABLE 269

Compounds of the formula I.1 where $R^3$ = methyl;
$R^5$ = E-3-chloroprop-2-en-1-yl;
$R^4$ = in each case one line of Table A.

TABLE 270

Compounds of the formula I.2 where $R^3$ = methyl;
$R^5$ = E-3-chloroprop-2-en-1-yl;
$R^4$ = in each case one line of Table A.

TABLE 271

Compounds of the formula I.3 where $R^3$ = methyl;
$R^5$ = E-3-chloroprop-2-en-1-yl;
$R^4$ = in each case one line of Table A.

TABLE 272

Compounds of the formula I.4 where $R^3$ = methyl;
$R^5$ = E-3-chloroprop-2-en-1-yl;
$R^4$ = in each case one line of Table A.

TABLE 273

Compounds of the formula I.1 where $R^3$ = methyl;
$R^5$ = Z-3-chloroprop-2-en-1-yl;
$R^4$ = in each case one line of Table A.

TABLE 274

Compounds of the formula I.2 where $R^3$ = methyl;
$R^5$ = Z-3-chloroprop-2-en-1-yl;
$R^4$ = in each case one line of Table A.

TABLE 275

Compounds of the formula I.3 where $R^3$ = methyl;
$R^5$ = Z-3-chloroprop-2-en-1-yl;
$R^4$ = in each case one line of Table A.

TABLE 276

Compounds of the formula I.4 where $R^3$ = methyl;
$R^5$ = Z-3-chloroprop-2-en-1-yl;
$R^4$ = in each case one line of Table A.

TABLE 277

Compounds of the formula I.1 where $R^3$ = methyl;
$R^5$ = prop-2-yn-1-yl;
$R^4$ = in each case one line of Table A.

TABLE 278

Compounds of the formula I.2 where $R^3$ = methyl;
$R^5$ = prop-2-yn-1-yl;
$R^4$ = in each case one line of Table A.

TABLE 279

Compounds of the formula I.3 where $R^3$ = methyl;
$R^5$ = prop-2-yn-1-yl;
$R^4$ = in each case one line of Table A.

TABLE 280

Compounds of the formula I.4 where $R^3$ = methyl;
$R^5$ = prop-2-yn-1-yl;
$R^4$ = in each case one line of Table A.

TABLE 281

Compounds of the formula I.1 where $R^3$ = methyl;
$R^5$ = 2-butyl;
$R^4$ = in each case one line of Table A.

TABLE 282

Compounds of the formula I.2 where $R^3$ = methyl;
$R^5$ = 2-butyl;
$R^4$ = in each case one line of Table A.

TABLE 283

Compounds of the formula I.3 where $R^3$ = methyl;
$R^5$ = 2-butyl;
$R^4$ = in each case one line of Table A.

TABLE 284

Compounds of the formula I.4 where $R^3$ = methyl;
$R^5$ = 2-butyl;
$R^4$ = in each case one line of Table A.

TABLE 285

Compounds of the formula I.1 where $R^3$ = methyl;
$R^5$ = 2-methylprop-1-yl;
$R^4$ = in each case one line of Table A.

TABLE 286

Compounds of the formula I.2 where $R^3$ = methyl;
$R^5$ = 2-methylprop-1-yl;
$R^4$ = in each case one line of Table A.

TABLE 287

Compounds of the formula I.3 where $R^3$ = methyl;
$R^5$ = 2-methylprop-1-yl;
$R^4$ = in each case one line of Table A.

TABLE 288

Compounds of the formula I.4 where $R^3$ = methyl;
$R^5$ = 2-methylprop-1-yl;
$R^4$ = in each case one line of Table A.

TABLE 289

Compounds of the formula I.1 where $R^3$ = methyl;
$R^5$ = 1,1-dimethyleth-1-yl;
$R^4$ = in each case one line of Table A.

TABLE 290

Compounds of the formula I.2 where $R^3$ = methyl;
$R^5$ = 1,1-dimethyleth-1-yl;
$R^4$ = in each case one line of Table A.

TABLE 291

Compounds of the formula I.3 where $R^3$ = methyl;
$R^5$ = 1,1-dimethyleth-1-yl;
$R^4$ = in each case one line of Table A.

TABLE 292

Compounds of the formula I.4 where $R^3$ = methyl;
$R^5$ = 1,1-dimethyleth-1-yl;
$R^4$ = in each case one line of Table A.

TABLE 293

Compounds of the formula I.1 where $R^3$ = methyl;
$R^5$ = 1-pentyl;
$R^4$ = in each case one line of Table A.

TABLE 294

Compounds of the formula I.2 where $R^3$ = methyl;
$R^5$ = 1-pentyl;
$R^4$ = in each case one line of Table A.

TABLE 295

Compounds of the formula I.3 where $R^3$ = methyl;
$R^5$ = 1-pentyl;
$R^4$ = in each case one line of Table A.

TABLE 296

Compounds of the formula I.4 where $R^3$ = methyl;
$R^5$ = 1-pentyl;
$R^4$ = in each case one line of Table A.

TABLE 297

Compounds of the formula I.1 where $R^3$ = methyl;
$R^5$ = 3-methylbut-1-yl;
$R^4$ = in each case one line of Table A.

TABLE 298

Compounds of the formula I.2 where $R^3$ = methyl;
$R^5$ = 3-methylbut-1-yl;
$R^4$ = in each case one line of Table A.

TABLE 299

Compounds of the formula I.3 where $R^3$ = methyl;
$R^5$ = 3-methylbut-1-yl;
$R^4$ = in each case one line of Table A.

TABLE 300

Compounds of the formula I.4 where $R^3$ = methyl;
$R^5$ = 3-methylbut-1-yl;
$R^4$ = in each case one line of Table A.

TABLE 301

Compounds of the formula I.1 where $R^3$ = methyl;
$R^5$ = 2,2-dimethylprop-1-yl;
$R^4$ = in each case one line of Table A.

TABLE 302

Compounds of the formula I.2 where $R^3$ = methyl;
$R^5$ = 2,2-dimethylprop-1-yl;
$R^4$ = in each case one line of Table A.

TABLE 303

Compounds of the formula I.3 where $R^3$ = methyl;
$R^5$ = 2,2-dimethylprop-1-yl;
$R^4$ = in each case one line of Table A.

TABLE 304

Compounds of the formula I.4 where $R^3$ = methyl;
$R^5$ = 2,2-dimethylprop-1-yl;
$R^4$ = in each case one line of Table A.

TABLE 305

Compounds of the formula I.1 where $R^3$ = methyl;
$R^5$ = 2-methylbut-1-yl;
$R^4$ = in each case one line of Table A.

TABLE 306

Compounds of the formula I.2 where $R^3$ = methyl;
$R^5$ = 2-methylbut-1-yl;
$R^4$ = in each case one line of Table A.

TABLE 307

Compounds of the formula I.3 where $R^3$ = methyl;
$R^5$ = 2-methylbut-1-yl;
$R^4$ = in each case one line of Table A.

TABLE 308

Compounds of the formula I.4 where $R^3$ = methyl;
$R^5$ = 2-methylbut-1-yl;
$R^4$ = in each case one line of Table A.

TABLE 309

Compounds of the formula I.1 where $R^3$ = methyl;
$R^5$ = 1-methylbut-1-yl;
$R^4$ = in each case one line of Table A.

TABLE 310

Compounds of the formula I.2 where $R^3$ = methyl;
$R^5$ = 1-methylbut-1-yl;
$R^4$ = in each case one line of Table A.

TABLE 311

Compounds of the formula I.3 where $R^3$ = methyl;
$R^5$ = 1-methylbut-1-yl;
$R^4$ = in each case one line of Table A.

TABLE 312

Compounds of the formula I.4 where $R^3$ = methyl;
$R^5$ = 1-methylbut-1-yl;
$R^4$ = in each case one line of Table A.

TABLE 313

Compounds of the formula I.1 where $R^3$ = methyl;
$R^5$ = 3-pentyl;
$R^4$ = in each case one line of Table A.

TABLE 314

Compounds of the formula I.2 where $R^3$ = methyl;
$R^5$ = 3-pentyl;
$R^4$ = in each case one line of Table A.

TABLE 315

Compounds of the formula I.3 where $R^3$ = methyl;
$R^5$ = 3-pentyl;
$R^4$ = in each case one line of Table A.

TABLE 316

Compounds of the formula I.4 where $R^3$ = methyl;
$R^5$ = 3-pentyl;
$R^4$ = in each case one line of Table A.

TABLE 317

Compounds of the formula I.1 where $R^3$ = methyl;
$R^5$ = 3-methylbut-2-yl;
$R^4$ = in each case one line of Table A.

TABLE 318

Compounds of the formula I.2 where $R^3$ = methyl;
$R^5$ = 3-methylbut-2-yl;
$R^4$ = in each case one line of Table A.

TABLE 319

Compounds of the formula I.3 where $R^3$ = methyl;
$R^5$ = 3-methylbut-2-yl;
$R^4$ = in each case one line of Table A.

TABLE 320

Compounds of the formula I.4 where $R^3$ = methyl;
$R^5$ = 3-methylbut-2-yl;
$R^4$ = in each case one line of Table A.

TABLE 321

Compounds of the formula I.1 where $R^3$ = methyl;
$R^5$ = 2-methylbut-2-yl;
$R^4$ = in each case one line of Table A.

TABLE 322

Compounds of the formula I.2 where $R^3$ = methyl;
$R^5$ = 2-methylbut-2-yl;
$R^4$ = in each case one line of Table A.

TABLE 323

Compounds of the formula I.3 where $R^3$ = methyl;
$R^5$ = 2-methylbut-2-yl;
$R^4$ = in each case one line of Table A.

TABLE 324

Compounds of the formula I.4 where $R^3$ = methyl;
$R^5$ = 2-methylbut-2-yl;
$R^4$ = in each case one line of Table A.

TABLE 325

Compounds of the formula I.1 where $R^3$ = methyl;
$R^5$ = 1-hexyl;
$R^4$ = in each case one line of Table A.

TABLE 326

Compounds of the formula I.2 where $R^3$ = methyl;
$R^5$ = 1-hexyl;
$R^4$ = in each case one line of Table A.

TABLE 327

Compounds of the formula I.3 where $R^3$ = methyl;
$R^5$ = 1-hexyl;
$R^4$ = in each case one line of Table A.

TABLE 328

Compounds of the formula I.4 where $R^3$ = methyl;
$R^5$ = 1-hexyl;
$R^4$ = in each case one line of Table A.

TABLE 329

Compounds of the formula I.1 where $R^3$ = methyl;
$R^5$ = 3,3-dimethylbut-1-yl;
$R^4$ = in each case one line of Table A.

TABLE 330

Compounds of the formula I.2 where $R^3$ = methyl;
$R^5$ = 3,3-dimethylbut-1-yl;
$R^4$ = in each case one line of Table A.

TABLE 331

Compounds of the formula I.3 where $R^3$ = methyl;
$R^5$ = 3,3-dimethylbut-1-yl;
$R^4$ = in each case one line of Table A.

TABLE 332

Compounds of the formula I.4 where $R^3$ = methyl;
$R^5$ = 3,3-dimethylbut-1-yl;
$R^4$ = in each case one line of Table A.

TABLE 333

Compounds of the formula I.1 where $R^3$ = methyl;
$R^5$ = 2-ethylbut-1-yl;
$R^4$ = in each case one line of Table A.

TABLE 334

Compounds of the formula I.2 where $R^3$ = methyl;
$R^5$ = 2-ethylbut-1-yl;
$R^4$ = in each case one line of Table A.

TABLE 335

Compounds of the formula I.3 where $R^3$ = methyl;
$R^5$ = 2-ethylbut-1-yl;
$R^4$ = in each case one line of Table A.

TABLE 336

Compounds of the formula I.4 where $R^3$ = methyl;
$R^5$ = 2-ethylbut-1-yl;
$R^4$ = in each case one line of Table A.

TABLE 337

Compounds of the formula I.1 where $R^3$ = methyl;
$R^5$ = 1-ethylbut-1-yl;
$R^4$ = in each case one line of Table A.

TABLE 338

Compounds of the formula I.2 where $R^3$ = methyl;
$R^5$ = 1-ethylbut-1-yl;
$R^4$ = in each case one line of Table A.

TABLE 339

Compounds of the formula I.3 where $R^3$ = methyl;
$R^5$ = 1-ethylbut-1-yl;
$R^4$ = in each case one line of Table A.

TABLE 340

Compounds of the formula I.4 where $R^3$ = methyl;
$R^5$ = 1-ethylbut-1-yl;
$R^4$ = in each case one line of Table A.

TABLE 341

Compounds of the formula I.1 where $R^3$ = methyl;
$R^5$ = 4-methylpent-1-yl;
$R^4$ = in each case one line of Table A.

TABLE 342

Compounds of the formula I.2 where $R^3$ = methyl;
$R^5$ = 4-methylpent-1-yl;
$R^4$ = in each case one line of Table A.

TABLE 343

Compounds of the formula I.3 where $R^3$ = methyl;
$R^5$ = 4-methylpent-1-yl;
$R^4$ = in each case one line of Table A.

TABLE 344

Compounds of the formula I.4 where $R^3$ = methyl;
$R^5$ = 4-methylpent-1-yl;
$R^4$ = in each case one line of Table A.

TABLE 345

Compounds of the formula I.1 where $R^3$ = methyl;
$R^5$ = cyclopropylmethyl;
$R^4$ = in each case one line of Table A.

TABLE 346

Compounds of the formula I.2 where $R^3$ = methyl;
$R^5$ = cyclopropylmethyl;
$R^4$ = in each case one line of Table A.

TABLE 347

Compounds of the formula I.3 where $R^3$ = methyl;
$R^5$ = cyclopropylmethyl;
$R^4$ = in each case one line of Table A.

TABLE 348

Compounds of the formula I.4 where $R^3$ = methyl;
$R^5$ = cyclopropylmethyl;
$R^4$ = in each case one line of Table A.

TABLE 349

Compounds of the formula I.1 where $R^3$ = methyl;
$R^5$ = cyclopentylmethyl;
$R^4$ = in each case one line of Table A.

TABLE 350

Compounds of the formula I.2 where $R^3$ = methyl;
$R^5$ = cyclopentylmethyl;
$R^4$ = in each case one line of Table A.

TABLE 351

Compounds of the formula I.3 where $R^3$ = methyl;
$R^5$ = cyclopentylmethyl;
$R^4$ = in each case one line of Table A.

TABLE 352

Compounds of the formula I.4 where $R^3$ = methyl;
$R^5$ = cyclopentylmethyl;
$R^4$ = in each case one line of Table A.

TABLE 353

Compounds of the formula I.1 where $R^3$ = methyl;
$R^5$ = 2-cyclopropyleth-1-yl;
$R^4$ = in each case one line of Table A.

TABLE 354

Compounds of the formula I.2 where $R^3$ = methyl;
$R^5$ = 2-cyclopropyleth-1-yl;
$R^4$ = in each case one line of Table A.

TABLE 355

Compounds of the formula I.3 where $R^3$ = methyl;
$R^5$ = 2-cyclopropyleth-1-yl;
$R^4$ = in each case one line of Table A.

TABLE 356

Compounds of the formula I.4 where $R^3$ = methyl;
$R^5$ = 2-cyclopropyleth-1-yl;
$R^4$ = in each case one line of Table A.

TABLE 357

Compounds of the formula I.1 where $R^3$ = methyl;
$R^5$ = 2-cyclopentyleth-1-yl;
$R^4$ = in each case one line of Table A.

TABLE 358

Compounds of the formula I.2 where $R^3$ = methyl;
$R^5$ = 2-cyclopentyleth-1-yl;
$R^4$ = in each case one line of Table A.

TABLE 359

Compounds of the formula I.3 where $R^3$ = methyl;
$R^5$ = 2-cyclopentyleth-1-yl;
$R^4$ = in each case one line of Table A.

TABLE 360

Compounds of the formula I.4 where $R^3$ = methyl;
$R^5$ = 2-cyclopentyleth-1-yl;
$R^4$ = in each case one line of Table A.

TABLE 361

Compounds of the formula I.1 where $R^3$ = methyl;
$R^5$ = 2-cyclohexyleth-1-yl;
$R^4$ = in each case one line of Table A.

TABLE 362

Compounds of the formula I.2 where $R^3$ = methyl;
$R^5$ = 2-cyclohexyleth-1-yl;
$R^4$ = in each case one line of Table A.

TABLE 363

Compounds of the formula I.3 where $R^3$ = methyl;
$R^5$ = 2-cyclohexyleth-1-yl;
$R^4$ = in each case one line of Table A.

TABLE 364

Compounds of the formula I.4 where $R^3$ = methyl;
$R^5$ = 2-cyclohexyleth-1-yl;
$R^4$ = in each case one line of Table A.

TABLE 365

Compounds of the formula I.1 where $R^3$ = methyl;
$R^5$ = fluoromethyl;
$R^4$ = in each case one line of Table A.

TABLE 366

Compounds of the formula I.2 where $R^3$ = methyl;
$R^5$ = fluoromethyl;
$R^4$ = in each case one line of Table A.

TABLE 367

Compounds of the formula I.3 where $R^3$ = methyl;
$R^5$ = fluoromethyl;
$R^4$ = in each case one line of Table A.

TABLE 368

Compounds of the formula I.4 where $R^3$ = methyl;
$R^5$ = fluoromethyl;
$R^4$ = in each case one line of Table A.

TABLE 369

Compounds of the formula I.1 where $R^3$ = methyl;
$R^5$ = difluoromethyl;
$R^4$ = in each case one line of Table A.

TABLE 370

Compounds of the formula I.2 where $R^3$ = methyl;
$R^5$ = difluoromethyl;
$R^4$ = in each case one line of Table A.

TABLE 371

Compounds of the formula I.3 where $R^3$ = methyl;
$R^5$ = difluoromethyl;
$R^4$ = in each case one line of Table A.

TABLE 372

Compounds of the formula I.4 where $R^3$ = methyl;
$R^5$ = difluoromethyl;
$R^4$ = in each case one line of Table A.

TABLE 373

Compounds of the formula I.1 where $R^3$ = methyl;
$R^5$ = 2-fluoroeth-1-yl;
$R^4$ = in each case one line of Table A.

TABLE 374

Compounds of the formula I.2 where $R^3$ = methyl;
$R^5$ = 2-fluoroeth-1-yl;
$R^4$ = in each case one line of Table A.

TABLE 375

Compounds of the formula I.3 where $R^3$ = methyl;
$R^5$ = 2-fluoroeth-1-yl;
$R^4$ = in each case one line of Table A.

TABLE 376

Compounds of the formula I.4 where $R^3$ = methyl;
$R^5$ = 2-fluoroeth-1-yl;
$R^4$ = in each case one line of Table A.

TABLE 377

Compounds of the formula I.1 where $R^3$ = methyl;
$R^5$ = 3-fluoroprop-1-yl;
$R^4$ = in each case one line of Table A.

TABLE 378

Compounds of the formula I.2 where $R^3$ = methyl;
$R^5$ = 3-fluoroprop-1-yl;
$R^4$ = in each case one line of Table A.

TABLE 379

Compounds of the formula I.3 where $R^3$ = methyl;
$R^5$ = 3-fluoroprop-1-yl;
$R^4$ = in each case one line of Table A.

TABLE 380

Compounds of the formula I.4 where $R^3$ = methyl;
$R^5$ = 3-fluoroprop-1-yl;
$R^4$ = in each case one line of Table A.

TABLE 381

Compounds of the formula I.1 where $R^3$ = methyl;
$R^5$ = 2,2-difluoroeth-1-yl;
$R^4$ = in each case one line of Table A.

TABLE 382

Compounds of the formula I.2 where $R^3$ = methyl;
$R^5$ = 2,2-difluoroeth-1-yl;
$R^4$ = in each case one line of Table A.

TABLE 383

Compounds of the formula I.3 where $R^3$ = methyl;
$R^5$ = 2,2-difluoroeth-1-yl;
$R^4$ = in each case one line of Table A.

TABLE 384

Compounds of the formula I.4 where $R^3$ = methyl;
$R^5$ = 2,2-difluoroeth-1-yl;
$R^4$ = in each case one line of Table A.

TABLE 385

Compounds of the formula I.1 where $R^3$ = methyl;
$R^5$ = 2,2,2-trifluoroeth-1-yl;
$R^4$ = in each case one line of Table A.

TABLE 386

Compounds of the formula I.2 where $R^3$ = methyl;
$R^5$ = 2,2,2-trifluoroeth-1-yl;
$R^4$ = in each case one line of Table A.

TABLE 387

Compounds of the formula I.3 where $R^3$ = methyl;
$R^5$ = 2,2,2-trifluoroeth-1-yl;
$R^4$ = in each case one line of Table A.

TABLE 388

Compounds of the formula I.4 where $R^3$ = methyl;
$R^5$ = 2,2,2-trifluoroeth-1-yl;
$R^4$ = in each case one line of Table A.

TABLE 389

Compounds of the formula I.1 where $R^3$ = methyl;
$R^5$ = 2-bromoeth-1-yl;
$R^4$ = in each case one line of Table A.

TABLE 390

Compounds of the formula I.2 where $R^3$ = methyl;
$R^5$ = 2-bromoeth-1-yl;
$R^4$ = in each case one line of Table A.

TABLE 391

Compounds of the formula I.3 where $R^3$ = methyl;
$R^5$ = 2-bromoeth-1-yl;
$R^4$ = in each case one line of Table A.

TABLE 392

Compounds of the formula I.4 where $R^3$ = methyl;
$R^5$ = 2-bromoeth-1-yl;
$R^4$ = in each case one line of Table A.

TABLE 393

Compounds of the formula I.1 where $R^3$ = methyl;
$R^5$ = 3-bromoprop-1-yl;
$R^4$ = in each case one line of Table A.

TABLE 394

Compounds of the formula I.2 where $R^3$ = methyl;
$R^5$ = 3-bromoprop-1-yl;
$R^4$ = in each case one line of Table A.

TABLE 395

Compounds of the formula I.3 where $R^3$ = methyl;
$R^5$ = 3-bromoprop-1-yl;
$R^4$ = in each case one line of Table A.

TABLE 396

Compounds of the formula I.4 where $R^3$ = methyl;
$R^5$ = 3-bromoprop-1-yl;
$R^4$ = in each case one line of Table A.

TABLE 397

Compounds of the formula I.1 where $R^3$ = methyl;
$R^5$ = 4-bromobut-1-yl;
$R^4$ = in each case one line of Table A.

TABLE 398

Compounds of the formula I.2 where $R^3$ = methyl;
$R^5$ = 4-bromobut-1-yl;
$R^4$ = in each case one line of Table A.

TABLE 399

Compounds of the formula I.3 where $R^3$ = methyl;
$R^5$ = 4-bromobut-1-yl;
$R^4$ = in each case one line of Table A.

TABLE 400

Compounds of the formula I.4 where $R^3$ = methyl;
$R^5$ = 4-bromobut-1-yl;
$R^4$ = in each case one line of Table A.

TABLE 401

Compounds of the formula I.1 where $R^3$ = methyl;
$R^5$ = 2-iodoeth-1-yl;
$R^4$ = in each case one line of Table A.

TABLE 402

Compounds of the formula I.2 where $R^3$ = methyl;
$R^5$ = 2-iodoeth-1-yl;
$R^4$ = in each case one line of Table A.

TABLE 403

Compounds of the formula I.3 where $R^3$ = methyl;
$R^5$ = 2-iodoeth-1-yl;
$R^4$ = in each case one line of Table A.

TABLE 404

Compounds of the formula I.4 where $R^3$ = methyl;
$R^5$ = 2-iodoeth-1-yl;
$R^4$ = in each case one line of Table A.

TABLE 405

Compounds of the formula I.1 where $R^3$ = methyl;
$R^5$ = 2-chloroeth-1-yl;
$R^4$ = in each case one line of Table A.

TABLE 406

Compounds of the formula I.2 where $R^3$ = methyl;
$R^5$ = 2-chloroeth-1-yl;
$R^4$ = in each case one line of Table A.

TABLE 407

Compounds of the formula I.3 where $R^3$ = methyl;
$R^5$ = 2-chloroeth-1-yl;
$R^4$ = in each case one line of Table A.

TABLE 408

Compounds of the formula I.4 where $R^3$ = methyl;
$R^5$ = 2-chloroeth-1-yl;
$R^4$ = in each case one line of Table A.

TABLE 409

Compounds of the formula I.1 where $R^3$ = methyl;
$R^5$ = 3-chloroprop-1-yl;
$R^4$ = in each case one line of Table A.

TABLE 410

Compounds of the formula I.2 where $R^3$ = methyl;
$R^5$ = 3-chloroprop-1-yl;
$R^4$ = in each case one line of Table A.

TABLE 411

Compounds of the formula I.3 where $R^3$ = methyl;
$R^5$ = 3-chloroprop-1-yl;
$R^4$ = in each case one line of Table A.

TABLE 412

Compounds of the formula I.4 where $R^3$ = methyl;
$R^5$ = 3-chloroprop-1-yl;
$R^4$ = in each case one line of Table A.

TABLE 413

Compounds of the formula I.1 where $R^3$ = methyl;
$R^5$ = 4-chlorobut-1-yl;
$R^4$ = in each case one line of Table A.

TABLE 414

Compounds of the formula I.2 where $R^3$ = methyl;
$R^5$ = 4-chlorobut-1-yl;
$R^4$ = in each case one line of Table A.

TABLE 415

Compounds of the formula I.3 where $R^3$ = methyl;
$R^5$ = 4-chlorobut-1-yl;
$R^4$ = in each case one line of Table A.

TABLE 416

Compounds of the formula I.4 where $R^3$ = methyl;
$R^5$ = 4-chlorobut-1-yl;
$R^4$ = in each case one line of Table A.

TABLE 417

Compounds of the formula I.1 where $R^3$ = methyl;
$R^5$ = cyanomethyl;
$R^4$ = in each case one line of Table A.

TABLE 418

Compounds of the formula I.2 where $R^3$ = methyl;
$R^5$ = cyanomethyl;
$R^4$ = in each case one line of Table A.

TABLE 419

Compounds of the formula I.3 where $R^3$ = methyl;
$R^5$ = cyanomethyl;
$R^4$ = in each case one line of Table A.

TABLE 420

Compounds of the formula I.4 where $R^3$ = methyl;
$R^5$ = cyanomethyl;
$R^4$ = in each case one line of Table A.

TABLE 421

Compounds of the formula I.1 where $R^3$ = methyl;
$R^5$ = 2-cyanoeth-1-yl;
$R^4$ = in each case one line of Table A.

TABLE 422

Compounds of the formula I.2 where $R^3$ = methyl;
$R^5$ = 2-cyanoeth-1-yl;
$R^4$ = in each case one line of Table A.

TABLE 423

Compounds of the formula I.3 where $R^3$ = methyl;
$R^5$ = 2-cyanoeth-1-yl;
$R^4$ = in each case one line of Table A.

TABLE 424

Compounds of the formula I.4 where $R^3$ = methyl;
$R^5$ = 2-cyanoeth-1-yl;
$R^4$ = in each case one line of Table A.

TABLE 425

Compounds of the formula I.1 where $R^3$ = methyl;
$R^5$ = 3-cyanoprop-1-yl;
$R^4$ = in each case one line of Table A.

TABLE 426

Compounds of the formula I.2 where $R^3$ = methyl;
$R^5$ = 3-cyanoprop-1-yl;
$R^4$ = in each case one line of Table A.

TABLE 427

Compounds of the formula I.3 where $R^3$ = methyl;
$R^5$ = 3-cyanoprop-1-yl;
$R^4$ = in each case one line of Table A.

TABLE 428

Compounds of the formula I.4 where $R^3$ = methyl;
$R^5$ = 3-cyanoprop-1-yl;
$R^4$ = in each case one line of Table A.

TABLE 429

Compounds of the formula I.1 where $R^3$ = methyl;
$R^5$ = 4-cyanobut-1-yl;
$R^4$ = in each case one line of Table A.

TABLE 430

Compounds of the formula I.2 where $R^3$ = methyl;
$R^5$ = 4-cyanobut-1-yl;
$R^4$ = in each case one line of Table A.

TABLE 431

Compounds of the formula I.3 where $R^3$ = methyl;
$R^5$ = 4-cyanobut-1-yl;
$R^4$ = in each case one line of Table A.

TABLE 432

Compounds of the formula I.4 where $R^3$ = methyl;
$R^5$ = 4-cyanobut-1-yl;
$R^4$ = in each case one line of Table A.

TABLE 433

Compounds of the formula I.1 where $R^3$ = methyl;
$R^5$ = 2-ethoxyeth-1-yl;
$R^4$ = in each case one line of Table A.

TABLE 434

Compounds of the formula I.2 where $R^3$ = methyl;
$R^5$ = 2-ethoxyeth-1-yl;
$R^4$ = in each case one line of Table A.

TABLE 435

Compounds of the formula I.3 where $R^3$ = methyl;
$R^5$ = 2-ethoxyeth-1-yl;
$R^4$ = in each case one line of Table A.

TABLE 436

Compounds of the formula I.4 where $R^3$ = methyl;
$R^5$ = 2-ethoxyeth-1-yl;
$R^4$ = in each case one line of Table A.

TABLE 437

Compounds of the formula I.1 where $R^3$ = methyl;
$R^5$ = 2-isopropoxyeth-1-yl;
$R^4$ = in each case one line of Table A.

TABLE 438

Compounds of the formula I.2 where $R^3$ = methyl;
$R^5$ = 2-isopropoxyeth-1-yl;
$R^4$ = in each case one line of Table A.

TABLE 439

Compounds of the formula I.3 where $R^3$ = methyl;
$R^5$ = 2-isopropoxyeth-1-yl;
$R^4$ = in each case one line of Table A.

TABLE 440

Compounds of the formula I.4 where $R^3$ = methyl;
$R^5$ = 2-isopropoxyeth-1-yl;
$R^4$ = in each case one line of Table A.

TABLE 441

Compounds of the formula I.1 where $R^3$ = methyl;
$R^5$ = 3-methoxyprop-1-yl;
$R^4$ = in each case one line of Table A.

TABLE 442

Compounds of the formula I.2 where $R^3$ = methyl;
$R^5$ = 3-methoxyprop-1-yl;
$R^4$ = in each case one line of Table A.

TABLE 443

Compounds of the formula I.3 where $R^3$ = methyl;
$R^5$ = 3-methoxyprop-1-yl;
$R^4$ = in each case one line of Table A.

TABLE 444

Compounds of the formula I.4 where $R^3$ = methyl;
$R^5$ = 3-methoxyprop-1-yl;
$R^4$ = in each case one line of Table A.

TABLE 445

Compounds of the formula I.1 where $R^3$ = methyl;
$R^5$ = 3-ethoxyprop-1-yl;
$R^4$ = in each case one line of Table A.

TABLE 446

Compounds of the formula I.2 where $R^3$ = methyl;
$R^5$ = 3-ethoxyprop-1-yl;
$R^4$ = in each case one line of Table A.

TABLE 447

Compounds of the formula I.3 where $R^3$ = methyl;
$R^5$ = 3-ethoxyprop-1-yl;
$R^4$ = in each case one line of Table A.

TABLE 448

Compounds of the formula I.4 where $R^3$ = methyl;
$R^5$ = 3-ethoxyprop-1-yl;
$R^4$ = in each case one line of Table A.

TABLE 449

Compounds of the formula I.1 where $R^3$ = methyl;
$R^5$ = 3-isopropoxyprop-1-yl;
$R^4$ = in each case one line of Table A.

TABLE 450

Compounds of the formula I.2 where $R^3$ = methyl;
$R^5$ = 3-isopropoxyprop-1-yl;
$R^4$ = in each case one line of Table A.

TABLE 451

Compounds of the formula I.3 where $R^3$ = methyl;
$R^5$ = 3-isopropoxyprop-1-yl;
$R^4$ = in each case one line of Table A.

TABLE 452

Compounds of the formula I.4 where $R^3$ = methyl;
$R^5$ = 3-isopropoxypro#-1-yl;
$R^4$ = in each case one line of Table A.

TABLE 453

Compounds of the formula I.1 where $R^3$ = methyl;
$R^5$ = 4-methoxybut-1-yl;
$R^4$ = in each case one line of Table A.

TABLE 454

Compounds of the formula I.2 where $R^3$ = methyl;
$R^5$ = 4-methoxybut-1-yl;
$R^4$ = in each case one line of Table A.

TABLE 455

Compounds of the formula I.3 where $R^3$ = methyl;
$R^5$ = 4-methoxybut-1-y1;
$R^4$ = in each case one line of Table A.

TABLE 456

Compounds of the formula I.4 where $R^3$ = methyl;
$R^5$ = 4-methoxybut-1-yl;
$R^4$ = in each case one line of Table A.

TABLE 457

Compounds of the formula I.1 where $R^3$ = methyl;
$R^5$ = 4-ethoxybut-1-yl;
$R^4$ = in each case one line of Table A.

TABLE 458

Compounds of the formula I.2 where $R^3$ = methyl;
$R^5$ = 4-ethoxybut-1-yl;
$R^4$ = in each case one line of Table A.

TABLE 459

Compounds of the formula I.3 where $R^3$ = methyl;
$R^5$ = 4-ethoxybut-1-yl;
$R^4$ = in each case one line of Table A.

TABLE 460

Compounds of the formula I.4 where $R^3$ = methyl;
$R^5$ = 4-ethoxybut-1-yl;
$R^4$ = in each case one line of Table A.

TABLE 461

Compounds of the formula I.1 where $R^3$ = methyl;
$R^5$ = 4-isopropoxybut-1-yl;
$R^4$ = in each case one line of Table A.

TABLE 462

Compounds of the formula I.2 where $R^3$ = methyl;
$R^5$ = 4-isopropoxybut-1-yl;
$R^4$ = in each case one line of Table A.

TABLE 463

Compounds of the formula I.3 where $R^3$ = methyl;
$R^5$ = 4-isopropoxybut-1-yl;
$R^4$ = in each case one line of Table A.

TABLE 464

Compounds of the formula I.4 where $R^3$ = methyl;
$R^5$ = 4-isopropoxybut-1-yl;
$R^4$ = in each case one line of Table A.

TABLE 465

Compounds of the formula I.1 where $R^3$ = methyl;
$R^5$ = 3-methylbut-2-en-1-yl;
$R^4$ = in each case one line of Table A.

TABLE 466

Compounds of the formula I.2 where $R^3$ = methyl;
$R^5$ = 3-methylbut-2-en-1-yl;
$R^4$ = in each case one line of Table A.

TABLE 467

Compounds of the formula I.3 where $R^3$ = methyl;
$R^5$ = 3-methylbut-2-en-1-yl;
$R^4$ = in each case one line of Table A.

TABLE 468

Compounds of the formula I.4 where $R^3$ = methyl;
$R^5$ = 3-methylbut-2-en-1-yl;
$R^4$ = in each case one line of Table A.

TABLE 469

Compounds of the formula I.1 where $R^3$ = methyl;
$R^5$ = 2-methylprop-2-en-1-yl;
$R^4$ = in each case one line of Table A.

TABLE 470

Compounds of the formula I.2 where $R^3$ = methyl;
$R^5$ = 2-methylprop-2-en-1-yl;
$R^4$ = in each case one line of Table A.

TABLE 471

Compounds of the formula I.3 where $R^3$ = methyl;
$R^5$ = 2-methylprop-2-en-1-yl;
$R^4$ = in each case one line of Table A.

TABLE 472

Compounds of the formula I.4 where $R^3$ = methyl;
$R^5$ = 2-methylprop-2-en-1-yl;
$R^4$ = in each case one line of Table A.

TABLE 473

Compounds of the formula I.1 where $R^3$ = methyl;
$R^5$ = but-3-en-1-yl;
$R^4$ = in each case one line of Table A.

TABLE 474

Compounds of the formula I.2 where $R^3$ = methyl;
$R^5$ = but-3-en-1-yl;
$R^4$ = in each case one line of Table A.

TABLE 475

Compounds of the formula I.3 where $R^3$ = methyl;
$R^5$ = but-3-en-1-yl;
$R^4$ = in each case one line of Table A.

TABLE 476

Compounds of the formula I.4 where $R^3$ = methyl;
$R^5$ = but-3-en-1-yl;
$R^4$ = in each case one line of Table A.

TABLE 477

Compounds of the formula I.1 where $R^3$ = methyl;
$R^5$ = 2-chloroprop-2-en-1-yl;
$R^4$ = in each case one line of Table A.

TABLE 478

Compounds of the formula I.2 where $R^3$ = methyl;
$R^5$ = 2-chloroprop-2-en-1-yl;
$R^4$ = in each case one line of Table A.

TABLE 479

Compounds of the formula I.3 where $R^3$ = methyl;
$R^5$ = 2-chloroprop-2-en-1-yl;
$R^4$ = in each case one line of Table A.

TABLE 480

Compounds of the formula I.4 where $R^3$ = methyl;
$R^5$ = 2-chloroprop-2-en-1-yl;
$R^4$ = in each case one line of Table A.

TABLE 481

Compounds of the formula I.1 where $R^3$ = methyl;
$R^5$ = 3,3-dichloroprop-2-en-1-yl;
$R^4$ = in each case one line of Table A.

TABLE 482

Compounds of the formula I.2 where $R^3$ = methyl;
$R^5$ = 3,3-dichloroprop-2-en-1-yl;
$R^4$ = in each case one line of Table A.

TABLE 483

Compounds of the formula I.3 where $R^3$ = methyl;
$R^5$ = 3,3-dichloroprop-2-en-1-yl;
$R^4$ = in each case one line of Table A.

TABLE 484

Compounds of the formula I.4 where $R^3$ = methyl;
$R^5$ = 3,3-dichloroprop-2-en-1-yl;
$R^4$ = in each case one line of Table A.

TABLE 485

Compounds of the formula I.1 where $R^3$ = methyl;
$R^5$ = 2,3,3-trichloroprop-2-en-1-yl;
$R^4$ = in each case one line of Table A.

TABLE 486

Compounds of the formula I.2 where $R^3$ = methyl;
$R^5$ = 2,3,3-trichloroprop-2-en-1-yl;
$R^4$ = in each case one line of Table A.

TABLE 487

Compounds of the formula I.3 where $R^3$ = methyl;
$R^5$ = 2,3,3-trichloroprop-2-en-1-yl;
$R^4$ = in each case one line of Table A.

TABLE 488

Compounds of the formula I.4 where $R^3$ = methyl;
$R^5$ = 2,3,3-trichloroprop-2-en-1-yl;
$R^4$ = in each case one line of Table A.

TABLE 489

Compounds of the formula I.1 where $R^3$ = methyl;
$R^5$ = Z-2,3-dichloroprop-2-en-1-yl;
$R^4$ = in each case one line of Table A.

TABLE 490

Compounds of the formula I.2 where $R^3$ = methyl;
$R^5$ = Z-2,3-dichloroprop-2-en-1-yl;
$R^4$ = in each case one line of Table A.

TABLE 491

Compounds of the formula I.3 where $R^3$ = methyl;
$R^5$ = Z-2,3-dichloroprop-2-en-1-yl;
$R^4$ = in each case one line of Table A.

TABLE 492

Compounds of the formula I.4 where $R^3$ = methyl;
$R^5$ = Z-2,3-dichloroprop-2-en-1-yl;
$R^4$ = in each case one line of Table A.

TABLE 493

Compounds of the formula I.1 where $R^3$ = methyl;
$R^5$ = E-2,3-dichloroprop-2-en-1-yl;
$R^4$ = in each case one line of Table A.

TABLE 494

Compounds of the formula I.2 where $R^3$ = methyl;
$R^5$ = E-2,3-dichloroprop-2-en-1-yl;
$R^4$ = in each case one line of Table A.

TABLE 495

Compounds of the formula I.3 where $R^3$ = methyl;
$R^5$ = E-2,3-dichloroprop-2-en-1-yl;
$R^4$ = in each case one line of Table A.

TABLE 496

Compounds of the formula I.4 where $R^3$ = methyl;
$R^5$ = E-2,3-dichloroprop-2-en-1-yl;
$R^4$ = in each case one line of Table A.

TABLE 497

Compounds of the formula I.1 where $R^3$ = methyl;
$R^5$ = Z-3-bromoprop-2-en-1-yl;
$R^4$ = in each case one line of Table A.

TABLE 498

Compounds of the formula I.2 where $R^3$ = methyl;
$R^5$ = Z-3-bromoprop-2-en-1-yl;
$R^4$ = in each case one line of Table A.

TABLE 499

Compounds of the formula I.3 where $R^3$ = methyl;
$R^5$ = Z-3-bromoprop-2-en-1-yl;
$R^4$ = in each case one line of Table A.

TABLE 500

Compounds of the formula I.4 where $R^3$ = methyl;
$R^5$ = Z-3-bromoprop-2-en-1-yl;
$R^4$ = in each case one line of Table A.

TABLE 501

Compounds of the formula I.1 where $R^3$ = methyl;
$R^5$ = E-3-bromoprop-2-en-1-yl;
$R^4$ = in each case one line of Table A.

TABLE 502

Compounds of the formula I.2 where $R^3$ = methyl;
$R^5$ = E-3-bromoprop-2-en-1-yl;
$R^4$ = in each case one line of Table A.

TABLE 503

Compounds of the formula I.3 where $R^3$ = methyl;
$R^5$ = E-3-bromoprop-2-en-1-yl;
$R^4$ = in each case one line of Table A.

TABLE 504

Compounds of the formula I.4 where $R^3$ = methyl;
$R^5$ = E-3-bromoprop-2-en-1-yl;
$R^4$ = in each case one line of Table A.

TABLE 505

Compounds of the formula I.1 where $R^3$ = methyl;
$R^5$ = 2-bromoprop-2-en-1-yl;
$R^4$ = in each case one line of Table A.

TABLE 506

Compounds of the formula I.2 where $R^3$ = methyl;
$R^5$ = 2-bromoprop-2-en-1-yl;
$R^4$ = in each case one line of Table A.

TABLE 507

Compounds of the formula I.3 where $R^3$ = methyl;
$R^5$ = 2-bromoprop-2-en-1-yl;
$R^4$ = in each case one line of Table A.

TABLE 508

Compounds of the formula I.4 where $R^3$ = methyl;
$R^5$ = 2-bromoprop-2-en-1-yl;
$R^4$ = in each case one line of Table A.

TABLE 509

Compounds of the formula I.1 where $R^3$ = methyl;
$R^5$ = 3,3-dibromoprop-2-en-1-yl;
$R^4$ = in each case one line of Table A.

TABLE 510

Compounds of the formula I.2 where $R^3$ = methyl;
$R^5$ = 3,3-dibromoprop-2-en-1-yl;
$R^4$ = in each case one line of Table A.

TABLE 511

Compounds of the formula I.3 where $R^3$ = methyl;
$R^5$ = 3,3-dibromoprop-2-en-1-yl;
$R^4$ = in each case one line of Table A.

TABLE 512

Compounds of the formula I.4 where $R^3$ = methyl;
$R^5$ = 3,3-dibromoprop-2-en-1-yl;
$R^4$ = in each case one line of Table A.

TABLE 513

Compounds of the formula I.1 where $R^3$ = methyl;
$R^5$ = 2,3,3-tribromoprop-2-en-1-yl;
$R^4$ = in each case one line of Table A.

TABLE 514

Compounds of the formula I.2 where $R^3$ = methyl;
$R^5$ = 2,3,3-tribromoprop-2-en-1-yl;
$R^4$ = in each case one line of Table A.

TABLE 515

Compounds of the formula I.3 where $R^3$ = methyl;
$R^5$ = 2,3,3-tribromoprop-2-en-1-yl;
$R^4$ = in each case one line of Table A.

TABLE 516

Compounds of the formula I.4 where $R^3$ = methyl;
$R^5$ = 2,3,3-tribromoprop-2-en-1-yl;
$R^4$ = in each case one line of Table A.

TABLE 517

Compounds of the formula I.1 where $R^3$ = methyl;
$R^5$ = Z-2,3-dibromoprop-2-en-1-yl;
$R^4$ = in each case one line of Table A.

TABLE 518

Compounds of the formula I.2 where $R^3$ = methyl;
$R^5$ = Z-2,3-dibromoprop-2-en-1-yl;
$R^4$ = in each case one line of Table A.

TABLE 519

Compounds of the formula I.3 where $R^3$ = methyl;
$R^5$ = Z-2,3-dibromoprop-2-en-1-yl;
$R^4$ = in each case one line of Table A.

TABLE 520

Compounds of the formula I.4 where $R^3$ = methyl;
$R^5$ = Z-2,3-dibromoprop-2-en-1-yl;
$R^4$ = in each case one line of Table A.

TABLE 521

Compounds of the formula I.1 where $R^3$ = methyl;
$R^5$ = E-2,3-dibromoprop-2-en-1-yl;
$R^4$ = in each case one line of Table A.

TABLE 522

Compounds of the formula I.2 where $R^3$ = methyl;
$R^5$ = E-2,3-dibromoprop-2-en-1-yl;
$R^4$ = in each case one line of Table A.

TABLE 523

Compounds of the formula I.3 where $R^3$ = methyl;
$R^5$ = E-2,3-dibromoprop-2-en-1-yl;
$R^4$ = in each case one line of Table A.

TABLE 524

Compounds of the formula I.4 where $R^3$ = methyl;
$R^5$ = E-2,3-dibromoprop-2-en-1-yl;
$R^4$ = in each case one line of Table A.

TABLE 525

Compounds of the formula I.1 where $R^3$ = methyl;
$R^5$ = E-2-chlorobut-2-en-1-yl;
$R^4$ = in each case one line of Table A.

TABLE 526

Compounds of the formula I.2 where $R^3$ = methyl;
$R^5$ = E-2-chlorobut-2-en-1-yl;
$R^4$ = in each case one line of Table A.

TABLE 527

Compounds of the formula I.3 where $R^3$ = methyl;
$R^5$ = E-2-chlorobut-2-en-1-yl;
$R^4$ = in each case one line of Table A.

TABLE 528

Compounds of the formula I.4 where $R^3$ = methyl;
$R^5$ = E-2-chlorobut-2-en-1-yl;
$R^4$ = in each case one line of Table A.

TABLE 529

Compounds of the formula I.1 where $R^3$ = methyl;
$R^5$ = Z-2-chlorobut-2-en-1-yl;
$R^4$ = in each case one line of Table A.

TABLE 530

Compounds of the formula I.2 where $R^3$ = methyl;
$R^5$ = Z-2-chlorobut-2-en-1-yl;
$R^4$ = in each case one line of Table A.

TABLE 531

Compounds of the formula I.3 where $R^3$ = methyl;
$R^5$ = Z-2-chlorobut-2-en-1-yl;
$R^4$ = in each case one line of Table A.

TABLE 532

Compounds of the formula I.4 where $R^3$ = methyl;
$R^5$ = Z-2-chlorobut-2-en-1-yl;
$R^4$ = in each case one line of Table A.

TABLE 533

Compounds of the formula I.1 where $R^3$ = methyl;
$R^5$ = E-3-chlorobut-2-en-1-yl;
$R^4$ = in each case one line of Table A.

TABLE 534

Compounds of the formula I.2 where $R^3$ = methyl;
$R^5$ = E-3-chlorobut-2-en-1-yl;
$R^4$ = in each case one line of Table A.

TABLE 535

Compounds of the formula I.3 where $R^3$ = methyl;
$R^5$ = E-3-chlorobut-2-en-1-yl;
$R^4$ = in each case one line of Table A.

TABLE 536

Compounds of the formula I.4 where $R^3$ = methyl;
$R^5$ = E-3-chlorobut-2-en-1-yl;
$R^4$ = in each case one line of Table A.

TABLE 537

Compounds of the formula I.1 where $R^3$ = methyl;
$R^5$ = Z-3-chlorobut-2-en-1-yl;
$R^4$ = in each case one line of Table A.

TABLE 538

Compounds of the formula I.2 where $R^3$ = methyl;
$R^5$ = Z-3-chlorobut-2-en-1-yl;
$R^4$ = in each case one line of Table A.

TABLE 539

Compounds of the formula I.3 where $R^3$ = methyl;
$R^5$ = Z-3-chlorobut-2-en-1-yl;
$R^4$ = in each case one line of Table A.

TABLE 540

Compounds of the formula I.4 where $R^3$ = methyl;
$R^5$ = Z-3-chlorobut-2-en-1-yl;
$R^4$ = in each case one line of Table A.

TABLE 541

Compounds of the formula I.1 where $R^3$ = methyl;
$R^5$ = E-2-bromobut-2-en-1-yl;
$R^4$ = in each case one line of Table A.

TABLE 542

Compounds of the formula I.2 where $R^3$ = methyl;
$R^5$ = E-2-bromobut-2-en-1-yl;
$R^4$ = in each case one line of Table A.

TABLE 543

Compounds of the formula I.3 where $R^3$ = methyl;
$R^5$ = E-2-bromobut-2-en-1-yl;
$R^4$ = in each case one line of Table A.

TABLE 544

Compounds of the formula I.4 where $R^3$ = methyl;
$R^5$ = E-2-bromobut-2-en-1-yl;
$R^4$ = in each case one line of Table A.

TABLE 545

Compounds of the formula I.1 where $R^3$ = methyl;
$R^5$ = Z-2-bromobut-2-en-1-yl;
$R^4$ = in each case one line of Table A.

TABLE 546

Compounds of the formula I.2 where $R^3$ = methyl;
$R^5$ = Z-2-bromobut-2-en-1-yl;
$R^4$ = in each case one line of Table A.

TABLE 547

Compounds of the formula I.3 where $R^3$ = methyl;
$R^5$ = Z-2-bromobut-2-en-1-yl;
$R^4$ = in each case one line of Table A.

TABLE 548

Compounds of the formula I.4 where $R^3$ = methyl;
$R^5$ = Z-2-bromobut-2-en-1-yl;
$R^4$ = in each case one line of Table A.

TABLE 549

Compounds of the formula I.1 where $R^3$ = methyl;
$R^5$ = E-3-bromobut-2-en-1-yl;
$R^4$ = in each case one line of Table A.

TABLE 550

Compounds of the formula I.2 where $R^3$ = methyl;
$R^5$ = E-3-bromobut-2-en-1-yl;
$R^4$ = in each case one line of Table A.

TABLE 551

Compounds of the formula I.3 where $R^3$ = methyl;
$R^5$ = E-3-bromobut-2-en-1-yl;
$R^4$ = in each case one line of Table A.

TABLE 552

Compounds of the formula I.4 where $R^3$ = methyl;
$R^5$ = E-3-bromobut-2-en-1-yl;
$R^4$ = in each case one line of Table A.

TABLE 553

Compounds of the formula I.1 where $R^3$ = methyl;
$R^5$ = Z-3-bromobut-2-en-1-yl;
$R^4$ = in each case one line of Table A.

TABLE 554

Compounds of the formula I.2 where

R³ = methyl;
R⁵ = Z-3-bromobut-2-en-1-yl;
R⁴ = in each case one line of Table A.

TABLE 555

Compounds of the formula I.3 where

R³ = methyl;
R⁵ = Z-3-bromobut-2-en-1-yl;
R⁴ = in each case one line of Table A.

TABLE 556

Compounds of the formula I.4 where

R³ = methyl;
R⁵ = Z-3-bromobut-2-en-1-yl;
R⁴ = in each case one line of Table A.

TABLE 557

Compounds of the formula I.1 where

R³ = methyl;
R⁵ = 3-chloroprop-2-yn-1-yl;
R⁴ = in each case one line of Table A.

TABLE 558

Compounds of the formula I.2 where

R³ = methyl;
R⁵ = 3-chloroprop-2-yn-1-yl;
R⁴ = in each case one line of Table A.

TABLE 559

Compounds of the formula I.3 where

R³ = methyl;
R⁵ = 3-chloroprop-2-yn-1-yl;
R⁴ = in each case one line of Table A.

TABLE 560

Compounds of the formula I.4 where

R³ = methyl;
R⁵ = 3-chloroprop-2-yn-1-yl;
R⁴ = in each case one line of Table A.

TABLE 561

Compounds of the formula I.1 where

R³ = methyl;
R⁵ = 3-bromoprop-2-yn-1-yl;
R⁴ = in each case one line of Table A.

TABLE 562

Compounds of the formula I.2 where

R³ = methyl;
R⁵ = 3-bromoprop-2-yn-1-yl;
R⁴ = in each case one line of Table A.

TABLE 563

Compounds of the formula I.3 where

R³ = methyl;
R⁵ = 3-bromoprop-2-yn-1-yl;
R⁴ = in each case one line of Table A.

TABLE 564

Compounds of the formula I.4 where

R³ = methyl;
R⁵ = 3-bromoprop-2-yn-1-yl;
R⁴ = in each case one line of Table A.

TABLE 565

Compounds of the formula I.1 where

R³ = methyl;
R⁵ = 3-iodoprop-2-yn-1-yl;
R⁴ = in each case one line of Table A.

TABLE 566

Compounds of the formula I.2 where

R³ = methyl;
R⁵ = 3-iodoprop-2-yn-1-yl;
R⁴ = in each case one line of Table A.

TABLE 567

Compounds of the formula I.3 where

R³ = methyl;
R⁵ = 3-iodoprop-2-yn-1-yl;
R⁴ = in each case one line of Table A.

TABLE 568

Compounds of the formula I.4 where

R³ = methyl;
R⁵ = 3-iodoprop-2-yn-1-yl;
R⁴ = in each case one line of Table A.

TABLE 569

Compounds of the formula I.1 where

R³ = methyl;
R⁵ = but-2-yn-1-yl;
R⁴ = in each case one line of Table A.

TABLE 570

Compounds of the formula I.2 where $R^3$ = methyl;
$R^5$ = but-2-yn-1-yl;
$R^4$ = in each case one line of Table A.

TABLE 571

Compounds of the formula I.3 where $R^3$ = methyl;
$R^5$ = but-2-yn-1-yl;
$R^4$ = in each case one line of Table A.

TABLE 572

Compounds of the formula I.4 where $R^3$ = methyl;
$R^5$ = but-2-yn-1-yl;
$R^4$ = in each case one line of Table A.

TABLE 573

Compounds of the formula I.1 where $R^3$ = methyl;
$R^5$ = but-3-yn-1-yl;
$R^4$ = in each case one line of Table A.

TABLE 574

Compounds of the formula I.2 where $R^3$ = methyl;
$R^5$ = but-3-yn-1-yl;
$R^4$ = in each case one line of Table A.

TABLE 575

Compounds of the formula I.3 where $R^3$ = methyl;
$R^5$ = but-3-yn-1-yl;
$R^4$ = in each case one line of Table A.

TABLE 576

Compounds of the formula I.4 where $R^3$ = methyl;
$R^5$ = but-3-yn-1-yl;
$R^4$ = in each case one line of Table A.

TABLE 577

Compounds of the formula I.1 where $R^3$ = methyl;
$R^5$ = but-3-yn-2-yl;
$R^4$ = in each case one line of Table A.

TABLE 578

Compounds of the formula I.2 where $R^3$ = methyl;
$R^5$ = but-3-yn-2-yl;
$R^4$ = in each case one line of Table A.

TABLE 579

Compounds of the formula I.3 where $R^3$ = methyl;
$R^5$ = but-3-yn-2-yl;
$R^4$ = in each case one line of Table A.

TABLE 580

Compounds of the formula I.4 where $R^3$ = methyl;
$R^5$ = but-3-yn-2-yl;
$R^4$ = in each case one line of Table A.

TABLE 581

Compounds of the formula I.1 where $R^3$ = methyl;
$R^5$ = pent-3-yn-1-yl;
$R^4$ = in each case one line of Table A.

TABLE 582

Compounds of the formula I.2 where $R^3$ = methyl;
$R^5$ = pent-3-yn-1-yl;
$R^4$ = in each case one line of Table A.

TABLE 583

Compounds of the formula I.3 where $R^3$ = methyl;
$R^5$ = pent-3-yn-1-yl;
$R^4$ = in each case one line of Table A.

TABLE 584

Compounds of the formula I.4 where $R^3$ = methyl;
$R^5$ = pent-3-yn-1-yl;
$R^4$ = in each case one line of Table A.

TABLE 585

Compounds of the formula I.1 where $R^3$ = methyl;
$R^5$ = pent-4-yn-1-yl;
$R^4$ = in each case one line of Table A.

TABLE 586

Compounds of the formula I.2 where $R^3$ = methyl;
$R^5$ = pent-4-yn-1-yl;
$R^4$ = in each case one line of Table A.

TABLE 587

Compounds of the formula I.3 where $R^3$ = methyl;
$R^5$ = pent-4-yn-1-yl;
$R^4$ = in each case one line of Table A.

TABLE 588

Compounds of the formula I.4 where $R^3$ = methyl;
$R^5$ = pent-4-yn-1-yl;
$R^4$ = in each case one line of Table A.

TABLE 589

Compounds of the formula I.1 where $R^3$ = methyl;
$R^5$ = pent-3-yn-2-yl;
$R^4$ = in each case one line of Table A.

TABLE 590

Compounds of the formula I.2 where $R^3$ = methyl;
$R^5$ = pent-3-yn-2-yl;
$R^4$ = in each case one line of Table A.

TABLE 591

Compounds of the formula I.3 where $R^3$ = methyl;
$R^5$ = pent-3-yn-2-yl;
$R^4$ = in each case one line of Table A.

TABLE 592

Compounds of the formula I.4 where $R^3$ = methyl;
$R^5$ = pent-3-yn-2-yl;
$R^4$ = in each case one line of Table A.

TABLE 593

Compounds of the formula I.1 where $R^3$ = methyl;
$R^5$ = cyclohexylmethyl;
$R^4$ = in each case one line of Table A.

TABLE 594

Compounds of the formula I.2 where $R^3$ = methyl;
$R^5$ = cyclohexylmethyl;
$R^4$ = in each case one line of Table A.

TABLE 595

Compounds of the formula I.3 where $R^3$ = methyl;
$R^5$ = cyclohexylmethyl;
$R^4$ = in each case one line of Table A.

TABLE 596

Compounds of the formula I.4 where $R^3$ = methyl;
$R^5$ = cyclohexylmethyl;
$R^4$ = in each case one line of Table A.

TABLE A

| No. | Ap | $R^b$ | $R^a$ |
|---|---|---|---|
| | | | a) $R^4$ = 3-(C=O)—$R^a$ |
| 1 | | | H |
| 2 | | | $CH_3$ |
| 3 | | | $C_2H_5$ |
| 4 | | | n-$C_3H_7$ |
| 5 | | | i-$C_3H_7$ |
| 6 | | | cyclopropyl |
| 7 | | | n-$C_4H_9$ |
| 8 | | | s-$C_4H_9$ |
| 9 | | | i-$C_4H_9$ |
| 10 | | | t-$C_4H_9$ |
| 11 | | | n-$C_5H_{11}$ |
| 12 | | | i-$C_5H_{11}$ |
| 13 | | | neo-$C_5H_{11}$ |
| 14 | | | cyclopentyl |
| 15 | | | n-$C_6H_{13}$ |
| 16 | | | cyclohexyl |
| 17 | | | $CH_2CN$ |
| 18 | | | $CH_2OCH_3$ |
| 19 | | | $CH_2Cl$ |
| 20 | | | $CF_3$ |
| 21 | | | ethenyl |
| | | | b) $R^4$ = 4-(C=O)—$R^a$ |
| 22 | | | H |
| 23 | | | $CH_3$ |
| 24 | | | $C_2H_5$ |
| 25 | | | n-$C_3H_7$ |
| 26 | | | i-$C_3H_7$ |
| 27 | | | cyclopropyl |
| 28 | | | n-$C_4H_9$ |
| 29 | | | s-$C_4H_9$ |
| 30 | | | i-$C_4H_9$ |
| 31 | | | t-$C_4H_9$ |
| 32 | | | n-$C_5H_{11}$ |
| 33 | | | i-$C_5H_{11}$ |
| 34 | | | neo-$C_5H_{11}$ |
| 35 | | | cyclopentyl |
| 36 | | | n-$C_6H_{13}$ |
| 37 | | | cyclohexyl |
| 38 | | | $CH_2CN$ |
| 39 | | | $CH_2OCH_3$ |
| 40 | | | $CH_2Cl$ |
| 41 | | | $CF_3$ |
| 42 | | | ethenyl |

TABLE A-continued c) $R^4 = 3\text{-}C(=NOR^a)\text{—}Ap\text{—}R^b$

| | | | |
|---|---|---|---|
| 43 | — | CH$_3$ | H |
| 44 | — | CH$_3$ | CH$_3$ |
| 45 | — | CH$_3$ | C$_2$H$_5$ |
| 46 | — | CH$_3$ | n-C$_3$H$_7$ |
| 47 | — | CH$_3$ | i-C$_3$H$_7$ |
| 48 | — | CH$_3$ | cyclopropyl |
| 49 | — | CH$_3$ | n-C$_4$H$_9$ |
| 50 | — | CH$_3$ | s-C$_4$H$_9$ |
| 51 | — | CH$_3$ | i-C$_4$H$_9$ |
| 52 | — | CH$_3$ | t-C$_4$H$_9$ |
| 53 | — | CH$_3$ | n-C$_5$H$_{11}$ |
| 54 | — | CH$_3$ | i-C$_5$H$_{11}$ |
| 55 | — | CH$_3$ | neo-C$_5$H$_{11}$ |
| 56 | — | CH$_3$ | cyclopentyl |
| 57 | — | CH$_3$ | n-C$_6$H$_{13}$ |
| 58 | — | CH$_3$ | cyclohexyl |
| 59 | — | CH$_3$ | CH$_2$CH$_2$Cl |
| 60 | — | CH$_3$ | (CH$_2$)$_4$Cl |
| 61 | — | CH$_3$ | CH$_2$CN |
| 62 | — | CH$_3$ | CH$_2$CH$_2$CN |
| 63 | — | CH$_3$ | (CH$_2$)$_3$CN |
| 64 | — | CH$_3$ | (CH$_2$)$_4$CN |
| 65 | — | CH$_3$ | (CH$_2$)$_6$CN |
| 66 | — | CH$_3$ | cyclohexylmethyl |
| 67 | — | CH$_3$ | 2-cyclohexyleth-1-yl |
| 68 | — | CH$_3$ | cyclopropylmethyl |
| 69 | — | CH$_3$ | 2-cyclopropyleth-1-yl |
| 70 | — | CH$_3$ | 2-methoxyeth-1-yl |
| 71 | — | CH$_3$ | 2-ethoxyeth-1-yl |
| 72 | — | CH$_3$ | 2-isopropoxyeth-1-yl |
| 73 | — | CH$_3$ | 3-methoxyprop-1-yl |
| 74 | — | CH$_3$ | 3-ethoxyprop-1-yl |
| 75 | — | CH$_3$ | 3-isopropoxyprop-1-yl |
| 76 | — | CH$_3$ | 4-methoxybut-1-yl |
| 77 | — | CH$_3$ | 4-isopropoxybut-1-yl |
| 78 | — | CH$_3$ | propen-3-yl |
| 79 | — | CH$_3$ | but-2-en-1-yl |
| 80 | — | CH$_3$ | 3-methylbut-2-en-1-yl |
| 81 | — | CH$_3$ | 2-vinyloxyeth-1-yl |
| 82 | — | CH$_3$ | allyloxyeth-1-yl |
| 83 | — | CH$_3$ | 2-trifluoromethoxyeth-1-yl |
| 84 | — | CH$_3$ | 3-trifluoromethoxyprop-1-yl |
| 85 | — | CH$_3$ | 4-difluoromethoxybut-1-yl |
| 86 | — | CH$_3$ | hydroxycarbonylmethyl |
| 87 | — | CH$_3$ | methoxycarbonylmethyl |
| 88 | — | CH$_3$ | aminocarbonylmethyl |
| 89 | — | CH$_3$ | N-methylaminocarbonylmethyl |
| 90 | — | CH$_3$ | N,N-dimethylaminocarbonyl-methyl |
| 91 | — | CH$_3$ | 2-hydroxycarbonyleth-1-yl |
| 92 | — | CH$_3$ | 2-methoxycarbonyleth-1-yl |
| 93 | — | CH$_3$ | 2-aminocarbonyleth-1-yl |
| 94 | — | CH$_3$ | 2-N-methylaminocarbonyleth-1-yl |
| 95 | — | CH$_3$ | 2-dimethylaminocarbonyleth-1-yl |
| 96 | — | CH$_3$ | 2-aminoeth-1-yl |
| 97 | — | CH$_3$ | 2-aminoprop-1-yl |
| 98 | — | CH$_3$ | 4-aminobut-1-yl |
| 99 | — | CH$_3$ | 3-dimethylaminoprop-1-yl |
| 100 | — | CH$_3$ | 4-aminothiocarbonylbut-1-yl |
| 101 | — | CH$_3$ | 6-aminocarbonylhex-1-yl |
| 102 | — | CH$_3$ | 3-aminothiocarbonylprop-1-yl |
| 103 | — | CH$_3$ | 2-aminothiocarbonyleth-1-yl |
| 104 | — | CH$_3$ | aminothiocarbonylmethyl |
| 105 | — | CH$_3$ | 4-(N,N-dimethylamino)but-1-yl |
| 106 | — | CH$_3$ | 2-(methylthio)eth-1-yl |
| 107 | — | CH$_3$ | 2-(methylsulfonyl)eth-1-yl |
| 108 | — | CH$_3$ | 4-(methylthio)prop-1-yl |
| 109 | — | CH$_3$ | 4-(methylsulfonyl)prop-1-yl |
| 110 | — | CH$_3$ | benzyl [sic] |
| 111 | — | CH$_3$ | 2-F—C$_6$H$_4$—CH$_2$ |
| 112 | — | CH$_3$ | 3-F—C$_6$H$_4$—CH$_2$ |
| 113 | — | CH$_3$ | 4-F—C$_6$H$_4$—CH$_2$ |
| 114 | — | CH$_3$ | 2,3-F$_2$—C$_6$H$_3$—CH$_2$ |
| 115 | — | CH$_3$ | 2,4-F$_2$—C$_6$H$_3$—CH$_2$ |
| 116 | — | CH$_3$ | 2,5-F$_2$—C$_6$H$_3$—CH$_2$ |
| 117 | — | CH$_3$ | 2,6-F$_2$—C$_6$H$_3$—CH$_2$ |
| 118 | — | CH$_3$ | 3,4-F$_2$—C$_6$H$_3$—CH$_2$ |
| 119 | — | CH$_3$ | 3,5-F$_2$—C$_6$H$_3$—CH$_2$ |
| 120 | — | CH$_3$ | 2-Cl—C$_6$H$_4$—CH$_2$ |
| 121 | — | CH$_3$ | 3-Cl—C$_6$H$_4$—CH$_2$ |
| 122 | — | CH$_3$ | 4-Cl—C$_6$H$_4$—CH$_2$ |
| 123 | — | CH$_3$ | 2,3-Cl$_2$—C$_6$H$_3$—CH$_2$ |
| 124 | — | CH$_3$ | 2,4-Cl$_2$—C$_6$H$_3$—CH$_2$ |
| 125 | — | CH$_3$ | 2,5-Cl$_2$—C$_6$H$_3$—CH$_2$ |
| 126 | — | CH$_3$ | 2,6-Cl$_2$—C$_6$H$_3$—CH$_2$ |
| 127 | — | CH$_3$ | 3,4-Cl$_2$—C$_6$H$_3$—CH$_2$ |
| 128 | — | CH$_3$ | 3,5-Cl$_2$—C$_6$H$_3$—CH$_2$ |
| 129 | — | CH$_3$ | 2,3,4-Cl$_3$—C$_6$H$_2$—CH$_2$ |
| 130 | — | CH$_3$ | 2,3,5-Cl$_3$—C$_6$H$_2$—CH$_2$ |
| 131 | — | CH$_3$ | 2,3,6-Cl$_3$—C$_6$H$_2$—CH$_2$ |
| 132 | — | CH$_3$ | 2,4,5-Cl$_3$—C$_6$H$_2$—CH$_2$ |
| 133 | — | CH$_3$ | 2,4,6-Cl$_3$—C$_6$H$_2$—CH$_2$ |
| 134 | — | CH$_3$ | 3,4,5-Cl$_3$—C$_6$H$_2$—CH$_2$ |
| 135 | — | CH$_3$ | 2-Br—C$_6$H$_4$—CH$_2$ |
| 136 | — | CH$_3$ | 3-Br—C$_6$H$_4$—CH$_2$ |
| 137 | — | CH$_3$ | 4-Br—C$_6$H$_4$—CH$_2$ |
| 138 | — | CH$_3$ | 2,3-Br$_2$—C$_6$H$_3$—CH$_2$ |
| 139 | — | CH$_3$ | 2,4-Br$_2$—C$_6$H$_3$—CH$_2$ |
| 140 | — | CH$_3$ | 2,5-Br$_2$—C$_6$H$_3$—CH$_2$ |
| 141 | — | CH$_3$ | 2,6-Br$_2$—C$_6$H$_3$—CH$_2$ |
| 142 | — | CH$_3$ | 3,4-Br$_2$—C$_6$H$_3$—CH$_2$ |
| 143 | — | CH$_3$ | 3,5-Br$_2$—C$_6$H$_3$—CH$_2$ |
| 144 | — | CH$_3$ | 2-F, 3-Cl—C$_6$H$_3$—CH$_2$ |
| 145 | — | CH$_3$ | 2-F, 4-Cl—C$_6$H$_3$—CH$_2$ |
| 146 | — | CH$_3$ | 2-F, 5-Cl—C$_6$H$_3$—CH$_2$ |
| 147 | — | CH$_3$ | 2-F, 3-Br—C$_6$H$_3$—CH$_2$ |
| 148 | — | CH$_3$ | 2-F, 4-Br—C$_6$H$_3$—CH$_2$ |
| 149 | — | CH$_3$ | 2-F, 5-Br—C$_6$H$_3$—CH$_2$ |
| 150 | — | CH$_3$ | 2-Cl, 3-Br—C$_6$H$_3$—CH$_2$ |
| 151 | — | CH$_3$ | 2-Cl, 4-Br—C$_6$H$_3$—CH$_2$ |
| 152 | — | CH$_3$ | 2-Cl, 5-Br—C$_6$H$_3$—CH$_2$ |
| 153 | — | CH$_3$ | 3-F, 4-Cl—C$_6$H$_3$—CH$_2$ |
| 154 | — | CH$_3$ | 3-F, 5-Cl—C$_6$H$_3$—CH$_2$ |
| 155 | — | CH$_3$ | 3-F, 6-Cl—C$_6$H$_3$—CH$_2$ |
| 156 | — | CH$_3$ | 3-F, 4-Br—C$_6$H$_3$—CH$_2$ |
| 157 | — | CH$_3$ | 3-F, 5-Br—C$_6$H$_3$—CH$_2$ |
| 158 | — | CH$_3$ | 3-F, 6-Br—C$_6$H$_3$—CH$_2$ |
| 159 | — | CH$_3$ | 3-Cl, 4-Br—C$_6$H$_3$—CH$_2$ |
| 160 | — | CH$_3$ | 3-Cl, 5-Br—C$_6$H$_3$—CH$_2$ |
| 161 | — | CH$_3$ | 3-Cl, 6-Br—C$_6$H$_3$—CH$_2$ |
| 162 | — | CH$_3$ | 4-F, 5-Cl—C$_6$H$_3$—CH$_2$ |
| 163 | — | CH$_3$ | 4-F, 6-Cl—C$_6$H$_3$—CH$_2$ |
| 164 | — | CH$_3$ | 4-F, 5-Br—C$_6$H$_3$—CH$_2$ |
| 165 | — | CH$_3$ | 4-F, 6-Br—C$_6$H$_3$—CH$_2$ |
| 166 | — | CH$_3$ | 4-Cl, 5-Br—C$_6$H$_3$—CH$_2$ |
| 167 | — | CH$_3$ | 5-F, 6-Cl—C$_6$H$_3$—CH$_2$ |
| 168 | — | CH$_3$ | 5-F, 6-Br—C$_6$H$_3$—CH$_2$ |
| 169 | — | CH$_3$ | 5-Cl, 6-Br—C$_6$H$_3$—CH$_2$ |
| 170 | — | CH$_3$ | 3-Br, 4-Cl, 5-Br—C$_6$H$_2$—CH$_2$ |
| 171 | — | CH$_3$ | 2-CN—C$_6$H$_4$—CH$_2$ |
| 172 | — | CH$_3$ | 3-CN—C$_6$H$_4$—CH$_2$ |
| 173 | — | CH$_3$ | 4-CN—C$_6$H$_4$—CH$_2$ |
| 174 | — | CH$_3$ | 2-NO$_2$—C$_6$H$_4$—CH$_2$ |
| 175 | — | CH$_3$ | 3-NO$_2$—C$_6$H$_4$—CH$_2$ |
| 176 | — | CH$_3$ | 4-NO$_2$—C$_6$H$_4$—CH$_2$ |
| 177 | — | CH$_3$ | 2-CH$_3$—C$_6$H$_4$—CH$_2$ |
| 178 | — | CH$_3$ | 3-CH$_3$—C$_6$H$_4$—CH$_2$ |
| 179 | — | CH$_3$ | 4-CH$_3$—C$_6$H$_4$—CH$_2$ |
| 180 | — | CH$_3$ | 2,3-(CH$_3$)$_2$—C$_6$H$_3$—CH$_2$ |
| 181 | — | CH$_3$ | 2,4-(CH$_3$)$_2$—C$_6$H$_3$—CH$_2$ |
| 182 | — | CH$_3$ | 2,5-(CH$_3$)$_2$—C$_6$H$_3$—CH$_2$ |
| 183 | — | CH$_3$ | 2,6-(CH$_3$)$_2$—C$_6$H$_3$—CH$_2$ |
| 184 | — | CH$_3$ | 3,4-(CH$_3$)$_2$—C$_6$H$_3$—CH$_2$ |
| 185 | — | CH$_3$ | 3,5-(CH$_3$)$_2$—C$_6$H$_3$—CH$_2$ |
| 186 | — | CH$_3$ | 2-C$_2$H$_5$—C$_6$H$_4$—CH$_2$ |
| 187 | — | CH$_3$ | 3-C$_2$H$_5$—C$_6$H$_4$—CH$_2$ |
| 188 | — | CH$_3$ | 4-C$_2$H$_5$—C$_6$H$_4$—CH$_2$ |
| 189 | — | CH$_3$ | 2-i-C$_3$H$_7$—C$_6$H$_4$—CH$_2$ |
| 190 | — | CH$_3$ | 3-i-C$_3$H$_7$—C$_6$H$_4$—CH$_2$ |
| 191 | — | CH$_3$ | 4-i-C$_3$H$_7$—C$_6$H$_4$—CH$_2$ |
| 192 | — | CH$_3$ | 2-cyclohexyl-C$_6$H$_4$—CH$_2$ |
| 193 | — | CH$_3$ | 3-cyclohexyl-C$_6$H$_4$—CH$_2$ |
| 194 | — | CH$_3$ | 4-cyclohexyl-C$_6$H$_4$—CH$_2$ |
| 195 | — | CH$_3$ | 2-vinyl-C$_6$H$_4$—CH$_2$ |
| 196 | — | CH$_3$ | 3-vinyl-C$_6$H$_4$—CH$_2$ |
| 197 | — | CH$_3$ | 4-vinyl-C$_6$H$_4$—CH$_2$ |
| 198 | — | CH$_3$ | 2-allyl-C$_6$H$_4$—CH$_2$ |

TABLE A-continued

| | | | |
|---|---|---|---|
| 199 | — | CH₃ | 3-allyl-C₆H₄—CH₂ |
| 200 | — | CH₃ | 4-allyl-C₆H₄—CH₂ |
| 201 | — | CH₃ | 2-C₆H₅—C₆H₄—CH₂ |
| 202 | — | CH₃ | 3-C₆H₅—C₆H₄—CH₂ |
| 203 | — | CH₃ | 4-C₆H₅—C₆H₄—CH₂ |
| 204 | — | CH₃ | 3-CH₃, 5-t-C₄H₉—C₆H₃—CH₂ |
| 205 | — | CH₃ | 2-OH—C₆H₄—CH₂ |
| 206 | — | CH₃ | 3-OH—C₆H₄—CH₂ |
| 207 | — | CH₃ | 4-OH—C₆H₄—CH₂ |
| 208 | — | CH₃ | 2-OCH₃—C₆H₄—CH₂ |
| 209 | — | CH₃ | 3-OCH₃—C₆H₄—CH₂ |
| 210 | — | CH₃ | 4-OCH₃—C₆H₄—CH₂ |
| 211 | — | CH₃ | 2-O-allyl-C₆H₄—CH₂ |
| 212 | — | CH₃ | 3-O-allyl-C₆H₄—CH₂ |
| 213 | — | CH₃ | 4-O-allyl-C₆H₄—CH₂ |
| 214 | — | CH₃ | 2-CF₃—C₆H₄—CH₂ |
| 215 | — | CH₃ | 3-CF₃—C₆H₄—CH₂ |
| 216 | — | CH₃ | 4-CF₃—C₆H₄—CH₂ |
| 217 | — | CH₃ | 2-acetyl-C₆H₄—CH₂ |
| 218 | — | CH₃ | 3-acetyl-C₆H₄—CH₂ |
| 219 | — | CH₃ | 4-acetyl-C₆H₄—CH₂ |
| 220 | — | CH₃ | 2-methoxycarbonyl-C₆H₄—CH₂ |
| 221 | — | CH₃ | 3-methoxycarbonyl-C₆H₄—CH₂ |
| 222 | — | CH₃ | 4-methoxycarbonyl-C₆H₄—CH₂ |
| 223 | — | CH₃ | 2-aminocarbonyl-C₆H₄—CH₂ |
| 224 | — | CH₃ | 3-aminocarbonyl-C₆H₄—CH₂ |
| 225 | — | CH₃ | 4-aminocarbonyl-C₆H₄—CH₂ |
| 226 | — | CH₃ | 2-dimethylaminocarbonyl-C₆H₄—CH₂ |
| 227 | — | CH₃ | 3-dimethylaminocarbonyl-C₆H₄—CH₂ |
| 228 | — | CH₃ | 4-dimethylaminocarbonyl-C₆H₄—CH₂ |
| 229 | — | CH₃ | 2-(N-methylaminocarbonyl)-C₆H₄—CH₂ |
| 230 | — | CH₃ | 3-(N-methylaminocarbonyl)-C₆H₄—CH₂ |
| 231 | — | CH₃ | 4-(N-methylaminocarbonyl)-C₆H₄—CH₂ |
| 232 | — | CH₃ | 2-H₂N—C₆H₄—CH₂ |
| 233 | — | CH₃ | 3-H₂N—C₆H₄—CH₂ |
| 234 | — | CH₃ | 4-H₂N—C₆H₄—CH₂ |
| 235 | — | CH₃ | 2-aminothiocarbonyl-C₆H₄—CH₂ |
| 236 | — | CH₃ | 3-aminothiocarbonyl-C₆H₄—CH₂ |
| 237 | — | CH₃ | 4-aminothiocarbonyl-C₆H₄—CH₂ |
| 238 | — | CH₃ | 2-SCH₃—C₆H₄—CH₂ |
| 239 | — | CH₃ | 3-SCH₃—C₆H₄—CH₂ |
| 240 | — | CH₃ | 4-SCH₃—C₆H₄—CH₂ |
| 241 | — | CH₃ | 2-SO₂CH₃—C₆H₄—CH₂ |
| 242 | — | CH₃ | 3-SO₂CH₃—C₆H₄—CH₂ |
| 243 | — | CH₃ | 4-SO₂CH₃—C₆H₄—CH₂ |
| 244 | — | CH₃ | 2-OCF₃—C₆H₄—CH₂ |
| 245 | — | CH₃ | 3-OCF₃—C₆H₄—CH₂ |
| 246 | — | CH₃ | 4-OCF₃—C₆H₄—CH₂ |
| 247 | — | CH₃ | 2-OCHF₂—C₆H₄—CH₂ |
| 248 | — | CH₃ | 3-OCHF₂—C₆H₄—CH₂ |
| 249 | — | CH₃ | 4-OCHF₂—C₆H₄—CH₂ |
| 250 | — | CH₃ | 3-CF₃, 4-OCF₃—C₆H₃—CH₂ |
| 251 | — | CH₃ | 1-naphthyl-CH₂ |
| 252 | — | CH₃ | 2-naphthyl-CH₂ |
| 253 | — | CH₃ | 2-phenoxyeth-1-yl |
| 254 | — | CH₃ | 2-(2'-chlorophenoxy)eth-1-yl |
| 255 | — | CH₃ | 2-(3'-chlorophenoxy)eth-1-yl |
| 256 | — | CH₃ | 2-(4'-chlorophenoxy)eth-1-yl |
| 257 | — | CH₃ | 2-(3',5'-dichlorophenoxy)eth-1-yl |
| 258 | — | CH₃ | 2-(4'-cyanophenoxy)eth-1-yl |
| 259 | — | CH₃ | 2-(3'-methylphenoxy)eth-1-yl |
| 260 | — | CH₃ | 2-(2'-nitrophenoxy)eth-1-yl |
| 261 | — | CH₃ | 3-phenoxyprop-1-yl |
| 262 | — | CH₃ | 3-(4'-chlorophenoxy)prop-1-yl |
| 263 | — | CH₃ | 3-(3'-cyanophenoxy)prop-1-yl |
| 264 | — | CH₃ | 3-(2'-methylphenoxy)prop-1-yl |
| 265 | — | CH₃ | 4-phenoxybut-1-yl |
| 266 | — | CH₃ | 2-phenyleth-1-yl |
| 267 | — | CH₃ | 2-(4'-chlorophenyl)eth-1-yl |
| 268 | — | CH₃ | 2-(3'-cyanophenyl)eth-1-yl |
| 269 | — | CH₃ | 2-(2'-methylphenyl)eth-1-yl |
| 270 | — | CH₃ | 3-phenylprop-1-yl |
| 271 | — | CH₃ | 4-phenylbut-1-yl |
| 272 | — | CH₃ | 2-pyridylmethyl |
| 273 | — | CH₃ | 3-pyridylmethyl |
| 274 | — | CH₃ | 4-pyridylmethyl |
| 275 | — | CH₃ | 4-chloropyridin-2-ylmethyl |
| 276 | — | CH₃ | 5-chloropyridin-2-ylmethyl |
| 277 | — | CH₃ | 6-chloropyridin-2-ylmethyl |
| 278 | — | CH₃ | 5-chloropyridin-3-ylmethyl |
| 279 | — | CH₃ | 6-chloropyridin-3-ylmethyl |
| 280 | — | CH₃ | 2-chloropyridin-4-ylmethyl |
| 281 | — | CH₃ | 2-pyrimidinylmethyl |
| 282 | — | CH₃ | 4-chloropyrimidin-2-ylmethyl |
| 283 | — | CH₃ | 5-chloropyrimidin-2-ylmethyl |
| 284 | — | CH₃ | 2-chloropyrimidin-4-ylmethyl |
| 285 | — | CH₃ | 6-chloropyrimidin-4-ylmethyl |
| 286 | — | CH₃ | 2-chloropyrimidin-5-ylmethyl |
| 287 | — | CH₃ | 4-pyridazinylmethyl |
| 288 | — | CH₃ | 2-pyrazinylmethyl |
| 289 | — | CH₃ | 5-chloropyrazin-2-ylmethyl |
| 290 | — | CH₃ | 6-chloropyrazin-2-ylmethyl |
| 291 | — | CH₃ | 3-pyridazinylmethyl |
| 292 | — | CH₃ | 6-chloropyridazin-3-ylmethyl |
| 293 | — | CH₃ | 1,3,5-triazinylmethyl |
| 294 | — | CH₃ | 2-furylmethyl |
| 295 | — | CH₃ | 3-furylmethyl |
| 296 | — | CH₃ | 4-bromofur-2-ylmethyl |
| 297 | — | CH₃ | 5-chlorofur-2-ylmethyl |
| 298 | — | CH₃ | 2-thienylmethyl |
| 299 | — | CH₃ | 3-thienylmethyl |
| 300 | — | CH₃ | 5-methylthien-3-ylmethyl |
| 301 | — | CH₃ | 5-chlorothien-2-ylmethyl |
| 302 | — | CH₃ | 2-chlorothien-4-ylmethyl |
| 303 | — | CH₃ | 2-pyrrolylmethyl |
| 304 | — | CH₃ | 3-pyrrolylmethyl |
| 305 | — | CH₃ | 2-oxazolylmethyl |
| 306 | — | CH₃ | 4-methyloxazol-2-ylmethyl |
| 307 | — | CH₃ | 5-methyloxazol-2-ylmethyl |
| 308 | — | CH₃ | 4-chlorooxazol-2-ylmethyl |
| 309 | — | CH₃ | 5-chlorooxazol-2-ylmethyl |
| 310 | — | CH₃ | 4-oxazolylmethyl |
| 311 | — | CH₃ | 2-methyloxazol-4-ylmethyl |
| 312 | — | CH₃ | 5-methyloxazol-4-ylmethyl |
| 313 | — | CH₃ | 2-chlorooxazol-4-ylmethyl |
| 314 | — | CH₃ | 5-chlorooxazol-4-ylmethyl |
| 315 | — | CH₃ | 5-oxazolylmethyl |
| 316 | — | CH₃ | 2-methyloxazol-5-ylmethyl |
| 317 | — | CH₃ | 4-methyloxazol-5-ylmethyl |
| 318 | — | CH₃ | 2-chlorooxazol-5-ylmethyl |
| 319 | — | CH₃ | 4-chlorooxazol-5-ylmethyl |
| 320 | — | CH₃ | 2-thiazolylmethyl |
| 321 | — | CH₃ | 4-methylthiazol-2-ylmethyl |
| 322 | — | CH₃ | 5-methylthiazol-2-ylmethyl |
| 323 | — | CH₃ | 4-chlorothiazol-2-ylmethyl |
| 324 | — | CH₃ | 5-chlorothiazol-2-ylmethyl |
| 325 | — | CH₃ | 4-thiazolylmethyl |
| 326 | — | CH₃ | 2-methylthiazol-4-ylmethyl |
| 327 | — | CH₃ | 5-methylthiazol-4-ylmethyl |
| 328 | — | CH₃ | 2-chlorothiazol-4-ylmethyl |
| 329 | — | CH₃ | 5-chlorothiazol-4-ylmethyl |
| 330 | — | CH₃ | 5-thiazolylmethyl |
| 331 | — | CH₃ | 2-methylthiazol-5-ylmethyl |
| 332 | — | CH₃ | 4-methylthiazol-5-ylmethyl |
| 333 | — | CH₃ | 2-chlorothiazol-5-ylmethyl |
| 334 | — | CH₃ | 4-chlorothiazol-5-ylmethyl |
| 335 | — | CH₃ | 3-isoxazolylmethyl |
| 336 | — | CH₃ | 4-methylisoxazol-3-ylmethyl |
| 337 | — | CH₃ | 5-methylisoxazol-3-ylmethyl |
| 338 | — | CH₃ | 4-chloroisoxazol-3-ylmethyl |
| 339 | — | CH₃ | 5-chloroisoxazol-3-ylmethyl |
| 340 | — | CH₃ | 4-isoxazolylmethyl |
| 341 | — | CH₃ | 3-methylisoxazol-4-ylmethyl |
| 342 | — | CH₃ | 5-methylisoxazol-4-ylmethyl |
| 343 | — | CH₃ | 3-chloroisoxazol-4-ylmethyl |
| 344 | — | CH₃ | 5-chloroisoxazol-4-ylmethyl |
| 345 | — | CH₃ | 5-isoxazolylmethyl |
| 346 | — | CH₃ | 3-methylisoxazol-5-ylmethyl |
| 347 | — | CH₃ | 4-methylisoxazol-5-ylmethyl |
| 348 | — | CH₃ | 3-chloroisoxazol-5-ylmethyl |
| 349 | — | CH₃ | 4-chloroisoxazol-5-ylmethyl |
| 350 | — | CH₃ | 3-isothiazolylmethyl |
| 351 | — | CH₃ | 4-methylisothiazol-3-ylmethyl |
| 352 | — | CH₃ | 5-methylisothiazol-3-ylmethyl |
| 353 | — | CH₃ | 4-chloroisothiazol-3-ylmethyl |
| 354 | — | CH₃ | 5-chloroisothiazol-3-ylmethyl |
| 355 | — | CH₃ | 4-isothiazolylmethyl |
| 356 | — | CH₃ | 3-methylisothiazol-4-ylmethyl |

TABLE A-continued

| | | | |
|---|---|---|---|
| 357 | — | CH₃ | 5-methylisothiazol-4-ylmethyl |
| 358 | — | CH₃ | 3-chloroisothiazol-4-ylmethyl |
| 359 | — | CH₃ | 5-chloroisothiazol-4-ylmethyl |
| 360 | — | CH₃ | 5-isothiazolylmethyl |
| 361 | — | CH₃ | 3-methylisothiazol-5-ylmethyl |
| 362 | — | CH₃ | 4-methylisothiazol-5-ylmethyl |
| 363 | — | CH₃ | 3-chloroisothiazol-5-ylmethyl |
| 364 | — | CH₃ | 4-chloroisothiazol-5-ylmethyl |
| 365 | — | CH₃ | 4-imidazolylmethyl |
| 366 | — | CH₃ | 1-phenylpyrazol-3-ylmethyl |
| 367 | — | CH₃ | 1-methylimidazol-4-ylmethyl |
| 368 | — | CH₃ | 1-phenyl-1,2,4-triazol-3-ylmethyl |
| 369 | — | CH₃ | 1,2,4-oxadiazol-3-ylmethyl |
| 370 | — | CH₃ | 5-chloro-1,2,4-oxadiazol-3-ylmethyl |
| 371 | — | CH₃ | 5-methyl-1,2,4-oxadiazol-3-ylmethyl |
| 372 | — | CH₃ | 5-trifluoromethyl-1,2,4-oxadiazol-3-ylmethyl |
| 373 | — | CH₃ | 1,3,4-oxadiazol-2-ylmethyl |
| 374 | — | CH₃ | 5-chloro-1,3,4-oxadiazol-2-ylmethyl |
| 375 | — | CH₃ | 5-methyl-1,3,4-oxadiazol-2-ylmethyl |
| 376 | — | CH₃ | 5-methoxy-1,3,4-oxadiazol-2-ylmethyl |
| 377 | — | CH₃ | 1,2,4-thiadiazol-3-ylmethyl |
| 378 | — | CH₃ | 5-chloro-1,2,4-thiadiazol-3-ylmethyl |
| 379 | — | CH₃ | 5-methyl-1,2,4-thiadiazol-3-ylmethyl |
| 380 | — | CH₃ | 1,3,4-thiadiazol-2-ylmethyl |
| 381 | — | CH₃ | 5-chloro-1,3,4-thiadiazol-2-ylmethyl |
| 382 | — | CH₃ | 5-methyl-1,3,4-thiadiazol-2-ylmethyl |
| 383 | — | CH₃ | 5-cyano-1,3,4-thiadiazol-2-ylmethyl |
| 384 | — | CH₃ | 2-(2'-pyridinyloxy)eth-1-yl |
| 385 | — | CH₃ | 2-(3'-pyridinyloxy)eth-1-yl |
| 386 | — | CH₃ | 2-(4'-pyridinyloxy)eth-1-yl |
| 387 | — | CH₃ | C₆H₅ |
| 388 | — | CH₃ | 2-Cl—C₆H₄ |
| 389 | — | CH₃ | 3-Cl—C₆H₄ |
| 390 | — | CH₃ | 4-Cl—C₆H₄ |
| 391 | — | CH₃ | 2,3-Cl₂—C₆H₃ |
| 392 | — | CH₃ | 2,4-Cl₂—C₆H₃ |
| 393 | — | CH₃ | 2,5-Cl₂—C₆H₃ |
| 394 | — | CH₃ | 3,4-Cl₂—C₆H₃ |
| 395 | — | CH₃ | 3,5-Cl₂—C₆H₃ |
| 396 | — | CH₃ | 4-CN—C₆H₄ |
| 397 | — | CH₃ | 2-NO₂—C₆H₄ |
| 398 | — | CH₃ | 3-NO₂—C₆H₄ |
| 399 | — | CH₃ | 4-NO₂—C₆H₄ |
| 400 | — | CH₃ | 2,4-(NO₂)₂—C₆H₃ |
| 401 | — | CH₃ | 2-CH₃—C₆H₄ |
| 402 | — | CH₃ | 3-CH₃—C₆H₄ |
| 403 | — | CH₃ | 4-CH₃—C₆H₄ |
| 404 | — | CH₃ | 2,3-(CH₃)₂—C₆H₃ |
| 405 | — | CH₃ | 2,4-(CH₃)₂—C₆H₃ |
| 406 | — | CH₃ | 2,5-(CH₃)₂—C₆H₃ |
| 407 | — | CH₃ | 2,6-(CH₃)₂—C₆H₃ |
| 408 | — | CH₃ | 2-C₆H₅—C₆H₄ |
| 409 | — | CH₃ | 3-C₆H₅—C₆H₄ |
| 410 | — | CH₃ | 4-C₆H₅—C₆H₄ |
| 411 | — | CH₃ | 3-OCH₃—C₆H₄ |
| 412 | — | CH₃ | 4-OCH₃—C₆H₄ |
| 413 | — | CH₃ | 3-acetyl-C₆H₄ |
| 414 | — | CH₃ | 4-acetyl-C₆H₄ |
| 415 | — | CH₃ | 3-methoxycarbonyl-C₆H₄ |
| 416 | — | CH₃ | 4-methoxycarbonyl-C₆H₄ |
| 417 | — | CH₃ | 3-CF₃—C₆H₄ |
| 418 | — | CH₃ | 4-CF₃—C₆H₄ |
| 419 | — | CH₃ | 2-naphthyl |
| 420 | — | CH₃ | 6-chloropyridazin-3-yl |
| 421 | — | CH₃ | 5-chloropyrazin-2-yl |
| 422 | — | CH₃ | quinolin-2-yl |
| 423 | — | CH₃ | 2,5-dimethylpyrazin-3-yl |
| 424 | — | CH₃ | pyrazin-2-yl |
| 425 | — | CH₃ | 3-chloropyrid-2-yl |
| 426 | — | CH₃ | 6-chloropyrid-2-yl |
| 427 | — | CH₃ | 4-trifluoromethyl, 6-chloropyrid-2-yl |
| 428 | — | CH₃ | 4-trifluoromethylpyrid-2-yl |
| 429 | — | CH₃ | 6-trifluoromethylpyrid-2-yl |
| 430 | — | CH₃ | 6-methoxypyrid-2-yl |
| 431 | — | CH₃ | 5-chloropyrid-2-yl |
| 432 | — | CH₃ | pyrid-2-yl |
| 433 | — | CH₃ | benzothiazol-2-yl |
| 434 | — | CH₃ | 7-chloroquinolin-4-yl |
| 435 | — | CH₃ | 3-nitropyrid-2-yl |
| 436 | — | CH₃ | pyrrol-3-yl |
| 437 | — | CH₃ | pyrrol-2-yl |
| 438 | — | CH₃ | 2,6-dioctylpyrid-4-yl |
| 439 | — | CH₃ | 5-nitropyrid-2-yl |
| 440 | — | CH₃ | pyrid-4-yl |
| 441 | — | CH₃ | pyrid-3-yl |
| 442 | — | CH₃ | pyrimidin-2-yl |
| 443 | — | CH₃ | pyrimidin-4-yl |
| 444 | — | CH₃ | quinazolin-4-yl |
| 445 | — | CH₃ | 6-chloropyrimidin-4-yl |
| 446 | — | CH₃ | 6-methoxypyrimidin-4-yl |
| 447 | — | CH₃ | 2,5,6-trichloropyrimidin-4-yl |
| 448 | — | CH₃ | 2,6-dimethylpyrimidin-4-yl |
| 449 | — | CH₃ | 2-methyl, 6-chloropyrimidin-4-yl |
| 450 | — | CH₃ | 2-methyl, 6-ethoxypyrimidin-4-yl |
| 451 | — | CH₃ | 4,5,6-trichloropyrimidin-2-yl |
| 452 | — | CH₃ | 4,6-dimethoxypyrimidin-2-yl |
| 453 | — | CH₃ | 4,6-dimethylpyrimidin-2-yl |
| 454 | — | CH₃ | 4,6-dichloropyrimidin-2-yl |
| 455 | — | CH₃ | 4-methyl, 6-methoxypyrimidin-2-yl |
| 456 | — | CH₃ | 4-chloro, 6-methoxypyrimidin-2-yl |
| 457 | — | CH₃ | 6-chloroquinoxalin-2-yl |
| 458 | — | CH₃ | 3,6-dichloro-1,2,4-triazin-5-yl |
| 459 | — | CH₃ | 4-methoxy-1,3,5-triazin-2-yl |
| 460 | — | CH₃ | 4-ethoxy-1,3,5-triazin-2-yl |
| 461 | — | CH₃ | 4,6-dichloro-1,3,5-triazin-2-yl |
| 462 | — | CH₃ | 4-ethoxy, 6-chloro-1,3,5-triazin-2-yl |
| 463 | — | CH₃ | isoxazol-3-yl |
| 464 | — | CH₃ | thien-2-yl |
| 465 | — | CH₃ | fur-2-yl |
| 466 | — | CH₃ | thiatriazol-5-yl |
| 467 | — | CH₃ | (E)-1-chloropropen-3-yl |
| 468 | — | CH₃ | (E)-4-(4'-chlorophenyl)but-2-en-1-yl |
| 469 | — | CH₃ | propyn-3-yl |
| 470 | — | CH₃ | methylcarbonyl |
| 471 | — | CH₃ | 2-t-C₄H₉—C₆H₄—CH₂ |
| 472 | — | CH₃ | 3-t-C₄H₉—C₆H₄—CH₂ |
| 473 | — | CH₃ | 4-t-C₄H₉—C₆H₄—CH₂ |
| 474 | — | CH₃ | 2-(4'-chlorothiazol-2'-yloxy)eth-1-yl |
| 475 | — | CH₃ | 2-(1'-methylpyrazol-4'-yloxy)eth-1-yl |
| 476 | — | CH₃ | 4-Br—C₆H₄ |
| 477 | — | CH₃ | 3,5-(CH₃)₂—C₆H₃ |
| 478 | — | CH₃ | 4-C₂H₅—C₆H₄ |
| 479 | — | CH₃ | 3-dimethylaminocarbonyl-C₆H₄ |
| 480 | — | CH₃ | 4-dimethylaminocarbonyl-C₆H₄ |
| 481 | — | CH₃ | 2-hydroxyprop-1-yl |
| 482 | — | CH₃ | 6-hydroxy-2-methylpyrimidin-4-ylmethyl |
| 483 | — | CH₃ | [6-OH,2-CH(CH₃)₂-pyrimidin-4-yl]-CH₂ |
| 484 | — | CH₃ | [6-OH,2-CH(CH₂)₂-pyrimidin-4-yl]-CH₂ |
| 1 | — | CH₃ | 5-(2'-furan)pent-1-yl |
| 2 | — | CH₃ | 5-(2'-N-methylpyrrole)pent-1-yl |
| 3 | — | CH₃ | [2-(4-Cl—C₆H₄)-oxazol-4-yl]-CH₂ |
| 4 | — | CH₃ | 3-CF₃-pyridin-2-yl |
| 5 | — | CH₃ | 5-CF₃-pyridin-2-yl |
| 6 | — | CH₃ | 6-(2'-thienyl)hex-1-yl |
| 7 | — | H | H |
| 8 | — | H | CH₃ |
| 9 | — | H | C₂H₅ |
| 10 | — | H | n-C₃H₇ |
| 11 | — | H | i-C₃H₇ |
| 12 | — | H | cyclopropyl |
| 13 | — | H | n-C₄H₉ |
| 14 | — | H | s-C₄H₉ |
| 15 | — | H | i-C₄H₉ |
| 16 | — | H | t-C₄H₉ |
| 17 | — | H | n-C₅H₁₁ |
| 18 | — | H | i-C₅H₁₁ |
| 19 | — | H | neo-C₅H₁₁ |
| 20 | — | H | cyclopentyl |
| 21 | — | H | n-C₆H₁₃ |
| 22 | — | H | cyclohexyl |
| 23 | — | H | CH₂CH₂Cl |
| 24 | — | H | (CH₂)₄Cl |
| 25 | — | H | CH₂CN |
| 26 | — | H | CH₂CH₂CN |
| 27 | — | H | (CH₂)₃CN |
| 28 | — | H | (CH₂)₄CN |
| 29 | — | H | (CH₂)₆CN |
| 30 | — | H | cyclohexylmethyl |

TABLE A-continued

| | | | |
|---|---|---|---|
| 31 | — | H | 2-cyclohexyleth-1-yl |
| 32 | — | H | cyclopropylmethyl |
| 33 | — | H | 2-cyclopropyleth-1-yl |
| 34 | — | H | 2-methoxyeth-1-yl |
| 35 | — | H | 2-ethoxyeth-1-yl |
| 36 | — | H | 2-isopropoxyeth-1-yl |
| 37 | — | H | 3-methoxyprop-1-yl |
| 38 | — | H | 3-ethoxyprop-1-yl |
| 39 | — | H | 3-isopropoxyprop-1-yl |
| 40 | — | H | 4-methoxybut-1-yl |
| 41 | — | H | 4-isopropoxybut-1-yl |
| 42 | — | H | propen-3-yl |
| 43 | — | H | but-2-en-1-yl |
| 44 | — | H | 3-methylbut-2-en-1-yl |
| 45 | — | H | 2-vinyloxyeth-1-yl |
| 46 | — | H | allyloxyeth-1-yl |
| 47 | — | H | 2-trifluoromethoxyeth-1-yl |
| 48 | — | H | 3-trifluoromethoxyprop-1-yl |
| 49 | — | H | 4-difluoromethoxybut-1-yl |
| 50 | — | H | hydroxycarbonylmethyl |
| 51 | — | H | methoxycarbonylmethyl |
| 52 | — | H | aminocarbonylmethyl |
| 53 | — | H | N-methylaminocarbonylmethyl |
| 54 | — | H | N,N-dimethylaminocarbonyl-methyl |
| 55 | — | H | 2-hydroxycarbonyleth-1-yl |
| 56 | — | H | 2-methoxycarbonyleth-1-yl |
| 57 | — | H | 2-aminocarbonyleth-1-yl |
| 58 | — | H | 2-N-methylaminocarbonyleth-1-yl |
| 59 | — | H | 2-dimethylaminocarbonyleth-1-yl |
| 60 | — | H | 2-aminoeth-1-yl |
| 61 | — | H | 2-aminoprop-1-yl |
| 62 | — | H | 4-aminobut-1-yl |
| 63 | — | H | 3-dimethylaminoprop-1-yl |
| 64 | — | H | 4-aminothiocarbonylbut-1-yl |
| 65 | — | H | 6-aminocarbonylhex-1-yl |
| 66 | — | H | 3-aminothiocarbonylprop-1-yl |
| 67 | — | H | 2-aminothiocarbonyleth-1-yl |
| 68 | — | H | aminothiocarbonylmethyl |
| 69 | — | H | 4-(N,N-dimethylamino)but-1-yl |
| 70 | — | H | 2-(methylthio)eth-1-yl |
| 71 | — | H | 2-(methylsulfonyl)eth-1-yl |
| 72 | — | H | 4-(methylthio)prop-1-yl |
| 73 | — | H | 4-(methylsulfonyl)prop-1-yl |
| 74 | — | H | benzyl |
| 75 | — | H | 2-F—$C_6H_4$—$CH_2$ |
| 76 | — | H | 3-F—$C_6H_4$—$CH_2$ |
| 77 | — | H | 4-F—$C_6H_4$—$CH_2$ |
| 78 | — | H | 2,3-$F_2$—$C_6H_3$—$CH_2$ |
| 79 | — | H | 2,4-$F_2$—$C_6H_3$—$CH_2$ |
| 80 | — | H | 2,5-$F_2$—$C_6H_3$—$CH_2$ |
| 81 | — | H | 2,6-$F_2$—$C_6H_3$—$CH_2$ |
| 82 | — | H | 3,4-$F_2$—$C_6H_3$—$CH_2$ |
| 83 | — | H | 3,5-$F_2$—$C_6H_3$—$CH_2$ |
| 84 | — | H | 2-Cl—$C_6H_4$—$CH_2$ |
| 85 | — | H | 3-Cl—$C_6H_4$—$CH_2$ |
| 86 | — | H | 4-Cl—$C_6H_4$—$CH_2$ |
| 87 | — | H | 2,3-$Cl_2$—$C_6H_3$—$CH_2$ |
| 88 | — | H | 2,4-$Cl_2$—$C_6H_3$—$CH_2$ |
| 89 | — | H | 2,5-$Cl_2$—$C_6H_3$—$CH_2$ |
| 90 | — | H | 2,6-$Cl_2$—$C_6H_3$—$CH_2$ |
| 91 | — | H | 3,4-$Cl_2$—$C_6H_3$—$CH_2$ |
| 92 | — | H | 3,5-$Cl_2$—$C_6H_3$—$CH_2$ |
| 93 | — | H | 2,3,4-$Cl_3$—$C_6H_2$—$CH_2$ |
| 94 | — | H | 2,3,5-$Cl_3$—$C_6H_2$—$CH_2$ |
| 95 | — | H | 2,3,6-$Cl_3$—$C_6H_2$—$CH_2$ |
| 96 | — | H | 2,4,5-$Cl_3$—$C_6H_2$—$CH_2$ |
| 97 | — | H | 2,4,6-$Cl_3$—$C_6H_2$—$CH_2$ |
| 98 | — | H | 3,4,5-$Cl_3$—$C_6H_2$—$CH_2$ |
| 99 | — | H | 2-Br—$C_6H_4$—$CH_2$ |
| 100 | — | H | 3-Br—$C_6H_4$—$CH_2$ |
| 101 | — | H | 4-Br—$C_6H_4$—$CH_2$ |
| 102 | — | H | 2,3-$Br_2$—$C_6H_3$—$CH_2$ |
| 103 | — | H | 2,4-$Br_2$—$C_6H_3$—$CH_2$ |
| 104 | — | H | 2,5-$Br_2$—$C_6H_3$—$CH_2$ |
| 105 | — | H | 2,6-$Br_2$—$C_6H_3$—$CH_2$ |
| 106 | — | H | 3,4-$Br_2$—$C_6H_3$—$CH_2$ |
| 107 | — | H | 3,5-$Br_2$—$C_6H_3$—$CH_2$ |
| 108 | — | H | 2-F, 3-Cl—$C_6H_3$—$CH_2$ |
| 109 | — | H | 2-F, 4-Cl—$C_6H_3$—$CH_2$ |
| 110 | — | H | 2-F, 5-Cl—$C_6H_3$—$CH_2$ |
| 111 | — | H | 2-F, 3-Br—$C_6H_3$—$CH_2$ |
| 112 | — | H | 2-F, 4-Br—$C_6H_3$—$CH_2$ |
| 113 | — | H | 2-F, 5-Br—$C_6H_3$—$CH_2$ |
| 114 | — | H | 2-Cl, 3-Br—$C_6H_3$—$CH_2$ |
| 115 | — | H | 2-Cl, 4-Br—$C_6H_3$—$CH_2$ |
| 116 | — | H | 2-Cl, 5-Br—$C_6H_3$—$CH_2$ |
| 117 | — | H | 3-F, 4-Cl—$C_6H_3$—$CH_2$ |
| 118 | — | H | 3-F, 5-Cl—$C_6H_3$—$CH_2$ |
| 119 | — | H | 3-F, 6-Cl—$C_6H_3$—$CH_2$ |
| 120 | — | H | 3-F, 4-Br—$C_6H_3$—$CH_2$ |
| 121 | — | H | 3-F, 5-Br—$C_6H_3$—$CH_2$ |
| 122 | — | H | 3-F, 6-Br—$C_6H_3$—$CH_2$ |
| 123 | — | H | 3-Cl, 4-Br—$C_6H_3$—$CH_2$ |
| 124 | — | H | 3-Cl, 5-Br—$C_6H_3$—$CH_2$ |
| 125 | — | H | 3-Cl, 6-Br—$C_6H_3$—$CH_2$ |
| 126 | — | H | 4-F, 5-Cl—$C_6H_3$—$CH_2$ |
| 127 | — | H | 4-F, 6-Cl—$C_6H_3$—$CH_2$ |
| 128 | — | H | 4-F, 5-Br—$C_6H_3$—$CH_2$ |
| 129 | — | H | 4-F, 6-Br—$C_6H_3$—$CH_2$ |
| 130 | — | H | 4-Cl, 5-Br—$C_6H_3$—$CH_2$ |
| 131 | — | H | 5-F, 6-Cl—$C_6H_3$—$CH_2$ |
| 132 | — | H | 5-F, 6-Br—$C_6H_3$—$CH_2$ |
| 133 | — | H | 5-Cl, 6-Br—$C_6H_3$—$CH_2$ |
| 134 | — | H | 3-Br, 4-Cl, 5-Br—$C_6H_2$—$CH_2$ |
| 135 | — | H | 2-CN—$C_6H_4$—$CH_2$ |
| 136 | — | H | 3-CN—$C_6H_4$—$CH_2$ |
| 137 | — | H | 4-CN—$C_6H_4$—$CH_2$ |
| 138 | — | H | 2-$NO_2$—$C_6H_4$—$CH_2$ |
| 139 | — | H | 3-$NO_2$—$C_6H_4$—$CH_2$ |
| 140 | — | H | 4-$NO_2$—$C_6H_4$—$CH_2$ |
| 141 | — | H | 2-$CH_3$—$C_6H_4$—$CH_2$ |
| 142 | — | H | 3-$CH_3$—$C_6H_4$—$CH_2$ |
| 143 | — | H | 4-$CH_3$—$C_6H_4$—$CH_2$ |
| 144 | — | H | 2,3-$(CH_3)_2$—$C_6H_3$—$CH_2$ |
| 145 | — | H | 2,4-$(CH_3)_2$—$C_6H_3$—$CH_2$ |
| 146 | — | H | 2,5-$(CH_3)_2$—$C_6H_3$—$CH_2$ |
| 147 | — | H | 2,6-$(CH_3)_2$—$C_6H_3$—$CH_2$ |
| 148 | — | H | 3,4-$(CH_3)_2$—$C_6H_3$—$CH_2$ |
| 149 | — | H | 3,5-$(CH_3)_2$—$C_6H_3$—$CH_2$ |
| 150 | — | H | 2-$C_2H_5$—$C_6H_4$—$CH_2$ |
| 151 | — | H | 3-$C_2H_5$—$C_6H_4$—$CH_2$ |
| 152 | — | H | 4-$C_2H_5$—$C_6H_4$—$CH_2$ |
| 153 | — | H | 2-i-$C_3H_7$—$C_6H_4$—$CH_2$ |
| 154 | — | H | 3-i-$C_3H_7$—$C_6H_4$—$CH_2$ |
| 155 | — | H | 4-i-$C_3H_7$—$C_6H_4$—$CH_2$ |
| 156 | — | H | 2-cyclohexyl-$C_6H_4$—$CH_2$ |
| 157 | — | H | 3-cyclohexyl-$C_6H_4$—$CH_2$ |
| 158 | — | H | 4-cyclohexyl-$C_6H_4$—$CH_2$ |
| 159 | — | H | 2-vinyl-$C_6H_4$—$CH_2$ |
| 160 | — | H | 3-vinyl-$C_6H_4$—$CH_2$ |
| 161 | — | H | 4-vinyl-$C_6H_4$—$CH_2$ |
| 162 | — | H | 2-allyl-$C_6H_4$—$CH_2$ |
| 163 | — | H | 3-allyl-$C_6H_4$—$CH_2$ |
| 164 | — | H | 4-allyl-$C_6H_4$—$CH_2$ |
| 165 | — | H | 2-$C_6H_5$—$C_6H_4$—$CH_2$ |
| 166 | — | H | 3-$C_6H_5$—$C_6H_4$—$CH_2$ |
| 167 | — | H | 4-$C_6H_5$—$C_6H_4$—$CH_2$ |
| 168 | — | H | 3-$CH_3$, 5-t-$C_4H_9$—$C_6H_3$—$CH_2$ |
| 169 | — | H | 2-OH—$C_6H_4$—$CH_2$ |
| 170 | — | H | 3-OH—$C_6H_4$—$CH_2$ |
| 171 | — | H | 4-OH—$C_6H_4$—$CH_2$ |
| 172 | — | H | 2-$OCH_3$—$C_6H_4$—$CH_2$ |
| 173 | — | H | 3-$OCH_3$—$C_6H_4$—$CH_2$ |
| 174 | — | H | 4-$OCH_3$—$C_6H_4$—$CH_2$ |
| 175 | — | H | 2-O-allyl-$C_6H_4$—$CH_2$ |
| 176 | — | H | 3-O-allyl-$C_6H_4$—$CH_2$ |
| 177 | — | H | 4-O-allyl-$C_6H_4$—$CH_2$ |
| 178 | — | H | 2-$CF_3$—$C_6H_4$—$CH_2$ |
| 179 | — | H | 3-$CF_3$—$C_6H_4$—$CH_2$ |
| 180 | — | H | 4-$CF_3$—$C_6H_4$—$CH_2$ |
| 181 | — | H | 2-acetyl-$C_6H_4$—$CH_2$ |
| 182 | — | H | 3-acetyl-$C_6H_4$—$CH_2$ |
| 183 | — | H | 4-acetyl-$C_6H_4$—$CH_2$ |
| 184 | — | H | 2-methoxycarbonyl-$C_6H_4$—$CH_2$ |
| 185 | — | H | 3-methoxycarbonyl-$C_6H_4$—$CH_2$ |
| 186 | — | H | 4-methoxycarbonyl-$C_6H_4$—$CH_2$ |
| 187 | — | H | 2-aminocarbonyl-$C_6H_4$—$CH_2$ |
| 188 | — | H | 3-aminocarbonyl-$C_6H_4$—$CH_2$ |

TABLE A-continued

| | | | |
|---|---|---|---|
| 189 | — | H | 4-aminocarbonyl-C₆H₄—CH₂ |
| 190 | — | H | 2-dimethylaminocarbonyl-C₆H₄—CH₂ |
| 191 | — | H | 3-dimethylaminocarbonyl-C₆H₄—CH₂ |
| 192 | — | H | 4-dimethylaminocarbonyl-C₆H₄—CH₂ |
| 193 | — | H | 2-(N-methylaminocarbonyl)-C₆H₄—CH₂ |
| 194 | — | H | 3-(N-methylaminocarbonyl)-C₆H₄—CH₂ |
| 195 | — | H | 4-(N-methylaminocarbonyl)-C₆H₄—CH₂ |
| 196 | — | H | 2-H₂N—C₆H₄—CH₂ |
| 197 | — | H | 3-H₂N—C₆H₄—CH₂ |
| 198 | — | H | 4-H₂N—C₆H₄—CH₂ |
| 199 | — | H | 2-aminothiocarbonyl-C₆H₄—CH₂ |
| 200 | — | H | 3-aminothiocarbonyl-C₆H₄—CH₂ |
| 201 | — | H | 4-aminothiocarbonyl-C₆H₄—CH₂ |
| 202 | — | H | 2-SCH₃—C₆H₄—CH₂ |
| 203 | — | H | 3-SCH₃—C₆H₄—CH₂ |
| 204 | — | H | 4-SCH₃—C₆H₄—CH₂ |
| 205 | — | H | 2-SO₂CH₃—C₆H₄—CH₂ |
| 206 | — | H | 3-SO₂CH₃—C₆H₄—CH₂ |
| 207 | — | H | 4-SO₂CH₃—C₆H₄—CH₂ |
| 208 | — | H | 2-OCF₃—C₆H₄—CH₂ |
| 209 | — | H | 3-OCF₃—C₆H₄—CH₂ |
| 210 | — | H | 4-OCF₃—C₆H₄—CH₂ |
| 211 | — | H | 2-OCHF₂—C₆H₄—CH₂ |
| 212 | — | H | 3-OCHF₂—C₆H₄—CH₂ |
| 213 | — | H | 4-OCHF₂—C₆H₄—CH₂ |
| 214 | — | H | 3-CF₃, 4-OCF₃—C₆H₃—CH₂ |
| 215 | — | H | 1-naphthyl-CH₂ |
| 216 | — | H | 2-naphthyl-CH₂ |
| 217 | — | H | 2-phenoxyeth-1-yl |
| 218 | — | H | 2-(2'-chlorophenoxy)eth-1-yl |
| 219 | — | H | 2-(3'-chlorophenoxy)eth-1-yl |
| 220 | — | H | 2-(4'-chlorophenoxy)eth-1-yl |
| 221 | — | H | 2-(3',5'-dichlorophenoxy)eth-1-yl |
| 222 | — | H | 2-(4'-cyanophenoxy)eth-1-yl |
| 223 | — | H | 2-(3'-methylphenoxy)eth-1-yl |
| 224 | — | H | 2-(2'-nitrophenoxy)eth-1-yl |
| 225 | — | H | 3-phenoxyprop-1-yl |
| 226 | — | H | 3-(4'-chlorophenoxy)prop-1-yl |
| 227 | — | H | 3-(3'-cyanophenoxy)prop-1-yl |
| 228 | — | H | 3-(2'-methylphenoxy)prop-1-yl |
| 229 | — | H | 4-phenoxybut-1-yl |
| 230 | — | H | 2-phenyleth-1-yl |
| 231 | — | H | 2-(4'-chlorophenyl)eth-1-yl |
| 232 | — | H | 2-(3'-cyanophenyl)eth-1-yl |
| 233 | — | H | 2-(2'-methylphenyl)eth-1-yl |
| 234 | — | H | 3-phenylprop-1-yl |
| 235 | — | H | 4-phenylbut-1-yl |
| 236 | — | H | 2-pyridylmethyl |
| 237 | — | H | 3-pyridylmethyl |
| 238 | — | H | 4-pyridylmethyl |
| 239 | — | H | 4-chloropyridin-2-ylmethyl |
| 240 | — | H | 5-chloropyridin-2-ylmethyl |
| 241 | — | H | 6-chloropyridin-2-ylmethyl |
| 242 | — | H | 5-chloropyridin-3-ylmethyl |
| 243 | — | H | 6-chloropyridin-3-ylmethyl |
| 244 | — | H | 2-chloropyridin-4-ylmethyl |
| 245 | — | H | 2-pyrimidinylmethyl |
| 246 | — | H | 4-chloropyrimidin-2-ylmethyl |
| 247 | — | H | 5-chloropyrimidin-2-ylmethyl |
| 248 | — | H | 2-chloropyrimidin-4-ylmethyl |
| 249 | — | H | 6-chloropyrimidin-4-ylmethyl |
| 250 | — | H | 2-chloropyrimidin-5-ylmethyl |
| 251 | — | H | 4-pyridazinylmethyl |
| 252 | — | H | 2-pyrazinylmethyl |
| 253 | — | H | 5-chloropyrazin-2-ylmethyl |
| 254 | — | H | 6-chloropyrazin-2-ylmethyl |
| 255 | — | H | 3-pyridazinylmethyl |
| 256 | — | H | 6-chloropyridazin-3-ylmethyl |
| 257 | — | H | 1,3,5-triazinylmethyl |
| 258 | — | H | 2-furylmethyl |
| 259 | — | H | 3-furylmethyl |
| 260 | — | H | 4-bromofur-2-ylmethyl |
| 261 | — | H | 5-chlorofur-2-ylmethyl |
| 262 | — | H | 2-thienylmethyl |
| 263 | — | H | 3-thienylmethyl |
| 264 | — | H | 5-methylthien-3-ylmethyl |
| 265 | — | H | 5-chlorothien-2-ylmethyl |
| 266 | — | H | 2-chlorothien-4-ylmethyl |
| 267 | — | H | 2-pyrrolylmethyl |
| 268 | — | H | 3-pyrrolylmethyl |
| 269 | — | H | 2-oxazolylmethyl |
| 270 | — | H | 4-methyloxazol-2-ylmethyl |
| 271 | — | H | 5-methyloxazol-2-ylmethyl |
| 272 | — | H | 4-chlorooxazol-2-ylmethyl |
| 273 | — | H | 5-chlorooxazol-2-ylmethyl |
| 274 | — | H | 4-oxazolylmethyl |
| 275 | — | H | 2-methyloxazol-4-ylmethyl |
| 276 | — | H | 5-methyloxazol-4-ylmethyl |
| 277 | — | H | 2-chlorooxazol-4-ylmethyl |
| 278 | — | H | 5-chlorooxazol-4-ylmethyl |
| 279 | — | H | 5-oxazolylmethyl |
| 280 | — | H | 2-methyloxazol-5-ylmethyl |
| 281 | — | H | 4-methyloxazol-5-ylmethyl |
| 282 | — | H | 2-chlorooxazol-5-ylmethyl |
| 283 | — | H | 4-chlorooxazol-5-ylmethyl |
| 284 | — | H | 2-thiazolylmethyl |
| 285 | — | H | 4-methylthiazol-2-ylmethyl |
| 286 | — | H | 5-methylthiazol-2-ylmethyl |
| 287 | — | H | 4-chlorothiazol-2-ylmethyl |
| 288 | — | H | 5-chlorothiazol-2-ylmethyl |
| 289 | — | H | 4-thiazolylmethyl |
| 290 | — | H | 2-methylthiazol-4-ylmethyl |
| 291 | — | H | 5-methylthiazol-4-ylmethyl |
| 292 | — | H | 2-chlorothiazol-4-ylmethyl |
| 293 | — | H | 5-chlorothiazol-4-ylmethyl |
| 294 | — | H | 5-thiazolylmethyl |
| 295 | — | H | 2-methylthiazol-5-ylmethyl |
| 296 | — | H | 4-methylthiazol-5-ylmethyl |
| 297 | — | H | 2-chlorothiazol-5-ylmethyl |
| 298 | — | H | 4-chlorothiazol-5-ylmethyl |
| 299 | — | H | 3-isoxazolylmethyl |
| 300 | — | H | 4-methylisoxazol-3-ylmethyl |
| 301 | — | H | 5-methylisoxazol-3-ylmethyl |
| 302 | — | H | 4-chloroisoxazol-3-ylmethyl |
| 303 | — | H | 5-chloroisoxazol-3-ylmethyl |
| 304 | — | H | 4-isoxazolylmethyl |
| 305 | — | H | 3-methylisoxazol-4-ylmethyl |
| 306 | — | H | 5-methylisoxazol-4-ylmethyl |
| 307 | — | H | 3-chloroisoxazol-4-ylmethyl |
| 308 | — | H | 5-chloroisoxazol-4-ylmethyl |
| 309 | — | H | 5-isoxazolylmethyl |
| 310 | — | H | 3-methylisoxazol-5-ylmethyl |
| 311 | — | H | 4-methylisoxazol-5-ylmethyl |
| 312 | — | H | 3-chloroisoxazol-5-ylmethyl |
| 313 | — | H | 4-chloroisoxazol-5-ylmethyl |
| 314 | — | H | 3-isothiazolylmethyl |
| 315 | — | H | 4-methylisothiazol-3-ylmethyl |
| 316 | — | H | 5-methylisothiazol-3-ylmethyl |
| 317 | — | H | 4-chloroisothiazol-3-ylmethyl |
| 318 | — | H | 5-chloroisothiazol-3-ylmethyl |
| 319 | — | H | 4-isothiazolylmethyl |
| 320 | — | H | 3-methylisothiazol-4-ylmethyl |
| 321 | — | H | 5-methylisothiazol-4-ylmethyl |
| 322 | — | H | 3-chloroisothiazol-4-ylmethyl |
| 323 | — | H | 5-chloroisothiazol-4-ylmethyl |
| 324 | — | H | 5-isothiazolylmethyl |
| 325 | — | H | 3-methylisothiazol-5-ylmethyl |
| 326 | — | H | 4-methylisothiazol-5-ylmethyl |
| 327 | — | H | 3-chloroisothiazol-5-ylmethyl |
| 328 | — | H | 4-chloroisothiazol-5-ylmethyl |
| 329 | — | H | 4-imidazolylmethyl |
| 330 | — | H | 1-phenylpyrazol-3-ylmethyl |
| 331 | — | H | 1-methylimidazol-4-ylmethyl |
| 332 | — | H | 1-phenyl-1,2,4-triazol-3-ylmethyl |
| 333 | — | H | 1,2,4-oxadiazol-3-ylmethyl |
| 334 | — | H | 5-chloro-1,2,4-oxadiazol-3-ylmethyl |
| 335 | — | H | 5-methyl-1,2,4-oxadiazol-3-ylmethyl |
| 336 | — | H | 5-trifluoromethyl-1,2,4-oxadiazol-3-ylmethyl |
| 337 | — | H | 1,3,4-oxadiazol-2-ylmethyl |
| 338 | — | H | 5-chloro-1,3,4-oxadiazol-2-ylmethyl |
| 339 | — | H | 5-methyl-1,3,4-oxadiazol-2-ylmethyl |
| 340 | — | H | 5-methoxy-1,3,4-oxadiazol-2-ylmethyl |
| 341 | — | H | 1,2,4-thiadiazol-3-ylmethyl |
| 342 | — | H | 5-chloro-1,2,4-thiadiazol-3-ylmethyl |
| 343 | — | H | 5-methyl-1,2,4-thiadiazol-3-ylmethyl |
| 344 | — | H | 1,3,4-thiadiazol-2-ylmethyl |
| 345 | — | H | 5-chloro-1,3,4-thiadiazol-2-ylmethyl |
| 346 | — | H | 5-methyl-1,3,4-thiadiazol-2-ylmethyl |

TABLE A-continued

| | | | |
|---|---|---|---|
| 347 | — | H | 5-cyano-1,3,4-thiadiazol-2-ylmethyl |
| 348 | — | H | 2-(2'-pyridinyloxy)eth-1-yl |
| 349 | — | H | 2-(3'-pyridinyloxy)eth-1-yl |
| 350 | — | H | 2-(4'-pyridinyloxy)eth-1-yl |
| 351 | — | H | $C_6H_5$ |
| 352 | — | H | 2-Cl—$C_6H_4$ |
| 353 | — | H | 3-Cl—$C_6H_4$ |
| 354 | — | H | 4-Cl—$C_6H_4$ |
| 355 | — | H | 2,3-$Cl_2$—$C_6H_3$ |
| 356 | — | H | 2,4-$Cl_2$—$C_6H_3$ |
| 357 | — | H | 2,5-$Cl_2$—$C_6H_3$ |
| 358 | — | H | 3,4-$Cl_2$—$C_6H_3$ |
| 359 | — | H | 3,5-$Cl_2$—$C_6H_3$ |
| 360 | — | H | 4-CN—$C_6H_4$ |
| 361 | — | H | 2-$NO_2$—$C_6H_4$ |
| 362 | — | H | 3-$NO_2$—$C_6H_4$ |
| 363 | — | H | 4-$NO_2$—$C_6H_4$ |
| 364 | — | H | 2,4-$(NO_2)_2$—$C_6H_3$ |
| 365 | — | H | 2-$CH_3$—$C_6H_4$ |
| 366 | — | H | 3-$CH_3$—$C_6H_4$ |
| 367 | — | H | 4-$CH_3$—$C_6H_4$ |
| 368 | — | H | 2,3-$(CH_3)_2$—$C_6H_3$ |
| 369 | — | H | 2,4-$(CH_3)_2$—$C_6H_3$ |
| 370 | — | H | 2,5-$(CH_3)_2$—$C_6H_3$ |
| 371 | — | H | 2,6-$(CH_3)_2$—$C_6H_3$ |
| 372 | — | H | 2-$C_6H_5$—$C_6H_4$ |
| 373 | — | H | 3-$C_6H_5$—$C_6H_4$ |
| 374 | — | H | 4-$C_6H_5$—$C_6H_4$ |
| 375 | — | H | 3-$OCH_3$—$C_6H_4$ |
| 376 | — | H | 4-$OCH_3$—$C_6H_4$ |
| 377 | — | H | 3-acetyl-$C_6H_4$ |
| 378 | — | H | 4-acetyl-$C_6H_4$ |
| 379 | — | H | 3-methoxycarbonyl-$C_6H_4$ |
| 380 | — | H | 4-methoxycarbonyl-$C_6H_4$ |
| 381 | — | H | 3-$CF_3$—$C_6H_4$ |
| 382 | — | H | 4-$CF_3$—$C_6H_4$ |
| 383 | — | H | 2-naphthyl |
| 384 | — | H | 6-chloropyridazin-3-yl |
| 385 | — | H | 5-chloropyrazin-2-yl |
| 386 | — | H | quinolin-2-yl |
| 387 | — | H | 2,5-dimethylpyrazin-3-yl |
| 388 | — | H | pyrazin-2-yl |
| 389 | — | H | 3-chloropyrid-2-yl |
| 390 | — | H | 6-chloropyrid-2-yl |
| 391 | — | H | 4-trifluoromethyl, 6-chloropyrid-2-yl |
| 392 | — | H | 4-trifluoromethylpyrid-2-yl |
| 393 | — | H | 6-trifluoromethylpyrid-2-yl |
| 394 | — | H | 6-methoxypyrid-2-yl |
| 395 | — | H | 5-chloropyrid-2-yl |
| 396 | — | H | pyrid-2-yl |
| 397 | — | H | benzothiazol-2-yl |
| 398 | — | H | 7-chloroquinolin-4-yl |
| 399 | — | H | 3-nitropyrid-2-yl |
| 400 | — | H | pyrrol-3-yl |
| 401 | — | H | pyrrol-2-yl |
| 402 | — | H | 2,6-dioctylpyrid-4-yl |
| 403 | — | H | 5-nitropyrid-2-yl |
| 404 | — | H | pyrid-4-yl |
| 405 | — | H | pyrid-3-yl |
| 406 | — | H | pyrimidin-2-yl |
| 407 | — | H | pyrimidin-4-yl |
| 408 | — | H | quinazolin-4-yl |
| 409 | — | H | 6-chloropyrimidin-4-yl |
| 410 | — | H | 6-methoxypyrimidin-4-yl |
| 411 | — | H | 2,5,6-trichloropyrimidin-4-yl |
| 412 | — | H | 2,6-dimethylpyrimidin-4-yl |
| 413 | — | H | 2-methyl, 6-chloropyrimidin-4-yl |
| 414 | — | H | 2-methyl, 6-ethoxypyrimidin-4-yl |
| 415 | — | H | 4,5,6-trichloropyrimidin-2-yl |
| 416 | — | H | 4,6-dimethoxypyrimidin-2-yl |
| 417 | — | H | 4,6-dimethylpyrimidin-2-yl |
| 418 | — | H | 4,6-dichloropyrimidin-2-yl |
| 419 | — | H | 4-methyl, 6-methoxypyrimidin-2-yl |
| 420 | — | H | 4-chloro, 6-methoxypyrimidin-2-yl |
| 421 | — | H | 6-chloroquinoxalin-2-yl |
| 422 | — | H | 3,6-dichloro-1,2,4-triazin-5-yl |
| 423 | — | H | 4-methoxy-1,3,5-triazin-2-yl |
| 424 | — | H | 4-ethoxy-1,3,5-triazin-2-yl |
| 425 | — | H | 4,6-dichloro-1,3,5-triazin-2-yl |
| 426 | — | H | 4-ethoxy, 6-chloro-1,3,5-triazin-2-yl |
| 427 | — | H | isoxazol-3-yl |
| 428 | — | H | thien-2-yl |
| 429 | — | H | fur-2-yl |
| 430 | — | H | thiatriazol-5-yl |
| 431 | — | H | (E)-1-chloropropen-3-yl |
| 432 | — | H | (E)-4-(4'-chlorophenyl)but-2-en-1-yl |
| 433 | — | H | propyn-3-yl |
| 434 | — | H | methylcarbonyl |
| 435 | — | H | 2-t-$C_4H_9$—$C_6H_4$—$CH_2$ |
| 436 | — | H | 3-t-$C_4H_9$—$C_6H_4$—$CH_2$ |
| 437 | — | H | 4-t-$C_4H_9$—$C_6H_4$—$CH_2$ |
| 438 | — | H | 2-(4'-chlorothiazol-2'-yloxy)eth-1-yl |
| 439 | — | H | 2-(1'-methylpyrazol-4'-yloxy)eth-1-yl |
| 440 | — | H | 4-Br—$C_6H_4$ |
| 441 | — | H | 3,5-$(CH_3)_2$—$C_6H_3$ |
| 442 | — | H | 4-$C_2H_5$—$C_6H_4$ |
| 443 | — | H | 3-dimethylaminocarbonyl-$C_6H_4$ |
| 444 | — | H | 4-dimethylaminocarbonyl-$C_6H_4$ |
| 445 | — | H | 2-hydroxyprop-1-yl |
| 446 | — | H | 6-hydroxy-2-methylpyrimidin-4-ylmethyl |
| 447 | — | H | [6-OH,2-$CH(CH_3)_2$-pyrimidin-4-yl]-$CH_2$ |
| 448 | — | H | [6-OH,2-$CH(CH_2)_2$-pyrimidin-4-yl]-$CH_2$ |
| 449 | — | H | 5-(2'-furan)pent-1-yl |
| 450 | — | H | 5-(2'-N-methylpyrrole)pent-1-yl |
| 451 | — | H | [2-(4-Cl—$C_6H_4$)-oxazol-4-yl]-$CH_2$ |
| 452 | — | H | 3-$CF_3$-pyridin-2-yl |
| 453 | — | H | 5-$CF_3$-pyridin-2-yl |
| 454 | — | H | 6-(2'-thienyl)hex-1-yl |
| 455 | O | $CH_3$ | H |
| 456 | O | $CH_3$ | $CH_3$ |
| 457 | O | $CH_3$ | $C_2H_5$ |
| 458 | O | $CH_3$ | n-$C_3H_7$ |
| 459 | O | $CH_3$ | i-$C_3H_7$ |
| 460 | O | $CH_3$ | cyclopropyl |
| 461 | O | $CH_3$ | n-$C_4H_9$ |
| 462 | O | $CH_3$ | s-$C_4H_9$ |
| 463 | O | $CH_3$ | i-$C_4H_9$ |
| 464 | O | $CH_3$ | t-$C_4H_9$ |
| 465 | O | $CH_3$ | n-$C_5H_{11}$ |
| 466 | O | $CH_3$ | i-$C_5H_{11}$ |
| 467 | O | $CH_3$ | neo-$C_5H_{11}$ |
| 468 | O | $CH_3$ | cyclopentyl |
| 469 | O | $CH_3$ | n-$C_6H_{13}$ |
| 470 | O | $CH_3$ | cyclohexyl |
| 471 | O | $CH_3$ | $CH_2CH_2Cl$ |
| 472 | O | $CH_3$ | $(CH_2)_4Cl$ |
| 473 | O | $CH_3$ | $CH_2CN$ |
| 474 | O | $CH_3$ | $CH_2CH_2CN$ |
| 475 | O | $CH_3$ | $(CH_2)_3CN$ |
| 476 | O | $CH_3$ | $(CH_2)_4CN$ |
| 477 | O | $CH_3$ | $(CH_2)_6CN$ |
| 478 | O | $CH_3$ | cyclohexylmethyl |
| 479 | O | $CH_3$ | 2-cyclohexyleth-1-yl |
| 480 | O | $CH_3$ | cyclopropylmethyl |
| 481 | O | $CH_3$ | 2-cyclopropyleth-1-yl |
| 482 | O | $CH_3$ | 2-methoxyeth-1-yl |
| 483 | O | $CH_3$ | 2-ethoxyeth-1-yl |
| 484 | O | $CH_3$ | 2-isopropoxyeth-1-yl |
| 485 | O | $CH_3$ | 3-methoxyprop-1-yl |
| 486 | O | $CH_3$ | 3-ethoxyprop-1-yl |
| 487 | O | $CH_3$ | 3-isopropoxyprop-1-yl |
| 488 | O | $CH_3$ | 4-methoxybut-1-yl |
| 489 | O | $CH_3$ | 4-isopropoxybut-1-yl |
| 490 | O | $CH_3$ | propen-3-yl |
| 491 | O | $CH_3$ | but-2-en-1-yl |
| 492 | O | $CH_3$ | 3-methylbut-2-en-1-yl |
| 493 | O | $CH_3$ | 2-vinyloxyeth-1-yl |
| 494 | O | $CH_3$ | allyloxyeth-1-yl |
| 495 | O | $CH_3$ | 2-trifluoromethoxyeth-1-yl |
| 496 | O | $CH_3$ | 3-trifluoromethoxyprop-1-yl |
| 497 | O | $CH_3$ | 4-difluoromethoxybut-1-yl |
| 498 | O | $CH_3$ | hydroxycarbonylmethyl |
| 499 | O | $CH_3$ | methoxycarbonylmethyl |
| 500 | O | $CH_3$ | aminocarbonylmethyl |
| 501 | O | $CH_3$ | N-methylaminocarbonylmethyl |
| 502 | O | $CH_3$ | N,N-dimethylaminocarbonyl-methyl |
| 503 | O | $CH_3$ | 2-hydroxycarbonyleth-1-yl |
| 504 | O | $CH_3$ | 2-methoxycarbonyleth-1-yl |

TABLE A-continued

| | | | |
|---|---|---|---|
| 505 | O | CH₃ | 2-aminocarbonyleth-1-yl |
| 506 | O | CH₃ | 2-N-methylaminocarbonyleth-1-yl |
| 507 | O | CH₃ | 2-dimethylaminocarbonyleth-1-yl |
| 508 | O | CH₃ | 2-aminoeth-1-yl |
| 509 | O | CH₃ | 2-aminoprop-1-yl |
| 510 | O | CH₃ | 4-aminobut-1-yl |
| 511 | O | CH₃ | 3-dimethylaminoprop-1-yl |
| 512 | O | CH₃ | 4-aminothiocarbonylbut-1-yl |
| 513 | O | CH₃ | 6-aminocarbonylhex-1-yl |
| 514 | O | CH₃ | 3-aminothiocarbonylprop-1-yl |
| 515 | O | CH₃ | 2-aminothiocarbonyleth-1-yl |
| 516 | O | CH₃ | aminothiocarbonylmethyl |
| 517 | O | CH₃ | 4-(N,N-dimethylamino)but-1-yl |
| 518 | O | CH₃ | 2-(methylthio)eth-1-yl |
| 519 | O | CH₃ | 2-(methylsulfonyl)eth-1-yl |
| 520 | O | CH₃ | 4-(methylthio)prop-1-yl |
| 521 | O | CH₃ | 4-(methylsulfonyl)prop-1-yl |
| 522 | O | CH₃ | benzyl |
| 523 | O | CH₃ | 2-F—C₆H₄—CH₂ |
| 524 | O | CH₃ | 3-F—C₆H₄—CH₂ |
| 525 | O | CH₃ | 4-F—C₆H₄—CH₂ |
| 526 | O | CH₃ | 2,3-F₂—C₆H₃—CH₂ |
| 527 | O | CH₃ | 2,4-F₂—C₆H₃—CH₂ |
| 528 | O | CH₃ | 2,5-F₂—C₆H₃—CH₂ |
| 529 | O | CH₃ | 2,6-F₂—C₆H₃—CH₂ |
| 530 | O | CH₃ | 3,4-F₂—C₆H₃—CH₂ |
| 531 | O | CH₃ | 3,5-F₂—C₆H₃—CH₂ |
| 532 | O | CH₃ | 2-Cl—C₆H₄—CH₂ |
| 533 | O | CH₃ | 3-Cl—C₆H₄—CH₂ |
| 534 | O | CH₃ | 4-Cl—C₆H₄—CH₂ |
| 535 | O | CH₃ | 2,3-Cl₂—C₆H₃—CH₂ |
| 536 | O | CH₃ | 2,4-Cl₂—C₆H₃—CH₂ |
| 537 | O | CH₃ | 2,5-Cl₂—C₆H₃—CH₂ |
| 538 | O | CH₃ | 2,6-Cl₂—C₆H₃—CH₂ |
| 539 | O | CH₃ | 3,4-Cl₂—C₆H₃—CH₂ |
| 540 | O | CH₃ | 3,5-Cl₂—C₆H₃—CH₂ |
| 541 | O | CH₃ | 2,3,4-Cl₃—C₆H₂—CH₂ |
| 542 | O | CH₃ | 2,3,5-Cl₃—C₆H₂—CH₂ |
| 543 | O | CH₃ | 2,3,6-Cl₃—C₆H₂—CH₂ |
| 544 | O | CH₃ | 2,4,5-Cl₃—C₆H₂—CH₂ |
| 545 | O | CH₃ | 2,4,6-Cl₃—C₆H₂—CH₂ |
| 546 | O | CH₃ | 3,4,5-Cl₃—C₆H₂—CH₂ |
| 547 | O | CH₃ | 2-Br—C₆H₄—CH₂ |
| 548 | O | CH₃ | 3-Br—C₆H₄—CH₂ |
| 549 | O | CH₃ | 4-Br—C₆H₄—CH₂ |
| 550 | O | CH₃ | 2,3-Br₂—C₆H₃—CH₂ |
| 551 | O | CH₃ | 2,4-Br₂—C₆H₃—CH₂ |
| 552 | O | CH₃ | 2,5-Br₂—C₆H₃—CH₂ |
| 553 | O | CH₃ | 2,6-Br₂—C₆H₃—CH₂ |
| 554 | O | CH₃ | 3,4-Br₂—C₆H₃—CH₂ |
| 555 | O | CH₃ | 3,5-Br₂—C₆H₃—CH₂ |
| 556 | O | CH₃ | 2-F, 3-Cl—C₆H₃—CH₂ |
| 557 | O | CH₃ | 2-F, 4-Cl—C₆H₃—CH₂ |
| 558 | O | CH₃ | 2-F, 5-Cl—C₆H₃—CH₂ |
| 559 | O | CH₃ | 2-F, 3-Br—C₆H₃—CH₂ |
| 560 | O | CH₃ | 2-F, 4-Br—C₆H₃—CH₂ |
| 561 | O | CH₃ | 2-F, 5-Br—C₆H₃—CH₂ |
| 562 | O | CH₃ | 2-Cl, 3-Br—C₆H₃—CH₂ |
| 563 | O | CH₃ | 2-Cl, 4-Br—C₆H₃—CH₂ |
| 564 | O | CH₃ | 2-Cl, 5-Br—C₆H₃—CH₂ |
| 565 | O | CH₃ | 3-F, 4-Cl—C₆H₃—CH₂ |
| 566 | O | CH₃ | 3-F, 5-Cl—C₆H₃—CH₂ |
| 567 | O | CH₃ | 3-F, 6-Cl—C₆H₃—CH₂ |
| 568 | O | CH₃ | 3-F, 4-Br—C₆H₃—CH₂ |
| 569 | O | CH₃ | 3-F, 5-Br—C₆H₃—CH₂ |
| 570 | O | CH₃ | 3-F, 6-Br—C₆H₃—CH₂ |
| 571 | O | CH₃ | 3-Cl, 4-Br—C₆H₃—CH₂ |
| 572 | O | CH₃ | 3-Cl, 5-Br—C₆H₃—CH₂ |
| 573 | O | CH₃ | 3-Cl, 6-Br—C₆H₃—CH₂ |
| 574 | O | CH₃ | 4-F, 5-Cl—C₆H₃—CH₂ |
| 575 | O | CH₃ | 4-F, 6-Cl—C₆H₃—CH₂ |
| 576 | O | CH₃ | 4-F, 5-Br—C₆H₃—CH₂ |
| 577 | O | CH₃ | 4-F, 6-Br—C₆H₃—CH₂ |
| 578 | O | CH₃ | 4-Cl, 5-Br—C₆H₃—CH₂ |
| 579 | O | CH₃ | 5-F, 6-Cl—C₆H₃—CH₂ |
| 580 | O | CH₃ | 5-F, 6-Br—C₆H₃—CH₂ |
| 581 | O | CH₃ | 5-Cl, 6-Br—C₆H₃—CH₂ |
| 582 | O | CH₃ | 3-Br, 4-Cl, 5-Br—C₆H₂—CH₂ |
| 583 | O | CH₃ | 2-CN—C₆H₄—CH₂ |
| 584 | O | CH₃ | 3-CN—C₆H₄—CH₂ |
| 585 | O | CH₃ | 4-CN—C₆H₄—CH₂ |
| 586 | O | CH₃ | 2-NO₂—C₆H₄—CH₂ |
| 587 | O | CH₃ | 3-NO₂—C₆H₄—CH₂ |
| 588 | O | CH₃ | 4-NO₂—C₆H₄—CH₂ |
| 589 | O | CH₃ | 2-CH₃—C₆H₄—CH₂ |
| 590 | O | CH₃ | 3-CH₃—C₆H₄—CH₂ |
| 591 | O | CH₃ | 4-CH₃—C₆H₄—CH₂ |
| 592 | O | CH₃ | 2,3-(CH₃)₂—C₆H₃—CH₂ |
| 593 | O | CH₃ | 2,4-(CH₃)₂—C₆H₃—CH₂ |
| 594 | O | CH₃ | 2,5-(CH₃)₂—C₆H₃—CH₂ |
| 595 | O | CH₃ | 2,6-(CH₃)₂—C₆H₃—CH₂ |
| 596 | O | CH₃ | 3,4-(CH₃)₂—C₆H₃—CH₂ |
| 597 | O | CH₃ | 3,5-(CH₃)₂—C₆H₃—CH₂ |
| 598 | O | CH₃ | 2-C₂H₅—C₆H₄—CH₂ |
| 599 | O | CH₃ | 3-C₂H₅—C₆H₄—CH₂ |
| 600 | O | CH₃ | 4-C₂H₅—C₆H₄—CH₂ |
| 601 | O | CH₃ | 2-i-C₃H₇—C₆H₄—CH₂ |
| 602 | O | CH₃ | 3-i-C₃H₇—C₆H₄—CH₂ |
| 603 | O | CH₃ | 4-i-C₃H₇—C₆H₄—CH₂ |
| 604 | O | CH₃ | 2-cyclohexyl-C₆H₄—CH₂ |
| 605 | O | CH₃ | 3-cyclohexyl-C₆H₄—CH₂ |
| 606 | O | CH₃ | 4-cyclohexyl-C₆H₄—CH₂ |
| 607 | O | CH₃ | 2-vinyl-C₆H₄—CH₂ |
| 608 | O | CH₃ | 3-vinyl-C₆H₄—CH₂ |
| 609 | O | CH₃ | 4-vinyl-C₆H₄—CH₂ |
| 610 | O | CH₃ | 2-allyl-C₆H₄—CH₂ |
| 611 | O | CH₃ | 3-allyl-C₆H₄—CH₂ |
| 612 | O | CH₃ | 4-allyl-C₆H₄—CH₂ |
| 613 | O | CH₃ | 2-C₆H₅—C₆H₄—CH₂ |
| 614 | O | CH₃ | 3-C₆H₅—C₆H₄—CH₂ |
| 615 | O | CH₃ | 4-C₆H₅—C₆H₄—CH₂ |
| 616 | O | CH₃ | 3-CH₃, 5-t-C₄H₉—C₆H₃—CH₂ |
| 617 | O | CH₃ | 2-OH—C₆H₄—CH₂ |
| 618 | O | CH₃ | 3-OH—C₆H₄—CH₂ |
| 619 | O | CH₃ | 4-OH—C₆H₄—CH₂ |
| 620 | O | CH₃ | 2-OCH₃—C₆H₄—CH₂ |
| 621 | O | CH₃ | 3-OCH₃—C₆H₄—CH₂ |
| 622 | O | CH₃ | 4-OCH₃—C₆H₄—CH₂ |
| 623 | O | CH₃ | 2-O-allyl-C₆H₄—CH₂ |
| 624 | O | CH₃ | 3-O-allyl-C₆H₄—CH₂ |
| 625 | O | CH₃ | 4-O-allyl-C₆H₄—CH₂ |
| 626 | O | CH₃ | 2-CF₃—C₆H₄—CH₂ |
| 627 | O | CH₃ | 3-CF₃—C₆H₄—CH₂ |
| 628 | O | CH₃ | 4-CF₃—C₆H₄—CH₂ |
| 629 | O | CH₃ | 2-acetyl-C₆H₄—CH₂ |
| 630 | O | CH₃ | 3-acetyl-C₆H₄—CH₂ |
| 631 | O | CH₃ | 4-acetyl-C₆H₄—CH₂ |
| 632 | O | CH₃ | 2-methoxycarbonyl-C₆H₄—CH₂ |
| 633 | O | CH₃ | 3-methoxycarbonyl-C₆H₄—CH₂ |
| 634 | O | CH₃ | 4-methoxycarbonyl-C₆H₄—CH₂ |
| 635 | O | CH₃ | 2-aminocarbonyl-C₆H₄—CH₂ |
| 636 | O | CH₃ | 3-aminocarbonyl-C₆H₄—CH₂ |
| 637 | O | CH₃ | 4-aminocarbonyl-C₆H₄—CH₂ |
| 638 | O | CH₃ | 2-dimethylaminocarbonyl-C₆H₄—CH₂ |
| 639 | O | CH₃ | 3-dimethylaminocarbonyl-C₆H₄—CH₂ |
| 640 | O | CH₃ | 4-dimethylaminocarbonyl-C₆H₄—CH₂ |
| 641 | O | CH₃ | 2-(N-methylaminocarbonyl)-C₆H₄—CH₂ |
| 642 | O | CH₃ | 3-(N-methylaminocarbonyl)-C₆H₄—CH₂ |
| 643 | O | CH₃ | 4-(N-methylaminocarbonyl)-C₆H₄—CH₂ |
| 644 | O | CH₃ | 2-H₂N—C₆H₄—CH₂ |
| 645 | O | CH₃ | 3-H₂N—C₆H₄—CH₂ |
| 646 | O | CH₃ | 4-H₂N—C₆H₄—CH₂ |
| 647 | O | CH₃ | 2-aminothiocarbonyl-C₆H₄—CH₂ |
| 648 | O | CH₃ | 3-aminothiocarbonyl-C₆H₄—CH₂ |
| 649 | O | CH₃ | 4-aminothiocarbonyl-C₆H₄—CH₂ |
| 650 | O | CH₃ | 2-SCH₃—C₆H₄—CH₂ |
| 651 | O | CH₃ | 3-SCH₃—C₆H₄—CH₂ |
| 652 | O | CH₃ | 4-SCH₃—C₆H₄—CH₂ |
| 653 | O | CH₃ | 2-SO₂CH₃—C₆H₄—CH₂ |
| 654 | O | CH₃ | 3-SO₂CH₃—C₆H₄—CH₂ |
| 655 | O | CH₃ | 4-SO₂CH₃—C₆H₄—CH₂ |
| 656 | O | CH₃ | 2-OCF₃—C₆H₄—CH₂ |
| 657 | O | CH₃ | 3-OCF₃—C₆H₄—CH₂ |
| 658 | O | CH₃ | 4-OCF₃—C₆H₄—CH₂ |
| 659 | O | CH₃ | 2-OCHF₂—C₆H₄—CH₂ |
| 660 | O | CH₃ | 3-OCHF₂—C₆H₄—CH₂ |
| 661 | O | CH₃ | 4-OCHF₂—C₆H₄—CH₂ |
| 662 | O | CH₃ | 3-CF₃, 4-OCF₃—C₆H₃—CH₂ |

TABLE A-continued

| | | | |
|---|---|---|---|
| 663 | O | $CH_3$ | 1-naphthyl-$CH_2$ |
| 664 | O | $CH_3$ | 2-naphthyl-$CH_2$ |
| 665 | O | $CH_3$ | 2-phenoxyeth-1-yl |
| 666 | O | $CH_3$ | 2-(2'-chlorophenoxy)eth-1-yl |
| 667 | O | $CH_3$ | 2-(3'-chlorophenoxy)eth-1-yl |
| 668 | O | $CH_3$ | 2-(4'-chlorophenoxy)eth-1-yl |
| 669 | O | $CH_3$ | 2-(3',5'-dichlorophenoxy)eth-1-yl |
| 670 | O | $CH_3$ | 2-(4'-cyanophenoxy)eth-1-yl |
| 671 | O | $CH_3$ | 2-(3'-methylphenoxy)eth-1-yl |
| 672 | O | $CH_3$ | 2-(2'-nitrophenoxy)eth-1-yl |
| 673 | O | $CH_3$ | 3-phenoxyprop-1-yl |
| 674 | O | $CH_3$ | 3-(4'-chlorophenoxy)prop-1-yl |
| 675 | O | $CH_3$ | 3-(3'-cyanophenoxy)prop-1-yl |
| 676 | O | $CH_3$ | 3-(2'-methylphenoxy)prop-1-yl |
| 677 | O | $CH_3$ | 4-phenoxybut-1-yl |
| 678 | O | $CH_3$ | 2-phenyleth-1-yl |
| 679 | O | $CH_3$ | 2-(4'-chlorophenyl)eth-1-yl |
| 680 | O | $CH_3$ | 2-(3'-cyanophenyl)eth-1-yl |
| 1 | O | $CH_3$ | 2-(2'-methylphenyl)eth-1-yl |
| 2 | O | $CH_3$ | 3-phenylprop-1-yl |
| 3 | O | $CH_3$ | 4-phenylbut-1-yl |
| 4 | O | $CH_3$ | 2-pyridylmethyl |
| 5 | O | $CH_3$ | 3-pyridylmethyl |
| 6 | O | $CH_3$ | 4-pyridylmethyl |
| 7 | O | $CH_3$ | 4-chloropyridin-2-ylmethyl |
| 8 | O | $CH_3$ | 5-chloropyridin-2-ylmethyl |
| 9 | O | $CH_3$ | 6-chloropyridin-2-ylmethyl |
| 10 | O | $CH_3$ | 5-chloropyridin-3-ylmethyl |
| 11 | O | $CH_3$ | 6-chloropyridin-3-ylmethyl |
| 12 | O | $CH_3$ | 2-chloropyridin-4-ylmethyl |
| 13 | O | $CH_3$ | 2-pyrimidinylmethyl |
| 14 | O | $CH_3$ | 4-chloropyrimidin-2-ylmethyl |
| 15 | O | $CH_3$ | 5-chloropyrimidin-2-ylmethyl |
| 16 | O | $CH_3$ | 2-chloropyrimidin-4-ylmethyl |
| 17 | O | $CH_3$ | 6-chloropyrimidin-4-ylmethyl |
| 18 | O | $CH_3$ | 2-chloropyrimidin-5-ylmethyl |
| 19 | O | $CH_3$ | 4-pyridazinylmethyl |
| 20 | O | $CH_3$ | 2-pyrazinylmethyl |
| 21 | O | $CH_3$ | 5-chloropyrazin-2-ylmethyl |
| 22 | O | $CH_3$ | 6-chloropyrazin-2-ylmethyl |
| 23 | O | $CH_3$ | 3-pyridazinylmethyl |
| 24 | O | $CH_3$ | 6-chloropyridazin-3-ylmethyl |
| 25 | O | $CH_3$ | 1,3,5-triazinylmethyl |
| 26 | O | $CH_3$ | 2-furylmethyl |
| 27 | O | $CH_3$ | 3-furylmethyl |
| 28 | O | $CH_3$ | 4-bromofur-2-ylmethyl |
| 29 | O | $CH_3$ | 5-chlorofur-2-ylmethyl |
| 30 | O | $CH_3$ | 2-thienylmethyl |
| 31 | O | $CH_3$ | 3-thienylmethyl |
| 32 | O | $CH_3$ | 5-methylthien-3-ylmethyl |
| 33 | O | $CH_3$ | 5-chlorothien-2-ylmethyl |
| 34 | O | $CH_3$ | 2-chlorothien-4-ylmethyl |
| 35 | O | $CH_3$ | 2-pyrrolylmethyl |
| 36 | O | $CH_3$ | 3-pyrrolylmethyl |
| 37 | O | $CH_3$ | 2-oxazolylmethyl |
| 38 | O | $CH_3$ | 4-methyloxazol-2-ylmethyl |
| 39 | O | $CH_3$ | 5-methyloxazol-2-ylmethyl |
| 40 | O | $CH_3$ | 4-chlorooxazol-2-ylmethyl |
| 41 | O | $CH_3$ | 5-chlorooxazol-2-ylmethyl |
| 42 | O | $CH_3$ | 4-oxazolylmethyl |
| 43 | O | $CH_3$ | 2-methyloxazol-4-ylmethyl |
| 44 | O | $CH_3$ | 5-methyloxazol-4-ylmethyl |
| 45 | O | $CH_3$ | 2-chlorooxazol-4-ylmethyl |
| 46 | O | $CH_3$ | 5-chlorooxazol-4-ylmethyl |
| 47 | O | $CH_3$ | 5-oxazolylmethyl |
| 48 | O | $CH_3$ | 2-methyloxazol-5-ylmethyl |
| 49 | O | $CH_3$ | 4-methyloxazol-5-ylmethyl |
| 50 | O | $CH_3$ | 2-chlorooxazol-5-ylmethyl |
| 51 | O | $CH_3$ | 4-chlorooxazol-5-ylmethyl |
| 52 | O | $CH_3$ | 2-thiazolylmethyl |
| 53 | O | $CH_3$ | 4-methylthiazol-2-ylmethyl |
| 54 | O | $CH_3$ | 5-methylthiazol-2-ylmethyl |
| 55 | O | $CH_3$ | 4-chlorothiazol-2-ylmethyl |
| 56 | O | $CH_3$ | 5-chlorothiazol-2-ylmethyl |
| 57 | O | $CH_3$ | 4-thiazolylmethyl |
| 58 | O | $CH_3$ | 2-methylthiazol-4-ylmethyl |
| 59 | O | $CH_3$ | 5-methylthiazol-4-ylmethyl |
| 60 | O | $CH_3$ | 2-chlorothiazol-4-ylmethyl |
| 61 | O | $CH_3$ | 5-chlorothiazol-4-ylmethyl |
| 62 | O | $CH_3$ | 5-thiazolylmethyl |
| 63 | O | $CH_3$ | 2-methylthiazol-5-ylmethyl |
| 64 | O | $CH_3$ | 4-methylthiazol-5-ylmethyl |
| 65 | O | $CH_3$ | 2-chlorothiazol-5-ylmethyl |
| 66 | O | $CH_3$ | 4-chlorothiazol-5-ylmethyl |
| 67 | O | $CH_3$ | 3-isoxazolylmethyl |
| 68 | O | $CH_3$ | 4-methylisoxazol-3-ylmethyl |
| 69 | O | $CH_3$ | 5-methylisoxazol-3-ylmethyl |
| 70 | O | $CH_3$ | 4-chloroisoxazol-3-ylmethyl |
| 71 | O | $CH_3$ | 5-chloroisoxazol-3-ylmethyl |
| 72 | O | $CH_3$ | 4-isoxazolylmethyl |
| 73 | O | $CH_3$ | 3-methylisoxazol-4-ylmethyl |
| 74 | O | $CH_3$ | 5-methylisoxazol-4-ylmethyl |
| 75 | O | $CH_3$ | 3-chloroisoxazol-4-ylmethyl |
| 76 | O | $CH_3$ | 5-chloroisoxazol-4-ylmethyl |
| 77 | O | $CH_3$ | 5-isoxazolylmethyl |
| 78 | O | $CH_3$ | 3-methylisoxazol-5-ylmethyl |
| 79 | O | $CH_3$ | 4-methylisoxazol-5-ylmethyl |
| 80 | O | $CH_3$ | 3-chloroisoxazol-5-ylmethyl |
| 81 | O | $CH_3$ | 4-chloroisoxazol-5-ylmethyl |
| 82 | O | $CH_3$ | 3-isothiazolylmethyl |
| 83 | O | $CH_3$ | 4-methylisothiazol-3-ylmethyl |
| 84 | O | $CH_3$ | 5-methylisothiazol-3-ylmethyl |
| 85 | O | $CH_3$ | 4-chloroisothiazol-3-ylmethyl |
| 86 | O | $CH_3$ | 5-chloroisothiazol-3-ylmethyl |
| 87 | O | $CH_3$ | 4-isothiazolylmethyl |
| 88 | O | $CH_3$ | 3-methylisothiazol-4-ylmethyl |
| 89 | O | $CH_3$ | 5-methylisothiazol-4-ylmethyl |
| 90 | O | $CH_3$ | 3-chloroisothiazol-4-ylmethyl |
| 91 | O | $CH_3$ | 5-chloroisothiazol-4-ylmethyl |
| 92 | O | $CH_3$ | 5-isothiazolylmethyl |
| 93 | O | $CH_3$ | 3-methylisothiazol-5-ylmethyl |
| 94 | O | $CH_3$ | 4-methylisothiazol-5-ylmethyl |
| 95 | O | $CH_3$ | 3-chloroisothiazol-5-ylmethyl |
| 96 | O | $CH_3$ | 4-chloroisothiazol-5-ylmethyl |
| 97 | O | $CH_3$ | 4-imidazolylmethyl |
| 98 | O | $CH_3$ | 1-phenylpyrazol-3-ylmethyl |
| 99 | O | $CH_3$ | 1-methylimidazol-4-ylmethyl |
| 100 | O | $CH_3$ | 1-phenyl-1,2,4-triazol-3-ylmethyl |
| 101 | O | $CH_3$ | 1,2,4-oxadiazol-3-ylmethyl |
| 102 | O | $CH_3$ | 5-chloro-1,2,4-oxadiazol-3-ylmethyl |
| 103 | O | $CH_3$ | 5-methyl-1,2,4-oxadiazol-3-ylmethyl |
| 104 | O | $CH_3$ | 5-trifluoromethyl-1,2,4-oxadiazol-3-ylmethyl |
| 105 | O | $CH_3$ | 1,3,4-oxadiazol-2-ylmethyl |
| 106 | O | $CH_3$ | 5-chloro-1,3,4-oxadiazol-2-ylmethyl |
| 107 | O | $CH_3$ | 5-methyl-1,3,4-oxadiazol-2-ylmethyl |
| 108 | O | $CH_3$ | 5-methoxy-1,3,4-oxadiazol-2-ylmethyl |
| 109 | O | $CH_3$ | 1,2,4-thiadiazol-3-ylmethyl |
| 110 | O | $CH_3$ | 5-chloro-1,2,4-thiadiazol-3-ylmethyl |
| 111 | O | $CH_3$ | 5-methyl-1,2,4-thiadiazol-3-ylmethyl |
| 112 | O | $CH_3$ | 1,3,4-thiadiazol-2-ylmethyl |
| 113 | O | $CH_3$ | 5-chloro-1,3,4-thiadiazol-2-ylmethyl |
| 114 | O | $CH_3$ | 5-methyl-1,3,4-thiadiazol-2-ylmethyl |
| 115 | O | $CH_3$ | 5-cyano-1,3,4-thiadiazol-2-ylmethyl |
| 116 | O | $CH_3$ | 2-(2'-pyridinyloxy)eth-1-yl |
| 117 | O | $CH_3$ | 2-(3'-pyridinyloxy)eth-1-yl |
| 118 | O | $CH_3$ | 2-(4'-pyridinyloxy)eth-1-yl |
| 119 | O | $CH_3$ | $C_6H_5$ |
| 120 | O | $CH_3$ | 2-Cl—$C_6H_4$ |
| 121 | O | $CH_3$ | 3-Cl—$C_6H_4$ |
| 122 | O | $CH_3$ | 4-Cl—$C_6H_4$ |
| 123 | O | $CH_3$ | 2,3-$Cl_2$—$C_6H_3$ |
| 124 | O | $CH_3$ | 2,4-$Cl_2$—$C_6H_3$ |
| 125 | O | $CH_3$ | 2,5-$Cl_2$—$C_6H_3$ |
| 126 | O | $CH_3$ | 3,4-$Cl_2$—$C_6H_3$ |
| 127 | O | $CH_3$ | 3,5-$Cl_2$—$C_6H_3$ |
| 128 | O | $CH_3$ | 4-CN—$C_6H_4$ |
| 129 | O | $CH_3$ | 2-$NO_2$—$C_6H_4$ |
| 130 | O | $CH_3$ | 3-$NO_2$—$C_6H_4$ |
| 131 | O | $CH_3$ | 4-$NO_2$—$C_6H_4$ |
| 132 | O | $CH_3$ | 2,4-$(NO_2)_2$—$C_6H_3$ |
| 133 | O | $CH_3$ | 2-$CH_3$—$C_6H_4$ |
| 134 | O | $CH_3$ | 3-$CH_3$—$C_6H_4$ |
| 135 | O | $CH_3$ | 4-$CH_3$—$C_6H_4$ |
| 136 | O | $CH_3$ | 2,3-$(CH_3)_2$—$C_6H_3$ |
| 137 | O | $CH_3$ | 2,4-$(CH_3)_2$—$C_6H_3$ |
| 138 | O | $CH_3$ | 2,5-$(CH_3)_2$—$C_6H_3$ |
| 139 | O | $CH_3$ | 2,6-$(CH_3)_2$—$C_6H_3$ |
| 140 | O | $CH_3$ | 2-$C_6H_5$—$C_6H_4$ |

TABLE A-continued

| | | | |
|---|---|---|---|
| 141 | O | CH$_3$ | 3-C$_6$H$_5$—C$_6$H$_4$ |
| 142 | O | CH$_3$ | 4-C$_6$H$_5$—C$_6$H$_4$ |
| 143 | O | CH$_3$ | 3-OCH$_3$—C$_6$H$_4$ |
| 144 | O | CH$_3$ | 4-OCH$_3$—C$_6$H$_4$ |
| 145 | O | CH$_3$ | 3-acetyl-C$_6$H$_4$ |
| 146 | O | CH$_3$ | 4-acetyl-C$_6$H$_4$ |
| 147 | O | CH$_3$ | 3-methoxycarbonyl-C$_6$H$_4$ |
| 148 | O | CH$_3$ | 4-methoxycarbonyl-C$_6$H$_4$ |
| 149 | O | CH$_3$ | 3-CF$_3$—C$_6$H$_4$ |
| 150 | O | CH$_3$ | 4-CF$_3$—C$_6$H$_4$ |
| 151 | O | CH$_3$ | 2-naphthyl |
| 152 | O | CH$_3$ | 6-chloropyridazin-3-yl |
| 153 | O | CH$_3$ | 5-chloropyrazin-2-yl |
| 154 | O | CH$_3$ | quinolin-2-yl |
| 155 | O | CH$_3$ | 2,5-dimethylpyrazin-3-yl |
| 156 | O | CH$_3$ | pyrazin-2-yl |
| 157 | O | CH$_3$ | 3-chloropyrid-2-yl |
| 158 | O | CH$_3$ | 6-chloropyrid-2-yl |
| 159 | O | CH$_3$ | 4-trifluoromethyl, 6-chloropyrid-2-yl |
| 160 | O | CH$_3$ | 4-trifluoromethylpyrid-2-yl |
| 161 | O | CH$_3$ | 6-trifluoromethylpyrid-2-yl |
| 162 | O | CH$_3$ | 6-methoxypyrid-2-yl |
| 163 | O | CH$_3$ | 5-chloropyrid-2-yl |
| 164 | O | CH$_3$ | pyrid-2-yl |
| 165 | O | CH$_3$ | benzothiazol-2-yl |
| 166 | O | CH$_3$ | 7-chloroquinolin-4-yl |
| 167 | O | CH$_3$ | 3-nitropyrid-2-yl |
| 168 | O | CH$_3$ | pyrrol-3-yl |
| 169 | O | CH$_3$ | pyrrol-2-yl |
| 170 | O | CH$_3$ | 2,6-dioctylpyrid-4-yl |
| 171 | O | CH$_3$ | 5-nitropyrid-2-yl |
| 172 | O | CH$_3$ | pyrid-4-yl |
| 173 | O | CH$_3$ | pyrid-3-yl |
| 174 | O | CH$_3$ | pyrimidin-2-yl |
| 175 | O | CH$_3$ | pyrimidin-4-yl |
| 176 | O | CH$_3$ | quinazolin-4-yl |
| 177 | O | CH$_3$ | 6-chloropyrimidin-4-yl |
| 178 | O | CH$_3$ | 6-methoxypyrimidin-4-yl |
| 179 | O | CH$_3$ | 2,5,6-trichloropyrimidin-4-yl |
| 180 | O | CH$_3$ | 2,6-dimethylpyrimidin-4-yl |
| 181 | O | CH$_3$ | 2-methyl, 6-chloropyrimidin-4-yl |
| 182 | O | CH$_3$ | 2-methyl, 6-ethoxypyrimidin-4-yl |
| 183 | O | CH$_3$ | 4,5,6-trichloropyrimidin-2-yl |
| 184 | O | CH$_3$ | 4,6-dimethoxypyrimidin-2-yl |
| 185 | O | CH$_3$ | 4,6-dimethylpyrimidin-2-yl |
| 186 | O | CH$_3$ | 4,6-dichloropyrimidin-2-yl |
| 187 | O | CH$_3$ | 4-methyl, 6-methoxypyrimidin-2-yl |
| 188 | O | CH$_3$ | 4-chloro, 6-methoxypyrimidin-2-yl |
| 189 | O | CH$_3$ | 6-chloroquinoxalin-2-yl |
| 190 | O | CH$_3$ | 3,6-dichloro-1,2,4-triazin-5-yl |
| 191 | O | CH$_3$ | 4-methoxy-1,3,5-triazin-2-yl |
| 192 | O | CH$_3$ | 4-ethoxy-1,3,5-triazin-2-yl |
| 193 | O | CH$_3$ | 4,6-dichloro-1,3,5-triazin-2-yl |
| 194 | O | CH$_3$ | 4-ethoxy, 6-chloro-1,3,5-triazin-2-yl |
| 195 | O | CH$_3$ | isoxazol-3-yl |
| 196 | O | CH$_3$ | thien-2-yl |
| 197 | O | CH$_3$ | fur-2-yl |
| 198 | O | CH$_3$ | thiatriazol-5-yl |
| 199 | O | CH$_3$ | (E)-1-chloropropen-3-yl |
| 200 | O | CH$_3$ | (E)-4-(4'-chlorophenyl)but-2-en-1-yl |
| 201 | O | CH$_3$ | propyn-3-yl |
| 202 | O | CH$_3$ | methylcarbonyl |
| 203 | O | CH$_3$ | 2-t-C$_4$H$_9$—C$_6$H$_4$—CH$_2$ |
| 204 | O | CH$_3$ | 3-t-C$_4$H$_9$—C$_6$H$_4$—CH$_2$ |
| 205 | O | CH$_3$ | 4-t-C$_4$H$_9$—C$_6$H$_4$—CH$_2$ |
| 206 | O | CH$_3$ | 2-(4'-chlorothiazol-2'-yloxy)eth-1-yl |
| 207 | O | CH$_3$ | 2-(1'-methylpyrazol-4'-yloxy)eth-1-yl |
| 208 | O | CH$_3$ | 4-Br—C$_6$H$_4$ |
| 209 | O | CH$_3$ | 3,5-(CH$_3$)$_2$—C$_6$H$_3$ |
| 210 | O | CH$_3$ | 4-C$_2$H$_5$—C$_6$H$_4$ |
| 211 | O | CH$_3$ | 3-dimethylaminocarbonyl-C$_6$H$_4$ |
| 212 | O | CH$_3$ | 4-dimethylaminocarbonyl-C$_6$H$_4$ |
| 213 | O | CH$_3$ | 2-hydroxyprop-1-yl |
| 214 | O | CH$_3$ | 6-hydroxy-2-methylpyrimidin-4-ylmethyl |
| 215 | O | CH$_3$ | [6-OH,2-CH(CH$_3$)$_2$-pyrimidin-4-yl]-CH$_2$ |
| 216 | O | CH$_3$ | [6-OH,2-CH(CH$_2$)$_2$-pyrimidin-4-yl]-CH$_2$ |
| 217 | O | CH$_3$ | 5-(2'-furan)-pent-1-yl |
| 218 | O | CH$_3$ | 5-(2'-N-methylpyrrole)-pent-1-yl |
| 219 | O | CH$_3$ | [2-(4-Cl—C$_6$H$_4$)-oxazol-4-yl]-CH$_2$ |
| 220 | O | CH$_3$ | 3-CF$_3$-pyridin-2-yl |
| 221 | O | CH$_3$ | 5-CF$_3$-pyridin-2-yl |
| 222 | O | CH$_3$ | 6-(2'-thienyl)hex-1-yl |
| 223 | O | C$_2$H$_5$ | H |
| 224 | O | C$_2$H$_5$ | CH$_3$ |
| 225 | O | C$_2$H$_5$ | C$_6$H$_5$—CH$_2$ |
| 226 | O | i-C$_3$H$_7$ | CH$_3$ |
| 227 | NH | H | H |
| 228 | NH | H | CH$_3$ |
| 229 | NH | H | 4-Cl—C$_6$H$_4$—CH$_2$ |
| 230 | NH | CH$_3$ | CH$_3$ |
| 231 | NH | CH$_3$ | C$_6$H$_5$—CH$_2$ |
| 232 | NCH$_3$ | CH$_3$ | CH$_3$ |
| 233 | NCH$_3$ | CH$_3$ | 4-CH$_3$—C$_6$H$_4$—CH$_2$ |
| 234 | S | CH$_3$ | H |
| 235 | S | CH$_3$ | CH$_3$ |
| 236 | S | CH$_3$ | C$_2$H$_5$ |
| 237 | S | CH$_3$ | C$_6$H$_5$—CH$_2$ |
| 238 | — | C$_2$H$_5$ | H |
| 239 | — | C$_2$H$_5$ | CH$_3$ |
| 240 | — | C$_2$H$_5$ | C$_6$H$_5$—CH$_2$ |
| 241 | — | C$_2$H$_5$ | 3-CN—C$_6$H$_4$—CH$_2$ |
| 242 | — | C$_2$H$_5$ | prop-2-en-1-yl |
| 243 | — | n-C$_3$H$_7$ | H |
| 244 | — | n-C$_3$H$_7$ | CH$_3$ |
| 245 | — | C$_6$H$_5$ | H |
| 246 | — | C$_6$H$_5$ | CH$_3$ |
| 247 | — | C$_6$H$_5$ | 3-OCH$_3$—C$_6$H$_4$—CH$_2$ | d) R$^4$ = 4-C(=NOR$^a$)—Ap—R$^b$

| | | | |
|---|---|---|---|
| 1 | — | CH$_3$ | H |
| 2 | — | CH$_3$ | CH$_3$ |
| 3 | — | CH$_3$ | C$_2$H$_5$ |
| 4 | — | CH$_3$ | n-C$_3$H$_7$ |
| 5 | — | CH$_3$ | i-C$_3$H$_7$ |
| 6 | — | CH$_3$ | cyclopropyl |
| 7 | — | CH$_3$ | n-C$_4$H$_9$ |
| 8 | — | CH$_3$ | s-C$_4$H$_9$ |
| 9 | — | CH$_3$ | i-C$_4$H$_9$ |
| 10 | — | CH$_3$ | t-C$_4$H$_9$ |
| 11 | — | CH$_3$ | n-C$_5$H$_{11}$ |
| 12 | — | CH$_3$ | i-C$_5$H$_{11}$ |
| 13 | — | CH$_3$ | neo-C$_5$H$_{11}$ |
| 14 | — | CH$_3$ | cyclopentyl |
| 15 | — | CH$_3$ | n-C$_6$H$_{13}$ |
| 16 | — | CH$_3$ | cyclohexyl |
| 17 | — | CH$_3$ | CH$_2$CH$_2$Cl |
| 18 | — | CH$_3$ | (CH$_2$)$_4$Cl |
| 19 | — | CH$_3$ | CH$_2$CN |
| 20 | — | CH$_3$ | CH$_2$CH$_2$CN |
| 21 | — | CH$_3$ | (CH$_2$)$_3$CN |
| 22 | — | CH$_3$ | (CH$_2$)$_4$CN |
| 23 | — | CH$_3$ | (CH$_2$)$_6$CN |
| 24 | — | CH$_3$ | cyclohexylmethyl |
| 25 | — | CH$_3$ | 2-cyclohexyleth-1-yl |
| 26 | — | CH$_3$ | cyclopropylmethyl |
| 27 | — | CH$_3$ | 2-cyclopropyleth-1-yl |
| 28 | — | CH$_3$ | 2-methoxyeth-1-yl |
| 29 | — | CH$_3$ | 2-ethoxyeth-1-yl |
| 30 | — | CH$_3$ | 2-isopropoxyeth-1-yl |
| 31 | — | CH$_3$ | 3-methoxyprop-1-yl |
| 32 | — | CH$_3$ | 3-ethoxyprop-1-yl |
| 33 | — | CH$_3$ | 3-isopropoxyprop-1-yl |
| 34 | — | CH$_3$ | 4-methoxybut-1-yl |
| 35 | — | CH$_3$ | 4-isopropoxybut-1-yl |
| 36 | — | CH$_3$ | propen-3-yl |
| 37 | — | CH$_3$ | but-2-en-1-yl |
| 38 | — | CH$_3$ | 3-methylbut-2-en-1-yl |
| 39 | — | CH$_3$ | 2-vinyloxyeth-1-yl |
| 40 | — | CH$_3$ | allyloxyeth-1-yl |
| 41 | — | CH$_3$ | 2-trifluoromethoxyeth-1-yl |
| 42 | — | CH$_3$ | 3-trifluoromethoxyprop-1-yl |
| 43 | — | CH$_3$ | 4-difluoromethoxybut-1-yl |
| 44 | — | CH$_3$ | hydroxymethyl |
| 45 | — | CH$_3$ | methoxycarbonylmethyl |
| 46 | — | CH$_3$ | aminocarbonylmethyl |
| 47 | — | CH$_3$ | N-methylaminocarbonylmethyl |
| 48 | — | CH$_3$ | N,N-dimethylaminocarbonyl-methyl |
| 49 | — | CH$_3$ | 2-hydroxycarbonyleth-1-yl |

TABLE A-continued

| | | | |
|---|---|---|---|
| 50 | — | CH₃ | 2-methoxycarbonyleth-1-yl |
| 51 | — | CH₃ | 2-aminocarbonyleth-1-yl |
| 52 | — | CH₃ | 2-N-methylaminocarbonyleth-1-yl |
| 53 | — | CH₃ | 2-dimethylaminocarbonyleth-1-yl |
| 54 | — | CH₃ | 2-aminoeth-1-yl |
| 55 | — | CH₃ | 2-aminoprop-1-yl |
| 56 | — | CH₃ | 4-aminobut-1-yl |
| 57 | — | CH₃ | 3-dimethylaminoprop-1-yl |
| 58 | — | CH₃ | 4-aminothiocarbonylbut-1-yl |
| 59 | — | CH₃ | 6-aminocarbonylhex-1-yl |
| 60 | — | CH₃ | 3-aminothiocarbonylprop-1-yl |
| 61 | — | CH₃ | 2-aminothiocarbonyleth-1-yl |
| 62 | — | CH₃ | aminothiocarbonylmethyl |
| 63 | — | CH₃ | 4-(N,N-dimethylamino)but-1-yl |
| 64 | — | CH₃ | 2-(methylthio)eth-1-yl |
| 65 | — | CH₃ | 2-(methylsulfonyl)eth-1-yl |
| 66 | — | CH₃ | 4-(methylthio)prop-1-yl |
| 67 | — | CH₃ | 4-(methylsulfonyl)prop-1-yl |
| 68 | — | CH₃ | benzyl |
| 69 | — | CH₃ | 2-F—C₆H₄—CH₂ |
| 70 | — | CH₃ | 3-F—C₆H₄—CH₂ |
| 71 | — | CH₃ | 4-F—C₆H₄—CH₂ |
| 72 | — | CH₃ | 2,3-F₂—C₆H₃—CH₂ |
| 73 | — | CH₃ | 2,4-F₂—C₆H₃—CH₂ |
| 74 | — | CH₃ | 2,5-F₂—C₆H₃—CH₂ |
| 75 | — | CH₃ | 2,6-F₂—C₆H₃—CH₂ |
| 76 | — | CH₃ | 3,4-F₂—C₆H₃—CH₂ |
| 77 | — | CH₃ | 3,5-F₂—C₆H₃—CH₂ |
| 78 | — | CH₃ | 2-Cl—C₆H₄—CH₂ |
| 79 | — | CH₃ | 3-Cl—C₆H₄—CH₂ |
| 80 | — | CH₃ | 4-Cl—C₆H₄—CH₂ |
| 81 | — | CH₃ | 2,3-Cl₂—C₆H₃—CH₂ |
| 82 | — | CH₃ | 2,4-Cl₂—C₆H₃—CH₂ |
| 83 | — | CH₃ | 2,5-Cl₂—C₆H₃—CH₂ |
| 84 | — | CH₃ | 2,6-Cl₂—C₆H₃—CH₂ |
| 85 | — | CH₃ | 3,4-Cl₂—C₆H₃—CH₂ |
| 86 | — | CH₃ | 3,5-Cl₂—C₆H₃—CH₂ |
| 87 | — | CH₃ | 2,3,4-Cl₃—C₆H₂—CH₂ |
| 88 | — | CH₃ | 2,3,5-Cl₃—C₆H₂—CH₂ |
| 89 | — | CH₃ | 2,3,6-Cl₃—C₆H₂—CH₂ |
| 90 | — | CH₃ | 2,4,5-Cl₃—C₆H₂—CH₂ |
| 91 | — | CH₃ | 2,4,6-Cl₃—C₆H₂—CH₂ |
| 92 | — | CH₃ | 3,4,5-Cl₃—C₆H₂—CH₂ |
| 93 | — | CH₃ | 2-Br—C₆H₄—CH₂ |
| 94 | — | CH₃ | 3-Br—C₆H₄—CH₂ |
| 95 | — | CH₃ | 4-Br—C₆H₄—CH₂ |
| 96 | — | CH₃ | 2,3-Br₂—C₆H₃—CH₂ |
| 97 | — | CH₃ | 2,4-Br₂—C₆H₃—CH₂ |
| 98 | — | CH₃ | 2,5-Br₂—C₆H₃—CH₂ |
| 99 | — | CH₃ | 2,6-Br₂—C₆H₃—CH₂ |
| 100 | — | CH₃ | 3,4-Br₂—C₆H₃—CH₂ |
| 101 | — | CH₃ | 3,5-Br₂—C₆H₃—CH₂ |
| 102 | — | CH₃ | 2-F, 3-Cl—C₆H₃—CH₂ |
| 103 | — | CH₃ | 2-F, 4-Cl—C₆H₃—CH₂ |
| 104 | — | CH₃ | 2-F, 5-Cl—C₆H₃—CH₂ |
| 105 | — | CH₃ | 2-F, 3-Br—C₆H₃—CH₂ |
| 106 | — | CH₃ | 2-F, 4-Br—C₆H₃—CH₂ |
| 107 | — | CH₃ | 2-F, 5-Br—C₆H₃—CH₂ |
| 108 | — | CH₃ | 2-Cl, 3-Br—C₆H₃—CH₂ |
| 109 | — | CH₃ | 2-Cl, 4-Br—C₆H₃—CH₂ |
| 110 | — | CH₃ | 2-Cl, 5-Br—C₆H₃—CH₂ |
| 111 | — | CH₃ | 3-F, 4-Cl—C₆H₃—CH₂ |
| 112 | — | CH₃ | 3-F, 5-Cl—C₆H₃—CH₂ |
| 113 | — | CH₃ | 3-F, 6-Cl—C₆H₃—CH₂ |
| 114 | — | CH₃ | 3-F, 4-Br—C₆H₃—CH₂ |
| 115 | — | CH₃ | 3-F, 5-Br—C₆H₃—CH₂ |
| 116 | — | CH₃ | 3-F, 6-Br—C₆H₃—CH₂ |
| 117 | — | CH₃ | 3-Cl, 4-Br—C₆H₃—CH₂ |
| 118 | — | CH₃ | 3-Cl, 5-Br—C₆H₃—CH₂ |
| 119 | — | CH₃ | 3-Cl, 6-Br—C₆H₃—CH₂ |
| 120 | — | CH₃ | 4-F, 5-Cl—C₆H₃—CH₂ |
| 121 | — | CH₃ | 4-F, 6-Cl—C₆H₃—CH₂ |
| 122 | — | CH₃ | 4-F, 5-Br—C₆H₃—CH₂ |
| 123 | — | CH₃ | 4-F, 6-Br—C₆H₃—CH₂ |
| 124 | — | CH₃ | 4-Cl, 5-Br—C₆H₃—CH₂ |
| 125 | — | CH₃ | 5-F, 6-Cl—C₆H₃—CH₂ |
| 126 | — | CH₃ | 5-F, 6-Br—C₆H₃—CH₂ |
| 127 | — | CH₃ | 5-Cl, 6-Br—C₆H₃—CH₂ |
| 128 | — | CH₃ | 3-Br, 4-Cl, 5-Br—C₆H₂—CH₂ |
| 129 | — | CH₃ | 2-CN—C₆H₄—CH₂ |
| 130 | — | CH₃ | 3-CN—C₆H₄—CH₂ |
| 131 | — | CH₃ | 4-CN—C₆H₄—CH₂ |
| 132 | — | CH₃ | 2-NO₂—C₆H₄—CH₂ |
| 133 | — | CH₃ | 3-NO₂—C₆H₄—CH₂ |
| 134 | — | CH₃ | 4-NO₂—C₆H₄—CH₂ |
| 135 | — | CH₃ | 2-CH₃—C₆H₄—CH₂ |
| 136 | — | CH₃ | 3-CH₃—C₆H₄—CH₂ |
| 137 | — | CH₃ | 4-CH₃—C₆H₄—CH₂ |
| 138 | — | CH₃ | 2,3-(CH₃)₂—C₆H₃—CH₂ |
| 139 | — | CH₃ | 2,4-(CH₃)₂—C₆H₃—CH₂ |
| 140 | — | CH₃ | 2,5-(CH₃)₂—C₆H₃—CH₂ |
| 141 | — | CH₃ | 2,6-(CH₃)₂—C₆H₃—CH₂ |
| 142 | — | CH₃ | 3,4-(CH₃)₂—C₆H₃—CH₂ |
| 143 | — | CH₃ | 3,5-(CH₃)₂—C₆H₃—CH₂ |
| 144 | — | CH₃ | 2-C₂H₅—C₆H₄—CH₂ |
| 145 | — | CH₃ | 3-C₂H₅—C₆H₄—CH₂ |
| 146 | — | CH₃ | 4-C₂H₅—C₆H₄—CH₂ |
| 147 | — | CH₃ | 2-i-C₃H₇—C₆H₄—CH₂ |
| 148 | — | CH₃ | 3-i-C₃H₇—C₆H₄—CH₂ |
| 149 | — | CH₃ | 4-i-C₃H₇—C₆H₄—CH₂ |
| 150 | — | CH₃ | 2-cyclohexyl-C₆H₄—CH₂ |
| 151 | — | CH₃ | 3-cyclohexyl-C₆H₄—CH₂ |
| 152 | — | CH₃ | 4-cyclohexyl-C₆H₄—CH₂ |
| 153 | — | CH₃ | 2-vinyl-C₆H₄—CH₂ |
| 154 | — | CH₃ | 3-vinyl-C₆H₄—CH₂ |
| 155 | — | CH₃ | 4-vinyl-C₆H₄—CH₂ |
| 156 | — | CH₃ | 2-allyl-C₆H₄—CH₂ |
| 157 | — | CH₃ | 3-allyl-C₆H₄—CH₂ |
| 158 | — | CH₃ | 4-allyl-C₆H₄—CH₂ |
| 159 | — | CH₃ | 2-C₆H₅—C₆H₄—CH₂ |
| 160 | — | CH₃ | 3-C₆H₅—C₆H₄—CH₂ |
| 161 | — | CH₃ | 4-C₆H₅—C₆H₄—CH₂ |
| 162 | — | CH₃ | 3-CH₃, 5-t-C₄H₉—C₆H₃—CH₂ |
| 163 | — | CH₃ | 2-OH—C₆H₄—CH₂ |
| 164 | — | CH₃ | 3-OH—C₆H₄—CH₂ |
| 165 | — | CH₃ | 4-OH—C₆H₄—CH₂ |
| 166 | — | CH₃ | 2-OCH₃—C₆H₄—CH₂ |
| 167 | — | CH₃ | 3-OCH₃—C₆H₄—CH₂ |
| 168 | — | CH₃ | 4-OCH₃—C₆H₄—CH₂ |
| 169 | — | CH₃ | 2-O-allyl-C₆H₄—CH₂ |
| 170 | — | CH₃ | 3-O-allyl-C₆H₄—CH₂ |
| 171 | — | CH₃ | 4-O-allyl-C₆H₄—CH₂ |
| 172 | — | CH₃ | 2-CF₃—C₆H₄—CH₂ |
| 173 | — | CH₃ | 3-CF₃—C₆H₄—CH₂ |
| 174 | — | CH₃ | 4-CF₃—C₆H₄—CH₂ |
| 175 | — | CH₃ | 2-acetyl-C₆H₄—CH₂ |
| 176 | — | CH₃ | 3-acetyl-C₆H₄—CH₂ |
| 177 | — | CH₃ | 4-acetyl-C₆H₄—CH₂ |
| 178 | — | CH₃ | 2-methoxycarbonyl-C₆H₄—CH₂ |
| 179 | — | CH₃ | 3-methoxycarbonyl-C₆H₄—CH₂ |
| 180 | — | CH₃ | 4-methoxycarbonyl-C₆H₄—CH₂ |
| 181 | — | CH₃ | 2-aminocarbonyl-C₆H₄—CH₂ |
| 182 | — | CH₃ | 3-aminocarbonyl-C₆H₄—CH₂ |
| 183 | — | CH₃ | 4-aminocarbonyl-C₆H₄—CH₂ |
| 184 | — | CH₃ | 2-dimethylaminocarbonyl-C₆H₄—CH₂ |
| 185 | — | CH₃ | 3-dimethylaminocarbonyl-C₆H₄—CH₂ |
| 186 | — | CH₃ | 4-dimethylaminocarbonyl-C₆H₄—CH₂ |
| 187 | — | CH₃ | 2-(N-methylaminocarbonyl)-C₆H₄—CH₂ |
| 188 | — | CH₃ | 3-(N-methylaminocarbonyl)-C₆H₄—CH₂ |
| 189 | — | CH₃ | 4-(N-methylaminocarbonyl)-C₆H₄—CH₂ |
| 190 | — | CH₃ | 2-H₂N—C₆H₄—CH₂ |
| 191 | — | CH₃ | 3-H₂N—C₆H₄—CH₂ |
| 192 | — | CH₃ | 4-H₂N—C₆H₄—CH₂ |
| 193 | — | CH₃ | 2-aminothiocarbonyl-C₆H₄—CH₂ |
| 194 | — | CH₃ | 3-aminothiocarbonyl-C₆H₄—CH₂ |
| 195 | — | CH₃ | 4-aminothiocarbonyl-C₆H₄—CH₂ |
| 196 | — | CH₃ | 2-SCH₃—C₆H₄—CH₂ |
| 197 | — | CH₃ | 3-SCH₃—C₆H₄—CH₂ |
| 198 | — | CH₃ | 4-SCH₃—C₆H₄—CH₂ |
| 199 | — | CH₃ | 2-SO₂CH₃—C₆H₄—CH₂ |
| 200 | — | CH₃ | 3-SO₂CH₃—C₆H₄—CH₂ |
| 201 | — | CH₃ | 4-SO₂CH₃—C₆H₄—CH₂ |
| 202 | — | CH₃ | 2-OCF₃—C₆H₄—CH₂ |
| 203 | — | CH₃ | 3-OCF₃—C₆H₄—CH₂ |
| 204 | — | CH₃ | 4-OCF₃—C₆H₄—CH₂ |
| 205 | — | CH₃ | 2-OCHF₂—C₆H₄—CH₂ |
| 206 | — | CH₃ | 3-OCHF₂—C₆H₄—CH₂ |
| 207 | — | CH₃ | 4-OCHF₂—C₆H₄—CH₂ |

TABLE A-continued

| | | | |
|---|---|---|---|
| 208 | — | CH$_3$ | 3-CF$_3$, 4-OCF$_3$—C$_6$H$_3$—CH$_2$ |
| 209 | — | CH$_3$ | 1-naphthyl-CH$_2$ |
| 210 | — | CH$_3$ | 2-naphthyl-CH$_2$ |
| 211 | — | CH$_3$ | 2-phenoxyeth-1-yl |
| 212 | — | CH$_3$ | 2-(2'-chlorophenoxy)eth-1-yl |
| 213 | — | CH$_3$ | 2-(3'-chlorophenoxy)eth-1-yl |
| 214 | — | CH$_3$ | 2-(4'-chlorophenoxy)eth-1-yl |
| 215 | — | CH$_3$ | 2-(3',5'-dichlorophenoxy)eth-1-yl |
| 216 | — | CH$_3$ | 2-(4'-cyanophenoxy)eth-1-yl |
| 217 | — | CH$_3$ | 2-(3'-methylphenoxy)eth-1-yl |
| 218 | — | CH$_3$ | 2-(2'-nitrophenoxy)eth-1-yl |
| 219 | — | CH$_3$ | 3-phenoxyprop-1-yl |
| 220 | — | CH$_3$ | 3-(4'-chlorophenoxy)prop-1-yl |
| 221 | — | CH$_3$ | 3-(3'-cyanophenoxy)prop-1-yl |
| 222 | — | CH$_3$ | 3-(2'-methylphenoxy)prop-1-yl |
| 223 | — | CH$_3$ | 4-phenoxybut-1-yl |
| 224 | — | CH$_3$ | 2-phenyleth-1-yl |
| 225 | — | CH$_3$ | 2-(4'-chlorophenyl)eth-1-yl |
| 226 | — | CH$_3$ | 2-(3'-cyanophenyl)eth-1-yl |
| 227 | — | CH$_3$ | 2-(2'-methylphenyl)eth-1-yl |
| 228 | — | CH$_3$ | 3-phenylprop-1-yl |
| 229 | — | CH$_3$ | 4-phenylbut-1-yl |
| 230 | — | CH$_3$ | 2-pyridylmethyl |
| 231 | — | CH$_3$ | 3-pyridylmethyl |
| 232 | — | CH$_3$ | 4-pyridylmethyl |
| 233 | — | CH$_3$ | 4-chloropyridin-2-ylmethyl |
| 234 | — | CH$_3$ | 5-chloropyridin-2-ylmethyl |
| 235 | — | CH$_3$ | 6-chloropyridin-2-ylmethyl |
| 236 | — | CH$_3$ | 5-chloropyridin-3-ylmethyl |
| 237 | — | CH$_3$ | 6-chloropyridin-3-ylmethyl |
| 238 | — | CH$_3$ | 2-chloropyridin-4-ylmethyl |
| 239 | — | CH$_3$ | 2-pyrimidinylmethyl |
| 240 | — | CH$_3$ | 4-chloropyrimidin-2-ylmethyl |
| 241 | — | CH$_3$ | 5-chloropyrimidin-2-ylmethyl |
| 242 | — | CH$_3$ | 2-chloropyrimidin-4-ylmethyl |
| 243 | — | CH$_3$ | 6-chloropyrimidin-4-ylmethyl |
| 244 | — | CH$_3$ | 2-chloropyrimidin-5-ylmethyl |
| 245 | — | CH$_3$ | 4-pyridazinylmethyl |
| 246 | — | CH$_3$ | 2-pyrazinylmethyl |
| 247 | — | CH$_3$ | 5-chloropyrazin-2-ylmethyl |
| 248 | — | CH$_3$ | 6-chloropyrazin-2-ylmethyl |
| 249 | — | CH$_3$ | 3-pyridazinylmethyl |
| 250 | — | CH$_3$ | 6-chloropyridazin-3-ylmethyl |
| 251 | — | CH$_3$ | 1,3,5-triazinylmethyl |
| 252 | — | CH$_3$ | 2-furylmethyl |
| 253 | — | CH$_3$ | 3-furylmethyl |
| 254 | — | CH$_3$ | 4-bromofur-2-ylmethyl |
| 255 | — | CH$_3$ | 5-chlorofur-2-ylmethyl |
| 256 | — | CH$_3$ | 2-thienylmethyl |
| 257 | — | CH$_3$ | 3-thienylmethyl |
| 258 | — | CH$_3$ | 5-methylthien-3-ylmethyl |
| 259 | — | CH$_3$ | 5-chlorothien-2-ylmethyl |
| 260 | — | CH$_3$ | 2-chlorothien-4-ylmethyl |
| 261 | — | CH$_3$ | 2-pyrrolylmethyl |
| 262 | — | CH$_3$ | 3-pyrrolylmethyl |
| 263 | — | CH$_3$ | 2-oxazolylmethyl |
| 264 | — | CH$_3$ | 4-methyloxazol-2-ylmethyl |
| 265 | — | CH$_3$ | 5-methyloxazol-2-ylmethyl |
| 266 | — | CH$_3$ | 4-chlorooxazol-2-ylmethyl |
| 267 | — | CH$_3$ | 5-chlorooxazol-2-ylmethyl |
| 268 | — | CH$_3$ | 4-oxazolylmethyl |
| 269 | — | CH$_3$ | 2-methyloxazol-4-ylmethyl |
| 270 | — | CH$_3$ | 5-methyloxazol-4-ylmethyl |
| 271 | — | CH$_3$ | 2-chlorooxazol-4-ylmethyl |
| 272 | — | CH$_3$ | 5-chlorooxazol-4-ylmethyl |
| 273 | — | CH$_3$ | 5-oxazolylmethyl |
| 274 | — | CH$_3$ | 2-methyloxazol-5-ylmethyl |
| 275 | — | CH$_3$ | 4-methyloxazol-5-ylmethyl |
| 276 | — | CH$_3$ | 2-chlorooxazol-5-ylmethyl |
| 277 | — | CH$_3$ | 4-chlorooxazol-5-ylmethyl |
| 278 | — | CH$_3$ | 2-thiazolylmethyl |
| 279 | — | CH$_3$ | 4-methylthiazol-2-ylmethyl |
| 280 | — | CH$_3$ | 5-methylthiazol-2-ylmethyl |
| 281 | — | CH$_3$ | 4-chlorothiazol-2-ylmethyl |
| 282 | — | CH$_3$ | 5-chlorothiazol-2-ylmethyl |
| 283 | — | CH$_3$ | 4-thiazolylmethyl |
| 284 | — | CH$_3$ | 2-methylthiazol-4-ylmethyl |
| 285 | — | CH$_3$ | 5-methylthiazol-4-ylmethyl |
| 286 | — | CH$_3$ | 2-chlorothiazol-4-ylmethyl |
| 287 | — | CH$_3$ | 5-chlorothiazol-4-ylmethyl |
| 288 | — | CH$_3$ | 5-thiazolylmethyl |
| 289 | — | CH$_3$ | 2-methylthiazol-5-ylmethyl |
| 290 | — | CH$_3$ | 4-methylthiazol-5-ylmethyl |
| 291 | — | CH$_3$ | 2-chlorothiazol-5-ylmethyl |
| 292 | — | CH$_3$ | 4-chlorothiazol-5-ylmethyl |
| 293 | — | CH$_3$ | 3-isoxazolylmethyl |
| 294 | — | CH$_3$ | 4-methylisoxazol-3-ylmethyl |
| 295 | — | CH$_3$ | 5-methylisoxazol-3-ylmethyl |
| 296 | — | CH$_3$ | 4-chloroisoxazol-3-ylmethyl |
| 297 | — | CH$_3$ | 5-chloroisoxazol-3-ylmethyl |
| 298 | — | CH$_3$ | 4-isoxazolylmethyl |
| 299 | — | CH$_3$ | 3-methylisoxazol-4-ylmethyl |
| 300 | — | CH$_3$ | 5-methylisoxazol-4-ylmethyl |
| 301 | — | CH$_3$ | 3-chloroisoxazol-4-ylmethyl |
| 302 | — | CH$_3$ | 5-chloroisoxazol-4-ylmethyl |
| 303 | — | CH$_3$ | 5-isoxazolylmethyl |
| 304 | — | CH$_3$ | 3-methylisoxazol-5-ylmethyl |
| 305 | — | CH$_3$ | 4-methylisoxazol-5-ylmethyl |
| 306 | — | CH$_3$ | 3-chloroisoxazol-5-ylmethyl |
| 307 | — | CH$_3$ | 4-chloroisoxazol-5-ylmethyl |
| 308 | — | CH$_3$ | 3-isothiazolylmethyl |
| 309 | — | CH$_3$ | 4-methylisothiazol-3-ylmethyl |
| 310 | — | CH$_3$ | 5-methylisothiazol-3-ylmethyl |
| 311 | — | CH$_3$ | 4-chloroisothiazol-3-ylmethyl |
| 312 | — | CH$_3$ | 5-chloroisothiazol-3-ylmethyl |
| 313 | — | CH$_3$ | 4-isothiazolylmethyl |
| 314 | — | CH$_3$ | 3-methylisothiazol-4-ylmethyl |
| 315 | — | CH$_3$ | 5-methylisothiazol-4-ylmethyl |
| 316 | — | CH$_3$ | 3-chloroisothiazol-4-ylmethyl |
| 317 | — | CH$_3$ | 5-chloroisothiazol-4-ylmethyl |
| 318 | — | CH$_3$ | 5-isothiazolylmethyl |
| 319 | — | CH$_3$ | 3-methylisothiazol-5-ylmethyl |
| 320 | — | CH$_3$ | 4-methylisothiazol-5-ylmethyl |
| 321 | — | CH$_3$ | 3-chloroisothiazol-5-ylmethyl |
| 322 | — | CH$_3$ | 4-chloroisothiazol-5-ylmethyl |
| 323 | — | CH$_3$ | 4-imidazolylmethyl |
| 324 | — | CH$_3$ | 1-phenylpyrazol-3-ylmethyl |
| 325 | — | CH$_3$ | 1-methylimidazol-4-ylmethyl |
| 326 | — | CH$_3$ | 1-phenyl-1,2,4-triazol-3-ylmethyl |
| 327 | — | CH$_3$ | 1,2,4-oxadiazol-3-ylmethyl |
| 328 | — | CH$_3$ | 5-chloro-1,2,4-oxadiazol-3-ylmethyl |
| 329 | — | CH$_3$ | 5-methyl-1,2,4-oxadiazol-3-ylmethyl |
| 330 | — | CH$_3$ | 5-trifluoromethyl-1,2,4-oxadiazol-3-ylmethyl |
| 331 | — | CH$_3$ | 1,3,4-oxadiazol-2-ylmethyl |
| 332 | — | CH$_3$ | 5-chloro-1,3,4-oxadiazol-2-ylmethyl |
| 333 | — | CH$_3$ | 5-methyl-1,3,4-oxadiazol-2-ylmethyl |
| 334 | — | CH$_3$ | 5-methoxy-1,3,4-oxadiazol-2-ylmethyl |
| 335 | — | CH$_3$ | 1,2,4-thiadiazol-3-ylmethyl |
| 336 | — | CH$_3$ | 5-chloro-1,2,4-thiadiazol-3-ylmethyl |
| 337 | — | CH$_3$ | 5-methyl-1,2,4-thiadiazol-3-ylmethyl |
| 338 | — | CH$_3$ | 1,3,4-thiadiazol-2-ylmethyl |
| 339 | — | CH$_3$ | 5-chloro-1,3,4-thiadiazol-2-ylmethyl |
| 340 | — | CH$_3$ | 5-methyl-1,3,4-thiadiazol-2-ylmethyl |
| 341 | — | CH$_3$ | 5-cyano-1,3,4-thiadiazol-2-ylmethyl |
| 342 | — | CH$_3$ | 2-(2'-pyridinyloxy)eth-1-yl |
| 343 | — | CH$_3$ | 2-(3'-pyridinyloxy)eth-1-yl |
| 344 | — | CH$_3$ | 2-(4'-pyridinyloxy)eth-1-yl |
| 345 | — | CH$_3$ | C$_6$H$_5$ |
| 346 | — | CH$_3$ | 2-Cl—C$_6$H$_4$ |
| 347 | — | CH$_3$ | 3-Cl—C$_6$H$_4$ |
| 348 | — | CH$_3$ | 4-Cl—C$_6$H$_4$ |
| 349 | — | CH$_3$ | 2,3-Cl$_2$—C$_6$H$_3$ |
| 350 | — | CH$_3$ | 2,4-Cl$_2$—C$_6$H$_3$ |
| 351 | — | CH$_3$ | 2,5-Cl$_2$—C$_6$H$_3$ |
| 352 | — | CH$_3$ | 3,4-Cl$_2$—C$_6$H$_3$ |
| 353 | — | CH$_3$ | 3,5-Cl$_2$—C$_6$H$_3$ |
| 354 | — | CH$_3$ | 4-CN—C$_6$H$_4$ |
| 355 | — | CH$_3$ | 2-NO$_2$—C$_6$H$_4$ |
| 356 | — | CH$_3$ | 3-NO$_2$—C$_6$H$_4$ |
| 357 | — | CH$_3$ | 4-NO$_2$—C$_6$H$_4$ |
| 358 | — | CH$_3$ | 2,4-(NO$_2$)$_2$—C$_6$H$_3$ |
| 359 | — | CH$_3$ | 2-CH$_3$—C$_6$H$_4$ |
| 360 | — | CH$_3$ | 3-CH$_3$—C$_6$H$_4$ |
| 361 | — | CH$_3$ | 4-CH$_3$—C$_6$H$_4$ |
| 362 | — | CH$_3$ | 2,3-(CH$_3$)$_2$—C$_6$H$_3$ |
| 363 | — | CH$_3$ | 2,4-(CH$_3$)$_2$—C$_6$H$_3$ |
| 364 | — | CH$_3$ | 2,5-(CH$_3$)$_2$—C$_6$H$_3$ |
| 365 | — | CH$_3$ | 2,6-(CH$_3$)$_2$—C$_6$H$_3$ |

TABLE A-continued

| | | | |
|---|---|---|---|
| 366 | — | CH$_3$ | 2-C$_6$H$_5$—C$_6$H$_4$ |
| 367 | — | CH$_3$ | 3-C$_6$H$_5$—C$_6$H$_4$ |
| 368 | — | CH$_3$ | 4-C$_6$H$_5$—C$_6$H$_4$ |
| 369 | — | CH$_3$ | 3-OCH$_3$—C$_6$H$_4$ |
| 370 | — | CH$_3$ | 4-OCH$_3$—C$_6$H$_4$ |
| 371 | — | CH$_3$ | 3-acetyl-C$_6$H$_4$ |
| 372 | — | CH$_3$ | 4-acetyl-C$_6$H$_4$ |
| 373 | — | CH$_3$ | 3-methoxycarbonyl-C$_6$H$_4$ |
| 374 | — | CH$_3$ | 4-methoxycarbonyl-C$_6$H$_4$ |
| 375 | — | CH$_3$ | 3-CF$_3$—C$_6$H$_4$ |
| 376 | — | CH$_3$ | 4-CF$_3$—C$_6$H$_4$ |
| 377 | — | CH$_3$ | 2-naphthyl |
| 378 | — | CH$_3$ | 6-chloropyridazin-3-yl |
| 379 | — | CH$_3$ | 5-chloropyrazin-2-yl |
| 380 | — | CH$_3$ | quinolin-2-yl |
| 381 | — | CH$_3$ | 2,5-dimethylpyrazin-3-yl |
| 382 | — | CH$_3$ | pyrazin-2-yl |
| 383 | — | CH$_3$ | 3-chloropyrid-2-yl |
| 384 | — | CH$_3$ | 6-chloropyrid-2-yl |
| 385 | — | CH$_3$ | 4-trifluoromethyl, 6-chloropyrid-2-yl |
| 386 | — | CH$_3$ | 4-trifluoromethylpyrid-2-yl |
| 387 | — | CH$_3$ | 6-trifluoromethylpyrid-2-yl |
| 388 | — | CH$_3$ | 6-methoxypyrid-2-yl |
| 389 | — | CH$_3$ | 5-chloropyrid-2-yl |
| 390 | — | CH$_3$ | pyrid-2-yl |
| 391 | — | CH$_3$ | benzothiazol-2-yl |
| 392 | — | CH$_3$ | 7-chloroquinolin-4-yl |
| 393 | — | CH$_3$ | 3-nitropyrid-2-yl |
| 394 | — | CH$_3$ | pyrrol-3-yl |
| 395 | — | CH$_3$ | pyrrol-2-yl |
| 396 | — | CH$_3$ | 2,6-dioctylpyrid-4-yl |
| 397 | — | CH$_3$ | 5-nitropyrid-2-yl |
| 398 | — | CH$_3$ | pyrid-4-yl |
| 399 | — | CH$_3$ | pyrid-3-yl |
| 400 | — | CH$_3$ | pyrimidin-2-yl |
| 401 | — | CH$_3$ | pyrimidin-4-yl |
| 402 | — | CH$_3$ | quinazolin-4-yl |
| 403 | — | CH$_3$ | 6-chloropyrimidin-4-yl |
| 404 | — | CH$_3$ | 6-methoxypyrimidin-4-yl |
| 405 | — | CH$_3$ | 2,5,6-trichloropyrimidin-4-yl |
| 406 | — | CH$_3$ | 2,6-dimethylpyrimidin-4-yl |
| 407 | — | CH$_3$ | 2-methyl, 6-chloropyrimidin-4-yl |
| 408 | — | CH$_3$ | 2-methyl, 6-ethoxypyrimidin-4-yl |
| 409 | — | CH$_3$ | 4,5,6-trichloropyrimidin-2-yl |
| 410 | — | CH$_3$ | 4,6-dimethoxypyrimidin-2-yl |
| 411 | — | CH$_3$ | 4,6-dimethylpyrimidin-2-yl |
| 412 | — | CH$_3$ | 4,6-dichloropyrimidin-2-yl |
| 413 | — | CH$_3$ | 4-methyl, 6-methoxypyrimidin-2-yl |
| 414 | — | CH$_3$ | 4-chloro, 6-methoxypyrimidin-2-yl |
| 415 | — | CH$_3$ | 6-chloroquinoxalin-2-yl |
| 416 | — | CH$_3$ | 3,6-dichloro-1,2,4-triazin-5-yl |
| 417 | — | CH$_3$ | 4-methoxy-1,3,5-triazin-2-yl |
| 418 | — | CH$_3$ | 4-ethoxy-1,3,5-triazin-2-yl |
| 419 | — | CH$_3$ | 4,6-dichloro-1,3,5-triazin-2-yl |
| 420 | — | CH$_3$ | 4-ethoxy, 6-chloro-1,3,5-triazin-2-yl |
| 421 | — | CH$_3$ | isoxazol-3-yl |
| 422 | — | CH$_3$ | thien-2-yl |
| 423 | — | CH$_3$ | fur-2-yl |
| 424 | — | CH$_3$ | thiatriazol-5-yl |
| 425 | — | CH$_3$ | (E)-1-chloropropen-3-yl |
| 426 | — | CH$_3$ | (E)-1-(4'-chlorophenyl)but-2-en-1-yl |
| 427 | — | CH$_3$ | propyn-3-yl |
| 428 | — | CH$_3$ | methylcarbonyl |
| 429 | — | CH$_3$ | 2-t-C$_4$H$_9$—C$_6$H$_4$—CH$_2$ |
| 430 | — | CH$_3$ | 3-t-C$_4$H$_9$—C$_6$H$_4$—CH$_2$ |
| 431 | — | CH$_3$ | 4-t-C$_4$H$_9$—C$_6$H$_4$—CH$_2$ |
| 432 | — | CH$_3$ | 2-(4'-chlorothiazol-2'-yloxy)eth-1-yl |
| 433 | — | CH$_3$ | 2-(1'-methylpyrazol-4'-yloxy)eth-1-yl |
| 434 | — | CH$_3$ | 4-Br—C$_6$H$_4$ |
| 435 | — | CH$_3$ | 3,5-(CH$_3$)$_2$—C$_6$H$_3$ |
| 436 | — | CH$_3$ | 4-C$_2$H$_5$—C$_6$H$_4$ |
| 437 | — | CH$_3$ | 3-dimethylaminocarbonyl-C$_6$H$_4$ |
| 438 | — | CH$_3$ | 4-dimethylaminocarbonyl-C$_6$H$_4$ |
| 439 | — | CH$_3$ | 2-hydroxyprop-1-yl |
| 440 | — | CH$_3$ | 6-hydroxy-2-methylpyrimidin-4-ylmethyl |
| 441 | — | CH$_3$ | [6-OH,2-CH(CH$_3$)$_2$-pyrimidin-4-yl]-CH$_2$ |
| 442 | — | CH$_3$ | [6-OH,2-CH(CH$_2$)$_2$-pyrimidin-4-yl]-CH$_2$ |
| 443 | — | CH$_3$ | 5-(2'-furan)-pent-1-yl |
| 444 | — | CH$_3$ | 5-(2'-N-methylpyrrole)-pent-1-yl |
| 445 | — | CH$_3$ | [2-(4-Cl—C$_6$H$_4$)-oxazol-4-yl]-CH$_2$ |
| 446 | — | CH$_3$ | 3-CF$_3$-pyridin-2-yl |
| 447 | — | CH$_3$ | 5-CF$_3$-pyridin-2-yl |
| 448 | — | CH$_3$ | 6-(2'-thienyl)hex-1-yl |
| 449 | — | H | H |
| 450 | — | H | CH$_3$ |
| 451 | — | H | C$_2$H$_5$ |
| 452 | — | H | n-C$_3$H$_7$ |
| 453 | — | H | i-C$_3$H$_7$ |
| 454 | — | H | cyclopropyl |
| 455 | — | H | n-C$_4$H$_9$ |
| 456 | — | H | s-C$_4$H$_9$ |
| 457 | — | H | i-C$_4$H$_9$ |
| 458 | — | H | t-C$_4$H$_9$ |
| 459 | — | H | n-C$_5$H$_{11}$ |
| 460 | — | H | i-C$_5$H$_{11}$ |
| 461 | — | H | neo-C$_5$H$_{11}$ |
| 462 | — | H | cyclopentyl |
| 463 | — | H | n-C$_6$H$_{13}$ |
| 464 | — | H | cyclohexyl |
| 465 | — | H | CH$_2$CH$_2$Cl |
| 466 | — | H | (CH$_2$)$_4$Cl |
| 467 | — | H | CH$_2$CN |
| 468 | — | H | CH$_2$CH$_2$CN |
| 469 | — | H | (CH$_2$)$_3$CN |
| 470 | — | H | (CH$_2$)$_4$CN |
| 471 | — | H | (CH$_2$)$_6$CN |
| 472 | — | H | cyclohexylmethyl |
| 473 | — | H | 2-cyclohexyleth-1-yl |
| 474 | — | H | cyclopropylmethyl |
| 475 | — | H | 2-cyclopropyleth-1-yl |
| 476 | — | H | 2-methoxyeth-1-yl |
| 477 | — | H | 2-ethoxyeth-1-yl |
| 478 | — | H | 2-isopropoxyeth-1-yl |
| 479 | — | H | 3-methoxyprop-1-yl |
| 480 | — | H | 3-ethoxyprop-1-yl |
| 481 | — | H | 3-isopropoxyprop-1-yl |
| 482 | — | H | 4-methoxybut-1-yl |
| 483 | — | H | 4-isopropoxybut-1-yl |
| 484 | — | H | propen-3-yl |
| 485 | — | H | but-2-en-1-yl |
| 486 | — | H | 3-methylbut-2-en-1-yl |
| 487 | — | H | 2-vinyloxyeth-1-yl |
| 488 | — | H | allyloxyeth-1-yl |
| 489 | — | H | 2-trifluoromethoxyeth-1-yl |
| 490 | — | H | 3-trifluoromethoxyprop-1-yl |
| 491 | — | H | 4-difluoromethoxybut-1-yl |
| 492 | — | H | hydroxycarbonylmethyl |
| 493 | — | H | methoxycarbonylmethyl |
| 494 | — | H | aminocarbonylmethyl |
| 495 | — | H | N-methylaminocarbonylmethyl |
| 496 | — | H | N,N-dimethylaminocarbonyl-methyl |
| 497 | — | H | 2-hydroxycarbonyleth-1-yl |
| 498 | — | H | 2-methoxycarbonyleth-1-yl |
| 499 | — | H | 2-aminocarbonyleth-1-yl |
| 500 | — | H | 2-N-methylaminocarbonyleth-1-yl |
| 501 | — | H | 2-dimethylaminocarbonyleth-1-yl |
| 502 | — | H | 2-aminoeth-1-yl |
| 503 | — | H | 2-aminoprop-1-yl |
| 504 | — | H | 4-aminobut-1-yl |
| 505 | — | H | 3-dimethylaminoprop-1-yl |
| 506 | — | H | 4-aminothiocarbonylbut-1-yl |
| 507 | — | H | 6-aminocarbonylhex-1-yl |
| 508 | — | H | 3-aminothiocarbonylprop-1-yl |
| 509 | — | H | 2-aminothiocarbonyleth-1-yl |
| 510 | — | H | aminothiocarbonylmethyl |
| 511 | — | H | 4-(N,N-dimethylamino)but-1-yl |
| 512 | — | H | 2-(methylthio)eth-1-yl |
| 513 | — | H | 2-(methylsulfonyl)eth-1-yl |
| 514 | — | H | 4-(methylthio)prop-1-yl |
| 515 | — | H | 4-(methylsulfonyl)prop-1-yl |
| 516 | — | H | benzyl |
| 517 | — | H | 2-F—C$_6$H$_4$—CH$_2$ |
| 518 | — | H | 3-F—C$_6$H$_4$—CH$_2$ |
| 519 | — | H | 4-F—C$_6$H$_4$—CH$_2$ |
| 520 | — | H | 2,3-F$_2$—C$_6$H$_3$—CH$_2$ |
| 521 | — | H | 2,4-F$_2$—C$_6$H$_3$—CH$_2$ |
| 522 | — | H | 2,5-F$_2$—C$_6$H$_3$—CH$_2$ |
| 523 | — | H | 2,6-F$_2$—C$_6$H$_3$—CH$_2$ |

TABLE A-continued

| | | | |
|---|---|---|---|
| 524 | — | H | 3,4-F$_2$—C$_6$H$_3$—CH$_2$ |
| 525 | — | H | 3,5-F$_2$—C$_6$H$_3$—CH$_2$ |
| 526 | — | H | 2-Cl—C$_6$H$_4$—CH$_2$ |
| 527 | — | H | 3-Cl—C$_6$H$_4$—CH$_2$ |
| 528 | — | H | 4-Cl—C$_6$H$_4$—CH$_2$ |
| 529 | — | H | 2,3-Cl$_2$—C$_6$H$_3$—CH$_2$ |
| 530 | — | H | 2,4-Cl$_2$—C$_6$H$_3$—CH$_2$ |
| 531 | — | H | 2,5-Cl$_2$—C$_6$H$_3$—CH$_2$ |
| 532 | — | H | 2,6-Cl$_2$—C$_6$H$_3$—CH$_2$ |
| 533 | — | H | 3,4-Cl$_2$—C$_6$H$_3$—CH$_2$ |
| 534 | — | H | 3,5-Cl$_2$—C$_6$H$_3$—CH$_2$ |
| 535 | — | H | 2,3,4-Cl$_3$—C$_6$H$_2$—CH$_2$ |
| 536 | — | H | 2,3,5-Cl$_3$—C$_6$H$_2$—CH$_2$ |
| 537 | — | H | 2,3,6-Cl$_3$—C$_6$H$_2$—CH$_2$ |
| 538 | — | H | 2,4,5-Cl$_3$—C$_6$H$_2$—CH$_2$ |
| 539 | — | H | 2,4,6-Cl$_3$—C$_6$H$_2$—CH$_2$ |
| 540 | — | H | 3,4,5-Cl$_3$—C$_6$H$_2$—CH$_2$ |
| 541 | — | H | 2-Br—C$_6$H$_4$—CH$_2$ |
| 542 | — | H | 3-Br—C$_6$H$_4$—CH$_2$ |
| 543 | — | H | 4-Br—C$_6$H$_4$—CH$_2$ |
| 544 | — | H | 2,3-Br$_2$—C$_6$H$_3$—CH$_2$ |
| 545 | — | H | 2,4-Br$_2$—C$_6$H$_3$—CH$_2$ |
| 546 | — | H | 2,5-Br$_2$—C$_6$H$_3$—CH$_2$ |
| 547 | — | H | 2,6-Br$_2$—C$_6$H$_3$—CH$_2$ |
| 548 | — | H | 3,4-Br$_2$—C$_6$H$_3$—CH$_2$ |
| 549 | — | H | 3,5-Br$_2$—C$_6$H$_3$—CH$_2$ |
| 550 | — | H | 2-F, 3-Cl—C$_6$H$_3$—CH$_2$ |
| 551 | — | H | 2-F, 4-Cl—C$_6$H$_3$—CH$_2$ |
| 552 | — | H | 2-F, 5-Cl—C$_6$H$_3$—CH$_2$ |
| 553 | — | H | 2-F, 3-Br—C$_6$H$_3$—CH$_2$ |
| 554 | — | H | 2-F, 4-Br—C$_6$H$_3$—CH$_2$ |
| 555 | — | H | 2-F, 5-Br—C$_6$H$_3$—CH$_2$ |
| 556 | — | H | 2-Cl, 3-Br—C$_6$H$_3$—CH$_2$ |
| 557 | — | H | 2-Cl, 4-Br—C$_6$H$_3$—CH$_2$ |
| 558 | — | H | 2-Cl, 5-Br—C$_6$H$_3$—CH$_2$ |
| 559 | — | H | 3-F, 4-Cl—C$_6$H$_3$—CH$_2$ |
| 560 | — | H | 3-F, 5-Cl—C$_6$H$_3$—CH$_2$ |
| 561 | — | H | 3-F, 6-Cl—C$_6$H$_3$—CH$_2$ |
| 562 | — | H | 3-F, 4-Br—C$_6$H$_3$—CH$_2$ |
| 563 | — | H | 3-F, 5-Br—C$_6$H$_3$—CH$_2$ |
| 564 | — | H | 3-F, 6-Br—C$_6$H$_3$—CH$_2$ |
| 565 | — | H | 3-Cl, 4-Br—C$_6$H$_3$—CH$_2$ |
| 566 | — | H | 3-Cl, 5-Br—C$_6$H$_3$—CH$_2$ |
| 567 | — | H | 3-Cl, 6-Br—C$_6$H$_3$—CH$_2$ |
| 568 | — | H | 4-F, 5-Cl—C$_6$H$_3$—CH$_2$ |
| 569 | — | H | 4-F, 6-Cl—C$_6$H$_3$—CH$_2$ |
| 570 | — | H | 4-F, 5-Br—C$_6$H$_3$—CH$_2$ |
| 571 | — | H | 4-F, 6-Br—C$_6$H$_3$—CH$_2$ |
| 572 | — | H | 4-Cl, 5-Br—C$_6$H$_3$—CH$_2$ |
| 573 | — | H | 5-F, 6-Cl—C$_6$H$_3$—CH$_2$ |
| 574 | — | H | 5-F, 6-Br—C$_6$H$_3$—CH$_2$ |
| 575 | — | H | 5-Cl, 6-Br—C$_6$H$_3$—CH$_2$ |
| 576 | — | H | 3-Br, 4-Cl, 5-Br—C$_6$H$_2$—CH$_2$ |
| 577 | — | H | 2-CN—C$_6$H$_4$—CH$_2$ |
| 578 | — | H | 3-CN—C$_6$H$_4$—CH$_2$ |
| 579 | — | H | 4-CN—C$_6$H$_4$—CH$_2$ |
| 580 | — | H | 2-NO$_2$—C$_6$H$_4$—CH$_2$ |
| 581 | — | H | 3-NO$_2$—C$_6$H$_4$—CH$_2$ |
| 582 | — | H | 4-NO$_2$—C$_6$H$_4$—CH$_2$ |
| 583 | — | H | 2-CH$_3$—C$_6$H$_4$—CH$_2$ |
| 584 | — | H | 3-CH$_3$—C$_6$H$_4$—CH$_2$ |
| 585 | — | H | 4-CH$_3$—C$_6$H$_4$—CH$_2$ |
| 586 | — | H | 2,3-(CH$_3$)$_2$—C$_6$H$_3$—CH$_2$ |
| 587 | — | H | 2,4-(CH$_3$)$_2$—C$_6$H$_3$—CH$_2$ |
| 588 | — | H | 2,5-(CH$_3$)$_2$—C$_6$H$_3$—CH$_2$ |
| 589 | — | H | 2,6-(CH$_3$)$_2$—C$_6$H$_3$—CH$_2$ |
| 590 | — | H | 3,4-(CH$_3$)$_2$—C$_6$H$_3$—CH$_2$ |
| 591 | — | H | 3,5-(CH$_3$)$_2$—C$_6$H$_3$—CH$_2$ |
| 592 | — | H | 2-C$_2$H$_5$—C$_6$H$_4$—CH$_2$ |
| 593 | — | H | 3-C$_2$H$_5$—C$_6$H$_4$—CH$_2$ |
| 594 | — | H | 4-C$_2$H$_5$—C$_6$H$_4$—CH$_2$ |
| 595 | — | H | 2-i-C$_3$H$_7$—C$_6$H$_4$—CH$_2$ |
| 596 | — | H | 3-i-C$_3$H$_7$—C$_6$H$_4$—CH$_2$ |
| 597 | — | H | 4-i-C$_3$H$_7$—C$_6$H$_4$—CH$_2$ |
| 598 | — | H | 2-cyclohexyl-C$_6$H$_4$—CH$_2$ |
| 599 | — | H | 3-cyclohexyl-C$_6$H$_4$—CH$_2$ |
| 600 | — | H | 4-cyclohexyl-C$_6$H$_4$—CH$_2$ |
| 601 | — | H | 2-vinyl-C$_6$H$_4$—CH$_2$ |
| 602 | — | H | 3-vinyl-C$_6$H$_4$—CH$_2$ |
| 603 | — | H | 4-vinyl-C$_6$H$_4$—CH$_2$ |
| 604 | — | H | 2-allyl-C$_6$H$_4$—CH$_2$ |
| 605 | — | H | 3-allyl-C$_6$H$_4$—CH$_2$ |
| 606 | — | H | 4-allyl-C$_6$H$_4$—CH$_2$ |
| 607 | — | H | 2-C$_6$H$_5$—C$_6$H$_4$—CH$_2$ |
| 608 | — | H | 3-C$_6$H$_5$—C$_6$H$_4$—CH$_2$ |
| 609 | — | H | 4-C$_6$H$_5$—C$_6$H$_4$—CH$_2$ |
| 610 | — | H | 3-CH$_3$, 5-t-C$_4$H$_9$—C$_6$H$_3$—CH$_2$ |
| 611 | — | H | 2-OH—C$_6$H$_4$—CH$_2$ |
| 612 | — | H | 3-OH—C$_6$H$_4$—CH$_2$ |
| 613 | — | H | 4-OH—C$_6$H$_4$—CH$_2$ |
| 614 | — | H | 2-OCH$_3$—C$_6$H$_4$—CH$_2$ |
| 615 | — | H | 3-OCH$_3$—C$_6$H$_4$—CH$_2$ |
| 616 | — | H | 4-OCH$_3$—C$_6$H$_4$—CH$_2$ |
| 617 | — | H | 2-O-allyl-C$_6$H$_4$—CH$_2$ |
| 618 | — | H | 3-O-allyl-C$_6$H$_4$—CH$_2$ |
| 619 | — | H | 4-O-allyl-C$_6$H$_4$—CH$_2$ |
| 620 | — | H | 2-CF$_3$—C$_6$H$_4$—CH$_2$ |
| 621 | — | H | 3-CF$_3$—C$_6$H$_4$—CH$_2$ |
| 622 | — | H | 4-CF$_3$—C$_6$H$_4$—CH$_2$ |
| 623 | — | H | 2-acetyl-C$_6$H$_4$—CH$_2$ |
| 624 | — | H | 3-acetyl-C$_6$H$_4$—CH$_2$ |
| 625 | — | H | 4-acetyl-C$_6$H$_4$—CH$_2$ |
| 626 | — | H | 2-methoxycarbonyl-C$_6$H$_4$—CH$_2$ |
| 627 | — | H | 3-methoxycarbonyl-C$_6$H$_4$—CH$_2$ |
| 628 | — | H | 4-methoxycarbonyl-C$_6$H$_4$—CH$_2$ |
| 629 | — | H | 2-aminocarbonyl-C$_6$H$_4$—CH$_2$ |
| 630 | — | H | 3-aminocarbonyl-C$_6$H$_4$—CH$_2$ |
| 631 | — | H | 4-aminocarbonyl-C$_6$H$_4$—CH$_2$ |
| 632 | — | H | 2-dimethylaminocarbonyl-C$_6$H$_4$—CH$_2$ |
| 633 | — | H | 3-dimethylaminocarbonyl-C$_6$H$_4$—CH$_2$ |
| 634 | — | H | 4-dimethylaminocarbonyl-C$_6$H$_4$—CH$_2$ |
| 635 | — | H | 2-(N-methylaminocarbonyl)-C$_6$H$_4$—CH$_2$ |
| 636 | — | H | 3-(N-methylaminocarbonyl)-C$_6$H$_4$—CH$_2$ |
| 637 | — | H | 4-(N-methylaminocarbonyl)-C$_6$H$_4$—CH$_2$ |
| 638 | — | H | 2-H$_2$N—C$_6$H$_4$—CH$_2$ |
| 639 | — | H | 3-H$_2$N—C$_6$H$_4$—CH$_2$ |
| 640 | — | H | 4-H$_2$N—C$_6$H$_4$—CH$_2$ |
| 641 | — | H | 2-aminothiocarbonyl-C$_6$H$_4$—CH$_2$ |
| 642 | — | H | 3-aminothiocarbonyl-C$_6$H$_4$—CH$_2$ |
| 643 | — | H | 4-aminothiocarbonyl-C$_6$H$_4$—CH$_2$ |
| 644 | — | H | 2-SCH$_3$—C$_6$H$_4$—CH$_2$ |
| 645 | — | H | 3-SCH$_3$—C$_6$H$_4$—CH$_2$ |
| 646 | — | H | 4-SCH$_3$—C$_6$H$_4$—CH$_2$ |
| 647 | — | H | 2-SO$_2$CH$_3$—C$_6$H$_4$—CH$_2$ |
| 648 | — | H | 3-SO$_2$CH$_3$—C$_6$H$_4$—CH$_2$ |
| 649 | — | H | 4-SO$_2$CH$_3$—C$_6$H$_4$—CH$_2$ |
| 650 | — | H | 2-OCF$_3$—C$_6$H$_4$—CH$_2$ |
| 651 | — | H | 3-OCF$_3$—C$_6$H$_4$—CH$_2$ |
| 652 | — | H | 4-OCF$_3$—C$_6$H$_4$—CH$_2$ |
| 653 | — | H | 2-OCHF$_2$—C$_6$H$_4$—CH$_2$ |
| 654 | — | H | 3-OCHF$_2$—C$_6$H$_4$—CH$_2$ |
| 655 | — | H | 4-OCHF$_2$—C$_6$H$_4$—CH$_2$ |
| 656 | — | H | 3-CF$_3$, 4-OCF$_3$—C$_6$H$_3$—CH$_2$ |
| 657 | — | H | 1-naphthyl-CH$_2$ |
| 658 | — | H | 2-naphthyl-CH$_2$ |
| 659 | — | H | 2-phenoxyeth-1-yl |
| 660 | — | H | 2-(2'-chlorophenoxy)eth-1-yl |
| 661 | — | H | 2-(3'-chlorophenoxy)eth-1-yl |
| 662 | — | H | 2-(4'-chlorophenoxy)eth-1-yl |
| 663 | — | H | 2-(3',5'-dichlorophenoxy)eth-1-yl |
| 664 | — | H | 2-(4'-cyanophenoxy)eth-1-yl |
| 665 | — | H | 2-(3'-methylphenoxy)eth-1-yl |
| 666 | — | H | 2-(2'-nitrophenoxy)eth-1-yl |
| 667 | — | H | 3-phenoxyprop-1-yl |
| 668 | — | H | 3-(4'-chlorophenoxy)prop-1-yl |
| 669 | — | H | 3-(3'-cyanophenoxy)prop-1-yl |
| 670 | — | H | 3-(2'-methylphenoxy)prop-1-yl |
| 671 | — | H | 4-phenoxybut-1-yl |
| 672 | — | H | 2-phenyleth-1-yl |
| 673 | — | H | 2-(4'-chlorophenyl)eth-1-yl |
| 674 | — | H | 2-(3'-cyanophenyl)eth-1-yl |
| 675 | — | H | 2-(2'-methylphenyl)eth-1-yl |
| 676 | — | H | 3-phenylprop-1-yl |
| 677 | — | H | 4-phenylbut-1-yl |
| 678 | — | H | 2-pyridylmethyl |
| 679 | — | H | 3-pyridylmethyl |
| 680 | — | H | 4-pyridylmethyl |
| 681 | — | H | 4-chloropyridin-2-ylmethyl |

TABLE A-continued

| | | | |
|---|---|---|---|
| 682 | — | H | 5-chloropyridin-2-ylmethyl |
| 683 | — | H | 6-chloropyridin-2-ylmethyl |
| 684 | — | H | 5-chloropyridin-3-ylmethyl |
| 685 | — | H | 6-chloropyridin-3-ylmethyl |
| 686 | — | H | 2-chloropyridin-4-ylmethyl |
| 687 | — | H | 2-pyrimidinylmethyl |
| 688 | — | H | 4-chloropyrimidin-2-ylmethyl |
| 689 | — | H | 5-chloropyrimidin-2-ylmethyl |
| 690 | — | H | 2-chloropyrimidin-4-ylmethyl |
| 691 | — | H | 6-chloropyrimidin-4-ylmethyl |
| 692 | — | H | 2-chloropyrimidin-5-ylmethyl |
| 693 | — | H | 4-pyridazinylmethyl |
| 694 | — | H | 2-pyrazinylmethyl |
| 695 | — | H | 5-chloropyrazin-2-ylmethyl |
| 696 | — | H | 6-chloropyrazin-2-ylmethyl |
| 697 | — | H | 3-pyridazinylmethyl |
| 698 | — | H | 6-chloropyridazin-3-ylmethyl |
| 699 | — | H | 1,3,5-triazinylmethyl |
| 700 | — | H | 2-furylmethyl |
| 701 | — | H | 3-furylmethyl |
| 702 | — | H | 4-bromofur-2-ylmethyl |
| 703 | — | H | 5-chlorofur-2-ylmethyl |
| 704 | — | H | 2-thienylmethyl |
| 705 | — | H | 3-thienylmethyl |
| 706 | — | H | 5-methylthien-3-ylmethyl |
| 707 | — | H | 5-chlorothien-2-ylmethyl |
| 708 | — | H | 2-chlorothien-4-ylmethyl |
| 709 | — | H | 2-pyrrolylmethyl |
| 710 | — | H | 3-pyrrolylmethyl |
| 711 | — | H | 2-oxazolylmethyl |
| 712 | — | H | 4-methyloxazol-2-ylmethyl |
| 713 | — | H | 5-methyloxazol-2-ylmethyl |
| 714 | — | H | 4-chlorooxazol-2-ylmethyl |
| 715 | — | H | 5-chlorooxazol-2-ylmethyl |
| 716 | — | H | 4-oxazolylmethyl |
| 717 | — | H | 2-methyloxazol-4-ylmethyl |
| 718 | — | H | 5-methyloxazol-4-ylmethyl |
| 719 | — | H | 2-chlorooxazol-4-ylmethyl |
| 720 | — | H | 5-chlorooxazol-4-ylmethyl |
| 721 | — | H | 5-oxazolylmethyl |
| 722 | — | H | 2-methyloxazol-5-ylmethyl |
| 723 | — | H | 4-methyloxazol-5-ylmethyl |
| 724 | — | H | 2-chlorooxazol-5-ylmethyl |
| 725 | — | H | 4-chlorooxazol-5-ylmethyl |
| 726 | — | H | 2-thiazolylmethyl |
| 727 | — | H | 4-methylthiazol-2-ylmethyl |
| 728 | — | H | 5-methylthiazol-2-ylmethyl |
| 729 | — | H | 4-chlorothiazol-2-ylmethyl |
| 730 | — | H | 5-chlorothiazol-2-ylmethyl |
| 731 | — | H | 4-thiazolylmethyl |
| 732 | — | H | 2-methylthiazol-4-ylmethyl |
| 733 | — | H | 5-methylthiazol-4-ylmethyl |
| 734 | — | H | 2-chlorothiazol-4-ylmethyl |
| 735 | — | H | 5-chlorothiazol-4-ylmethyl |
| 736 | — | H | 5-thiazolylmethyl |
| 737 | — | H | 2-methylthiazol-5-ylmethyl |
| 738 | — | H | 4-methylthiazol-5-ylmethyl |
| 739 | — | H | 2-chlorothiazol-5-ylmethyl |
| 740 | — | H | 4-chlorothiazol-5-ylmethyl |
| 741 | — | H | 3-isoxazolylmethyl |
| 742 | — | H | 4-methylisoxazol-3-ylmethyl |
| 743 | — | H | 5-methylisoxazol-3-ylmethyl |
| 744 | — | H | 4-chloroisoxazol-3-ylmethyl |
| 745 | — | H | 5-chloroisoxazol-3-ylmethyl |
| 746 | — | H | 4-isoxazolylmethyl |
| 747 | — | H | 3-methylisoxazol-4-ylmethyl |
| 748 | — | H | 5-methylisoxazol-4-ylmethyl |
| 749 | — | H | 3-chloroisoxazol-4-ylmethyl |
| 750 | — | H | 5-chloroisoxazol-4-ylmethyl |
| 751 | — | H | 5-isoxazolylmethyl |
| 752 | — | H | 3-methylisoxazol-5-ylmethyl |
| 753 | — | H | 4-methylisoxazol-5-ylmethyl |
| 754 | — | H | 3-chloroisoxazol-5-ylmethyl |
| 755 | — | H | 4-chloroisoxazol-5-ylmethyl |
| 756 | — | H | 3-isothiazolylmethyl |
| 757 | — | H | 4-methylisothiazol-3-ylmethyl |
| 758 | — | H | 5-methylisothiazol-3-ylmethyl |
| 759 | — | H | 4-chloroisothiazol-3-ylmethyl |
| 760 | — | H | 5-chloroisothiazol-3-ylmethyl |
| 761 | — | H | 4-isothiazolylmethyl |
| 762 | — | H | 3-methylisothiazol-4-ylmethyl |
| 763 | — | H | 5-methylisothiazol-4-ylmethyl |
| 764 | — | H | 3-chloroisothiazol-4-ylmethyl |
| 765 | — | H | 5-chloroisothiazol-4-ylmethyl |
| 766 | — | H | 5-isothiazolylmethyl |
| 767 | — | H | 3-methylisothiazol-5-ylmethyl |
| 768 | — | H | 4-methylisothiazol-5-ylmethyl |
| 769 | — | H | 3-chloroisothiazol-5-ylmethyl |
| 770 | — | H | 4-chloroisothiazol-5-ylmethyl |
| 771 | — | H | 4-imidazolylmethyl |
| 772 | — | H | 1-phenylpyrazol-3-ylmethyl |
| 773 | — | H | 1-methylimidazol-4-ylmethyl |
| 774 | — | H | 1-phenyl-1,2,4-triazol-3-ylmethyl |
| 775 | — | H | 1,2,4-oxadiazol-3-ylmethyl |
| 776 | — | H | 5-chloro-1,2,4-oxadiazol-3-ylmethyl |
| 777 | — | H | 5-methyl-1,2,4-oxadiazol-3-ylmethyl |
| 778 | — | H | 5-trifluoromethyl-1,2,4-oxadiazol-3-ylmethyl |
| 779 | — | H | 1,3,4-oxadiazol-2-ylmethyl |
| 780 | — | H | 5-chloro-1,3,4-oxadiazol-2-ylmethyl |
| 781 | — | H | 5-methyl-1,3,4-oxadiazol-2-ylmethyl |
| 782 | — | H | 5-methoxy-1,3,4-oxadiazol-2-ylmethyl |
| 783 | — | H | 1,2,4-thiadiazol-3-ylmethyl |
| 784 | — | H | 5-chloro-1,2,4-thiadiazol-3-ylmethyl |
| 785 | — | H | 5-methyl-1,2,4-thiadiazol-3-ylmethyl |
| 786 | — | H | 1,3,4-thiadiazol-2-ylmethyl |
| 787 | — | H | 5-chloro-1,3,4-thiadiazol-2-ylmethyl |
| 788 | — | H | 5-methyl-1,3,4-thiadiazol-2-ylmethyl |
| 789 | — | H | 5-cyano-1,3,4-thiadiazol-2-ylmethyl |
| 790 | — | H | 2-(2'-pyridinyloxy)eth-1-yl |
| 791 | — | H | 2-(3'-pyridinyloxy)eth-1-yl |
| 792 | — | H | 2-(4'-pyridinyloxy)eth-1-yl |
| 793 | — | H | $C_6H_5$ |
| 794 | — | H | $2\text{-Cl}\text{—}C_6H_4$ |
| 795 | — | H | $3\text{-Cl}\text{—}C_6H_4$ |
| 796 | — | H | $4\text{-Cl}\text{—}C_6H_4$ |
| 797 | — | H | $2,3\text{-Cl}_2\text{—}C_6H_3$ |
| 798 | — | H | $2,4\text{-Cl}_2\text{—}C_6H_3$ |
| 799 | — | H | $2,5\text{-Cl}_2\text{—}C_6H_3$ |
| 800 | — | H | $3,4\text{-Cl}_2\text{—}C_6H_3$ |
| 801 | — | H | $3,5\text{-Cl}_2\text{—}C_6H_3$ |
| 802 | — | H | $4\text{-CN}\text{—}C_6H_4$ |
| 803 | — | H | $2\text{-NO}_2\text{—}C_6H_4$ |
| 804 | — | H | $3\text{-NO}_2\text{—}C_6H_4$ |
| 805 | — | H | $4\text{-NO}_2\text{—}C_6H_4$ |
| 806 | — | H | $2,4\text{-(NO}_2)_2\text{—}C_6H_3$ |
| 807 | — | H | $2\text{-CH}_3\text{—}C_6H_4$ |
| 808 | — | H | $3\text{-CH}_3\text{—}C_6H_4$ |
| 809 | — | H | $4\text{-CH}_3\text{—}C_6H_4$ |
| 810 | — | H | $2,3\text{-(CH}_3)_2\text{—}C_6H_3$ |
| 811 | — | H | $2,4\text{-(CH}_3)_2\text{—}C_6H_3$ |
| 812 | — | H | $2,5\text{-(CH}_3)_2\text{—}C_6H_3$ |
| 813 | — | H | $2,6\text{-(CH}_3)_2\text{—}C_6H_3$ |
| 814 | — | H | $2\text{-}C_6H_5\text{—}C_6H_4$ |
| 815 | — | H | $3\text{-}C_6H_5\text{—}C_6H_4$ |
| 816 | — | H | $4\text{-}C_6H_5\text{—}C_6H_4$ |
| 817 | — | H | $3\text{-OCH}_3\text{—}C_6H_4$ |
| 818 | — | H | $4\text{-OCH}_3\text{—}C_6H_4$ |
| 819 | — | H | $3\text{-acetyl-}C_6H_4$ |
| 820 | — | H | $4\text{-acetyl-}C_6H_4$ |
| 821 | — | H | $3\text{-methoxycarbonyl-}C_6H_4$ |
| 822 | — | H | $4\text{-methoxycarbonyl-}C_6H_4$ |
| 823 | — | H | $3\text{-CF}_3\text{—}C_6H_4$ |
| 824 | — | H | $4\text{-CF}_3\text{—}C_6H_4$ |
| 825 | — | H | 2-naphthyl |
| 826 | — | H | 6-chloropyridazin-3-yl |
| 827 | — | H | 5-chloropyrazin-2-yl |
| 828 | — | H | quinolin-2-yl |
| 829 | — | H | 2,5-dimethylpyrazin-3-yl |
| 830 | — | H | pyrazin-2-yl |
| 831 | — | H | 3-chloropyrid-2-yl |
| 832 | — | H | 6-chloropyrid-2-yl |
| 833 | — | H | 4-trifluoromethyl, 6-chloropyrid-2-yl |
| 834 | — | H | 4-trifluoromethylpyrid-2-yl |
| 835 | — | H | 6-trifluoromethylpyrid-2-yl |
| 836 | — | H | 6-methoxypyrid-2-yl |
| 837 | — | H | 5-chloropyrid-2-yl |
| 838 | — | H | pyrid-2-yl |
| 839 | — | H | benzothiazol-2-yl |

TABLE A-continued

| | | | |
|---|---|---|---|
| 840 | — | H | 7-chloroquinolin-4-yl |
| 841 | — | H | 3-nitropyrid-2-yl |
| 842 | — | H | pyrrol-3-yl |
| 843 | — | H | pyrrol-2-yl |
| 844 | — | H | 2,6-dioctylpyrid-4-yl |
| 845 | — | H | 5-nitropyrid-2-yl |
| 846 | — | H | pyrid-4-yl |
| 847 | — | H | pyrid-3-yl |
| 848 | — | H | pyrimidin-2-yl |
| 849 | — | H | pyrimidin-4-yl |
| 850 | — | H | quinazolin-4-yl |
| 851 | — | H | 6-chloropyrimidin-4-yl |
| 852 | — | H | 6-methoxypyrimidin-4-yl |
| 853 | — | H | 2,5,6-trichloropyrimidin-4-yl |
| 854 | — | H | 2,6-dimethylpyrimidin-4-yl |
| 855 | — | H | 2-methyl, 6-chloropyrimidin-4-yl |
| 856 | — | H | 2-methyl, 6-ethoxypyrimidin-4-yl |
| 857 | — | H | 4,5,6-trichloropyrimidin-2-yl |
| 858 | — | H | 4,6-dimethoxypyrimidin-2-yl |
| 859 | — | H | 4,6-dimethylpyrimidin-2-yl |
| 860 | — | H | 4,6-dichloropyrimidin-2-yl |
| 861 | — | H | 4-methyl, 6-methoxypyrimidin-2-yl |
| 862 | — | H | 4-chloro, 6-methoxypyrimidin-2-yl |
| 863 | — | H | 6-chloroquinoxalin-2-yl |
| 864 | — | H | 3,6-dichloro-1,2,4-triazin-5-yl |
| 865 | — | H | 4-methoxy-1,3,5-triazin-2-yl |
| 866 | — | H | 4-ethoxy-1,3,5-triazin-2-yl |
| 867 | — | H | 4,6-dichloro-1,3,5-triazin-2-yl |
| 868 | — | H | 4-ethoxy, 6-chloro-1,3,5-triazin-2-yl |
| 869 | — | H | isoxazol-3-yl |
| 870 | — | H | thien-2-yl |
| 871 | — | H | fur-2-yl |
| 872 | — | H | thiatriazol-5-yl |
| 873 | — | H | (E)-1-chloropropen-3-yl |
| 874 | — | H | (E)-4-(4'-chlorophenyl)but-2-en-1-yl |
| 875 | — | H | propyn-3-yl |
| 876 | — | H | methylcarbonyl |
| 877 | — | H | 2-t-$C_4H_9$—$C_6H_4$—$CH_2$ |
| 878 | — | H | 3-t-$C_4H_9$—$C_6H_4$—$CH_2$ |
| 879 | — | H | 4-t-$C_4H_9$—$C_6H_4$—$CH_2$ |
| 880 | — | H | 2-(4'-chlorothiazol-2'-yloxy)eth-1-yl |
| 881 | — | H | 2-(1'-methylpyrazol-4'-yloxy)eth-1-yl |
| 882 | — | H | 4-Br—$C_6H_4$ |
| 883 | — | H | 3,5-$(CH_3)_2$—$C_6H_3$ |
| 884 | — | H | 4-$C_2H_5$—$C_6H_4$ |
| 885 | — | H | 3-dimethylaminocarbonyl-$C_6H_4$ |
| 886 | — | H | 4-dimethylaminocarbonyl-$C_6H_4$ |
| 887 | — | H | 2-hydroxyprop-1-yl |
| 888 | — | H | 6-hydroxy-2-methylpyrimidin-4-ylmethyl |
| 889 | — | H | [6-OH,2-CH($CH_3$)$_2$-pyrimidin-4-yl]-$CH_2$ |
| 890 | — | H | [6-OH,2-CH($CH_2$)$_2$-pyrimidin-4-yl]-$CH_2$ |
| 891 | — | H | 5-(2'-furan)-pent-1-yl |
| 892 | — | H | 5-(2'-N-methylpyrrole)-pent-1-yl |
| 893 | — | H | [2-(4-Cl—$C_6H_4$)-oxazol-4-yl]-$CH_2$ |
| 894 | — | H | 3-$CF_3$-pyridin-2-yl |
| 895 | — | H | 5-$CF_3$-pyridin-2-yl |
| 896 | — | H | 6-(2'-thienyl)hex-1-yl |
| 897 | O | $CH_3$ | H |
| 898 | O | $CH_3$ | $CH_3$ |
| 899 | O | $CH_3$ | $C_2H_5$ |
| 900 | O | $CH_3$ | n-$C_3H_7$ |
| 901 | O | $CH_3$ | i-$C_3H_7$ |
| 902 | O | $CH_3$ | cyclopropyl |
| 903 | O | $CH_3$ | n-$C_4H_9$ |
| 904 | O | $CH_3$ | s-$C_4H_9$ |
| 905 | O | $CH_3$ | i-$C_4H_9$ |
| 906 | O | $CH_3$ | t-$C_4H_9$ |
| 907 | O | $CH_3$ | n-$C_5H_{11}$ |
| 908 | O | $CH_3$ | i-$C_5H_{11}$ |
| 909 | O | $CH_3$ | neo-$C_5H_{11}$ |
| 910 | O | $CH_3$ | cyclopentyl |
| 911 | O | $CH_3$ | n-$C_6H_{13}$ |
| 912 | O | $CH_3$ | cyclohexyl |
| 913 | O | $CH_3$ | $CH_2CH_2Cl$ |
| 914 | O | $CH_3$ | $(CH_2)_4Cl$ |
| 915 | O | $CH_3$ | $CH_2CN$ |
| 916 | O | $CH_3$ | $CH_2CH_2CN$ |
| 917 | O | $CH_3$ | $(CH_2)_3CN$ |
| 918 | O | $CH_3$ | $(CH_2)_4CN$ |
| 919 | O | $CH_3$ | $(CH_2)_6CN$ |
| 920 | O | $CH_3$ | cyclohexylmethyl |
| 921 | O | $CH_3$ | 2-cyclohexyleth-1-yl |
| 922 | O | $CH_3$ | cyclopropylmethyl |
| 923 | O | $CH_3$ | 2-cyclopropyleth-1-yl |
| 924 | O | $CH_3$ | 2-methoxyeth-1-yl |
| 925 | O | $CH_3$ | 2-ethoxyeth-1-yl |
| 926 | O | $CH_3$ | 2-isopropoxyeth-1-yl |
| 927 | O | $CH_3$ | 3-methoxyprop-1-yl |
| 928 | O | $CH_3$ | 3-ethoxyprop-1-yl |
| 929 | O | $CH_3$ | 3-isopropoxyprop-1-yl |
| 930 | O | $CH_3$ | 4-methoxybut-1-yl |
| 931 | O | $CH_3$ | 4-isopropoxybut-1-yl |
| 932 | O | $CH_3$ | propen-3-yl |
| 933 | O | $CH_3$ | but-2-en-1-yl |
| 934 | O | $CH_3$ | 3-methylbut-2-en-1-yl |
| 935 | O | $CH_3$ | 2-vinyloxyeth-1-yl |
| 936 | O | $CH_3$ | allyloxyeth-1-yl |
| 937 | O | $CH_3$ | 2-trifluoromethoxyeth-1-yl |
| 938 | O | $CH_3$ | 3-trifluoromethoxyprop-1-yl |
| 939 | O | $CH_3$ | 4-difluoromethoxybut-1-yl |
| 940 | O | $CH_3$ | hydroxycarbonylmethyl |
| 941 | O | $CH_3$ | methoxycarbonylmethyl |
| 942 | O | $CH_3$ | aminocarbonylmethyl |
| 943 | O | $CH_3$ | N-methylaminocarbonylmethyl |
| 944 | O | $CH_3$ | N,N-dimethylaminocarbonyl-methyl |
| 945 | O | $CH_3$ | 2-hydroxycarbonyleth-1-yl |
| 946 | O | $CH_3$ | 2-methoxycarbonyleth-1-yl |
| 947 | O | $CH_3$ | 2-aminocarbonyleth-1-yl |
| 948 | O | $CH_3$ | 2-N-methylaminocarbonyleth-1-yl |
| 949 | O | $CH_3$ | 2-dimethylaminocarbonyleth-1-yl |
| 950 | O | $CH_3$ | 2-aminoeth-1-yl |
| 951 | O | $CH_3$ | 2-aminoprop-1-yl |
| 952 | O | $CH_3$ | 4-aminobut-1-yl |
| 953 | O | $CH_3$ | 3-dimethylaminoprop-1-yl |
| 954 | O | $CH_3$ | 4-aminothiocarbonylbut-1-yl |
| 955 | O | $CH_3$ | 6-aminocarbonylhex-1-yl |
| 956 | O | $CH_3$ | 3-aminothiocarbonylprop-1-yl |
| 957 | O | $CH_3$ | 2-aminothiocarbonyleth-1-yl |
| 958 | O | $CH_3$ | aminothiocarbonylmethyl |
| 959 | O | $CH_3$ | 4-(N,N-dimethylamino)but-1-yl |
| 960 | O | $CH_3$ | 2-(methylthio)eth-1-yl |
| 961 | O | $CH_3$ | 2-(methylsulfonyl)eth-1-yl |
| 962 | O | $CH_3$ | 4-(methylthio)prop-1-yl |
| 963 | O | $CH_3$ | 4-(methylsulfonyl)prop-1-yl |
| 964 | O | $CH_3$ | benzyl |
| 965 | O | $CH_3$ | 2-F—$C_6H_4$—$CH_2$ |
| 966 | O | $CH_3$ | 3-F—$C_6H_4$—$CH_2$ |
| 967 | O | $CH_3$ | 4-F—$C_6H_4$—$CH_2$ |
| 968 | O | $CH_3$ | 2,3-$F_2$—$C_6H_3$—$CH_2$ |
| 969 | O | $CH_3$ | 2,4-$F_2$—$C_6H_3$—$CH_2$ |
| 970 | O | $CH_3$ | 2,5-$F_2$—$C_6H_3$—$CH_2$ |
| 971 | O | $CH_3$ | 2,6-$F_2$—$C_6H_3$—$CH_2$ |
| 972 | O | $CH_3$ | 3,4-$F_2$—$C_6H_3$—$CH_2$ |
| 973 | O | $CH_3$ | 3,5-$F_2$—$C_6H_3$—$CH_2$ |
| 974 | O | $CH_3$ | 2-Cl—$C_6H_4$—$CH_2$ |
| 975 | O | $CH_3$ | 3-Cl—$C_6H_4$—$CH_2$ |
| 976 | O | $CH_3$ | 4-Cl—$C_6H_4$—$CH_2$ |
| 977 | O | $CH_3$ | 2,3-$Cl_2$—$C_6H_3$—$CH_2$ |
| 978 | O | $CH_3$ | 2,4-$Cl_2$—$C_6H_3$—$CH_2$ |
| 979 | O | $CH_3$ | 2,5-$Cl_2$—$C_6H_3$—$CH_2$ |
| 980 | O | $CH_3$ | 2,6-$Cl_2$—$C_6H_3$—$CH_2$ |
| 981 | O | $CH_3$ | 3,4-$Cl_2$—$C_6H_3$—$CH_2$ |
| 982 | O | $CH_3$ | 3,5-$Cl_2$—$C_6H_3$—$CH_2$ |
| 983 | O | $CH_3$ | 2,3,4-$Cl_3$—$C_6H_2$—$CH_2$ |
| 984 | O | $CH_3$ | 2,3,5-$Cl_3$—$C_6H_2$—$CH_2$ |
| 985 | O | $CH_3$ | 2,3,6-$Cl_3$—$C_6H_2$—$CH_2$ |
| 986 | O | $CH_3$ | 2,4,5-$Cl_3$—$C_6H_2$—$CH_2$ |
| 987 | O | $CH_3$ | 2,4,6-$Cl_3$—$C_6H_2$—$CH_2$ |
| 988 | O | $CH_3$ | 3,4,5-$Cl_3$—$C_6H_2$—$CH_2$ |
| 989 | O | $CH_3$ | 2-Br—$C_6H_4$—$CH_2$ |
| 990 | O | $CH_3$ | 3-Br—$C_6H_4$—$CH_2$ |
| 991 | O | $CH_3$ | 4-Br—$C_6H_4$—$CH_2$ |
| 992 | O | $CH_3$ | 2,3-$Br_2$—$C_6H_3$—$CH_2$ |
| 993 | O | $CH_3$ | 2,4-$Br_2$—$C_6H_3$—$CH_2$ |
| 994 | O | $CH_3$ | 2,5-$Br_2$—$C_6H_3$—$CH_2$ |
| 995 | O | $CH_3$ | 2,6-$Br_2$—$C_6H_3$—$CH_2$ |
| 996 | O | $CH_3$ | 3,4-$Br_2$—$C_6H_3$—$CH_2$ |
| 997 | O | $CH_3$ | 3,5-$Br_2$—$C_6H_3$—$CH_2$ |

TABLE A-continued

| | | | |
|---|---|---|---|
| 998 | O | CH$_3$ | 2-F, 3-Cl—C$_6$H$_3$—CH$_2$ |
| 999 | O | CH$_3$ | 2-F, 4-Cl—C$_6$H$_3$—CH$_2$ |
| 1000 | O | CH$_3$ | 2-F, 5-Cl—C$_6$H$_3$—CH$_2$ |
| 1001 | O | CH$_3$ | 2-F, 3-Br—C$_6$H$_3$—CH$_2$ |
| 1002 | O | CH$_3$ | 2-F, 4-Br—C$_6$H$_3$—CH$_2$ |
| 1003 | O | CH$_3$ | 2-F, 5-Br—C$_6$H$_3$—CH$_2$ |
| 1004 | O | CH$_3$ | 2-Cl, 3-Br—C$_6$H$_3$—CH$_2$ |
| 1005 | O | CH$_3$ | 2-Cl, 4-Br—C$_6$H$_3$—CH$_2$ |
| 1006 | O | CH$_3$ | 2-Cl, 5-Br—C$_6$H$_3$—CH$_2$ |
| 1007 | O | CH$_3$ | 3-F, 4-Cl—C$_6$H$_3$—CH$_2$ |
| 1008 | O | CH$_3$ | 3-F, 5-Cl—C$_6$H$_3$—CH$_2$ |
| 1009 | O | CH$_3$ | 3-F, 6-Cl—C$_6$H$_3$—CH$_2$ |
| 1010 | O | CH$_3$ | 3-F, 4-Br—C$_6$H$_3$—CH$_2$ |
| 1011 | O | CH$_3$ | 3-F, 5-Br—C$_6$H$_3$—CH$_2$ |
| 1012 | O | CH$_3$ | 3-F, 6-Br—C$_6$H$_3$—CH$_2$ |
| 1013 | O | CH$_3$ | 3-Cl, 4-Br—C$_6$H$_3$—CH$_2$ |
| 1014 | O | CH$_3$ | 3-Cl, 5-Br—C$_6$H$_3$—CH$_2$ |
| 1015 | O | CH$_3$ | 3-Cl, 6-Br—C$_6$H$_3$—CH$_2$ |
| 1016 | O | CH$_3$ | 4-F, 5-Cl—C$_6$H$_3$—CH$_2$ |
| 1017 | O | CH$_3$ | 4-F, 6-Cl—C$_6$H$_3$—CH$_2$ |
| 1018 | O | CH$_3$ | 4-F, 5-Br—C$_6$H$_3$—CH$_2$ |
| 1019 | O | CH$_3$ | 4-F, 6-Br—C$_6$H$_3$—CH$_2$ |
| 1020 | O | CH$_3$ | 4-Cl, 5-Br—C$_6$H$_3$—CH$_2$ |
| 1021 | O | CH$_3$ | 5-F, 6-Cl—C$_6$H$_3$—CH$_2$ |
| 1022 | O | CH$_3$ | 5-F, 6-Br—C$_6$H$_3$—CH$_2$ |
| 1023 | O | CH$_3$ | 5-Cl, 6-Br—C$_6$H$_3$—CH$_2$ |
| 1024 | O | CH$_3$ | 3-Br, 4-Cl, 5-Br—C$_6$H$_2$—CH$_2$ |
| 1025 | O | CH$_3$ | 2-CN—C$_6$H$_4$—CH$_2$ |
| 1026 | O | CH$_3$ | 3-CN—C$_6$H$_4$—CH$_2$ |
| 1027 | O | CH$_3$ | 4-CN—C$_6$H$_4$—CH$_2$ |
| 1028 | O | CH$_3$ | 2-NO$_2$—C$_6$H$_4$—CH$_2$ |
| 1029 | O | CH$_3$ | 3-NO$_2$—C$_6$H$_4$—CH$_2$ |
| 1030 | O | CH$_3$ | 4-NO$_2$—C$_6$H$_4$—CH$_2$ |
| 1031 | O | CH$_3$ | 2-CH$_3$—C$_6$H$_4$—CH$_2$ |
| 1032 | O | CH$_3$ | 3-CH$_3$—C$_6$H$_4$—CH$_2$ |
| 1033 | O | CH$_3$ | 4-CH$_3$—C$_6$H$_4$—CH$_2$ |
| 1034 | O | CH$_3$ | 2,3-(CH$_3$)$_2$—C$_6$H$_3$—CH$_2$ |
| 1035 | O | CH$_3$ | 2,4-(CH$_3$)$_2$—C$_6$H$_3$—CH$_2$ |
| 1036 | O | CH$_3$ | 2,5-(CH$_3$)$_2$—C$_6$H$_3$—CH$_2$ |
| 1037 | O | CH$_3$ | 2,6-(CH$_3$)$_2$—C$_6$H$_3$—CH$_2$ |
| 1038 | O | CH$_3$ | 3,4-(CH$_3$)$_2$—C$_6$H$_3$—CH$_2$ |
| 1039 | O | CH$_3$ | 3,5-(CH$_3$)$_2$—C$_6$H$_3$—CH$_2$ |
| 1040 | O | CH$_3$ | 2-C$_2$H$_5$—C$_6$H$_4$—CH$_2$ |
| 1041 | O | CH$_3$ | 3-C$_2$H$_5$—C$_6$H$_4$—CH$_2$ |
| 1042 | O | CH$_3$ | 4-C$_2$H$_5$—C$_6$H$_4$—CH$_2$ |
| 1043 | O | CH$_3$ | 2-i-C$_3$H$_7$—C$_6$H$_4$—CH$_2$ |
| 1044 | O | CH$_3$ | 3-i-C$_3$H$_7$—C$_6$H$_4$—CH$_2$ |
| 1045 | O | CH$_3$ | 4-i-C$_3$H$_7$—C$_6$H$_4$—CH$_2$ |
| 1046 | O | CH$_3$ | 2-cyclohexyl-C$_6$H$_4$—CH$_2$ |
| 1047 | O | CH$_3$ | 3-cyclohexyl-C$_6$H$_4$—CH$_2$ |
| 1048 | O | CH$_3$ | 4-cyclohexyl-C$_6$H$_4$—CH$_2$ |
| 1049 | O | CH$_3$ | 2-vinyl-C$_6$H$_4$—CH$_2$ |
| 1050 | O | CH$_3$ | 3-vinyl-C$_6$H$_4$—CH$_2$ |
| 1051 | O | CH$_3$ | 4-vinyl-C$_6$H$_4$—CH$_2$ |
| 1052 | O | CH$_3$ | 2-allyl-C$_6$H$_4$—CH$_2$ |
| 1053 | O | CH$_3$ | 3-allyl-C$_6$H$_4$—CH$_2$ |
| 1054 | O | CH$_3$ | 4-allyl-C$_6$H$_4$—CH$_2$ |
| 1055 | O | CH$_3$ | 2-C$_6$H$_5$—C$_6$H$_4$—CH$_2$ |
| 1056 | O | CH$_3$ | 3-C$_6$H$_5$—C$_6$H$_4$—CH$_2$ |
| 1057 | O | CH$_3$ | 4-C$_6$H$_5$—C$_6$H$_4$—CH$_2$ |
| 1058 | O | CH$_3$ | 3-CH$_3$, 5-t-C$_4$H$_9$—C$_6$H$_3$—CH$_2$ |
| 1059 | O | CH$_3$ | 2-OH—C$_6$H$_4$—CH$_2$ |
| 1060 | O | CH$_3$ | 3-OH—C$_6$H$_4$—CH$_2$ |
| 1061 | O | CH$_3$ | 4-OH—C$_6$H$_4$—CH$_2$ |
| 1062 | O | CH$_3$ | 2-OCH$_3$—C$_6$H$_4$—CH$_2$ |
| 1063 | O | CH$_3$ | 3-OCH$_3$—C$_6$H$_4$—CH$_2$ |
| 1064 | O | CH$_3$ | 4-OCH$_3$—C$_6$H$_4$—CH$_2$ |
| 1065 | O | CH$_3$ | 2-O-allyl-C$_6$H$_4$—CH$_2$ |
| 1066 | O | CH$_3$ | 3-O-allyl-C$_6$H$_4$—CH$_2$ |
| 1067 | O | CH$_3$ | 4-O-allyl-C$_6$H$_4$—CH$_2$ |
| 1068 | O | CH$_3$ | 2-CF$_3$—C$_6$H$_4$—CH$_2$ |
| 1069 | O | CH$_3$ | 3-CF$_3$—C$_6$H$_4$—CH$_2$ |
| 1070 | O | CH$_3$ | 4-CF$_3$—C$_6$H$_4$—CH$_2$ |
| 1071 | O | CH$_3$ | 2-acetyl-C$_6$H$_4$—CH$_2$ |
| 1072 | O | CH$_3$ | 3-acetyl-C$_6$H$_4$—CH$_2$ |
| 1073 | O | CH$_3$ | 4-acetyl-C$_6$H$_4$—CH$_2$ |
| 1074 | O | CH$_3$ | 2-methoxycarbonyl-C$_6$H$_4$—CH$_2$ |
| 1075 | O | CH$_3$ | 3-methoxycarbonyl-C$_6$H$_4$—CH$_2$ |
| 1076 | O | CH$_3$ | 4-methoxycarbonyl-C$_6$H$_4$—CH$_2$ |
| 1077 | O | CH$_3$ | 2-aminocarbonyl-C$_6$H$_4$—CH$_2$ |
| 1078 | O | CH$_3$ | 3-aminocarbonyl-C$_6$H$_4$—CH$_2$ |
| 1079 | O | CH$_3$ | 4-aminocarbonyl-C$_6$H$_4$—CH$_2$ |
| 1080 | O | CH$_3$ | 2-dimethylaminocarbonyl-C$_6$H$_4$—CH$_2$ |
| 1081 | O | CH$_3$ | 3-dimethylaminocarbonyl-C$_6$H$_4$—CH$_2$ |
| 1082 | O | CH$_3$ | 4-dimethylaminocarbonyl-C$_6$H$_4$—CH$_2$ |
| 1083 | O | CH$_3$ | 2-(N-methylaminocarbonyl)-C$_6$H$_4$—CH$_2$ |
| 1084 | O | CH$_3$ | 3-(N-methylaminocarbonyl)-C$_6$H$_4$—CH$_2$ |
| 1085 | O | CH$_3$ | 4-(N-methylaminocarbonyl)-C$_6$H$_4$—CH$_2$ |
| 1086 | O | CH$_3$ | 2-H$_2$N—C$_6$H$_4$—CH$_2$ |
| 1087 | O | CH$_3$ | 3-H$_2$N—C$_6$H$_4$—CH$_2$ |
| 1088 | O | CH$_3$ | 4-H$_2$N—C$_6$H$_4$—CH$_2$ |
| 1089 | O | CH$_3$ | 2-aminothiocarbonyl-C$_6$H$_4$—CH$_2$ |
| 1090 | O | CH$_3$ | 3-aminothiocarbonyl-C$_6$H$_4$—CH$_2$ |
| 1091 | O | CH$_3$ | 4-aminothiocarbonyl-C$_6$H$_4$—CH$_2$ |
| 1092 | O | CH$_3$ | 2-SCH$_3$—C$_6$H$_4$—CH$_2$ |
| 1093 | O | CH$_3$ | 3-SCH$_3$—C$_6$H$_4$—CH$_2$ |
| 1094 | O | CH$_3$ | 4-SCH$_3$—C$_6$H$_4$—CH$_2$ |
| 1095 | O | CH$_3$ | 2-SO$_2$CH$_3$—C$_6$H$_4$—CH$_2$ |
| 1096 | O | CH$_3$ | 3-SO$_2$CH$_3$—C$_6$H$_4$—CH$_2$ |
| 1097 | O | CH$_3$ | 4-SO$_2$CH$_3$—C$_6$H$_4$—CH$_2$ |
| 1098 | O | CH$_3$ | 2-OCF$_3$—C$_6$H$_4$—CH$_2$ |
| 1099 | O | CH$_3$ | 3-OCF$_3$—C$_6$H$_4$—CH$_2$ |
| 1100 | O | CH$_3$ | 4-OCF$_3$—C$_6$H$_4$—CH$_2$ |
| 1101 | O | CH$_3$ | 2-OCHF$_2$—C$_6$H$_4$—CH$_2$ |
| 1102 | O | CH$_3$ | 3-OCHF$_2$—C$_6$H$_4$—CH$_2$ |
| 1103 | O | CH$_3$ | 4-OCHF$_2$—C$_6$H$_4$—CH$_2$ |
| 1104 | O | CH$_3$ | 3-CF$_3$, 4-OCF$_3$—C$_6$H$_3$—CH$_2$ |
| 1105 | O | CH$_3$ | 1-naphthyl-CH$_2$ |
| 1106 | O | CH$_3$ | 2-naphthyl-CH$_2$ |
| 1107 | O | CH$_3$ | 2-phenoxyeth-1-yl |
| 1108 | O | CH$_3$ | 2-(2'-chlorophenoxy)eth-1-yl |
| 1109 | O | CH$_3$ | 2-(3'-chlorophenoxy)eth-1-yl |
| 1110 | O | CH$_3$ | 2-(4'-chlorophenoxy)eth-1-yl |
| 1111 | O | CH$_3$ | 2-(3',5'-dichlorophenoxy)eth-1-yl |
| 1112 | O | CH$_3$ | 2-(4'-cyanophenoxy)eth-1-yl |
| 1113 | O | CH$_3$ | 2-(3'-methylphenoxy)eth-1-yl |
| 1114 | O | CH$_3$ | 2-(2'-nitrophenoxy)eth-1-yl |
| 1115 | O | CH$_3$ | 3-phenoxyprop-1-yl |
| 1116 | O | CH$_3$ | 3-(4'-chlorophenoxy)prop-1-yl |
| 1117 | O | CH$_3$ | 3-(3'-cyanophenoxy)prop-1-yl |
| 1118 | O | CH$_3$ | 3-(2'-methylphenoxy)prop-1-yl |
| 1119 | O | CH$_3$ | 4-phenoxybut-1-yl |
| 1120 | O | CH$_3$ | 2-phenyleth-1-yl |
| 1121 | O | CH$_3$ | 2-(4'-chlorophenyl)eth-1-yl |
| 1122 | O | CH$_3$ | 2-(3'-cyanophenyl)eth-1-yl |
| 1123 | O | CH$_3$ | 2-(2'-methylphenyl)eth-1-yl |
| 1124 | O | CH$_3$ | 3-phenylprop-1-yl |
| 1125 | O | CH$_3$ | 4-phenylbut-1-yl |
| 1126 | O | CH$_3$ | 2-pyridylmethyl |
| 1127 | O | CH$_3$ | 3-pyridylmethyl |
| 1128 | O | CH$_3$ | 4-pyridylmethyl |
| 1129 | O | CH$_3$ | 4-chloropyridin-2-ylmethyl |
| 1130 | O | CH$_3$ | 5-chloropyridin-2-ylmethyl |
| 1131 | O | CH$_3$ | 6-chloropyridin-2-ylmethyl |
| 1132 | O | CH$_3$ | 5-chloropyridin-3-ylmethyl |
| 1133 | O | CH$_3$ | 6-chloropyridin-3-ylmethyl |
| 1134 | O | CH$_3$ | 2-chloropyridin-4-ylmethyl |
| 1135 | O | CH$_3$ | 2-pyrimidinylmethyl |
| 1136 | O | CH$_3$ | 4-chloropyrimidin-2-ylmethyl |
| 1137 | O | CH$_3$ | 5-chloropyrimidin-2-ylmethyl |
| 1138 | O | CH$_3$ | 2-chloropyrimidin-4-ylmethyl |
| 1139 | O | CH$_3$ | 6-chloropyrimidin-4-ylmethyl |
| 1140 | O | CH$_3$ | 2-chloropyrimidin-5-ylmethyl |
| 1141 | O | CH$_3$ | 4-pyridazinylmethyl |
| 1142 | O | CH$_3$ | 2-pyrazinylmethyl |
| 1143 | O | CH$_3$ | 5-chloropyrazin-2-ylmethyl |
| 1144 | O | CH$_3$ | 6-chloropyrazin-2-ylmethyl |
| 1145 | O | CH$_3$ | 3-pyridazinylmethyl |
| 1146 | O | CH$_3$ | 6-chloropyridazin-3-ylmethyl |
| 1147 | O | CH$_3$ | 1,3,5-triazinylmethyl |
| 1148 | O | CH$_3$ | 2-furylmethyl |
| 1149 | O | CH$_3$ | 3-furylmethyl |
| 1150 | O | CH$_3$ | 4-bromofur-2-ylmethyl |
| 1151 | O | CH$_3$ | 5-chlorofur-2-ylmethyl |
| 1152 | O | CH$_3$ | 2-thienylmethyl |
| 1153 | O | CH$_3$ | 3-thienylmethyl |
| 1154 | O | CH$_3$ | 5-methylthien-3-ylmethyl |
| 1155 | O | CH$_3$ | 5-chlorothien-2-ylmethyl |

TABLE A-continued

| | | | |
|---|---|---|---|
| 1156 | O | CH₃ | 2-chlorothien-4-ylmethyl |
| 1157 | O | CH₃ | 2-pyrrolylmethyl |
| 1158 | O | CH₃ | 3-pyrrolylmethyl |
| 1159 | O | CH₃ | 2-oxazolylmethyl |
| 1160 | O | CH₃ | 4-methyloxazol-2-ylmethyl |
| 1161 | O | CH₃ | 5-methyloxazol-2-ylmethyl |
| 1162 | O | CH₃ | 4-chlorooxazol-2-ylmethyl |
| 1163 | O | CH₃ | 5-chlorooxazol-2-ylmethyl |
| 1164 | O | CH₃ | 4-oxazolylmethyl |
| 1165 | O | CH₃ | 2-methyloxazol-4-ylmethyl |
| 1166 | O | CH₃ | 5-methyloxazol-4-ylmethyl |
| 1167 | O | CH₃ | 2-chlorooxazol-4-ylmethyl |
| 1168 | O | CH₃ | 5-chlorooxazol-4-ylmethyl |
| 1169 | O | CH₃ | 5-oxazolylmethyl |
| 1170 | O | CH₃ | 2-methyloxazol-5-ylmethyl |
| 1171 | O | CH₃ | 4-methyloxazol-5-ylmethyl |
| 1172 | O | CH₃ | 2-chlorooxazol-5-ylmethyl |
| 1173 | O | CH₃ | 4-chlorooxazol-5-ylmethyl |
| 1174 | O | CH₃ | 2-thiazolylmethyl |
| 1175 | O | CH₃ | 4-methylthiazol-2-ylmethyl |
| 1176 | O | CH₃ | 5-methylthiazol-2-ylmethyl |
| 1177 | O | CH₃ | 4-chlorothiazol-2-ylmethyl |
| 1178 | O | CH₃ | 5-chlorothiazol-2-ylmethyl |
| 1179 | O | CH₃ | 4-thiazolylmethyl |
| 1180 | O | CH₃ | 2-methylthiazol-4-ylmethyl |
| 1181 | O | CH₃ | 5-methylthiazol-4-ylmethyl |
| 1182 | O | CH₃ | 2-chlorothiazol-4-ylmethyl |
| 1183 | O | CH₃ | 5-chlorothiazol-4-ylmethyl |
| 1184 | O | CH₃ | 5-thiazolylmethyl |
| 1185 | O | CH₃ | 2-methylthiazol-5-ylmethyl |
| 1186 | O | CH₃ | 4-methylthiazol-5-ylmethyl |
| 1187 | O | CH₃ | 2-chlorothiazol-5-ylmethyl |
| 1188 | O | CH₃ | 4-chlorothiazol-5-ylmethyl |
| 1189 | O | CH₃ | 3-isoxazolylmethyl |
| 1190 | O | CH₃ | 4-methylisoxazol-3-ylmethyl |
| 1191 | O | CH₃ | 5-methylisoxazol-3-ylmethyl |
| 1192 | O | CH₃ | 4-chloroisoxazol-3-ylmethyl |
| 1193 | O | CH₃ | 5-chloroisoxazol-3-ylmethyl |
| 1194 | O | CH₃ | 4-isoxazolylmethyl |
| 1195 | O | CH₃ | 3-methylisoxazol-4-ylmethyl |
| 1196 | O | CH₃ | 5-methylisoxazol-4-ylmethyl |
| 1197 | O | CH₃ | 3-chloroisoxazol-4-ylmethyl |
| 1198 | O | CH₃ | 5-chloroisoxazol-4-ylmethyl |
| 1199 | O | CH₃ | 5-isoxazolylmethyl |
| 1200 | O | CH₃ | 3-methylisoxazol-5-ylmethyl |
| 1201 | O | CH₃ | 4-methylisoxazol-5-ylmethyl |
| 1202 | O | CH₃ | 3-chloroisoxazol-5-ylmethyl |
| 1203 | O | CH₃ | 4-chloroisoxazol-5-ylmethyl |
| 1204 | O | CH₃ | 3-isothiazolylmethyl |
| 1205 | O | CH₃ | 4-methylisothiazol-3-ylmethyl |
| 1206 | O | CH₃ | 5-methylisothiazol-3-ylmethyl |
| 1207 | O | CH₃ | 4-chloroisothiazol-3-ylmethyl |
| 1208 | O | CH₃ | 5-chloroisothiazol-3-ylmethyl |
| 1209 | O | CH₃ | 4-isothiazolylmethyl |
| 1210 | O | CH₃ | 3-methylisothiazol-4-ylmethyl |
| 1211 | O | CH₃ | 5-methylisothiazol-4-ylmethyl |
| 1212 | O | CH₃ | 3-chloroisothiazol-4-ylmethyl |
| 1213 | O | CH₃ | 5-chloroisothiazol-4-ylmethyl |
| 1214 | O | CH₃ | 5-isothiazolylmethyl |
| 1215 | O | CH₃ | 3-methylisothiazol-5-ylmethyl |
| 1216 | O | CH₃ | 4-methylisothiazol-5-ylmethyl |
| 1217 | O | CH₃ | 3-chloroisothiazol-5-ylmethyl |
| 1218 | O | CH₃ | 4-chloroisothiazol-5-ylmethyl |
| 1219 | O | CH₃ | 4-imidazolylmethyl |
| 1220 | O | CH₃ | 1-phenylpyrazol-3-ylmethyl |
| 1221 | O | CH₃ | 1-methylimidazol-4-ylmethyl |
| 1222 | O | CH₃ | 1-phenyl-1,2,4-triazol-3-ylmethyl |
| 1223 | O | CH₃ | 1,2,4-oxadiazol-3-ylmethyl |
| 1224 | O | CH₃ | 5-chloro-1,2,4-oxadiazol-3-ylmethyl |
| 1225 | O | CH₃ | 5-methyl-1,2,4-oxadiazol-3-ylmethyl |
| 1226 | O | CH₃ | 5-trifluoromethyl-1,2,4-oxadiazol-3-ylmethyl |
| 1227 | O | CH₃ | 1,3,4-oxadiazol-2-ylmethyl |
| 1228 | O | CH₃ | 5-chloro-1,3,4-oxadiazol-2-ylmethyl |
| 1229 | O | CH₃ | 5-methyl-1,3,4-oxadiazol-2-ylmethyl |
| 1230 | O | CH₃ | 5-methoxy-1,3,4-oxadiazol-2-ylmethyl |
| 1231 | O | CH₃ | 1,2,4-thiadiazol-3-ylmethyl |
| 1232 | O | CH₃ | 5-chloro-1,2,4-thiadiazol-3-ylmethyl |
| 1233 | O | CH₃ | 5-methyl-1,2,4-thiadiazol-3-ylmethyl |
| 1234 | O | CH₃ | 1,3,4-thiadiazol-2-ylmethyl |
| 1235 | O | CH₃ | 5-chloro-1,3,4-thiadiazol-2-ylmethyl |
| 1236 | O | CH₃ | 5-methyl-1,3,4-thiadiazol-2-ylmethyl |
| 1237 | O | CH₃ | 5-cyano-1,3,4-thiadiazol-2-ylmethyl |
| 1238 | O | CH₃ | 2-(2'-pyridinyloxy)eth-1-yl |
| 1239 | O | CH₃ | 2-(3'-pyridinyloxy)eth-1-yl |
| 1240 | O | CH₃ | 2-(4'-pyridinyloxy)eth-1-yl |
| 1241 | O | CH₃ | C₆H₅ |
| 1242 | O | CH₃ | 2-Cl—C₆H₄ |
| 1243 | O | CH₃ | 3-Cl—C₆H₄ |
| 1244 | O | CH₃ | 4-Cl—C₆H₄ |
| 1245 | O | CH₃ | 2,3-Cl₂—C₆H₃ |
| 1246 | O | CH₃ | 2,4-Cl₂—C₆H₃ |
| 1247 | O | CH₃ | 2,5-Cl₂—C₆H₃ |
| 1248 | O | CH₃ | 3,4-Cl₂—C₆H₃ |
| 1249 | O | CH₃ | 3,5-Cl₂—C₆H₃ |
| 1250 | O | CH₃ | 4-CN—C₆H₄ |
| 1251 | O | CH₃ | 2-NO₂—C₆H₄ |
| 1252 | O | CH₃ | 3-NO₂—C₆H₄ |
| 1253 | O | CH₃ | 4-NO₂—C₆H₄ |
| 1254 | O | CH₃ | 2,4-(NO₂)₂—C₆H₃ |
| 1255 | O | CH₃ | 2-CH₃—C₆H₄ |
| 1256 | O | CH₃ | 3-CH₃—C₆H₄ |
| 1257 | O | CH₃ | 4-CH₃—C₆H₄ |
| 1258 | O | CH₃ | 2,3-(CH₃)₂—C₆H₃ |
| 1259 | O | CH₃ | 2,4-(CH₃)₂—C₆H₃ |
| 1260 | O | CH₃ | 2,5-(CH₃)₂—C₆H₃ |
| 1261 | O | CH₃ | 2,6-(CH₃)₂—C₆H₃ |
| 1262 | O | CH₃ | 2-C₆H₅—C₆H₄ |
| 1263 | O | CH₃ | 3-C₆H₅—C₆H₄ |
| 1264 | O | CH₃ | 4-C₆H₅—C₆H₄ |
| 1265 | O | CH₃ | 3-OCH₃—C₆H₄ |
| 1266 | O | CH₃ | 4-OCH₃—C₆H₄ |
| 1267 | O | CH₃ | 3-acetyl-C₆H₄ |
| 1268 | O | CH₃ | 4-acetyl-C₆H₄ |
| 1269 | O | CH₃ | 3-methoxycarbonyl-C₆H₄ |
| 1270 | O | CH₃ | 4-methoxycarbonyl-C₆H₄ |
| 1271 | O | CH₃ | 3-CF₃—C₆H₄ |
| 1272 | O | CH₃ | 4-CF₃—C₆H₄ |
| 1273 | O | CH₃ | 2-naphthyl |
| 1274 | O | CH₃ | 6-chloropyridazin-3-yl |
| 1275 | O | CH₃ | 5-chloropyrazin-2-yl |
| 1276 | O | CH₃ | quinolin-2-yl |
| 1277 | O | CH₃ | 2,5-dimethylpyrazin-3-yl |
| 1278 | O | CH₃ | pyrazin-2-yl |
| 1279 | O | CH₃ | 3-chloropyrid-2-yl |
| 1280 | O | CH₃ | 6-chloropyrid-2-yl |
| 1281 | O | CH₃ | 4-trifluoromethyl, 6-chloropyrid-2-yl |
| 1282 | O | CH₃ | 4-trifluoromethylpyrid-2-yl |
| 1283 | O | CH₃ | 6-trifluoromethylpyrid-2-yl |
| 1284 | O | CH₃ | 6-methoxypyrid-2-yl |
| 1285 | O | CH₃ | 5-chloropyrid-2-yl |
| 1286 | O | CH₃ | pyrid-2-yl |
| 1287 | O | CH₃ | benzothiazol-2-yl |
| 1288 | O | CH₃ | 7-chloroquinolin-4-yl |
| 1289 | O | CH₃ | 3-nitropyrid-2-yl |
| 1290 | O | CH₃ | pyrrol-3-yl |
| 1291 | O | CH₃ | pyrrol-2-yl |
| 1292 | O | CH₃ | 2,6-dioctylpyrid-4-yl |
| 1293 | O | CH₃ | 5-nitropyrid-2-yl |
| 1294 | O | CH₃ | pyrid-4-yl |
| 1295 | O | CH₃ | pyrid-3-yl |
| 1296 | O | CH₃ | pyrimidin-2-yl |
| 1297 | O | CH₃ | pyrimidin-4-yl |
| 1298 | O | CH₃ | quinazolin-4-yl |
| 1299 | O | CH₃ | 6-chloropyrimidin-4-yl |
| 1300 | O | CH₃ | 6-methoxypyrimidin-4-yl |
| 1301 | O | CH₃ | 2,5,6-trichloropyrimidin-4-yl |
| 1302 | O | CH₃ | 2,6-dimethylpyrimidin-4-yl |
| 1303 | O | CH₃ | 2-methyl, 6-chloropyrimidin-4-yl |
| 1304 | O | CH₃ | 2-methyl, 6-ethoxypyrimidin-4-yl |
| 1305 | O | CH₃ | 4,5,6-trichloropyrimidin-2-yl |
| 1306 | O | CH₃ | 4,6-dimethoxypyrimidin-2-yl |
| 1307 | O | CH₃ | 4,6-dimethylpyrimidin-2-yl |
| 1308 | O | CH₃ | 4,6-dichloropyrimidin-2-yl |
| 1309 | O | CH₃ | 4-methyl, 6-methoxypyrimidin-2-yl |
| 1310 | O | CH₃ | 4-chloro, 6-methoxypyrimidin-2-yl |
| 1311 | O | CH₃ | 6-chloroquinoxalin-2-yl |
| 1312 | O | CH₃ | 3,6-dichloro-1,2,4-triazin-5-yl |
| 1313 | O | CH₃ | 4-methoxy-1,3,5-triazin-2-yl |

TABLE A-continued

| | | | |
|---|---|---|---|
| 1314 | O | $CH_3$ | 4-ethoxy-1,3,5-triazin-2-yl |
| 1315 | O | $CH_3$ | 4,6-dichloro-1,3,5-triazin-2-yl |
| 1316 | O | $CH_3$ | 4-ethoxy, 6-chloro-1,3,5-triazin-2-yl |
| 1317 | O | $CH_3$ | isoxazol-3-yl |
| 1318 | O | $CH_3$ | thien-2-yl |
| 1319 | O | $CH_3$ | fur-2-yl |
| 1320 | O | $CH_3$ | thiatriazol-5-yl |
| 1321 | O | $CH_3$ | (E)-1-chloropropen-3-yl |
| 1322 | O | $CH_3$ | (E)-4-(4'-chlorophenyl)but-2-en-1-yl |
| 1323 | O | $CH_3$ | propyn-3-yl |
| 1324 | O | $CH_3$ | methylcarbonyl |
| 1325 | O | $CH_3$ | 2-t-$C_4H_9$—$C_6H_4$—$CH_2$ |
| 1326 | O | $CH_3$ | 3-t-$C_4H_9$—$C_6H_4$—$CH_2$ |
| 1327 | O | $CH_3$ | 4-t-$C_4H_9$—$C_6H_4$—$CH_2$ |
| 1328 | O | $CH_3$ | 2-(4'-chlorothiazol-2'-yloxy)eth-1-yl |
| 1329 | O | $CH_3$ | 2-(1'-methylpyrazol-4'-yloxy)eth-1-yl |
| 1330 | O | $CH_3$ | 4-Br—$C_6H_4$ |
| 1331 | O | $CH_3$ | 3,5-$(CH_3)_2$—$C_6H_3$ |
| 1332 | O | $CH_3$ | 4-$C_2H_5$—$C_6H_4$ |
| 1333 | O | $CH_3$ | 3-dimethylaminocarbonyl-$C_6H_4$ |
| 1334 | O | $CH_3$ | 4-dimethylaminocarbonyl-$C_6H_4$ |
| 1335 | O | $CH_3$ | 2-hydroxyprop-1-yl |
| 1336 | O | $CH_3$ | 6-hydroxy-2-methylpyrimidin-4-ylmethyl |
| 1337 | O | $CH_3$ | [6-OH,2-CH($CH_3$)$_2$-pyrimidin-4-yl]-$CH_2$ |
| 1338 | O | $CH_3$ | [6-OH,2-CH($CH_2$)$_2$-pyrimidin-4-yl]-$CH_2$ |
| 1339 | O | $CH_3$ | 5-(2'-furan)pent-1-yl |
| 1340 | O | $CH_3$ | 5-(2'-N-methylpyrrole)pent-1-yl |
| 1341 | O | $CH_3$ | [2-(4-Cl—$C_6H_4$)-oxazol-4-yl]-$CH_2$ |
| 1342 | O | $CH_3$ | 3-$CF_3$-pyridin-2-yl |
| 1343 | O | $CH_3$ | 5-$CF_3$-pyridin-2-yl |
| 1344 | O | $CH_3$ | 6-(2'-thienyl)hex-1-yl |
| 1345 | O | $C_2H_5$ | H |
| 1346 | O | $C_2H_5$ | $CH_3$ |
| 1347 | O | $C_2H_5$ | $C_6H_5$—$CH_2$ |
| 1348 | O | i-$C_3H_7$ | $CH_3$ |
| 1349 | NH | H | H |
| 1350 | NH | H | $CH_3$ |
| 1351 | NH | H | 4-Cl—$C_6H_4$—$CH_2$ |
| 1352 | NH | $CH_3$ | $CH_3$ |
| 1353 | NH | $CH_3$ | $C_6H_5$—$CH_2$ |
| 1354 | $NCH_3$ | $CH_3$ | $CH_3$ |
| 1355 | $NCH_3$ | $CH_3$ | 4-$CH_3$—$C_6H_4$—$CH_2$ |
| 1356 | S | $CH_3$ | H |
| 1357 | S | $CH_3$ | $CH_3$ |
| 1358 | S | $CH_3$ | $C_2H_5$ |
| 1359 | S | $CH_3$ | $C_6H_5$—$CH_2$ |
| 1360 | — | $C_2H_5$ | H |
| 1361 | — | $C_2H_5$ | $CH_3$ |
| 1362 | — | $C_2H_5$ | $C_6H_5$—$CH_2$ |
| 1363 | — | $C_2H_5$ | 3-CN—$C_6H_4$—$CH_2$ |
| 1364 | — | $C_2H_5$ | prop-2-en-1-yl |
| 1365 | — | n-$C_3H_7$ | H |
| 1366 | — | n-$C_3H_7$ | $CH_3$ |
| 1367 | — | $C_6H_5$ | H |
| 1368 | — | $C_6H_5$ | $CH_3$ |
| 1369 | — | $C_6H_5$ | 3-$OCH_3$—$C_6H_4$—$CH_2$ |

| No. | $R^c$ | Ap | $R^a$ |
|---|---|---|---|
| e) $R^4$ = 3-$NR^c$—(C=O)—Ap—$R^a$ | | | |
| 1 | H | — | H |
| 2 | H | — | $CH_3$ |
| 3 | H | — | $C_2H_5$ |
| 4 | H | — | n-$C_3H_7$ |
| 5 | H | — | i-$C_3H_7$ |
| 6 | H | — | cyclopropyl |
| 7 | H | — | n-$C_4H_9$ |
| 8 | H | — | s-$C_4H_9$ |
| 9 | H | — | i-$C_4H_9$ |
| 10 | H | — | t-$C_4H_9$ |
| 11 | H | — | n-$C_5H_{11}$ |
| 12 | H | — | i-$C_5H_{11}$ |
| 13 | H | — | neo-$C_5H_{11}$ |
| 14 | H | — | cyclopentyl |
| 15 | H | — | n-$C_6H_{13}$ |
| 16 | H | — | cyclohexyl |
| 17 | H | — | $CF_3$ |
| 18 | H | — | ethenyl |
| 19 | H | — | propen-3-yl |
| 20 | H | — | benzyl |
| 21 | H | — | phenyl |
| 22 | H | O | H |
| 23 | H | O | $CH_3$ |
| 24 | H | O | $C_2H_5$ |
| 25 | H | O | n-$C_3H_7$ |
| 26 | H | O | i-$C_3H_7$ |
| 27 | H | O | cyclopropyl |
| 28 | H | O | n-$C_4H_9$ |
| 29 | H | O | s-$C_4H_9$ |
| 30 | H | O | i-$C_4H_9$ |
| 31 | H | O | t-$C_4H_9$ |
| 32 | H | O | n-$C_5H_{11}$ |
| 33 | H | O | i-$C_5H_{11}$ |
| 34 | H | O | neo-$C_5H_{11}$ |
| 35 | H | O | cyclopentyl |
| 36 | H | O | n-$C_6H_{13}$ |
| 37 | H | O | cyclohexyl |
| 38 | H | O | $CF_3$ |
| 39 | H | O | propyn-3-yl |
| 40 | H | O | propen-3-yl |
| 41 | H | O | benzyl |
| 42 | H | O | phenyl |
| 43 | H | NH | H |
| 44 | H | NH | $CH_3$ |
| 45 | H | NH | $C_2H_5$ |
| 46 | H | NH | n-$C_3H_7$ |
| 47 | H | NH | i-$C_3H_7$ |
| 48 | H | NH | cyclopropyl |
| 49 | H | NH | n-$C_4H_9$ |
| 50 | H | NH | s-$C_4H_9$ |
| 51 | H | NH | i-$C_4H_9$ |
| 52 | H | NH | t-$C_4H_9$ |
| 53 | H | NH | n-$C_5H_{11}$ |
| 54 | H | NH | i-$C_5H_{11}$ |
| 55 | H | NH | neo-$C_5H_{11}$ |
| 56 | H | NH | cyclopentyl |
| 57 | H | NH | n-$C_6H_{13}$ |
| 58 | H | NH | cyclohexyl |
| 59 | H | NH | cyclopropyl-$CH_2$ |
| 60 | H | NH | propyn-3-yl |
| 61 | H | NH | propen-3-yl |
| 62 | H | NH | benzyl |
| 63 | H | NH | phenyl |
| 64 | H | $NCH_3$ | $CH_3$ |
| 65 | H | $NCH_3$ | $C_2H_5$ |
| 66 | H | $NCH_3$ | n-$C_3H_7$ |
| 67 | H | $NCH_3$ | i-$C_3H_7$ |
| 68 | H | $NCH_3$ | cyclopropyl |
| 69 | H | $NCH_3$ | n-$C_4H_9$ |
| 70 | H | $NCH_3$ | s-$C_4H_9$ |
| 71 | H | $NCH_3$ | i-$C_4H_9$ |
| 72 | H | $NCH_3$ | t-$C_4H_9$ |
| 73 | H | $NCH_3$ | n-$C_5H_{11}$ |
| 74 | H | $NCH_3$ | i-$C_5H_{11}$ |
| 75 | H | $NCH_3$ | neo-$C_5H_{11}$ |
| 76 | H | $NCH_3$ | cyclopentyl |
| 77 | H | $NCH_3$ | n-$C_6H_{13}$ |
| 78 | H | $NCH_3$ | cyclohexyl |
| 79 | H | $NCH_3$ | cyclopropyl-$CH_2$ |
| 80 | H | $NCH_3$ | propyn-3-yl |
| 81 | H | $NCH_3$ | propen-3-yl |
| 82 | H | $NCH_3$ | benzyl |
| 83 | H | $NCH_3$ | phenyl |
| 84 | $CH_3$ | — | H |
| 85 | $CH_3$ | — | $CH_3$ |
| 86 | $CH_3$ | — | $C_2H_5$ |
| 87 | $CH_3$ | — | n-$C_3H_7$ |
| 88 | $CH_3$ | — | i-$C_3H_7$ |
| 89 | $CH_3$ | — | cyclopropyl |
| 90 | $CH_3$ | — | n-$C_4H_9$ |
| 91 | $CH_3$ | — | s-$C_4H_9$ |
| 92 | $CH_3$ | — | i-$C_4H_9$ |
| 93 | $CH_3$ | — | t-$C_4H_9$ |
| 94 | $CH_3$ | — | n-$C_5H_{11}$ |
| 95 | $CH_3$ | — | i-$C_5H_{11}$ |
| 96 | $CH_3$ | — | neo-$C_5H_{11}$ |
| 97 | $CH_3$ | — | cyclopentyl |

TABLE A-continued

| | | | |
|---|---|---|---|
| 98 | CH$_3$ | — | n-C$_6$H$_{13}$ |
| 99 | CH$_3$ | — | cyclohexyl |
| 100 | CH$_3$ | — | CF$_3$ |
| 101 | CH$_3$ | — | ethenyl |
| 102 | CH$_3$ | — | propen-3-yl |
| 103 | CH$_3$ | — | benzyl |
| 104 | CH$_3$ | — | phenyl |
| 105 | CH$_3$ | O | H |
| 106 | CH$_3$ | O | CH$_3$ |
| 107 | CH$_3$ | O | C$_2$H$_5$ |
| 108 | CH$_3$ | O | n-C$_3$H$_7$ |
| 109 | CH$_3$ | O | i-C$_3$H$_7$ |
| 110 | CH$_3$ | O | cyclopropyl |
| 111 | CH$_3$ | O | n-C$_4$H$_9$ |
| 112 | CH$_3$ | O | s-C$_4$H$_9$ |
| 113 | CH$_3$ | O | i-C$_4$H$_9$ |
| 114 | CH$_3$ | O | t-C$_4$H$_9$ |
| 115 | CH$_3$ | O | n-C$_5$H$_{11}$ |
| 116 | CH$_3$ | O | i-C$_5$H$_{11}$ |
| 117 | CH$_3$ | O | neo-C$_5$H$_{11}$ |
| 118 | CH$_3$ | O | cyclopentyl |
| 119 | CH$_3$ | O | n-C$_6$H$_{13}$ |
| 120 | CH$_3$ | O | cyclohexyl |
| 121 | CH$_3$ | O | CF$_3$ |
| 122 | CH$_3$ | O | propyn-3-yl |
| 123 | CH$_3$ | O | propen-3-yl |
| 124 | CH$_3$ | O | benzyl |
| 125 | CH$_3$ | O | phenyl |
| 126 | CH$_3$ | NH | H |
| 127 | CH$_3$ | NH | CH$_3$ |
| 128 | CH$_3$ | NH | C$_2$H$_5$ |
| 129 | CH$_3$ | NH | n-C$_3$H$_7$ |
| 130 | CH$_3$ | NH | i-C$_3$H$_7$ |
| 131 | CH$_3$ | NH | cyclopropyl |
| 132 | CH$_3$ | NH | n-C$_4$H$_9$ |
| 133 | CH$_3$ | NH | s-C$_4$H$_9$ |
| 134 | CH$_3$ | NH | i-C$_4$H$_9$ |
| 135 | CH$_3$ | NH | t-C$_4$H$_9$ |
| 136 | CH$_3$ | NH | n-C$_5$H$_{11}$ |
| 137 | CH$_3$ | NH | i-C$_5$H$_{11}$ |
| 138 | CH$_3$ | NH | neo-C$_5$H$_{11}$ |
| 139 | CH$_3$ | NH | cyclopentyl |
| 140 | CH$_3$ | NH | n-C$_6$H$_{13}$ |
| 141 | CH$_3$ | NH | cyclohexyl |
| 142 | CH$_3$ | NH | cyclopropyl-CH$_2$ |
| 143 | CH$_3$ | NH | propyn-3-yl |
| 144 | CH$_3$ | NH | propen-3-yl |
| 145 | CH$_3$ | NH | benzyl |
| 146 | CH$_3$ | NH | phenyl |
| 147 | CH$_3$ | NCH$_3$ | CH$_3$ |
| 148 | CH$_3$ | NCH$_3$ | C$_2$H$_5$ |
| 149 | CH$_3$ | NCH$_3$ | n-C$_3$H$_7$ |
| 150 | CH$_3$ | NCH$_3$ | i-C$_3$H$_7$ |
| 151 | CH$_3$ | NCH$_3$ | cyclopropyl |
| 152 | CH$_3$ | NCH$_3$ | n-C$_4$H$_9$ |
| 153 | CH$_3$ | NCH$_3$ | s-C$_4$H$_9$ |
| 154 | CH$_3$ | NCH$_3$ | i-C$_4$H$_9$ |
| 155 | CH$_3$ | NCH$_3$ | t-C$_4$H$_9$ |
| 156 | CH$_3$ | NCH$_3$ | n-C$_5$H$_{11}$ |
| 157 | CH$_3$ | NCH$_3$ | i-C$_5$H$_{11}$ |
| 158 | CH$_3$ | NCH$_3$ | neo-C$_5$H$_{11}$ |
| 159 | CH$_3$ | NCH$_3$ | cyclopentyl |
| 160 | CH$_3$ | NCH$_3$ | n-C$_6$H$_{13}$ |
| 161 | CH$_3$ | NCH$_3$ | cyclohexyl |
| 162 | CH$_3$ | NCH$_3$ | cyclopropyl-CH$_2$ |
| 163 | CH$_3$ | NCH$_3$ | propyn-3-yl |
| 164 | CH$_3$ | NCH$_3$ | propen-3-yl |
| 165 | CH$_3$ | NCH$_3$ | benzyl |
| 166 | CH$_3$ | NCH$_3$ | phenyl |
| 167 | C$_2$H$_5$ | — | H |
| 168 | C$_2$H$_5$ | — | CH$_3$ |
| 169 | C$_2$H$_5$ | — | C$_2$H$_5$ |
| 170 | C$_2$H$_5$ | — | n-C$_3$H$_7$ |
| 171 | C$_2$H$_5$ | — | i-C$_3$H$_7$ |
| 172 | C$_2$H$_5$ | — | cyclopropyl |
| 173 | C$_2$H$_5$ | — | n-C$_4$H$_9$ |
| 174 | C$_2$H$_5$ | — | s-C$_4$H$_9$ |
| 175 | C$_2$H$_5$ | — | i-C$_4$H$_9$ |
| 176 | C$_2$H$_5$ | — | t-C$_4$H$_9$ |
| 177 | C$_2$H$_5$ | — | n-C$_5$H$_{11}$ |
| 178 | C$_2$H$_5$ | — | i-C$_5$H$_{11}$ |
| 179 | C$_2$H$_5$ | — | neo-C$_5$H$_{11}$ |
| 180 | C$_2$H$_5$ | — | cyclopentyl |
| 181 | C$_2$H$_5$ | — | n-C$_6$H$_{13}$ |
| 182 | C$_2$H$_5$ | — | cyclohexyl |
| 183 | C$_2$H$_5$ | — | CF$_3$ |
| 184 | C$_2$H$_5$ | — | ethenyl |
| 185 | C$_2$H$_5$ | — | propen-3-yl |
| 186 | C$_2$H$_5$ | — | benzyl |
| 187 | C$_2$H$_5$ | — | phenyl |
| 188 | C$_2$H$_5$ | O | H |
| 189 | C$_2$H$_5$ | O | CH$_3$ |
| 190 | C$_2$H$_5$ | O | C$_2$H$_5$ |
| 191 | C$_2$H$_5$ | O | n-C$_3$H$_7$ |
| 192 | C$_2$H$_5$ | O | i-C$_3$H$_7$ |
| 193 | C$_2$H$_5$ | O | cyclopropyl |
| 194 | C$_2$H$_5$ | O | n-C$_4$H$_9$ |
| 195 | C$_2$H$_5$ | O | s-C$_4$H$_9$ |
| 196 | C$_2$H$_5$ | O | i-C$_4$H$_9$ |
| 197 | C$_2$H$_5$ | O | t-C$_4$H$_9$ |
| 198 | C$_2$H$_5$ | O | n-C$_5$H$_{11}$ |
| 199 | C$_2$H$_5$ | O | i-C$_5$H$_{11}$ |
| 200 | C$_2$H$_5$ | O | neo-C$_5$H$_{11}$ |
| 201 | C$_2$H$_5$ | O | cyclopentyl |
| 202 | C$_2$H$_5$ | O | n-C$_6$H$_{13}$ |
| 203 | C$_2$H$_5$ | O | cyclohexyl |
| 204 | C$_2$H$_5$ | O | CF$_3$ |
| 205 | C$_2$H$_5$ | O | propyn-3-yl |
| 206 | C$_2$H$_5$ | O | propen-3-yl |
| 207 | C$_2$H$_5$ | O | benzyl |
| 208 | C$_2$H$_5$ | O | phenyl |
| 209 | C$_2$H$_5$ | NH | H |
| 210 | C$_2$H$_5$ | NH | CH$_3$ |
| 211 | C$_2$H$_5$ | NH | C$_2$H$_5$ |
| 212 | C$_2$H$_5$ | NH | n-C$_3$H$_7$ |
| 213 | C$_2$H$_5$ | NH | i-C$_3$H$_7$ |
| 214 | C$_2$H$_5$ | NH | cyclopropyl |
| 215 | C$_2$H$_5$ | NH | n-C$_4$H$_9$ |
| 216 | C$_2$H$_5$ | NH | s-C$_4$H$_9$ |
| 217 | C$_2$H$_5$ | NH | i-C$_4$H$_9$ |
| 218 | C$_2$H$_5$ | NH | t-C$_4$H$_9$ |
| 219 | C$_2$H$_5$ | NH | n-C$_5$H$_{11}$ |
| 220 | C$_2$H$_5$ | NH | i-C$_5$H$_{11}$ |
| 221 | C$_2$H$_5$ | NH | neo-C$_5$H$_{11}$ |
| 222 | C$_2$H$_5$ | NH | cyclopentyl |
| 223 | C$_2$H$_5$ | NH | n-C$_6$H$_{13}$ |
| 224 | C$_2$H$_5$ | NH | cyclohexyl |
| 225 | C$_2$H$_5$ | NH | cyclopropyl-CH$_2$ |
| 226 | C$_2$H$_5$ | NH | propyn-3-yl |
| 227 | C$_2$H$_5$ | NH | propen-3-yl |
| 228 | C$_2$H$_5$ | NH | benzyl |
| 229 | C$_2$H$_5$ | NH | phenyl |
| 230 | C$_2$H$_5$ | NCH$_3$ | CH$_3$ |
| 231 | C$_2$H$_5$ | NCH$_3$ | C$_2$H$_5$ |
| 232 | C$_2$H$_5$ | NCH$_3$ | n-C$_3$H$_7$ |
| 233 | C$_2$H$_5$ | NCH$_3$ | i-C$_3$H$_7$ |
| 234 | C$_2$H$_5$ | NCH$_3$ | cyclopropyl |
| 235 | C$_2$H$_5$ | NCH$_3$ | n-C$_4$H$_9$ |
| 236 | C$_2$H$_5$ | NCH$_3$ | s-C$_4$H$_9$ |
| 237 | C$_2$H$_5$ | NCH$_3$ | i-C$_4$H$_9$ |
| 238 | C$_2$H$_5$ | NCH$_3$ | t-C$_4$H$_9$ |
| 239 | C$_2$H$_5$ | NCH$_3$ | n-C$_5$H$_{11}$ |
| 240 | C$_2$H$_5$ | NCH$_3$ | i-C$_5$H$_{11}$ |
| 241 | C$_2$H$_5$ | NCH$_3$ | neo-C$_5$H$_{11}$ |
| 242 | C$_2$H$_5$ | NCH$_3$ | cyclopentyl |
| 243 | C$_2$H$_5$ | NCH$_3$ | n-C$_6$H$_{13}$ |
| 244 | C$_2$H$_5$ | NCH$_3$ | cyclohexyl |
| 245 | C$_2$H$_5$ | NCH$_3$ | cyclopropyl-CH$_2$ |
| 246 | C$_2$H$_5$ | NCH$_3$ | propyn-3-yl |
| 247 | C$_2$H$_5$ | NCH$_3$ | propen-3-yl |
| 248 | C$_2$H$_5$ | NCH$_3$ | benzyl |
| 249 | C$_2$H$_5$ | NCH$_3$ | phenyl |
| 250 | n-C$_3$H$_7$ | — | H |
| 251 | n-C$_3$H$_7$ | — | CH$_3$ |
| 252 | n-C$_3$H$_7$ | — | C$_2$H$_5$ |
| 253 | n-C$_3$H$_7$ | — | n-C$_3$H$_7$ |
| 254 | n-C$_3$H$_7$ | — | i-C$_3$H$_7$ |
| 255 | n-C$_3$H$_7$ | — | cyclopropyl |

TABLE A-continued

| | | | |
|---|---|---|---|
| 256 | n-C$_3$H$_7$ | — | n-C$_4$H$_9$ |
| 257 | n-C$_3$H$_7$ | — | s-C$_4$H$_9$ |
| 258 | n-C$_3$H$_7$ | — | i-C$_4$H$_9$ |
| 259 | n-C$_3$H$_7$ | — | t-C$_4$H$_9$ |
| 260 | n-C$_3$H$_7$ | — | n-C$_5$H$_{11}$ |
| 261 | n-C$_3$H$_7$ | — | i-C$_5$H$_{11}$ |
| 262 | n-C$_3$H$_7$ | — | neo-C$_5$H$_{11}$ |
| 263 | n-C$_3$H$_7$ | — | cyclopentyl |
| 264 | n-C$_3$H$_7$ | — | n-C$_6$H$_{13}$ |
| 265 | n-C$_3$H$_7$ | — | cyclohexyl |
| 266 | n-C$_3$H$_7$ | — | CF$_3$ |
| 267 | n-C$_3$H$_7$ | — | ethenyl |
| 268 | n-C$_3$H$_7$ | — | propen-3-yl |
| 269 | n-C$_3$H$_7$ | — | benzyl |
| 270 | n-C$_3$H$_7$ | — | phenyl |
| 271 | n-C$_3$H$_7$ | O | H |
| 272 | n-C$_3$H$_7$ | O | CH$_3$ |
| 273 | n-C$_3$H$_7$ | O | C$_2$H$_5$ |
| 274 | n-C$_3$H$_7$ | O | n-C$_3$H$_7$ |
| 275 | n-C$_3$H$_7$ | O | i-C$_3$H$_7$ |
| 276 | n-C$_3$H$_7$ | O | cyclopropyl |
| 277 | n-C$_3$H$_7$ | O | n-C$_4$H$_9$ |
| 278 | n-C$_3$H$_7$ | O | s-C$_4$H$_9$ |
| 279 | n-C$_3$H$_7$ | O | i-C$_4$H$_9$ |
| 280 | n-C$_3$H$_7$ | O | t-C$_4$H$_9$ |
| 281 | n-C$_3$H$_7$ | O | n-C$_5$H$_{11}$ |
| 282 | n-C$_3$H$_7$ | O | i-C$_5$H$_{11}$ |
| 283 | n-C$_3$H$_7$ | O | neo-C$_5$H$_{11}$ |
| 284 | n-C$_3$H$_7$ | O | cyclopentyl |
| 285 | n-C$_3$H$_7$ | O | n-C$_6$H$_{13}$ |
| 286 | n-C$_3$H$_7$ | O | cyclohexyl |
| 287 | n-C$_3$H$_7$ | O | CF$_3$ |
| 288 | n-C$_3$H$_7$ | O | propyn-3-yl |
| 289 | n-C$_3$H$_7$ | O | propen-3-yl |
| 290 | n-C$_3$H$_7$ | O | benzyl |
| 291 | n-C$_3$H$_7$ | O | phenyl |
| 292 | n-C$_3$H$_7$ | NH | H |
| 293 | n-C$_3$H$_7$ | NH | CH$_3$ |
| 294 | n-C$_3$H$_7$ | NH | C$_2$H$_5$ |
| 295 | n-C$_3$H$_7$ | NH | n-C$_3$H$_7$ |
| 296 | n-C$_3$H$_7$ | NH | i-C$_3$H$_7$ |
| 297 | n-C$_3$H$_7$ | NH | cyclopropyl |
| 298 | n-C$_3$H$_7$ | NH | n-C$_4$H$_9$ |
| 299 | n-C$_3$H$_7$ | NH | s-C$_4$H$_9$ |
| 300 | n-C$_3$H$_7$ | NH | i-C$_4$H$_9$ |
| 301 | n-C$_3$H$_7$ | NH | t-C$_4$H$_9$ |
| 302 | n-C$_3$H$_7$ | NH | n-C$_5$H$_{11}$ |
| 303 | n-C$_3$H$_7$ | NH | i-C$_5$H$_{11}$ |
| 304 | n-C$_3$H$_7$ | NH | neo-C$_5$H$_{11}$ |
| 305 | n-C$_3$H$_7$ | NH | cyclopentyl |
| 306 | n-C$_3$H$_7$ | NH | n-C$_6$H$_{13}$ |
| 307 | n-C$_3$H$_7$ | NH | cyclohexyl |
| 308 | n-C$_3$H$_7$ | NH | cyclopropyl-CH$_2$ |
| 309 | n-C$_3$H$_7$ | NH | propyn-3-yl |
| 310 | n-C$_3$H$_7$ | NH | propen-3-yl |
| 311 | n-C$_3$H$_7$ | NH | benzyl |
| 312 | n-C$_3$H$_7$ | NH | phenyl |
| 313 | n-C$_3$H$_7$ | NCH$_3$ | CH$_3$ |
| 314 | n-C$_3$H$_7$ | NCH$_3$ | C$_2$H$_5$ |
| 315 | n-C$_3$H$_7$ | NCH$_3$ | n-C$_3$H$_7$ |
| 316 | n-C$_3$H$_7$ | NCH$_3$ | i-C$_3$H$_7$ |
| 317 | n-C$_3$H$_7$ | NCH$_3$ | cyclopropyl |
| 318 | n-C$_3$H$_7$ | NCH$_3$ | n-C$_4$H$_9$ |
| 319 | n-C$_3$H$_7$ | NCH$_3$ | s-C$_4$H$_9$ |
| 320 | n-C$_3$H$_7$ | NCH$_3$ | i-C$_4$H$_9$ |
| 321 | n-C$_3$H$_7$ | NCH$_3$ | t-C$_4$H$_9$ |
| 322 | n-C$_3$H$_7$ | NCH$_3$ | n-C$_5$H$_{11}$ |
| 323 | n-C$_3$H$_7$ | NCH$_3$ | i-C$_5$H$_{11}$ |
| 324 | n-C$_3$H$_7$ | NCH$_3$ | neo-C$_5$H$_{11}$ |
| 325 | n-C$_3$H$_7$ | NCH$_3$ | cyclopentyl |
| 326 | n-C$_3$H$_7$ | NCH$_3$ | n-C$_6$H$_{13}$ |
| 327 | n-C$_3$H$_7$ | NCH$_3$ | cyclohexyl |
| 328 | n-C$_3$H$_7$ | NCH$_3$ | cyclopropyl-CH$_2$ |
| 329 | n-C$_3$H$_7$ | NCH$_3$ | propyn-3-yl |
| 330 | n-C$_3$H$_7$ | NCH$_3$ | propen-3-yl |
| 331 | n-C$_3$H$_7$ | NCH$_3$ | benzyl |
| 332 | n-C$_3$H$_7$ | NCH$_3$ | phenyl |
| 333 | i-C$_3$H$_7$ | — | H |
| 334 | i-C$_3$H$_7$ | — | CH$_3$ |
| 335 | i-C$_3$H$_7$ | — | C$_2$H$_5$ |
| 336 | i-C$_3$H$_7$ | — | n-C$_3$H$_7$ |
| 337 | i-C$_3$H$_7$ | — | i-C$_3$H$_7$ |
| 338 | i-C$_3$H$_7$ | — | cyclopropyl |
| 339 | i-C$_3$H$_7$ | — | n-C$_4$H$_9$ |
| 340 | i-C$_3$H$_7$ | — | s-C$_4$H$_9$ |
| 341 | i-C$_3$H$_7$ | — | i-C$_4$H$_9$ |
| 342 | i-C$_3$H$_7$ | — | t-C$_4$H$_9$ |
| 343 | i-C$_3$H$_7$ | — | n-C$_5$H$_{11}$ |
| 344 | i-C$_3$H$_7$ | — | i-C$_5$H$_{11}$ |
| 345 | i-C$_3$H$_7$ | — | neo-C$_5$H$_{11}$ |
| 346 | i-C$_3$H$_7$ | — | cyclopentyl |
| 347 | i-C$_3$H$_7$ | — | n-C$_6$H$_{13}$ |
| 348 | i-C$_3$H$_7$ | — | cyclohexyl |
| 349 | i-C$_3$H$_7$ | — | CF$_3$ |
| 350 | i-C$_3$H$_7$ | — | ethenyl |
| 351 | i-C$_3$H$_7$ | — | propen-3-yl |
| 352 | i-C$_3$H$_7$ | — | benzyl |
| 353 | i-C$_3$H$_7$ | — | phenyl |
| 354 | i-C$_3$H$_7$ | O | H |
| 355 | i-C$_3$H$_7$ | O | CH$_3$ |
| 356 | i-C$_3$H$_7$ | O | C$_2$H$_5$ |
| 357 | i-C$_3$H$_7$ | O | n-C$_3$H$_7$ |
| 358 | i-C$_3$H$_7$ | O | i-C$_3$H$_7$ |
| 359 | i-C$_3$H$_7$ | O | cyclopropyl |
| 360 | i-C$_3$H$_7$ | O | n-C$_4$H$_9$ |
| 361 | i-C$_3$H$_7$ | O | s-C$_4$H$_9$ |
| 362 | i-C$_3$H$_7$ | O | i-C$_4$H$_9$ |
| 363 | i-C$_3$H$_7$ | O | t-C$_4$H$_9$ |
| 364 | i-C$_3$H$_7$ | O | n-C$_5$H$_{11}$ |
| 365 | i-C$_3$H$_7$ | O | i-C$_5$H$_{11}$ |
| 366 | i-C$_3$H$_7$ | O | neo-C$_5$H$_{11}$ |
| 367 | i-C$_3$H$_7$ | O | cyclopentyl |
| 368 | i-C$_3$H$_7$ | O | n-C$_6$H$_{13}$ |
| 369 | i-C$_3$H$_7$ | O | cyclohexyl |
| 370 | i-C$_3$H$_7$ | O | CF$_3$ |
| 371 | i-C$_3$H$_7$ | O | propyn-3-yl |
| 372 | i-C$_3$H$_7$ | O | propen-3-yl |
| 373 | i-C$_3$H$_7$ | O | benzyl |
| 374 | i-C$_3$H$_7$ | O | phenyl |
| 375 | i-C$_3$H$_7$ | NH | H |
| 376 | i-C$_3$H$_7$ | NH | CH$_3$ |
| 377 | i-C$_3$H$_7$ | NH | C$_2$H$_5$ |
| 378 | i-C$_3$H$_7$ | NH | n-C$_3$H$_7$ |
| 379 | i-C$_3$H$_7$ | NH | i-C$_3$H$_7$ |
| 380 | i-C$_3$H$_7$ | NH | cyclopropyl |
| 381 | i-C$_3$H$_7$ | NH | n-C$_4$H$_9$ |
| 382 | i-C$_3$H$_7$ | NH | s-C$_4$H$_9$ |
| 383 | i-C$_3$H$_7$ | NH | i-C$_4$H$_9$ |
| 384 | i-C$_3$H$_7$ | NH | t-C$_4$H$_9$ |
| 385 | i-C$_3$H$_7$ | NH | n-C$_5$H$_{11}$ |
| 386 | i-C$_3$H$_7$ | NH | i-C$_5$H$_{11}$ |
| 387 | i-C$_3$H$_7$ | NH | neo-C$_5$H$_{11}$ |
| 388 | i-C$_3$H$_7$ | NH | cyclopentyl |
| 389 | i-C$_3$H$_7$ | NH | n-C$_6$H$_{13}$ |
| 390 | i-C$_3$H$_7$ | NH | cyclohexyl |
| 391 | i-C$_3$H$_7$ | NH | cyclopropyl-CH$_2$ |
| 392 | i-C$_3$H$_7$ | NH | propyn-3-yl |
| 393 | i-C$_3$H$_7$ | NH | propen-3-yl |
| 394 | i-C$_3$H$_7$ | NH | benzyl |
| 395 | i-C$_3$H$_7$ | NH | phenyl |
| 396 | i-C$_3$H$_7$ | NCH$_3$ | CH$_3$ |
| 397 | i-C$_3$H$_7$ | NCH$_3$ | C$_2$H$_5$ |
| 398 | i-C$_3$H$_7$ | NCH$_3$ | n-C$_3$H$_7$ |
| 399 | i-C$_3$H$_7$ | NCH$_3$ | i-C$_3$H$_7$ |
| 400 | i-C$_3$H$_7$ | NCH$_3$ | cyclopropyl |
| 401 | i-C$_3$H$_7$ | NCH$_3$ | n-C$_4$H$_9$ |
| 402 | i-C$_3$H$_7$ | NCH$_3$ | s-C$_4$H$_9$ |
| 403 | i-C$_3$H$_7$ | NCH$_3$ | i-C$_4$H$_9$ |
| 404 | i-C$_3$H$_7$ | NCH$_3$ | t-C$_4$H$_9$ |
| 405 | i-C$_3$H$_7$ | NCH$_3$ | n-C$_5$H$_{11}$ |
| 406 | i-C$_3$H$_7$ | NCH$_3$ | i-C$_5$H$_{11}$ |
| 407 | i-C$_3$H$_7$ | NCH$_3$ | neo-C$_5$H$_{11}$ |
| 408 | i-C$_3$H$_7$ | NCH$_3$ | cyclopentyl |
| 409 | i-C$_3$H$_7$ | NCH$_3$ | n-C$_6$H$_{13}$ |
| 410 | i-C$_3$H$_7$ | NCH$_3$ | cyclohexyl |
| 411 | i-C$_3$H$_7$ | NCH$_3$ | cyclopropyl-CH$_2$ |
| 412 | i-C$_3$H$_7$ | NCH$_3$ | propyn-3-yl |
| 413 | i-C$_3$H$_7$ | NCH$_3$ | propen-3-yl |

TABLE A-continued

| | | | |
|---|---|---|---|
| 414 | i-C$_3$H$_7$ | NCH$_3$ | benzyl |
| 415 | i-C$_3$H$_7$ | NCH$_3$ | phenyl |
| 416 | benzyl | — | H |
| 417 | benzyl | — | CH$_3$ |
| 418 | benzyl | — | C$_2$H$_5$ |
| 419 | benzyl | — | n-C$_3$H$_7$ |
| 420 | benzyl | — | i-C$_3$H$_7$ |
| 421 | benzyl | — | cyclopropyl |
| 422 | benzyl | — | n-C$_4$H$_9$ |
| 423 | benzyl | — | s-C$_4$H$_9$ |
| 424 | benzyl | — | i-C$_4$H$_9$ |
| 425 | benzyl | — | t-C$_4$H$_9$ |
| 426 | benzyl | — | n-C$_5$H$_{11}$ |
| 427 | benzyl | — | i-C$_5$H$_{11}$ |
| 428 | benzyl | — | neo-C$_5$H$_{11}$ |
| 429 | benzyl | — | cyclopentyl |
| 430 | benzyl | — | n-C$_6$H$_{13}$ |
| 431 | benzyl | — | cyclohexyl |
| 432 | benzyl | — | CF$_3$ |
| 433 | benzyl | — | ethenyl |
| 434 | benzyl | — | propen-3-yl |
| 435 | benzyl | — | benzyl |
| 436 | benzyl | — | phenyl |
| 437 | benzyl | O | H |
| 438 | benzyl | O | CH$_3$ |
| 439 | benzyl | O | C$_2$H$_5$ |
| 440 | benzyl | O | n-C$_3$H$_7$ |
| 441 | benzyl | O | i-C$_3$H$_7$ |
| 442 | benzyl | O | cyclopropyl |
| 443 | benzyl | O | n-C$_4$H$_9$ |
| 444 | benzyl | O | s-C$_4$H$_9$ |
| 445 | benzyl | O | i-C$_4$H$_9$ |
| 446 | benzyl | O | t-C$_4$H$_9$ |
| 447 | benzyl | O | n-C$_5$H$_{11}$ |
| 448 | benzyl | O | i-C$_5$H$_{11}$ |
| 449 | benzyl | O | neo-C$_5$H$_{11}$ |
| 450 | benzyl | O | cyclopentyl |
| 451 | benzyl | O | n-C$_6$H$_{13}$ |
| 452 | benzyl | O | cyclohexyl |
| 453 | benzyl | O | CF$_3$ |
| 454 | benzyl | O | propyn-3-yl |
| 455 | benzyl | O | propen-3-yl |
| 456 | benzyl | O | benzyl |
| 457 | benzyl | O | phenyl |
| 458 | benzyl | NH | H |
| 459 | benzyl | NH | CH$_3$ |
| 460 | benzyl | NH | C$_2$H$_5$ |
| 461 | benzyl | NH | n-C$_3$H$_7$ |
| 462 | benzyl | NH | i-C$_3$H$_7$ |
| 463 | benzyl | NH | cyclopropyl |
| 464 | benzyl | NH | n-C$_4$H$_9$ |
| 465 | benzyl | NH | s-C$_4$H$_9$ |
| 466 | benzyl | NH | i-C$_4$H$_9$ |
| 467 | benzyl | NH | t-C$_4$H$_9$ |
| 468 | benzyl | NH | n-C$_5$H$_{11}$ |
| 469 | benzyl | NH | i-C$_5$H$_{11}$ |
| 470 | benzyl | NH | neo-C$_5$H$_{11}$ |
| 471 | benzyl | NH | cyclopentyl |
| 472 | benzyl | NH | n-C$_6$H$_{13}$ |
| 473 | benzyl | NH | cyclohexyl |
| 474 | benzyl | NH | cyclopropyl-CH$_2$ |
| 475 | benzyl | NH | propyn-3-yl |
| 476 | benzyl | NH | propen-3-yl |
| 477 | benzyl | NH | benzyl |
| 478 | benzyl | NH | phenyl |
| 479 | benzyl | NCH$_3$ | CH$_3$ |
| 480 | benzyl | NCH$_3$ | C$_2$H$_5$ |
| 481 | benzyl | NCH$_3$ | n-C$_3$H$_7$ |
| 482 | benzyl | NCH$_3$ | i-C$_3$H$_7$ |
| 483 | benzyl | NCH$_3$ | cyclopropyl |
| 484 | benzyl | NCH$_3$ | n-C$_4$H$_9$ |
| 485 | benzyl | NCH$_3$ | s-C$_4$H$_9$ |
| 486 | benzyl | NCH$_3$ | i-C$_4$H$_9$ |
| 487 | benzyl | NCH$_3$ | t-C$_4$H$_9$ |
| 488 | benzyl | NCH$_3$ | n-C$_5$H$_{11}$ |
| 489 | benzyl | NCH$_3$ | i-C$_5$H$_{11}$ |
| 490 | benzyl | NCH$_3$ | neo-C$_5$H$_{11}$ |
| 491 | benzyl | NCH$_3$ | cyclopentyl |
| 492 | benzyl | NCH$_3$ | n-C$_6$H$_{13}$ |
| 493 | benzyl | NCH$_3$ | cyclohexyl |
| 494 | benzyl | NCH$_3$ | cyclopropyl-CH$_2$ |
| 495 | benzyl | NCH$_3$ | propyn-3-yl |
| 496 | benzyl | NCH$_3$ | propen-3-yl |
| 497 | benzyl | NCH$_3$ | benzyl |
| 498 | benzyl | NCH$_3$ | phenyl |
| 499 | propen-3-yl | — | H |
| 500 | propen-3-yl | — | CH$_3$ |
| 501 | propen-3-yl | — | C$_2$H$_5$ |
| 502 | propen-3-yl | — | n-C$_3$H$_7$ |
| 503 | propen-3-yl | — | i-C$_3$H$_7$ |
| 504 | propen-3-yl | — | cyclopropyl |
| 505 | propen-3-yl | — | n-C$_4$H$_9$ |
| 506 | propen-3-yl | — | s-C$_4$H$_9$ |
| 507 | propen-3-yl | — | i-C$_4$H$_9$ |
| 508 | propen-3-yl | — | t-C$_4$H$_9$ |
| 509 | propen-3-yl | — | n-C$_5$H$_{11}$ |
| 510 | propen-3-yl | — | i-C$_5$H$_{11}$ |
| 511 | propen-3-yl | — | neo-C$_5$H$_{11}$ |
| 512 | propen-3-yl | — | cyclopentyl |
| 513 | propen-3-yl | — | n-C$_6$H$_{13}$ |
| 514 | propen-3-yl | — | cyclohexyl |
| 515 | propen-3-yl | — | CF$_3$ |
| 516 | propen-3-yl | — | ethenyl |
| 517 | propen-3-yl | — | propen-3-yl |
| 518 | propen-3-yl | — | benzyl |
| 519 | propen-3-yl | — | phenyl |
| 520 | propen-3-yl | O | H |
| 521 | propen-3-yl | O | CH$_3$ |
| 522 | propen-3-yl | O | C$_2$H$_5$ |
| 523 | propen-3-yl | O | n-C$_3$H$_7$ |
| 524 | propen-3-yl | O | i-C$_3$H$_7$ |
| 525 | propen-3-yl | O | cyclopropyl |
| 526 | propen-3-yl | O | n-C$_4$H$_9$ |
| 527 | propen-3-yl | O | s-C$_4$H$_9$ |
| 528 | propen-3-yl | O | i-C$_4$H$_9$ |
| 529 | propen-3-yl | O | t-C$_4$H$_9$ |
| 530 | propen-3-yl | O | n-C$_5$H$_{11}$ |
| 531 | propen-3-yl | O | i-C$_5$H$_{11}$ |
| 532 | propen-3-yl | O | neo-C$_5$H$_{11}$ |
| 533 | propen-3-yl | O | cyclopentyl |
| 534 | propen-3-yl | O | n-C$_6$H$_{13}$ |
| 535 | propen-3-yl | O | cyclohexyl |
| 536 | propen-3-yl | O | CF$_3$ |
| 537 | propen-3-yl | O | propyn-3-yl |
| 538 | propen-3-yl | O | propen-3-yl |
| 539 | propen-3-yl | O | benzyl |
| 540 | propen-3-yl | O | phenyl |
| 541 | propen-3-yl | NH | H |
| 542 | propen-3-yl | NH | CH$_3$ |
| 543 | propen-3-yl | NH | C$_2$H$_5$ |
| 544 | propen-3-yl | NH | n-C$_3$H$_7$ |
| 545 | propen-3-yl | NH | i-C$_3$H$_7$ |
| 546 | propen-3-yl | NH | cyclopropyl |
| 547 | propen-3-yl | NH | n-C$_4$H$_9$ |
| 548 | propen-3-yl | NH | s-C$_4$H$_9$ |
| 549 | propen-3-yl | NH | i-C$_4$H$_9$ |
| 550 | propen-3-yl | NH | t-C$_4$H$_9$ |
| 551 | propen-3-yl | NH | n-C$_5$H$_{11}$ |
| 552 | propen-3-yl | NH | i-C$_5$H$_{11}$ |
| 553 | propen-3-yl | NH | neo-C$_5$H$_{11}$ |
| 554 | propen-3-yl | NH | cyclopentyl |
| 555 | propen-3-yl | NH | n-C$_6$H$_{13}$ |
| 556 | propen-3-yl | NH | cyclohexyl |
| 557 | propen-3-yl | NH | cyclopropyl-CH$_2$ |
| 558 | propen-3-yl | NH | propyn-3-yl |
| 559 | propen-3-yl | NH | propen-3-yl |
| 560 | propen-3-yl | NH | benzyl |
| 561 | propen-3-yl | NH | phenyl |
| 562 | propen-3-yl | NCH$_3$ | CH$_3$ |
| 563 | propen-3-yl | NCH$_3$ | C$_2$H$_5$ |
| 564 | propen-3-yl | NCH$_3$ | n-C$_3$H$_7$ |
| 565 | propen-3-yl | NCH$_3$ | i-C$_3$H$_7$ |
| 566 | propen-3-yl | NCH$_3$ | cyclopropyl |
| 567 | propen-3-yl | NCH$_3$ | n-C$_4$H$_9$ |
| 568 | propen-3-yl | NCH$_3$ | s-C$_4$H$_9$ |
| 569 | propen-3-yl | NCH$_3$ | i-C$_4$H$_9$ |
| 570 | propen-3-yl | NCH$_3$ | t-C$_4$H$_9$ |
| 571 | propen-3-yl | NCH$_3$ | n-C$_5$H$_{11}$ |

TABLE A-continued

| | | | |
|---|---|---|---|
| 572 | propen-3-yl | NCH$_3$ | i-C$_5$H$_{11}$ |
| 573 | propen-3-yl | NCH$_3$ | neo-C$_5$H$_{11}$ |
| 574 | propen-3-yl | NCH$_3$ | cyclopentyl |
| 575 | propen-3-yl | NCH$_3$ | n-C$_6$H$_{13}$ |
| 576 | propen-3-yl | NCH$_3$ | cyclohexyl |
| 577 | propen-3-yl | NCH$_3$ | cyclopropyl-CH$_2$ |
| 578 | propen-3-yl | NCH$_3$ | propyn-3-yl |
| 579 | propen-3-yl | NCH$_3$ | propen-3-yl |
| 580 | propen-3-yl | NCH$_3$ | benzyl |
| 581 | propen-3-yl | NCH$_3$ | phenyl |
| 582 | H | NC$_2$H$_5$ | C$_2$H$_5$ |
| 583 | H | N-n-C$_3$H$_7$ | n-C$_3$H$_7$ |
| 584 | H | N—CH$_2$CH=CH$_2$ | CH$_2$CH=CH$_2$ |
| 585 | H | N—CH$_2$CH$_2$OH | CH$_2$CH=CH$_2$ |
| 586 | CH$_3$ | NC$_2$H$_5$ | C$_2$H$_5$ |
| 587 | CH$_3$ | N-n-C$_3$H$_7$ | n-C$_3$H$_7$ |
| 588 | CH$_3$ | N—CH$_2$CH=CH$_2$ | CH$_2$CH=CH$_2$ |
| 589 | CH$_3$ | N—CH$_2$CHOH | CH$_2$CH=CH$_2$ |
| 590 | C$_6$H$_5$—CH$_2$ | NC$_2$H$_5$ | C$_2$H$_5$ |
| 591 | C$_6$H$_5$—CH$_2$ | N-n-C$_3$H$_7$ | n-C$_3$H$_7$ |
| 592 | C$_6$H$_5$—CH$_2$ | N—CH$_2$CH=CH$_2$ | CH$_2$CH=CH$_2$ |
| 593 | C$_6$H$_5$—CH$_2$ | N—CH$_2$CH$_2$OH | CH$_2$CH=CH$_2$ | f) R$^4$ = 4-NR$^c$—(C=O)—Ap—R$^a$

| | | | |
|---|---|---|---|
| 1 | H | — | H |
| 2 | H | — | CH$_3$ |
| 3 | H | — | C$_2$H$_5$ |
| 4 | H | — | n-C$_3$H$_7$ |
| 5 | H | — | i-C$_3$H$_7$ |
| 6 | H | — | cyclopropyl |
| 7 | H | — | n-C$_4$H$_9$ |
| 8 | H | — | s-C$_4$H$_9$ |
| 9 | H | — | i-C$_4$H$_9$ |
| 10 | H | — | t-C$_4$H$_9$ |
| 11 | H | — | n-C$_5$H$_{11}$ |
| 12 | H | — | i-C$_5$H$_{11}$ |
| 13 | H | — | neo-C$_5$H$_{11}$ |
| 14 | H | — | cyclopentyl |
| 15 | H | — | n-C$_6$H$_{13}$ |
| 16 | H | — | cyclohexyl |
| 17 | H | — | CF$_3$ |
| 18 | H | — | ethenyl |
| 19 | H | — | propen-3-yl |
| 20 | H | — | benzyl |
| 21 | H | — | phenyl |
| 22 | H | O | H |
| 23 | H | O | CH$_3$ |
| 24 | H | O | C$_2$H$_5$ |
| 25 | H | O | n-C$_3$H$_7$ |
| 26 | H | O | i-C$_3$H$_7$ |
| 27 | H | O | cyclopropyl |
| 28 | H | O | n-C$_4$H$_9$ |
| 29 | H | O | s-C$_4$H$_9$ |
| 30 | H | O | i-C$_4$H$_9$ |
| 31 | H | O | t-C$_4$H$_9$ |
| 32 | H | O | n-C$_5$H$_{11}$ |
| 33 | H | O | i-C$_5$H$_{11}$ |
| 34 | H | O | neo-C$_5$H$_{11}$ |
| 35 | H | O | cyclopentyl |
| 36 | H | O | n-C$_6$H$_{13}$ |
| 37 | H | O | cyclohexyl |
| 38 | H | O | CF$_3$ |
| 39 | H | O | propyn-3-yl |
| 40 | H | O | propen-3-yl |
| 41 | H | O | benzyl |
| 42 | H | O | phenyl |
| 43 | H | NH | H |
| 44 | H | NH | CH$_3$ |
| 45 | H | NH | C$_2$H$_5$ |
| 46 | H | NH | n-C$_3$H$_7$ |
| 47 | H | NH | i-C$_3$H$_7$ |
| 48 | H | NH | cyclopropyl |
| 49 | H | NH | n-C$_4$H$_9$ |
| 50 | H | NH | s-C$_4$H$_9$ |
| 51 | H | NH | i-C$_4$H$_9$ |
| 52 | H | NH | t-C$_4$H$_9$ |
| 53 | H | NH | n-C$_5$H$_{11}$ |
| 54 | H | NH | i-C$_5$H$_{11}$ |
| 55 | H | NH | neo-C$_5$H$_{11}$ |
| 56 | H | NH | cyclopentyl |
| 57 | H | NH | n-C$_6$H$_{13}$ |
| 58 | H | NH | cyclohexyl |
| 59 | H | NH | cyclopropyl-CH$_2$ |
| 60 | H | NH | propyn-3-yl |
| 61 | H | NH | propen-3-yl |
| 62 | H | NH | benzyl |
| 63 | H | NH | phenyl |
| 64 | H | NCH$_3$ | CH$_3$ |
| 65 | H | NCH$_3$ | C$_2$H$_5$ |
| 66 | H | NCH$_3$ | n-C$_3$H$_7$ |
| 67 | H | NCH$_3$ | i-C$_3$H$_7$ |
| 68 | H | NCH$_3$ | cyclopropyl |
| 69 | H | NCH$_3$ | n-C$_4$H$_9$ |
| 70 | H | NCH$_3$ | s-C$_4$H$_9$ |
| 71 | H | NCH$_3$ | i-C$_4$H$_9$ |
| 72 | H | NCH$_3$ | t-C$_4$H$_9$ |
| 73 | H | NCH$_3$ | n-C$_5$H$_{11}$ |
| 74 | H | NCH$_3$ | i-C$_5$H$_{11}$ |
| 75 | H | NCH$_3$ | neo-C$_5$H$_{11}$ |
| 76 | H | NCH$_3$ | cyclopentyl |
| 77 | H | NCH$_3$ | n-C$_6$H$_{13}$ |
| 78 | H | NCH$_3$ | cyclohexyl |
| 79 | H | NCH$_3$ | cyclopropyl-CH$_2$ |
| 80 | H | NCH$_3$ | propyn-3-yl |
| 81 | H | NCH$_3$ | propen-3-yl |
| 82 | H | NCH$_3$ | benzyl |
| 83 | H | NCH$_3$ | phenyl |
| 84 | CH$_3$ | — | H |
| 85 | CH$_3$ | — | CH$_3$ |
| 86 | CH$_3$ | — | C$_2$H$_5$ |
| 87 | CH$_3$ | — | n-C$_3$H$_7$ |
| 88 | CH$_3$ | — | i-C$_3$H$_7$ |
| 89 | CH$_3$ | — | cyclopropyl |
| 90 | CH$_3$ | — | n-C$_4$H$_9$ |
| 91 | CH$_3$ | — | s-C$_4$H$_9$ |
| 92 | CH$_3$ | — | i-C$_4$H$_9$ |
| 93 | CH$_3$ | — | t-C$_4$H$_9$ |
| 94 | CH$_3$ | — | n-C$_5$H$_{11}$ |
| 95 | CH$_3$ | — | i-C$_5$H$_{11}$ |
| 96 | CH$_3$ | — | neo-C$_5$H$_{11}$ |
| 97 | CH$_3$ | — | cyclopentyl |
| 98 | CH$_3$ | — | n-C$_6$H$_{13}$ |
| 99 | CH$_3$ | — | cyclohexyl |
| 100 | CH$_3$ | — | CF$_3$ |
| 101 | CH$_3$ | — | ethenyl |
| 102 | CH$_3$ | — | propen-3-yl |
| 103 | CH$_3$ | — | benzyl |
| 104 | CH$_3$ | — | phenyl |
| 105 | CH$_3$ | O | H |
| 106 | CH$_3$ | O | CH$_3$ |
| 107 | CH$_3$ | O | C$_2$H$_5$ |
| 108 | CH$_3$ | O | n-C$_3$H$_7$ |
| 109 | CH$_3$ | O | i-C$_3$H$_7$ |
| 110 | CH$_3$ | O | cyclopropyl |
| 111 | CH$_3$ | O | n-C$_4$H$_9$ |
| 112 | CH$_3$ | O | s-C$_4$H$_9$ |
| 113 | CH$_3$ | O | i-C$_4$H$_9$ |
| 114 | CH$_3$ | O | t-C$_4$H$_9$ |
| 115 | CH$_3$ | O | n-C$_5$H$_{11}$ |
| 116 | CH$_3$ | O | i-C$_5$H$_{11}$ |
| 117 | CH$_3$ | O | neo-C$_5$H$_{11}$ |
| 118 | CH$_3$ | O | cyclopentyl |
| 119 | CH$_3$ | O | n-C$_6$H$_{13}$ |
| 120 | CH$_3$ | O | cyclohexyl |
| 121 | CH$_3$ | O | CF$_3$ |
| 122 | CH$_3$ | O | propyn-3-yl |
| 123 | CH$_3$ | O | propen-3-yl |
| 124 | CH$_3$ | O | benzyl |
| 125 | CH$_3$ | O | phenyl |
| 126 | CH$_3$ | NH | H |
| 127 | CH$_3$ | NH | CH$_3$ |
| 128 | CH$_3$ | NH | C$_2$H$_5$ |
| 129 | CH$_3$ | NH | n-C$_3$H$_7$ |
| 130 | CH$_3$ | NH | i-C$_3$H$_7$ |
| 131 | CH$_3$ | NH | cyclopropyl |
| 132 | CH$_3$ | NH | n-C$_4$H$_9$ |
| 133 | CH$_3$ | NH | s-C$_4$H$_9$ |
| 134 | CH$_3$ | NH | i-C$_4$H$_9$ |

TABLE A-continued

| | | | |
|---|---|---|---|
| 135 | CH₃ | NH | t-C₄H₉ |
| 136 | CH₃ | NH | n-C₅H₁₁ |
| 137 | CH₃ | NH | i-C₅H₁₁ |
| 138 | CH₃ | NH | neo-C₅H₁₁ |
| 139 | CH₃ | NH | cyclopentyl |
| 140 | CH₃ | NH | n-C₆H₁₃ |
| 141 | CH₃ | NH | cyclohexyl |
| 142 | CH₃ | NH | cyclopropyl-CH₂ |
| 143 | CH₃ | NH | propyn-3-yl |
| 144 | CH₃ | NH | propen-3-yl |
| 145 | CH₃ | NH | benzyl |
| 146 | CH₃ | NH | phenyl |
| 147 | CH₃ | NCH₃ | CH₃ |
| 148 | CH₃ | NCH₃ | C₂H₅ |
| 149 | CH₃ | NCH₃ | n-C₃H₇ |
| 150 | CH₃ | NCH₃ | i-C₃H₇ |
| 151 | CH₃ | NCH₃ | cyclopropyl |
| 152 | CH₃ | NCH₃ | n-C₄H₉ |
| 153 | CH₃ | NCH₃ | s-C₄H₉ |
| 154 | CH₃ | NCH₃ | i-C₄H₉ |
| 155 | CH₃ | NCH₃ | t-C₄H₉ |
| 156 | CH₃ | NCH₃ | n-C₅H₁₁ |
| 157 | CH₃ | NCH₃ | i-C₅H₁₁ |
| 158 | CH₃ | NCH₃ | neo-C₅H₁₁ |
| 159 | CH₃ | NCH₃ | cyclopentyl |
| 160 | CH₃ | NCH₃ | n-C₆H₁₃ |
| 161 | CH₃ | NCH₃ | cyclohexyl |
| 162 | CH₃ | NCH₃ | cyclopropyl-CH₂ |
| 163 | CH₃ | NCH₃ | propyn-3-yl |
| 164 | CH₃ | NCH₃ | propen-3-yl |
| 165 | CH₃ | NCH₃ | benzyl |
| 166 | CH₃ | NCH₃ | phenyl |
| 167 | C₂H₅ | — | H |
| 168 | C₂H₅ | — | CH₃ |
| 169 | C₂H₅ | — | C₂H₅ |
| 170 | C₂H₅ | — | n-C₃H₇ |
| 171 | C₂H₅ | — | i-C₃H₇ |
| 172 | C₂H₅ | — | cyclopropyl |
| 173 | C₂H₅ | — | n-C₄H₉ |
| 174 | C₂H₅ | — | s-C₄H₉ |
| 175 | C₂H₅ | — | i-C₄H₉ |
| 176 | C₂H₅ | — | t-C₄H₉ |
| 177 | C₂H₅ | — | n-C₅H₁₁ |
| 178 | C₂H₅ | — | i-C₅H₁₁ |
| 179 | C₂H₅ | — | neo-C₅H₁₁ |
| 180 | C₂H₅ | — | cyclopentyl |
| 181 | C₂H₅ | — | n-C₆H₁₃ |
| 182 | C₂H₅ | — | cyclohexyl |
| 183 | C₂H₅ | — | CF₃ |
| 184 | C₂H₅ | — | ethenyl |
| 185 | C₂H₅ | — | propen-3-yl |
| 186 | C₂H₅ | — | benzyl |
| 187 | C₂H₅ | — | phenyl |
| 188 | C₂H₅ | O | H |
| 189 | C₂H₅ | O | CH₃ |
| 190 | C₂H₅ | O | C₂H₅ |
| 191 | C₂H₅ | O | n-C₃H₇ |
| 192 | C₂H₅ | O | i-C₃H₇ |
| 193 | C₂H₅ | O | cyclopropyl |
| 194 | C₂H₅ | O | n-C₄H₉ |
| 195 | C₂H₅ | O | s-C₄H₉ |
| 196 | C₂H₅ | O | i-C₄H₉ |
| 197 | C₂H₅ | O | t-C₄H₉ |
| 198 | C₂H₅ | O | n-C₅H₁₁ |
| 199 | C₂H₅ | O | i-C₅H₁₁ |
| 200 | C₂H₅ | O | neo-C₅H₁₁ |
| 201 | C₂H₅ | O | cyclopentyl |
| 202 | C₂H₅ | O | n-C₆H₁₃ |
| 203 | C₂H₅ | O | cyclohexyl |
| 204 | C₂H₅ | O | CF₃ |
| 205 | C₂H₅ | O | propyn-3-yl |
| 206 | C₂H₅ | O | propen-3-yl |
| 207 | C₂H₅ | O | benzyl |
| 208 | C₂H₅ | O | phenyl |
| 209 | C₂H₅ | NH | H |
| 210 | C₂H₅ | NH | CH₃ |
| 211 | C₂H₅ | NH | C₂H₅ |
| 212 | C₂H₅ | NH | n-C₃H₇ |
| 213 | C₂H₅ | NH | i-C₃H₇ |
| 214 | C₂H₅ | NH | cyclopropyl |
| 215 | C₂H₅ | NH | n-C₄H₉ |
| 216 | C₂H₅ | NH | s-C₄H₉ |
| 217 | C₂H₅ | NH | i-C₄H₉ |
| 218 | C₂H₅ | NH | t-C₄H₉ |
| 219 | C₂H₅ | NH | n-C₅H₁₁ |
| 220 | C₂H₅ | NH | i-C₅H₁₁ |
| 221 | C₂H₅ | NH | neo-C₅H₁₁ |
| 222 | C₂H₅ | NH | cyclopentyl |
| 223 | C₂H₅ | NH | n-C₆H₁₃ |
| 224 | C₂H₅ | NH | cyclohexyl |
| 225 | C₂H₅ | NH | cyclopropyl-CH₂ |
| 226 | C₂H₅ | NH | propyn-3-yl |
| 227 | C₂H₅ | NH | propen-3-yl |
| 228 | C₂H₅ | NH | benzyl |
| 229 | C₂H₅ | NH | phenyl |
| 230 | C₂H₅ | NCH₃ | CH₃ |
| 231 | C₂H₅ | NCH₃ | C₂H₅ |
| 232 | C₂H₅ | NCH₃ | n-C₃H₇ |
| 233 | C₂H₅ | NCH₃ | i-C₃H₇ |
| 234 | C₂H₅ | NCH₃ | cyclopropyl |
| 235 | C₂H₅ | NCH₃ | n-C₄H₉ |
| 236 | C₂H₅ | NCH₃ | s-C₄H₉ |
| 237 | C₂H₅ | NCH₃ | i-C₄H₉ |
| 238 | C₂H₅ | NCH₃ | t-C₄H₉ |
| 239 | C₂H₅ | NCH₃ | n-C₅H₁₁ |
| 240 | C₂H₅ | NCH₃ | i-C₅H₁₁ |
| 241 | C₂H₅ | NCH₃ | neo-C₅H₁₁ |
| 242 | C₂H₅ | NCH₃ | cyclopentyl |
| 243 | C₂H₅ | NCH₃ | n-C₆H₁₃ |
| 244 | C₂H₅ | NCH₃ | cyclohexyl |
| 245 | C₂H₅ | NCH₃ | cyclopropyl-CH₂ |
| 246 | C₂H₅ | NCH₃ | propyn-3-yl |
| 247 | C₂H₅ | NCH₃ | propen-3-yl |
| 248 | C₂H₅ | NCH₃ | benzyl |
| 249 | C₂H₅ | NCH₃ | phenyl |
| 250 | n-C₃H₇ | — | H |
| 251 | n-C₃H₇ | — | CH₃ |
| 252 | n-C₃H₇ | — | C₂H₅ |
| 253 | n-C₃H₇ | — | n-C₃H₇ |
| 254 | n-C₃H₇ | — | i-C₃H₇ |
| 255 | n-C₃H₇ | — | cyclopropyl |
| 256 | n-C₃H₇ | — | n-C₄H₉ |
| 257 | n-C₃H₇ | — | s-C₄H₉ |
| 258 | n-C₃H₇ | — | i-C₄H₉ |
| 259 | n-C₃H₇ | — | t-C₄H₉ |
| 260 | n-C₃H₇ | — | n-C₅H₁₁ |
| 261 | n-C₃H₇ | — | i-C₅H₁₁ |
| 262 | n-C₃H₇ | — | neo-C₅H₁₁ |
| 263 | n-C₃H₇ | — | cyclopentyl |
| 264 | n-C₃H₇ | — | n-C₆H₁₃ |
| 265 | n-C₃H₇ | — | cyclohexyl |
| 266 | n-C₃H₇ | — | CF₃ |
| 267 | n-C₃H₇ | — | ethenyl |
| 268 | n-C₃H₇ | — | propen-3-yl |
| 269 | n-C₃H₇ | — | benzyl |
| 270 | n-C₃H₇ | — | phenyl |
| 271 | n-C₃H₇ | O | H |
| 272 | n-C₃H₇ | O | CH₃ |
| 273 | n-C₃H₇ | O | C₂H₅ |
| 274 | n-C₃H₇ | O | n-C₃H₇ |
| 275 | n-C₃H₇ | O | i-C₃H₇ |
| 276 | n-C₃H₇ | O | cyclopropyl |
| 277 | n-C₃H₇ | O | n-C₄H₉ |
| 278 | n-C₃H₇ | O | s-C₄H₉ |
| 279 | n-C₃H₇ | O | i-C₄H₉ |
| 280 | n-C₃H₇ | O | t-C₄H₉ |
| 281 | n-C₃H₇ | O | n-C₅H₁₁ |
| 282 | n-C₃H₇ | O | i-C₅H₁₁ |
| 283 | n-C₃H₇ | O | neo-C₅H₁₁ |
| 284 | n-C₃H₇ | O | cyclopentyl |
| 285 | n-C₃H₇ | O | n-C₆H₁₃ |
| 286 | n-C₃H₇ | O | cyclohexyl |
| 287 | n-C₃H₇ | O | CF₃ |
| 288 | n-C₃H₇ | O | propyn-3-yl |
| 289 | n-C₃H₇ | O | propen-3-yl |
| 290 | n-C₃H₇ | O | benzyl |
| 291 | n-C₃H₇ | O | phenyl |
| 292 | n-C₃H₇ | NH | H |

TABLE A-continued

| | | | |
|---|---|---|---|
| 293 | n-C$_3$H$_7$ | NH | CH$_3$ |
| 294 | n-C$_3$H$_7$ | NH | C$_2$H$_5$ |
| 295 | n-C$_3$H$_7$ | NH | n-C$_3$H$_7$ |
| 296 | n-C$_3$H$_7$ | NH | i-C$_3$H$_7$ |
| 297 | n-C$_3$H$_7$ | NH | cyclopropyl |
| 298 | n-C$_3$H$_7$ | NH | n-C$_4$H$_9$ |
| 299 | n-C$_3$H$_7$ | NH | s-C$_4$H$_9$ |
| 300 | n-C$_3$H$_7$ | NH | i-C$_4$H$_9$ |
| 301 | n-C$_3$H$_7$ | NH | t-C$_4$H$_9$ |
| 302 | n-C$_3$H$_7$ | NH | n-C$_5$H$_{11}$ |
| 303 | n-C$_3$H$_7$ | NH | i-C$_5$H$_{11}$ |
| 304 | n-C$_3$H$_7$ | NH | neo-C$_5$H$_{11}$ |
| 305 | n-C$_3$H$_7$ | NH | cyclopentyl |
| 306 | n-C$_3$H$_7$ | NH | n-C$_6$H$_{13}$ |
| 307 | n-C$_3$H$_7$ | NH | cyclohexyl |
| 308 | n-C$_3$H$_7$ | NH | cyclopropyl-CH$_2$ |
| 309 | n-C$_3$H$_7$ | NH | propyn-3-yl |
| 310 | n-C$_3$H$_7$ | NH | propen-3-yl |
| 311 | n-C$_3$H$_7$ | NH | benzyl |
| 312 | n-C$_3$H$_7$ | NH | phenyl |
| 313 | n-C$_3$H$_7$ | NCH$_3$ | CH$_3$ |
| 314 | n-C$_3$H$_7$ | NCH$_3$ | C$_2$H$_5$ |
| 315 | n-C$_3$H$_7$ | NCH$_3$ | n-C$_3$H$_7$ |
| 316 | n-C$_3$H$_7$ | NCH$_3$ | i-C$_3$H$_7$ |
| 317 | n-C$_3$H$_7$ | NCH$_3$ | cyclopropyl |
| 318 | n-C$_3$H$_7$ | NCH$_3$ | n-C$_4$H$_9$ |
| 319 | n-C$_3$H$_7$ | NCH$_3$ | s-C$_4$H$_9$ |
| 320 | n-C$_3$H$_7$ | NCH$_3$ | i-C$_4$H$_9$ |
| 321 | n-C$_3$H$_7$ | NCH$_3$ | t-C$_4$H$_9$ |
| 322 | n-C$_3$H$_7$ | NCH$_3$ | n-C$_5$H$_{11}$ |
| 323 | n-C$_3$H$_7$ | NCH$_3$ | i-C$_5$H$_{11}$ |
| 324 | n-C$_3$H$_7$ | NCH$_3$ | neo-C$_5$H$_{11}$ |
| 325 | n-C$_3$H$_7$ | NCH$_3$ | cyclopentyl |
| 326 | n-C$_3$H$_7$ | NCH$_3$ | n-C$_6$H$_{13}$ |
| 327 | n-C$_3$H$_7$ | NCH$_3$ | cyclohexyl |
| 328 | n-C$_3$H$_7$ | NCH$_3$ | cyclopropyl-CH$_2$ |
| 329 | n-C$_3$H$_7$ | NCH$_3$ | propyn-3-yl |
| 330 | n-C$_3$H$_7$ | NCH$_3$ | propen-3-yl |
| 331 | n-C$_3$H$_7$ | NCH$_3$ | benzyl |
| 332 | n-C$_3$H$_7$ | NCH$_3$ | phenyl |
| 333 | i-C$_3$H$_7$ | — | H |
| 334 | i-C$_3$H$_7$ | — | CH$_3$ |
| 335 | i-C$_3$H$_7$ | — | C$_2$H$_5$ |
| 336 | i-C$_3$H$_7$ | — | n-C$_3$H$_7$ |
| 337 | i-C$_3$H$_7$ | — | i-C$_3$H$_7$ |
| 338 | i-C$_3$H$_7$ | — | cyclopropyl |
| 339 | i-C$_3$H$_7$ | — | n-C$_4$H$_9$ |
| 340 | i-C$_3$H$_7$ | — | s-C$_4$H$_9$ |
| 341 | i-C$_3$H$_7$ | — | i-C$_4$H$_9$ |
| 342 | i-C$_3$H$_7$ | — | t-C$_4$H$_9$ |
| 343 | i-C$_3$H$_7$ | — | n-C$_5$H$_{11}$ |
| 344 | i-C$_3$H$_7$ | — | i-C$_5$H$_{11}$ |
| 345 | i-C$_3$H$_7$ | — | neo-C$_5$H$_{11}$ |
| 346 | i-C$_3$H$_7$ | — | cyclopentyl |
| 347 | i-C$_3$H$_7$ | — | n-C$_6$H$_{13}$ |
| 348 | i-C$_3$H$_7$ | — | cyclohexyl |
| 349 | i-C$_3$H$_7$ | — | CF$_3$ |
| 350 | i-C$_3$H$_7$ | — | ethenyl |
| 351 | i-C$_3$H$_7$ | — | propen-3-yl |
| 352 | i-C$_3$H$_7$ | — | benzyl |
| 353 | i-C$_3$H$_7$ | — | phenyl |
| 354 | i-C$_3$H$_7$ | O | H |
| 355 | i-C$_3$H$_7$ | O | CH$_3$ |
| 356 | i-C$_3$H$_7$ | O | C$_2$H$_5$ |
| 357 | i-C$_3$H$_7$ | O | n-C$_3$H$_7$ |
| 358 | i-C$_3$H$_7$ | O | i-C$_3$H$_7$ |
| 359 | i-C$_3$H$_7$ | O | cyclopropyl |
| 360 | i-C$_3$H$_7$ | O | n-C$_4$H$_9$ |
| 361 | i-C$_3$H$_7$ | O | s-C$_4$H$_9$ |
| 362 | i-C$_3$H$_7$ | O | i-C$_4$H$_9$ |
| 363 | i-C$_3$H$_7$ | O | t-C$_4$H$_9$ |
| 364 | i-C$_3$H$_7$ | O | n-C$_5$H$_{11}$ |
| 365 | i-C$_3$H$_7$ | O | i-C$_5$H$_{11}$ |
| 366 | i-C$_3$H$_7$ | O | neo-C$_5$H$_{11}$ |
| 367 | i-C$_3$H$_7$ | O | cyclopentyl |
| 368 | i-C$_3$H$_7$ | O | n-C$_6$H$_{13}$ |
| 369 | i-C$_3$H$_7$ | O | cyclohexyl |
| 370 | i-C$_3$H$_7$ | O | CF$_3$ |
| 371 | i-C$_3$H$_7$ | O | propyn-3-yl |
| 372 | i-C$_3$H$_7$ | O | propen-3-yl |
| 373 | i-C$_3$H$_7$ | O | benzyl |
| 374 | i-C$_3$H$_7$ | O | phenyl |
| 375 | i-C$_3$H$_7$ | NH | H |
| 376 | i-C$_3$H$_7$ | NH | CH$_3$ |
| 377 | i-C$_3$H$_7$ | NH | C$_2$H$_5$ |
| 378 | i-C$_3$H$_7$ | NH | n-C$_3$H$_7$ |
| 379 | i-C$_3$H$_7$ | NH | i-C$_3$H$_7$ |
| 380 | i-C$_3$H$_7$ | NH | cyclopropyl |
| 381 | i-C$_3$H$_7$ | NH | n-C$_4$H$_9$ |
| 382 | i-C$_3$H$_7$ | NH | s-C$_4$H$_9$ |
| 383 | i-C$_3$H$_7$ | NH | i-C$_4$H$_9$ |
| 384 | i-C$_3$H$_7$ | NH | t-C$_4$H$_9$ |
| 385 | i-C$_3$H$_7$ | NH | n-C$_5$H$_{11}$ |
| 386 | i-C$_3$H$_7$ | NH | i-C$_5$H$_{11}$ |
| 387 | i-C$_3$H$_7$ | NH | neo-C$_5$H$_{11}$ |
| 388 | i-C$_3$H$_7$ | NH | cyclopentyl |
| 389 | i-C$_3$H$_7$ | NH | n-C$_6$H$_{13}$ |
| 390 | i-C$_3$H$_7$ | NH | cyclohexyl |
| 391 | i-C$_3$H$_7$ | NH | cyclopropyl-CH$_2$ |
| 392 | i-C$_3$H$_7$ | NH | propyn-3-yl |
| 393 | i-C$_3$H$_7$ | NH | propen-3-yl |
| 394 | i-C$_3$H$_7$ | NH | benzyl |
| 395 | i-C$_3$H$_7$ | NH | phenyl |
| 396 | i-C$_3$H$_7$ | NCH$_3$ | CH$_3$ |
| 397 | i-C$_3$H$_7$ | NCH$_3$ | C$_2$H$_5$ |
| 398 | i-C$_3$H$_7$ | NCH$_3$ | n-C$_3$H$_7$ |
| 399 | i-C$_3$H$_7$ | NCH$_3$ | i-C$_3$H$_7$ |
| 400 | i-C$_3$H$_7$ | NCH$_3$ | cyclopropyl |
| 401 | i-C$_3$H$_7$ | NCH$_3$ | n-C$_4$H$_9$ |
| 402 | i-C$_3$H$_7$ | NCH$_3$ | s-C$_4$H$_9$ |
| 403 | i-C$_3$H$_7$ | NCH$_3$ | i-C$_4$H$_9$ |
| 404 | i-C$_3$H$_7$ | NCH$_3$ | t-C$_4$H$_9$ |
| 405 | i-C$_3$H$_7$ | NCH$_3$ | n-C$_5$H$_{11}$ |
| 406 | i-C$_3$H$_7$ | NCH$_3$ | i-C$_5$H$_{11}$ |
| 407 | i-C$_3$H$_7$ | NCH$_3$ | neo-C$_5$H$_{11}$ |
| 408 | i-C$_3$H$_7$ | NCH$_3$ | cyclopentyl |
| 409 | i-C$_3$H$_7$ | NCH$_3$ | n-C$_6$H$_{13}$ |
| 410 | i-C$_3$H$_7$ | NCH$_3$ | cyclohexyl |
| 411 | i-C$_3$H$_7$ | NCH$_3$ | cyclopropyl-CH$_2$ |
| 412 | i-C$_3$H$_7$ | NCH$_3$ | propyn-3-yl |
| 413 | i-C$_3$H$_7$ | NCH$_3$ | propen-3-yl |
| 414 | i-C$_3$H$_7$ | NCH$_3$ | benzyl |
| 415 | i-C$_3$H$_7$ | NCH$_3$ | phenyl |
| 416 | benzyl | — | H |
| 417 | benzyl | — | CH$_3$ |
| 418 | benzyl | — | C$_2$H$_5$ |
| 419 | benzyl | — | n-C$_3$H$_7$ |
| 420 | benzyl | — | i-C$_3$H$_7$ |
| 421 | benzyl | — | cyclopropyl |
| 422 | benzyl | — | n-C$_4$H$_9$ |
| 423 | benzyl | — | s-C$_4$H$_9$ |
| 424 | benzyl | — | i-C$_4$H$_9$ |
| 425 | benzyl | — | t-C$_4$H$_9$ |
| 426 | benzyl | — | n-C$_5$H$_{11}$ |
| 427 | benzyl | — | i-C$_5$H$_{11}$ |
| 428 | benzyl | — | neo-C$_5$H$_{11}$ |
| 429 | benzyl | — | cyclopentyl |
| 430 | benzyl | — | n-C$_6$H$_{13}$ |
| 431 | benzyl | — | cyclohexyl |
| 432 | benzyl | — | CF$_3$ |
| 433 | benzyl | — | ethenyl |
| 434 | benzyl | — | propen-3-yl |
| 435 | benzyl | — | benzyl |
| 436 | benzyl | — | phenyl |
| 437 | benzyl | O | H |
| 438 | benzyl | O | CH$_3$ |
| 439 | benzyl | O | C$_2$H$_5$ |
| 440 | benzyl | O | n-C$_3$H$_7$ |
| 441 | benzyl | O | i-C$_3$H$_7$ |
| 442 | benzyl | O | cyclopropyl |
| 443 | benzyl | O | n-C$_4$H$_9$ |
| 444 | benzyl | O | s-C$_4$H$_9$ |
| 445 | benzyl | O | i-C$_4$H$_9$ |
| 446 | benzyl | O | t-C$_4$H$_9$ |
| 447 | benzyl | O | n-C$_5$H$_{11}$ |
| 448 | benzyl | O | i-C$_5$H$_{11}$ |
| 449 | benzyl | O | neo-C$_5$H$_{11}$ |
| 450 | benzyl | O | cyclopentyl |

TABLE A-continued

| | | | |
|---|---|---|---|
| 451 | benzyl | O | n-C$_6$H$_{13}$ |
| 452 | benzyl | O | cyclohexyl |
| 453 | benzyl | O | CF$_3$ |
| 454 | benzyl | O | propyn-3-yl |
| 455 | benzyl | O | propen-3-yl |
| 456 | benzyl | O | benzyl |
| 457 | benzyl | O | phenyl |
| 458 | benzyl | NH | H |
| 459 | benzyl | NH | CH$_3$ |
| 460 | benzyl | NH | C$_2$H$_5$ |
| 461 | benzyl | NH | n-C$_3$H$_7$ |
| 462 | benzyl | NH | i-C$_3$H$_7$ |
| 463 | benzyl | NH | cyclopropyl |
| 464 | benzyl | NH | n-C$_4$H$_9$ |
| 465 | benzyl | NH | s-C$_4$H$_9$ |
| 466 | benzyl | NH | i-C$_4$H$_9$ |
| 467 | benzyl | NH | t-C$_4$H$_9$ |
| 468 | benzyl | NH | n-C$_5$H$_{11}$ |
| 469 | benzyl | NH | i-C$_5$H$_{11}$ |
| 470 | benzyl | NH | neo-C$_5$H$_{11}$ |
| 471 | benzyl | NH | cyclopentyl |
| 472 | benzyl | NH | n-C$_6$H$_{13}$ |
| 473 | benzyl | NH | cyclohexyl |
| 474 | benzyl | NH | cyclopropyl-CH$_2$ |
| 475 | benzyl | NH | propyn-3-yl |
| 476 | benzyl | NH | propen-3-yl |
| 477 | benzyl | NH | benzyl |
| 478 | benzyl | NH | phenyl |
| 479 | benzyl | NCH$_3$ | CH$_3$ |
| 480 | benzyl | NCH$_3$ | C$_2$H$_5$ |
| 481 | benzyl | NCH$_3$ | n-C$_3$H$_7$ |
| 482 | benzyl | NCH$_3$ | i-C$_3$H$_7$ |
| 483 | benzyl | NCH$_3$ | cyclopropyl |
| 484 | benzyl | NCH$_3$ | n-C$_4$H$_9$ |
| 485 | benzyl | NCH$_3$ | s-C$_4$H$_9$ |
| 486 | benzyl | NCH$_3$ | i-C$_4$H$_9$ |
| 487 | benzyl | NCH$_3$ | t-C$_4$H$_9$ |
| 488 | benzyl | NCH$_3$ | n-C$_5$H$_{11}$ |
| 489 | benzyl | NCH$_3$ | i-C$_5$H$_{11}$ |
| 490 | benzyl | NCH$_3$ | neo-C$_5$H$_{11}$ |
| 491 | benzyl | NCH$_3$ | cyclopentyl |
| 492 | benzyl | NCH$_3$ | n-C$_6$H$_{13}$ |
| 493 | benzyl | NCH$_3$ | cyclohexyl |
| 494 | benzyl | NCH$_3$ | cyclopropyl-CH$_2$ |
| 495 | benzyl | NCH$_3$ | propyn-3-yl |
| 496 | benzyl | NCH$_3$ | propen-3-yl |
| 497 | benzyl | NCH$_3$ | benzyl |
| 498 | benzyl | NCH$_3$ | phenyl |
| 499 | propen-3-yl | — | H |
| 500 | propen-3-yl | — | CH$_3$ |
| 501 | propen-3-yl | — | C$_2$H$_5$ |
| 502 | propen-3-yl | — | n-C$_3$H$_7$ |
| 503 | propen-3-yl | — | i-C$_3$H$_7$ |
| 504 | propen-3-yl | — | cyclopropyl |
| 505 | propen-3-yl | — | n-C$_4$H$_9$ |
| 506 | propen-3-yl | — | s-C$_4$H$_9$ |
| 507 | propen-3-yl | — | i-C$_4$H$_9$ |
| 508 | propen-3-yl | — | t-C$_4$H$_9$ |
| 509 | propen-3-yl | — | n-C$_5$H$_{11}$ |
| 510 | propen-3-yl | — | i-C$_5$H$_{11}$ |
| 511 | propen-3-yl | — | neo-C$_5$H$_{11}$ |
| 512 | propen-3-yl | — | cyclopentyl |
| 513 | propen-3-yl | — | n-C$_6$H$_{13}$ |
| 514 | propen-3-yl | — | cyclohexyl |
| 515 | propen-3-yl | — | CF$_3$ |
| 516 | propen-3-yl | — | ethenyl |
| 517 | propen-3-yl | — | propen-3-yl |
| 518 | propen-3-yl | — | benzyl |
| 519 | propen-3-yl | — | phenyl |
| 520 | propen-3-yl | O | H |
| 521 | propen-3-yl | O | CH$_3$ |
| 522 | propen-3-yl | O | C$_2$H$_5$ |
| 523 | propen-3-yl | O | n-C$_3$H$_7$ |
| 524 | propen-3-yl | O | i-C$_3$H$_7$ |
| 525 | propen-3-yl | O | cyclopropyl |
| 526 | propen-3-yl | O | n-C$_4$H$_9$ |
| 527 | propen-3-yl | O | s-C$_4$H$_9$ |
| 528 | propen-3-yl | O | i-C$_4$H$_9$ |
| 529 | propen-3-yl | O | t-C$_4$H$_9$ |
| 530 | propen-3-yl | O | n-C$_5$H$_{11}$ |
| 531 | propen-3-yl | O | i-C$_5$H$_{11}$ |
| 532 | propen-3-yl | O | neo-C$_5$H$_{11}$ |
| 533 | propen-3-yl | O | cyclopentyl |
| 534 | propen-3-yl | O | n-C$_6$H$_{13}$ |
| 535 | propen-3-yl | O | cyclohexyl |
| 536 | propen-3-yl | O | CF$_3$ |
| 537 | propen-3-yl | O | propyn-3-yl |
| 538 | propen-3-yl | O | propen-3-yl |
| 539 | propen-3-yl | O | benzyl |
| 540 | propen-3-yl | O | phenyl |
| 541 | propen-3-yl | NH | H |
| 542 | propen-3-yl | NH | CH$_3$ |
| 543 | propen-3-yl | NH | C$_2$H$_5$ |
| 544 | propen-3-yl | NH | n-C$_3$H$_7$ |
| 545 | propen-3-yl | NH | i-C$_3$H$_7$ |
| 546 | propen-3-yl | NH | cyclopropyl |
| 547 | propen-3-yl | NH | n-C$_4$H$_9$ |
| 548 | propen-3-yl | NH | s-C$_4$H$_9$ |
| 549 | propen-3-yl | NH | i-C$_4$H$_9$ |
| 550 | propen-3-yl | NH | t-C$_4$H$_9$ |
| 551 | propen-3-yl | NH | n-C$_5$H$_{11}$ |
| 552 | propen-3-yl | NH | i-C$_5$H$_{11}$ |
| 553 | propen-3-yl | NH | neo-C$_5$H$_{11}$ |
| 554 | propen-3-yl | NH | cyclopentyl |
| 555 | propen-3-yl | NH | n-C$_6$H$_{13}$ |
| 556 | propen-3-yl | NH | cyclohexyl |
| 557 | propen-3-yl | NH | cyclopropyl-CH$_2$ |
| 558 | propen-3-yl | NH | propyn-3-yl |
| 559 | propen-3-yl | NH | propen-3-yl |
| 560 | propen-3-yl | NH | benzyl |
| 561 | propen-3-yl | NH | phenyl |
| 562 | propen-3-yl | NCH$_3$ | CH$_3$ |
| 563 | propen-3-yl | NCH$_3$ | C$_2$H$_5$ |
| 564 | propen-3-yl | NCH$_3$ | n-C$_3$H$_7$ |
| 565 | propen-3-yl | NCH$_3$ | i-C$_3$H$_7$ |
| 566 | propen-3-yl | NCH$_3$ | cyclopropyl |
| 567 | propen-3-yl | NCH$_3$ | n-C$_4$H$_9$ |
| 568 | propen-3-yl | NCH$_3$ | s-C$_4$H$_9$ |
| 569 | propen-3-yl | NCH$_3$ | i-C$_4$H$_9$ |
| 570 | propen-3-yl | NCH$_3$ | t-C$_4$H$_9$ |
| 571 | propen-3-yl | NCH$_3$ | n-C$_5$H$_{11}$ |
| 572 | propen-3-yl | NCH$_3$ | i-C$_5$H$_{11}$ |
| 573 | propen-3-yl | NCH$_3$ | neo-C$_5$H$_{11}$ |
| 574 | propen-3-yl | NCH$_3$ | cyclopentyl |
| 575 | propen-3-yl | NCH$_3$ | n-C$_6$H$_{13}$ |
| 576 | propen-3-yl | NCH$_3$ | cyclohexyl |
| 577 | propen-3-yl | NCH$_3$ | cyclopropyl-CH$_2$ |
| 578 | propen-3-yl | NCH$_3$ | propyn-3-yl |
| 579 | propen-3-yl | NCH$_3$ | propen-3-yl |
| 580 | propen-3-yl | NCH$_3$ | benzyl |
| 581 | propen-3-yl | NCH$_3$ | phenyl |
| 582 | H | NC$_2$H$_5$ | C$_2$H$_5$ |
| 583 | H | N—N—C$_3$H$_7$ | n-C$_3$H$_7$ |
| 584 | H | N—CH$_2$CH=CH$_2$ | CH$_2$CH=CH$_2$ |
| 585 | H | N—CH$_2$CH$_2$OH | CH$_2$CH=CH$_2$ |
| 586 | CH$_3$ | NC$_2$H$_5$ | C$_2$H$_5$ |
| 587 | CH$_3$ | N-n-C$_3$H$_7$ | n-C$_3$H$_7$ |
| 588 | CH$_3$ | N—CH$_2$CH=CH$_2$ | CH$_2$CH=CH$_2$ |
| 589 | CH$_3$ | N—CH$_2$CHOH | CH$_2$CH=CH$_2$ |
| 590 | C$_6$H$_5$—CH$_2$ | NC$_2$H$_5$ | C$_2$H$_5$ |
| 591 | C$_6$H$_5$—CH$_2$ | N-n-C$_3$H$_7$ | n-C$_3$H$_7$ |
| 592 | C$_6$H$_5$—CH$_2$ | N—CH$_2$CH=CH$_2$ | CH$_2$CH=CH$_2$ |
| 593 | C$_6$H$_5$—CH$_2$ | N—CH$_2$CH$_2$OH | CH$_2$CH=CH$_2$ |

| No. | R$^a$ | R$^b$ |
|---|---|---|
| g) R$^4$ = 3-O(C=O)—NR$^a$R$^b$ | | |
| 1 | H | H |
| 2 | H | CH$_3$ |
| 3 | H | C$_2$H$_5$ |
| 4 | H | n-C$_3$H$_7$ |
| 5 | H | i-C$_3$H$_7$ |
| 6 | H | cyclopropyl |
| 7 | H | n-C$_4$H$_9$ |
| 8 | H | s-C$_4$H$_9$ |
| 9 | H | i-C$_4$H$_9$ |
| 10 | H | t-C$_4$H$_9$ |

TABLE A-continued

| | | |
|---|---|---|
| 11 | H | n-$C_5H_{11}$ |
| 12 | H | i-$C_5H_{11}$ |
| 13 | H | neo-$C_5H_{11}$ |
| 14 | H | cyclopentyl |
| 15 | H | n-$C_6H_{13}$ |
| 16 | H | cyclohexyl |
| 17 | H | cyclopropyl-$CH_2$ |
| 18 | H | propyn-3-yl |
| 19 | H | propen-3-yl |
| 20 | H | benzyl |
| 21 | H | phenyl |
| 22 | $CH_3$ | $CH_3$ |
| 23 | $CH_3$ | $C_2H_5$ |
| 24 | $CH_3$ | n-$C_3H_7$ |
| 25 | $CH_3$ | i-$C_3H_7$ |
| 26 | $CH_3$ | cyclopropyl |
| 27 | $CH_3$ | n-$C_4H_9$ |
| 28 | $CH_3$ | s-$C_4H_9$ |
| 29 | $CH_3$ | i-$C_4H_9$ |
| 30 | $CH_3$ | t-$C_4H_9$ |
| 31 | $CH_3$ | n-$C_5H_{11}$ |
| 32 | $CH_3$ | i-$C_5H_{11}$ |
| 33 | $CH_3$ | neo-$C_5H_{11}$ |
| 34 | $CH_3$ | cyclopentyl |
| 35 | $CH_3$ | n-$C_6H_{13}$ |
| 36 | $CH_3$ | cyclohexyl |
| 37 | $CH_3$ | cyclopropyl-$CH_2$ |
| 38 | $CH_3$ | propyn-3-yl |
| 39 | $CH_3$ | propen-3-yl |
| 40 | $CH_3$ | benzyl |
| 41 | $CH_3$ | phenyl |
| 42 | $C_2H_5$ | $C_2H_5$ |
| 43 | $C_2H_5$ | n-$C_3H_7$ |
| 44 | $C_2H_5$ | i-$C_3H_7$ |
| 45 | $C_2H_5$ | cyclopropyl |
| 46 | $C_2H_5$ | n-$C_4H_9$ |
| 47 | $C_2H_5$ | s-$C_4H_9$ |
| 48 | $C_2H_5$ | i-$C_4H_9$ |
| 49 | $C_2H_5$ | t-$C_4H_9$ |
| 50 | $C_2H_5$ | n-$C_5H_{11}$ |
| 51 | $C_2H_5$ | i-$C_5H_{11}$ |
| 52 | $C_2H_5$ | neo-$C_5H_{11}$ |
| 53 | $C_2H_5$ | cyclopentyl |
| 54 | $C_2H_5$ | n-$C_6H_{13}$ |
| 55 | $C_2H_5$ | cyclohexyl |
| 56 | $C_2H_5$ | cyclopropyl-$CH_2$ |
| 57 | $C_2H_5$ | propyn-3-yl |
| 58 | $C_2H_5$ | propen-3-yl |
| 59 | $C_2H_5$ | benzyl |
| 60 | $C_2H_5$ | phenyl |
| 61 | propen-3-yl | propen-3-yl |
| 62 | propyn-3-yl | propyn-3-yl |
| 63 | $CH_2CH_2OH$ | $CH_2CH=CH_2$ |
| 64 | t-$C_4H_9$ | t-$C_4H_9$ |
| 65 | i-$C_3H_7$ | i-$C_3H_7$ |
| 66 | n-$C_3H_7$ | 4-Cl—$C_6H_4$—$CH_2$ | h) $R^4 = 4$-O(C=O)—$N^aR^b$

| | | |
|---|---|---|
| 67 | H | H |
| 68 | H | $CH_3$ |
| 69 | H | $C_2H_5$ |
| 70 | H | n-$C_3H_7$ |
| 71 | H | i-$C_3H_7$ |
| 72 | H | cyclopropyl |
| 73 | H | n-$C_4H_9$ |
| 74 | H | s-$C_4H_9$ |
| 75 | H | i-$C_4H_9$ |
| 76 | H | t-$C_4H_9$ |
| 77 | H | n-$C_5H_{11}$ |
| 78 | H | i-$C_5H_{11}$ |
| 79 | H | neo-$C_5H_{11}$ |
| 80 | H | cyclopentyl |
| 81 | H | n-$C_6H_{13}$ |
| 82 | H | cyclohexyl |
| 83 | H | cyclopropyl-$CH_2$ |
| 84 | H | propyn-3-yl |
| 85 | H | propen-3-yl |
| 86 | H | benzyl |
| 87 | H | phenyl |

TABLE A-continued

| | | |
|---|---|---|
| 88 | $CH_3$ | $CH_3$ |
| 89 | $CH_3$ | $C_2H_5$ |
| 90 | $CH_3$ | n-$C_3H_7$ |
| 91 | $CH_3$ | i-$C_3H_7$ |
| 92 | $CH_3$ | cyclopropyl |
| 93 | $CH_3$ | n-$C_4H_9$ |
| 94 | $CH_3$ | s-$C_4H_9$ |
| 95 | $CH_3$ | i-$C_4H_9$ |
| 96 | $CH_3$ | t-$C_4H_9$ |
| 97 | $CH_3$ | n-$C_5H_{11}$ |
| 98 | $CH_3$ | i-$C_5H_{11}$ |
| 99 | $CH_3$ | neo-$C_5H_{11}$ |
| 100 | $CH_3$ | cyclopentyl |
| 101 | $CH_3$ | n-$C_6H_{13}$ |
| 102 | $CH_3$ | cyclohexyl |
| 103 | $CH_3$ | cyclopropyl-$CH_2$ |
| 104 | $CH_3$ | propyn-3-yl |
| 105 | $CH_3$ | propen-3-yl |
| 106 | $CH_3$ | benzyl |
| 107 | $CH_3$ | phenyl |
| 108 | $C_2H_5$ | $C_2H_5$ |
| 109 | $C_2H_5$ | n-$C_3H_7$ |
| 110 | $C_2H_5$ | i-$C_3H_7$ |
| 111 | $C_2H_5$ | cyclopropyl |
| 112 | $C_2H_5$ | n-$C_4H_9$ |
| 113 | $C_2H_5$ | s-$C_4H_9$ |
| 114 | $C_2H_5$ | i-$C_4H_9$ |
| 115 | $C_2H_5$ | t-$C_4H_9$ |
| 116 | $C_2H_5$ | n-$C_5H_{11}$ |
| 117 | $C_2H_5$ | i-$C_5H_{11}$ |
| 118 | $C_2H_5$ | neo-$C_5H_{11}$ |
| 119 | $C_2H_5$ | cyclopentyl |
| 120 | $C_2H_5$ | n-$C_6H_{13}$ |
| 121 | $C_2H_5$ | cyclohexyl |
| 122 | $C_2H_5$ | cyclopropyl-$CH_2$ |
| 123 | $C_2H_5$ | propyn-3-yl |
| 124 | $C_2H_5$ | propen-3-yl |
| 125 | $C_2H_5$ | benzyl |
| 126 | $C_2H_5$ | phenyl |
| 127 | propen-3-yl | propen-3-yl |
| 128 | propyn-3-yl | propyn-3-yl |
| 129 | $CH_2CH_2OH$ | $CH_2CH=CH_2$ |
| 130 | t-$C_4H_9$ | t-$C_4H_9$ |
| 131 | i-$C_3H_7$ | i-$C_3H_7$ |
| 132 | n-$C_3H_7$ | 4-Cl—$C_6H_4$—$CH_2$ |

| No. | $R^c$ | $R^d$ |
|---|---|---| i) $R^4 = 3$-N($R^c$)—O$R^d$

| | | |
|---|---|---|
| 133 | $CO_2CH_3$ | H |
| 134 | $CO_2CH_3$ | $CH_3$ |
| 135 | $CO_2CH_3$ | $C_2H_5$ |
| 136 | $CO_2CH_3$ | n-$C_3H_7$ |
| 137 | $CO_2CH_3$ | i-$C_3H_7$ |
| 138 | $CO_2CH_3$ | cyclopropyl |
| 139 | $CO_2CH_3$ | n-$C_4H_9$ |
| 140 | $CO_2CH_3$ | s-$C_4H_9$ |
| 141 | $CO_2CH_3$ | i-$C_4H_9$ |
| 142 | $CO_2CH_3$ | t-$C_4H_9$ |
| 143 | $CO_2CH_3$ | n-$C_5H_{11}$ |
| 144 | $CO_2CH_3$ | i-$C_5H_{11}$ |
| 145 | $CO_2CH_3$ | neo-$C_5H_{11}$ |
| 146 | $CO_2CH_3$ | cyclopentyl |
| 147 | $CO_2CH_3$ | n-$C_6H_{13}$ |
| 148 | $CO_2CH_3$ | cyclohexyl |
| 149 | $CO_2CH_3$ | cyclopropyl-$CH_2$ |
| 150 | $CO_2CH_3$ | propyn-3-yl |
| 151 | $CO_2CH_3$ | propen-3-yl |
| 152 | $CO_2CH_3$ | benzyl |
| 153 | $CO_2CH_3$ | $CH_2CH_2$—$OCH_3$ |
| 154 | $CO_2CH_2CH_3$ | H |
| 155 | $CO_2CH_2CH_3$ | $CH_3$ |
| 156 | $CO_2CH_2CH_3$ | $C_2H_5$ |
| 157 | $CO_2CH_2CH_3$ | n-$C_3H_7$ |
| 158 | $CO_2CH_2CH_3$ | i-$C_3H_7$ |
| 159 | $CO_2CH_2CH_3$ | cyclopropyl |
| 160 | $CO_2CH_2CH_3$ | n-$C_4H_9$ |
| 161 | $CO_2CH_2CH_3$ | s-$C_4H_9$ |

TABLE A-continued

| | | |
|---|---|---|
| 162 | $CO_2CH_2CH_3$ | $i\text{-}C_4H_9$ |
| 163 | $CO_2CH_2CH_3$ | $t\text{-}C_4H_9$ |
| 164 | $CO_2CH_2CH_3$ | $n\text{-}C_5H_{11}$ |
| 165 | $CO_2CH_2CH_3$ | $i\text{-}C_5H_{11}$ |
| 166 | $CO_2CH_2CH_3$ | $neo\text{-}C_5H_{11}$ |
| 167 | $CO_2CH_2CH_3$ | cyclopentyl |
| 168 | $CO_2CH_2CH_3$ | $n\text{-}C_6H_{13}$ |
| 169 | $CO_2CH_2CH_3$ | cyclohexyl |
| 170 | $CO_2CH_2CH_3$ | cyclopropyl-$CH_2$ |
| 171 | $CO_2CH_2CH_3$ | propyn-3-yl |
| 172 | $CO_2CH_2CH_3$ | propen-3-yl |
| 173 | $CO_2CH_2CH_3$ | benzyl |
| 174 | $CO_2CH_2CH_3$ | $CH_2CH_2\text{—}OCH_3$ |
| 175 | $CO_2CH(CH_3)_2$ | H |
| 176 | $CO_2CH(CH_3)_2$ | $CH_3$ |
| 177 | $CO_2CH(CH_3)_2$ | $C_2H_5$ |
| 178 | $CO_2CH(CH_3)_2$ | $n\text{-}C_3H_7$ |
| 179 | $CO_2CH(CH_3)_2$ | $i\text{-}C_3H_7$ |
| 180 | $CO_2CH(CH_3)_2$ | cyclopropyl |
| 181 | $CO_2CH(CH_3)_2$ | $n\text{-}C_4H_9$ |
| 182 | $CO_2CH(CH_3)_2$ | $s\text{-}C_4H_9$ |
| 183 | $CO_2CH(CH_3)_2$ | $i\text{-}C_4H_9$ |
| 184 | $CO_2CH(CH_3)_2$ | $t\text{-}C_4H_9$ |
| 185 | $CO_2CH(CH_3)_2$ | $n\text{-}C_5H_{11}$ |
| 186 | $CO_2CH(CH_3)_2$ | $i\text{-}C_5H_{11}$ |
| 187 | $CO_2CH(CH_3)_2$ | $neo\text{-}C_5H_{11}$ |
| 188 | $CO_2CH(CH_3)_2$ | cyclopentyl |
| 189 | $CO_2C(CH_3)_3$ | $n\text{-}C_6H_{13}$ |
| 190 | $CO_2CH(CH_3)_2$ | cyclohexyl |
| 191 | $CO_2CH(CH_3)_2$ | cyclopropyl-$CH_2$ |
| 192 | $CO_2CH(CH_3)_2$ | propyn-3-yl |
| 193 | $CO_2CH(CH_3)_2$ | propen-3-yl |
| 194 | $CO_2CH(CH_3)_2$ | benzyl |
| 195 | $CO_2CH(CH_3)_2$ | $CH_2CH_2\text{—}OCH_3$ |
| 196 | $CO_2C(CH_3)_3$ | H |
| 197 | $CO_2C(CH_3)_3$ | $CH_3$ |
| 198 | $CO_2C(CH_3)_3$ | $C_2H_5$ |
| 199 | $CO_2C(CH_3)_3$ | $n\text{-}C_3H_7$ |
| 200 | $CO_2C(CH_3)_3$ | $i\text{-}C_3H_7$ |
| 201 | $CO_2C(CH_3)_3$ | cyclopropyl |
| 202 | $CO_2C(CH_3)_3$ | $n\text{-}C_4H_9$ |
| 203 | $CO_2C(CH_3)_3$ | $s\text{-}C_4H_9$ |
| 204 | $CO_2C(CH_3)_3$ | $i\text{-}C_4H_9$ |
| 205 | $CO_2C(CH_3)_3$ | $t\text{-}C_4H_9$ |
| 206 | $CO_2C(CH_3)_3$ | $n\text{-}C_5H_{11}$ |
| 207 | $CO_2C(CH_3)_3$ | $i\text{-}C_5H_{11}$ |
| 208 | $CO_2C(CH_3)_3$ | $neo\text{-}C_5H_{11}$ |
| 209 | $CO_2C(CH_3)_3$ | cyclopentyl |
| 210 | $CO_2C(CH_3)_3$ | $n\text{-}C_6H_{13}$ |
| 211 | $CO_2C(CH_3)_3$ | cyclohexyl |
| 212 | $CO_2C(CH_3)_3$ | cyclopropyl-$CH_2$ |
| 213 | $CO_2C(CH_3)_3$ | propyn-3-yl |
| 214 | $CO_2C(CH_3)_3$ | propen-3-yl |
| 215 | $CO_2C(CH_3)_3$ | benzyl |
| 216 | $CO_2C(CH_3)_3$ | $CH_2CH_2\text{—}OCH_3$ |
| 217 | $CH_3$ | H |
| 218 | $CH_3$ | $CH_3$ |
| 219 | $CH_3$ | $C_2H_5$ |
| 220 | $CH_3$ | $n\text{-}C_3H_7$ |
| 221 | $CH_3$ | $i\text{-}C_3H_7$ |
| 222 | $CH_3$ | cyclopropyl |
| 223 | $CH_3$ | $n\text{-}C_4H_9$ |
| 224 | $CH_3$ | $s\text{-}C_4H_9$ |
| 225 | $CH_3$ | $i\text{-}C_4H_9$ |
| 226 | $CH_3$ | $t\text{-}C_4H_9$ |
| 227 | $CH_3$ | $n\text{-}C_5H_{11}$ |
| 228 | $CH_3$ | $i\text{-}C_5H_{11}$ |
| 229 | $CH_3$ | $neo\text{-}C_5H_{11}$ |
| 230 | $CH_3$ | cyclopentyl |
| 231 | $CH_3$ | $n\text{-}C_6H_{13}$ |
| 232 | $CH_3$ | cyclohexyl |
| 233 | $CH_3$ | cyclopropyl-$CH_2$ |
| 234 | $CH_3$ | propyn-3-yl |
| 235 | $CH_3$ | propen-3-yl |
| 236 | $CH_3$ | benzyl |
| 237 | $CH_3$ | $CH_2CH_2\text{—}OCH_3$ |
| 238 | $C_2H_5$ | H |
| 239 | $C_2H_5$ | $CH_3$ |
| 240 | $C_2H_5$ | $C_2H_5$ |
| 241 | $C_2H_5$ | $n\text{-}C_3H_7$ |
| 242 | $C_2H_5$ | $i\text{-}C_3H_7$ |
| 243 | $C_2H_5$ | cyclopropyl |
| 244 | $C_2H_5$ | $n\text{-}C_4H_9$ |
| 245 | $C_2H_5$ | $s\text{-}C_4H_9$ |
| 246 | $C_2H_5$ | $i\text{-}C_4H_9$ |
| 247 | $C_2H_5$ | $t\text{-}C_4H_9$ |
| 248 | $C_2H_5$ | $n\text{-}C_5H_{11}$ |
| 249 | $C_2H_5$ | $i\text{-}C_5H_{11}$ |
| 250 | $C_2H_5$ | $neo\text{-}C_5H_{11}$ |
| 251 | $C_2H_5$ | cyclopentyl |
| 252 | $C_2H_5$ | $n\text{-}C_6H_{13}$ |
| 253 | $C_2H_5$ | cyclohexyl |
| 254 | $C_2H_5$ | cyclopropyl-$CH_2$ |
| 255 | $C_2H_5$ | propyn-3-yl |
| 256 | $C_2H_5$ | propen-3-yl |
| 257 | $C_2H_5$ | benzyl |
| 258 | $C_2H_5$ | $CH_2CH_2\text{—}OCH_3$ |
| 259 | benzyl | H |
| 260 | benzyl | $CH_3$ |
| 261 | benzyl | $C_2H_5$ |
| 262 | benzyl | $n\text{-}C_3H_7$ |
| 263 | benzyl | $i\text{-}C_3H_7$ |
| 264 | benzyl | cyclopropyl |
| 265 | benzyl | $n\text{-}C_4H_9$ |
| 266 | benzyl | $s\text{-}C_4H_9$ |
| 267 | benzyl | $i\text{-}C_4H_9$ |
| 268 | benzyl | $t\text{-}C_4H_9$ |
| 269 | benzyl | $n\text{-}C_5H_{11}$ |
| 270 | benzyl | $i\text{-}C_5H_{11}$ |
| 271 | benzyl | $neo\text{-}C_5H_{11}$ |
| 272 | benzyl | cyclopentyl |
| 273 | benzyl | $n\text{-}C_6H_{13}$ |
| 274 | benzyl | cyclohexyl |
| 275 | benzyl | cyclopropyl-$CH_2$ |
| 276 | benzyl | propyn-3-yl |
| 277 | benzyl | propen-3-yl |
| 278 | benzyl | benzyl |
| 279 | benzyl | $CH_2CH_2\text{—}OCH_3$ | j) $R^4 = 4\text{-}N(R^c)\text{—}OR^d$

| | | |
|---|---|---|
| 280 | $CO_2CH_3$ | H |
| 281 | $CO_2CH_3$ | $CH_3$ |
| 282 | $CO_2CH_3$ | $C_2H_5$ |
| 283 | $CO_2CH_3$ | $n\text{-}C_3H_7$ |
| 284 | $CO_2CH_3$ | $i\text{-}C_3H_7$ |
| 285 | $CO_2CH_3$ | cyclopropyl |
| 286 | $CO_2CH_3$ | $n\text{-}C_4H_9$ |
| 287 | $CO_2CH_3$ | $s\text{-}C_4H_9$ |
| 288 | $CO_2CH_3$ | $i\text{-}C_4H_9$ |
| 289 | $CO_2CH_3$ | $t\text{-}C_4H_9$ |
| 290 | $CO_2CH_3$ | $n\text{-}C_5H_{11}$ |
| 291 | $CO_2CH_3$ | $i\text{-}C_5H_{11}$ |
| 292 | $CO_2CH_3$ | $neo\text{-}C_5H_{11}$ |
| 293 | $CO_2CH_3$ | cyclopentyl |
| 294 | $CO_2CH_3$ | $n\text{-}C_6H_{13}$ |
| 295 | $CO_2CH_3$ | cyclohexyl |
| 296 | $CO_2CH_3$ | cyclopropyl-$CH_2$ |
| 297 | $CO_2CH_3$ | propyn-3-yl |
| 298 | $CO_2CH_3$ | propen-3-yl |
| 299 | $CO_2CH_3$ | benzyl |
| 300 | $CO_2CH_3$ | $CH_2CH_2\text{—}OCH_3$ |
| 301 | $CO_2CH_2CH_3$ | H |
| 302 | $CO_2CH_2CH_3$ | $CH_3$ |
| 303 | $CO_2CH_2CH_3$ | $C_2H_5$ |
| 304 | $CO_2CH_2CH_3$ | $n\text{-}C_3H_7$ |
| 305 | $CO_2CH_2CH_3$ | $i\text{-}C_3H_7$ |
| 306 | $CO_2CH_2CH_3$ | cyclopropyl |
| 307 | $CO_2CH_2CH_3$ | $n\text{-}C_4H_9$ |
| 308 | $CO_2CH_2CH_3$ | $s\text{-}C_4H_9$ |
| 309 | $CO_2CH_2CH_3$ | $i\text{-}C_4H_9$ |
| 310 | $CO_2CH_2CH_3$ | $t\text{-}C_4H_9$ |
| 311 | $CO_2CH_2CH_3$ | $n\text{-}C_5H_{11}$ |
| 312 | $CO_2CH_2CH_3$ | $i\text{-}C_5H_{11}$ |
| 313 | $CO_2CH_2CH_3$ | $neo\text{-}C_5H_{11}$ |
| 314 | $CO_2CH_2CH_3$ | cyclopentyl |
| 315 | $CO_2CH_2CH_3$ | $n\text{-}C_6H_{13}$ |
| 316 | $CO_2CH_2CH_3$ | cyclohexyl |
| 317 | $CO_2CH_2CH_3$ | cyclopropyl-$CH_2$ |

| No. | | |
|---|---|---|
| 318 | CO$_2$CH$_2$CH$_3$ | propyn-3-yl |
| 319 | CO$_2$CH$_2$CH$_3$ | propen-3-yl |
| 320 | CO$_2$CH$_2$CH$_3$ | benzyl |
| 321 | CO$_2$CH$_2$CH$_3$ | CH$_2$CH$_2$—OCH$_3$ |
| 322 | CO$_2$CH(CH$_3$)$_2$ | H |
| 323 | CO$_2$CH(CH$_3$)$_2$ | CH$_3$ |
| 324 | CO$_2$CH(CH$_3$)$_2$ | C$_2$H$_5$ |
| 325 | CO$_2$CH(CH$_3$)$_2$ | n-C$_3$H$_7$ |
| 326 | CO$_2$CH(CH$_3$)$_2$ | i-C$_3$H$_7$ |
| 327 | CO$_2$CH(CH$_3$)$_2$ | cyclopropyl |
| 328 | CO$_2$CH(CH$_3$)$_2$ | n-C$_4$H$_9$ |
| 329 | CO$_2$CH(CH$_3$)$_2$ | s-C$_4$H$_9$ |
| 330 | CO$_2$CH(CH$_3$)$_2$ | i-C$_4$H$_9$ |
| 331 | CO$_2$CH(CH$_3$)$_2$ | t-C$_4$H$_9$ |
| 332 | CO$_2$CH(CH$_3$)$_2$ | n-C$_5$H$_{11}$ |
| 333 | CO$_2$CH(CH$_3$)$_2$ | i-C$_5$H$_{11}$ |
| 334 | CO$_2$CH(CH$_3$)$_2$ | neo-C$_5$H$_{11}$ |
| 335 | CO$_2$CH(CH$_3$)$_2$ | cyclopentyl |
| 336 | CO$_2$CH(CH$_3$)$_2$ | n-C$_6$H$_{13}$ |
| 337 | CO$_2$CH(CH$_3$)$_2$ | cyclohexyl |
| 338 | CO$_2$CH(CH$_3$)$_2$ | cyclopropyl-CH$_2$ |
| 339 | CO$_2$CH(CH$_3$)$_2$ | propyn-3-yl |
| 340 | CO$_2$CH(CH$_3$)$_2$ | propen-3-yl |
| 341 | CO$_2$CH(CH$_3$)$_2$ | benzyl |
| 342 | CO$_2$C(CH$_3$)$_3$ | H |
| 343 | CO$_2$C(CH$_3$)$_3$ | CH$_3$ |
| 344 | CO$_2$C(CH$_3$)$_3$ | C$_2$H$_5$ |
| 345 | CO$_2$C(CH$_3$)$_3$ | n-C$_3$H$_7$ |
| 346 | CO$_2$C(CH$_3$)$_3$ | i-C$_3$H$_7$ |
| 347 | CO$_2$C(CH$_3$)$_3$ | cyclopropyl |
| 348 | CO$_2$C(CH$_3$)$_3$ | n-C$_4$H$_9$ |
| 349 | CO$_2$C(CH$_3$)$_3$ | s-C$_4$H$_9$ |
| 350 | CO$_2$C(CH$_3$)$_3$ | i-C$_4$H$_9$ |
| 351 | CO$_2$C(CH$_3$)$_3$ | t-C$_4$H$_9$ |
| 352 | CO$_2$C(CH$_3$)$_3$ | n-C$_5$H$_{11}$ |
| 353 | CO$_2$C(CH$_3$)$_3$ | i-C$_5$H$_{11}$ |
| 354 | CO$_2$C(CH$_3$)$_3$ | neo-C$_5$H$_{11}$ |
| 355 | CO$_2$C(CH$_3$)$_3$ | cyclopentyl |
| 356 | CO$_2$C(CH$_3$)$_3$ | n-C$_6$H$_{13}$ |
| 357 | CO$_2$C(CH$_3$)$_3$ | cyclohexyl |
| 358 | CO$_2$C(CH$_3$)$_3$ | cyclopropyl-CH$_2$ |
| 359 | CO$_2$C(CH$_3$)$_3$ | propyn-3-yl |
| 360 | CO$_2$C(CH$_3$)$_3$ | propen-3-yl |
| 361 | CO$_2$C(CH$_3$)$_3$ | benzyl |
| 362 | CO$_2$C(CH$_3$)$_3$ | CH$_2$CH$_2$—OCH$_3$ |
| 363 | CH$_3$ | H |
| 364 | CH$_3$ | CH$_3$ |
| 365 | CH$_3$ | C$_2$H$_5$ |
| 366 | CH$_3$ | n-C$_3$H$_7$ |
| 367 | CH$_3$ | i-C$_3$H$_7$ |
| 368 | CH$_3$ | cyclopropyl |
| 369 | CH$_3$ | n-C$_4$H$_9$ |
| 370 | CH$_3$ | s-C$_4$H$_9$ |
| 371 | CH$_3$ | i-C$_4$H$_9$ |
| 372 | CH$_3$ | t-C$_4$H$_9$ |
| 373 | CH$_3$ | n-C$_5$H$_{11}$ |
| 374 | CH$_3$ | i-C$_5$H$_{11}$ |
| 375 | CH$_3$ | neo-C$_5$H$_{11}$ |
| 376 | CH$_3$ | cyclopentyl |
| 377 | CH$_3$ | n-C$_6$H$_{13}$ |
| 378 | CH$_3$ | cyclohexyl |
| 379 | CH$_3$ | cyclopropyl-CH$_2$ |
| 380 | CH$_3$ | propyn-3-yl |
| 381 | CH$_3$ | propen-3-yl |
| 382 | CH$_3$ | benzyl |
| 383 | CH$_3$ | CH$_2$CH$_2$—OCH$_3$ |
| 384 | C$_2$H$_5$ | H |
| 385 | C$_2$H$_5$ | CH$_3$ |
| 386 | C$_2$H$_5$ | C$_2$H$_5$ |
| 387 | C$_2$H$_5$ | n-C$_3$H$_7$ |
| 388 | C$_2$H$_5$ | i-C$_3$H$_7$ |
| 389 | C$_2$H$_5$ | cyclopropyl |
| 390 | C$_2$H$_5$ | n-C$_4$H$_9$ |
| 391 | C$_2$H$_5$ | s-C$_4$H$_9$ |
| 392 | C$_2$H$_5$ | i-C$_4$H$_9$ |
| 393 | C$_2$H$_5$ | t-C$_4$H$_9$ |
| 394 | C$_2$H$_5$ | n-C$_5$H$_{11}$ |
| 395 | C$_2$H$_5$ | i-C$_5$H$_{11}$ |
| 396 | C$_2$H$_5$ | neo-C$_5$H$_{11}$ |
| 397 | C$_2$H$_5$ | cyclopentyl |
| 398 | C$_2$H$_5$ | n-C$_6$H$_{13}$ |
| 399 | C$_2$H$_5$ | cyclohexyl |
| 400 | C$_2$H$_5$ | cyclopropyl-CH$_2$ |
| 401 | C$_2$H$_5$ | propyn-3-yl |
| 402 | C$_2$H$_5$ | propen-3-yl |
| 403 | C$_2$H$_5$ | benzyl |
| 404 | C$_2$H$_5$ | CH$_2$CH$_2$—OCH$_3$ |
| 405 | benzyl | H |
| 406 | benzyl | CH$_3$ |
| 407 | benzyl | C$_2$H$_5$ |
| 408 | benzyl | n-C$_3$H$_7$ |
| 409 | benzyl | i-C$_3$H$_7$ |
| 410 | benzyl | cyclopropyl |
| 411 | benzyl | n-C$_4$H$_9$ |
| 412 | benzyl | s-C$_4$H$_9$ |
| 413 | benzyl | i-C$_4$H$_9$ |
| 414 | benzyl | t-C$_4$H$_9$ |
| 415 | benzyl | n-C$_5$H$_{11}$ |
| 416 | benzyl | i-C$_5$H$_{11}$ |
| 417 | benzyl | neo-C$_5$H$_{11}$ |
| 418 | benzyl | cyclopentyl |
| 419 | benzyl | n-C$_6$H$_{13}$ |
| 420 | benzyl | cyclohexyl |
| 421 | benzyl | cyclopropyl-CH$_2$ |
| 422 | benzyl | propyn-3-yl |
| 423 | benzyl | propen-3-yl |
| 424 | benzyl | benzyl |
| 425 | benzyl | CH$_2$CH$_2$—OCH$_3$ |

| No. | R$^4$ |
|---|---|
| 426 | 2,3-O—CHF—O |
| 427 | 3,4-O—CHF—O |
| 428 | 2,3-O—CF$_2$—O |
| 429 | 3,4-O—CF$_2$—O |
| 430 | 2,3-*O—CF$_2$—CHF—O |
| 431 | 3,4-•O—CF$_2$—CHF—O |
| 432 | 2,3-*O—CHF—CF$_2$—O |
| 433 | 3,4-•O—CHF—CF$_2$—O |

*Linkage site in the 2-position of the R$^4$-substituted phenyl ring
•Linkage site in the 3-position of the R$^4$-substituted phenyl ring The compounds I are suitable as fungicides.

The compounds I are distinguished by an outstanding activity against a broad spectrum of phytopathogenic fungi, in particular from the classes of the Ascomycetes and Basidiomycetes. Some of them act systemically and can be employed as foliar- and soilacting fungicides.

They are especially important for controlling a large number of fungi on a variety of crop plants such as wheat, rye, barley, oats, rice, maize, grass, cotton, soybeans, coffee, sugar cane, grapevines, fruit species, ornamentals and vegetable species such as cucumbers, beans and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, Uncinula necator on grapevines, Puccinia species on cereals, Rhizoctonia species on cotton, rice and lawns, ustilago species on cereals and sugar cane, *Venturia inaequalis* (scab) on apples, Helminthosporium species on cereals, *Septoria nodorum* on wheat, *Botrytis cinerea* (gray mold) on strawberries, grapevines, vegetables and ornamentals, Cercospora arachidicola on peanuts, *Pseudocercosporella herpotrichoides* on wheat, barley, *Pyricularia oryzae* on rice, Phytophthora infestans on potatoes and tomatoes, Fusarium and Verticillium species on a variety of plants, Plasmopara viticola on grapevines, Pseudoperonospora species in hops and cucumbers, Alternaria species on vegetables and fruit.

The compounds I are applied by treating the fungi, or the plants, seeds, materials or the soil to be protected against fungal infection, with a fungicidally active amount of the active ingredients. Application is effected before or after infection of the materials, plants or seeds by the fungi.

Using formulation auxiliaries known per se, they can be converted into the customary formulations (compositions), such as solutions, emulsions, suspensions, dusts, powders, pastes and granules. The use form depends on the intended purpose; in any case, it should guarantee fine and uniform distribution of the compounds I. The formulations are prepared in a known manner, eg. by extending the active ingredient with solvents and/or carriers, if desired using emulsifiers and dispersants, it also being possible for other organic solvents to be used as auxiliary solvents if water is used as the diluent. Suitable auxiliaries are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

In general, the fungicidal compositions comprise between 0.1 and 95, preferably between 0.5 and 90, % by weight of active ingredient.

Depending on the nature of the desired effect, the rates of application are between 0.01 and 2.0 kg of active ingredient per ha.

In the treatment of seed, amounts of active ingredient of from 0.001 to 0.1 g, preferably 0.01 to 0.05 g, are generally required per kilogram of seed.

In the use form as fungicides, the agents according to the invention can also be present together with other active ingredients, the [sic] eg. with herbicides, insecticides, growth regulators, fungicides or else with fertilizers.

A mixture with fungicides frequently results in a widened spectrum of fungicidal action.

The following list of fungicides together with which the compounds according to the invention can be used is intended to illustrate the possible combinations but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide; nitro derivatives, such as dinitro(1-methylheptyl)phenyl crotonate, 2-sec-butyl-4,6-dinitrophenyl-3,3-dimethyl acrylate, 2-sec-butyl-4,6-dinitrophenylisopropyl carbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis-(dimethylamino)-phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2))benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-(1-(2,2,2-trichloroethyl)formamide [sic], 1-(3,4-dichloroanilino)-1-formylamino-2,2,2-trichloroethane, 2,6-dimethyl-N-tridecyl-morpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethyl-phenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxy-methyl]-1,3-oxazolidine-2,4-dione [sic], 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)-pentyl]-1H-1,2,4-triazole, 2,4-difluoro-α-(1H-1,2,4-triazolyl-1-methyl)-benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

Strobilurins such as methyl E-methoximino-[α-(o-tolyloxy)-o-tolyl]acetate, methyl E-2-{2-[6-(2-cyanophenoxy)-pyrimidin-4-yloxy]phenyl}-3-methoxyacrylate, N-methyl-E-methoximino-[α-(2-phenoxyphenyl)]acetamide, N-methyl-E-methoximino-[α-(2,5-dimethylphenoxy)-o-tolyl]acetamide.

Anilinopyrimidines, such as N-(4,6-dimethylpyrimidin-2-yl)aniline, N-[4-methyl-6-(1-propynyl)pyrimidin-2-yl]aniline, N-(4-methyl-6-cyclopropylpyrimidin-2-yl)aniline.

Phenylpyrroles, such as 4-(2,2-difluoro-1,3-benzodioxol-4-yl)pyrrole-3-carbonitrile.

Cinnamamides, such as N-3-(4-chlorophenyl)-3-(3,4-dimethoxyphenyl)-acryloylmorpholine.

(2RS,3RS)-1-[3-(2-Chlorophenyl)-2-[4-fluorophenyl] oxiran-2-yl-methyl]1H-1,2,4-triazole [sic].

Moreover, the compounds of the formula I are suitable for efficiently controlling pests from the classes of the insects, arachnids and nematodes. They can be employed as pesticides in crop protection and in the hygiene, stored-product and veterinary sectors.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens,* Heliothis zea, *Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana,* Trichoplusia ni, *Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis,* Diabrotica 12-punctata, *Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotretastriolata, popillia japonica, Sitona lineatus, sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala,*Sappaphis mali, Schizaphis graminum, Schizoneura lanuginosa, Trialeurodes vaporariorum, Viteus vitifolii.

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina), such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root-knot nematodes, eg. *Meloidogyne hapla, Meloidogyne incognita, Meloidogyne javanica*, cyst-forming nematodes, eg. *Globodera rostochiensis, Heterodera avenae, Heterodera glycines, Heterodera schachtii, Heterodera trifolii*, stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi*.

The compounds I, as such, in the form of their formulations (compositions) which have been obtained using formulation auxiliaries known per se or in the form of the use forms prepared therefrom, can be applied by spraying, atomizing, dusting, spreading or pouring, for example in the form of directly sprayable solutions, powders, suspensions or dispersions, emulsions, oil dispersions, pastes, dusts, materials for spreading, or granules. The use forms depend entirely on the intended purposes; in any case, they should guarantee the finest possible distribution of the active ingredients according to the invention.

The concentrations of active ingredient in the ready-to-use preparations can be varied within substantial ranges.

They are in general between 0.0001 and 10%, preferably between 0.01 and 1%.

The active ingredients can also be used very successfully in the ultra-low volume method (ULV), it being possible to apply formulations comprising over 95% by weight of active ingredient, or even the active ingredient without additives.

The rate of application of active ingredient for controlling pests is from 0.1 to 2.0, preferably 0.2 to 1.0, kg/ha under field conditions.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, and strongly polar solvents, eg. dimethylformamide, dimethyl sulfoxide, N-methylpyrrolidone and water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetting agent, tackifier, dispersant or emulsifier. Alternatively, it is possible to prepare concentrates composed of active substance, wetting agent, tackifier, dispersant or emulsifier and, if desired, oil or solvent, and these concentrates are suitable for dilution with water.

Suitable surfactants are alkali metal, alkaline earth metal and ammonium salts of lignosulfonic acid, naphthalenesulfonic acid, phenolsulfonic acid, dibutylnaphthalenesulfonic acid, or alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene, or of naphthalenesulfonic acid, with phenol and formaldehyde, polyoxyethylene octylphenol [sic] ether, ethoxylated isooctylphenol, octylphenol, nonylphenol, alkylphenol [sic] polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, materials for spreading and dusts can be prepared by mixing or concomitantly grinding the active substances together with a solid carrier.

In general, the formulations comprise from 0.01 to 95% by weight, preferably from 0.1 to 90% by weight, of the active ingredient. The active ingredients are employed in a purity of from 90% to 100%, preferably 95% to 100% (according to the NMR spectrum).

The following are examples of formulations:

I. 5 parts by weight of a compound I according to the invention 25 are mixed intimately with 95 parts by weight of finely divided kaolin. This gives a dust which comprises 5% by weight of the active ingredient.

II. 30 parts by weight of a compound I according to the invention are mixed intimately with a mixture of 92 parts by weight of puverulent silica gel and 8 parts by weight of paraffin oil which had been sprayed onto the surface of this silica gel. This gives a preparation of the active ingredient with good adhesion properties (comprises 23% by weight of active ingredient).

III. 10 parts by weight of a compound I according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound I according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide to 1 mol of castor oil (comprises 16% by weight of active ingredient).

V. 80 parts by weight of a compound I according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound I according to the invention are mixed with 10 parts by weight of N-methyl-α-pyrrolidone, resulting in a solution which is suitable for use in the form of microdrops (comprises 90% by weight of active ingredient).

VII. 20 parts by weight of a compound I according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

VIII. 20 parts by weight of a compound I according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredients to solid carriers. Examples of solid carriers are mineral earths, such as silica gel, silicas, silica gels [sic], silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders, and other solid carriers.

Various types of oils, or herbicides, fungicides, other pesticides, or bactericides, can be added to the active ingredients, if desired only immediately prior to use (tank mix). These agents can be admixed with the agents according to the invention in a weight ratio of 1:10 to 10:1.

SYNTHESIS EXAMPLE 1

Synthesis of Compound I.11 of Table 1

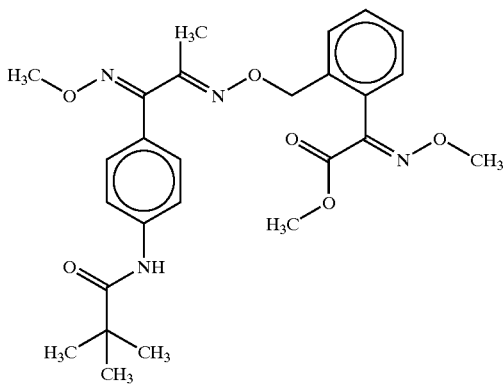

1a) Synthesis of

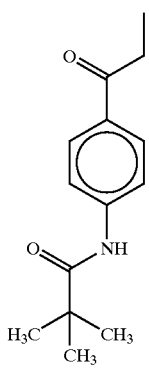

(1a)

162 g (1.2 mol) of AlCl₃ were added, a little at a time, to a stirred mixture of 82 g (0.45 ml) of pivalanilide and 40 g (0.43 mol) of propionyl chloride, during which process the temperature of the reaction mixture climbed to approximately 100° C. and hydrochloric acid was evolved.

The reaction mixture was subsequently stirred for 6 hours at 80° C. The reaction mixture was carefully poured onto ice, and the aqueous phase was extracted with methyl t-butyl ether and ethyl acetate.

The combined organic phases were extracted 2× with water, and the aqueous phase was dried over MgSO₄ and concentrated. The residue was purified by column chromatography with cyclohexane/ethyl acetate mixtures. This gave 22.3 g (22%) of the title Compound 1a as a colorless solid (m.p.=121° C.).

$^1$H NMR (CDCl₃; δ in ppm): 7.95 (d, 2H, phenyl); 7.65 (d, broad, 3H, NH, 2×phenyl); 2.95 (q, 2H, CH₂); 1.35 (s, 9H, t-butyl); 1.2 (t, 3H, CH₃).

1b) Synthesis of

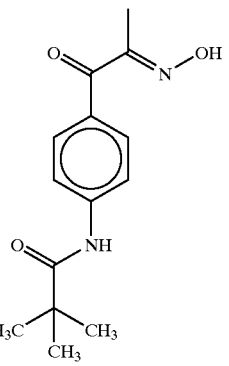

(1b)

A mixture of 22 g (94 mmol) of Compound 1a in 200 ml of toluene was treated at −20° C. with 80 ml of hydrochloric acid solution in ether (approximately 4N) and 12 g (115 mmol) of n-butyl nitrite in 50 ml of ether are subsequently added dropwise. The mixture was then stirred overnight at room temperature. The title compound crystallized out of the reaction mixture. The solid which had precipitated was filtered off with suction, washed with methyl t-butyl ether, ethyl acetate and methylene chloride and dried in a stream of nitrogen. This gave 17 g (69%) of the title Compound 1b as a colorless solid (m.p. 198° C.). Work-up of the mother liquor yielded a second crystal fraction of 3.5 g (14%).

$^1$H NMR (DMSO-d₆; δ in ppm): 12.3; 9.5 (2s, in each case 1H, OH, NH); 7.85 (d, 2H, phenyl); 7.75 (d, 2H, phenyl); 2.0 (s, 3H, CH₃); 1.25 (s, 9H, t-butyl).

1c) Synthesis of

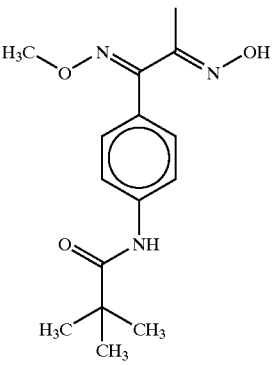

(1c)

A mixture of 16 g (61 mmol) of Compound 1b, 12 g (150 mmol) of pyridine and 6.5 g (78 mmol) of O-methylhydroxylamine hydrochloride in 100 ml of methanol was stirred overnight at room temperature. The reaction mixture was subsequently concentrated and the residue taken up in methylene chloride. The organic phase was washed with dilute hydrochloric acid and water, dried over MgSO$_4$ and concentrated. The residue crystallized and was obtained by stirring with methylene chloride. This gave 3.6 g (20%) of the title Compound 1c as a colorless solid (m.p.=208° C.). Work-up of the mother liquor yielded a second crystal fraction of 5.2 g of 1c (29%).

$^1$H NMR (DMSO-d$_6$; δ in ppm): 11.6; 9.25 (2s, in each case 1H, OH, NH); 7.6 (d, 2H, phenyl); 7.1 (d, 2H, phenyl); 3.8 (s, 3H, OCH$_3$); 2.05 (s, 3H, CH$_3$); 1.25 (s, 9H, t-butyl).

Synthesis of I.11

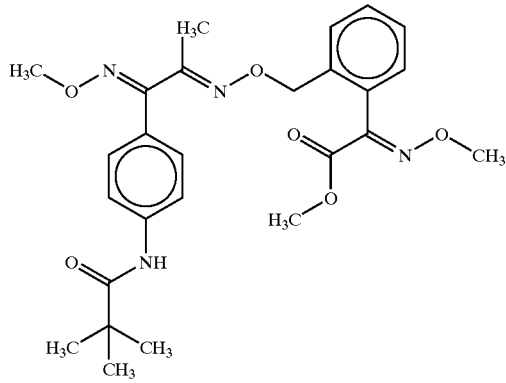
(I.11)

A mixture of 2 g (6.8 mmol) of the Compound 1c and 0.25 g (10 mmol) of sodium hydride in 20 ml of dimethylformamide was stirred for 15 minutes at room temperature. 2 g (7 mmol) of methyl 2-bromomethylphenylglyoxylate trans-O-methyloxime (EP 254 426) were subsequently added, and the mixture was stirred for one hour at room temperature. The reaction mixture was then diluted with water and the aqueous phase extracted with methyl t-butyl ether. The combined organic phases were washed with water, dried over MgSO$_4$ and concentrated. The residue crystallized, and the crystals were filtered off with suction and dried in a stream of nitrogen. This gave 2.8 g (83%) of the title Compound I.11 as a pale yellow solid (m.p.=114–116° C.).

$^1$H NMR (CDCl$_3$-d$_6$; δ in ppm): 7.55; (2s, 2H, phenyl); 7.4 (m, 4H, phenyl); 7.15 (d, broad, NH, 2×phenyl); 4.95 (s, 2H, OCH$_2$); 4.0; 3.9; 3.8 (3s, in each case 3H, 3×OCH$_3$); 2.1 (s, 3H, CH$_3$); 1.25 (s, 9H, t-butyl).

SYNTHESIS EXAMPLE 2

Synthesis of Compound I.12 of Table 1

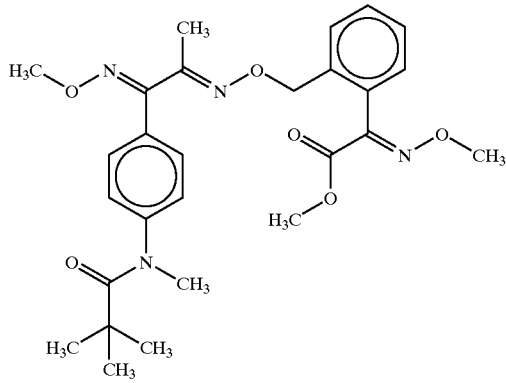
(I.12)

A mixture of 1.5 g (3 mmol) of Compound I.11 of Synthesis Example 1 and 0.1 g (4 mmol) of sodium hydride in 20 ml of dimethylformamide was stirred for 10 minutes at room temperature. 0.7 g (5 mmol) of methyl iodide was subsequently added and the mixture was stirred at room temperature for approximately 2 hours. The reaction mixture was subsequently diluted with water and the aqueous phase extracted with methyl t-butyl ether. The combined organic phases were extracted with water, dried over MgSO$_4$ and concentrated. The residue was purified by column chromatography with cyclohexane/ethyl acetate mixture. This gave 1.2 g (78%) of the title Compound I.12 as pale yellow crystals (m.p.=111–113° C.).

$^1$H NMR (CDCl$_3$; δ in ppm): 7.35; (m, 2H, phenyl); 7.2 (m, 6H, phenyl); 4.9 (s, 2H, OCH$_2$); 4.0; 3.9; 3.8 (3s, in each case 3H, 3×OCH$_3$); 3.2 (s, 3H, NCH$_3$); 2.1 (s, 3H, CH$_3$); 1.05 (s, 9H, t-butyl).

SYNTHESIS EXAMPLE 3

Synthesis of Compound I.10 of Table 1

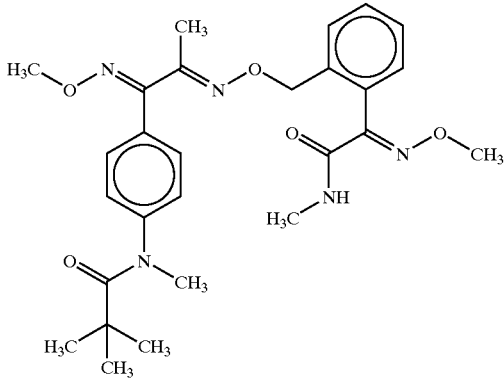
(I.10)

A mixture of 0.9 g (1.8 mmol) of Compound I.12 of Synthesis Example 2 and 3 ml of tetrahydrofuran in 20 ml of 40% strength methylamine solution was stirred for 1 hour at 50° C. Excess methylamine was subsequently evaporated in vacuo and the remaining aqueous phase was extracted with methylene chloride. The combined organic phases were washed with water, dried over MgSO$_4$ and concentrated. The residue crystallized and was obtained by stirring with methyl t-butyl ether. This gave 0.7 g (76%) of the title Compound I.10 as a colorless solid m.p.=168–170° C.).

$^1$H NMR (CDCl$_3$; δ in ppm): 7.35; (m, 2H, phenyl); 7.2 (m, 6H, phenyl); 6.75 (s, broad, 1H, NH); 4.9 (s, 2H, OCH$_2$); 3.9 (2s, in each case 3H, 2×OCH$_3$); 3.2 (s, 3H, NCH$_3$); 2.9 (d, 3H, HNCH$_3$); 2.1 (s, 3H, CH$_3$); 1.05 (s, 9H, t-butyl).

SYNTHESIS EXAMPLE 4

Synthesis of Compound I.52 of Table 1

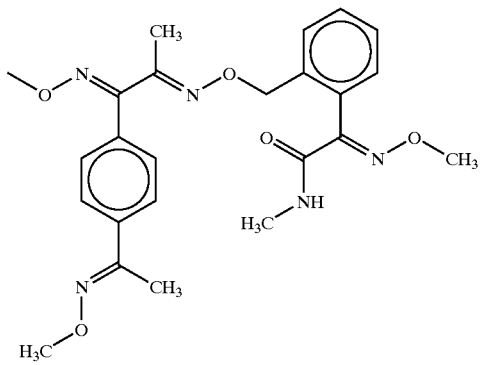
(I.52)

4a. Synthesis of

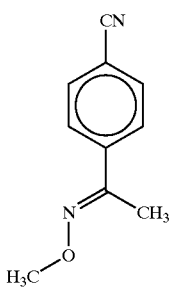
(4a)

17.5 g (0.21 mol) of O-methylhydroxylamine hydrochloride were added to a solution of 20 g (0.14 mol) of 4-cyanoacetophenone in 200 ml of methanol, and the mixture was first stirred for 2 hours at room temperature and subsequently for 2 hours at 60° C. The reaction mixture was poured onto water and extracted with methyl tert-butyl ether. The combined organic phases were washed with water, dried over Na$_2$SO$_4$ and concentrated. The residue was purified by column chromatography on silica gel (n-hexane). This gave 23.3 g (97% yield) of Compound 4a as a white powder (m.p.=58–60° C.).

$^1$H NMR (CDCl$_3$; δ in ppm): 2.21 (s, 3H); 4.02 (s, 3H); 7.61–7.75 (AA'BB', 4H).

4b. Synthesis of

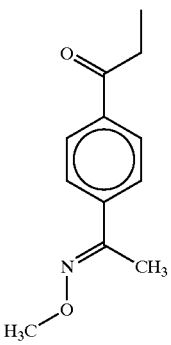
(4b)

At −15° C., 53 ml (0.15 mol) of an ethylmagnesium bromide solution (3M in diethyl ether) was added dropwise to a solution of 17.6 g (0.10 mol) of Compound 4a in 200 ml of tetrahydrofuran, and the reaction mixture was allowed to come to room temperature and was subsequently heated for 2.5 hours at 40° C. The reaction mixture was cooled to 0–5° C., hydrolyzed with 100 ml of ice-water and brought to pH=6 with glacial acetic acid. After a further addition of water, the mixture was extracted with methyl tert-butyl ether, and the organic phase was washed with water, dried over Na$_2$SO$_4$ and concentrated. The residue was purified by column chromatography on silica gel (n-hexane). This gave 13.9 g (67% yield) of Compound 4b as a pale yellow powder (m.p.=75–77° C.).

$^1$H NMR (CDCl$_3$; δ in ppm): 1.23 (t, 3H); 2.24 (s, 3H); 3.00 (q, 2H); 4.02 (s, 3H); 7.71–7.95 (AA'BB',4H).

4c) Synthesis of

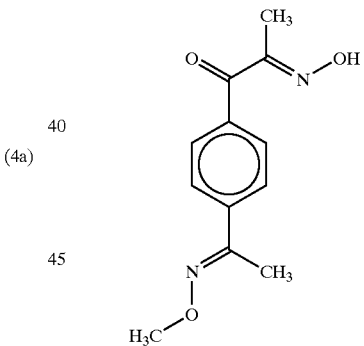
(4c)

80 ml of saturated HCl solution in ether were added at −20° C. to 13.2 g (0.064 mol) of Compound 4b in 150 ml of toluene. At this temperature, a solution of 7.3 g (0.071 mol) of n-butyl nitrite in 60 ml of diethyl ether was subsequently added dropwise. The mixture was stirred for 1 hour at −10° C. and subsequently allowed to come to room temperature. After a total of 16 hours, the reaction batch was washed with ice-water and subsequently extracted with 1M sodium hydroxide solution. The alkaline phase was separated off and rendered neutral with 20% strength sulfuric acid. The batch was subsequently extracted with methylene chloride, and the organic phase was washed with water, dried over Na$_2$SO$_4$ and concentrated. The residue was dissolved in a small amount of methylene chloride and purified by column chromatography on silica gel (n-hexane). This gave 13.2 g (88% yield) of Compound 4c as a colorless oil.

$^1$H NMR (CDCl$_3$; δ in ppm): 2.16 (s, 3H); 2.24 (s, 3H); 4.03 (s, 3H); 7.66–7.88 (AA'BB',4H); 8.92 (s, br, 1H).

4d) Synthesis of

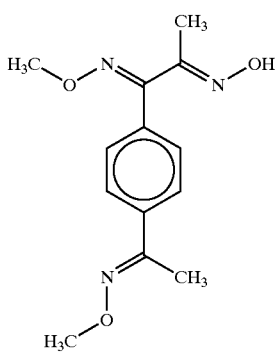

5 g (0.021 mol) of Compound 4c in 100 ml of methanol and 5 g of pyridine were treated with a solution of 2.7 g (0.032 mol) of O-methylhydroxylamine hydrochloride in 20 ml of methanol. The reaction mixture was stirred for 16 hours at room temperature and subsequently for 2 hours at 60° C. The reaction batch was poured into a mixture of methyl tert-butyl ether and 10% strength hydrochloric acid and extracted with methyl tert-butyl ether. The combined organic phases were washed with 10% hydrochloric acid and water, dried over $Na_2SO_4$ and concentrated. The residue was dissolved in 100 ml of toluene and treated with 0.9 g (6.3 mmol) $AlCl_3$. After 5 hours at 40° C. and a further 12 hours at room temperature, the reaction mixture was added to a mixture of ethyl acetate and 10% hydrochloric acid. The mixture was extracted with ethyl acetate and the organic phase was washed with water, dried over $Na_2SO_4$ and concentrated. After triturating the residue with methanol, 3.7 g (66% yield) of Compound 4d were obtained as a pale yellow powder (m.p.=162–165° C.).

$^1$H NMR ($CDCl_3$; δ in ppm): 2.11 (s, 3H); 2.21 (s, 3H); 3.89 (s, 3H); 3.99 (s, 3H); 7.15–7.67 (AA'BB',4H); 8.43 (s, 1H).

4e) Synthesis of Compound I.51 of Table 1

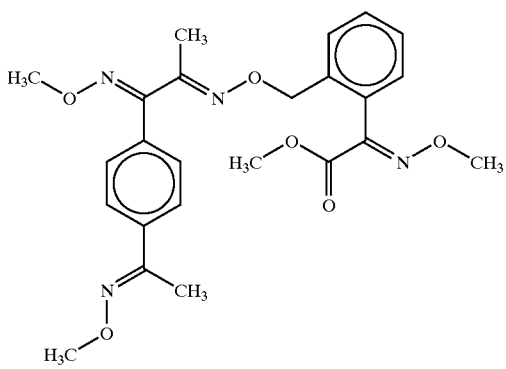

A solution of 3.0 g (11.4 mmol) of Compound 4d in 50 ml of N,N-dimethylformamide was treated with 2.1 g (11.4 mmol) of 30% strength sodium methoxide solution (in methanol) and stirred for 15 minutes at room temperature. After the addition of 3.3 g (11.4 mmol) of methyl 2-bromomethylphenylglyoxylate trans-O-methyloxime (EP 254 426) in 30 ml of N,N-dimethylformamide, the mixture was stirred for 0.5 hour at room temperature. The mixture was subsequently poured into ice-water and extracted with methyl tert-butyl ether. The organic phase was washed with water, dried over $Na_2SO_4$ and concentrated. Crystallization of the residue from methanol gave 4.7 g (88% yield) of the title Compound I.51 as colorless crystals (m.p.=112–114° C.).

$^1$H NMR ($CDCl_3$; δ in ppm): 2.10 (s, 3H); 2.22 (s, 3H); 3.82 (s, 3H); 3.90 (s, 3H); 3.99 (s, 6H); 4.90 (s, 2H); 7.08–7.60 (m, 8H).

4f) Synthesis of Compound I.52 of Table 1

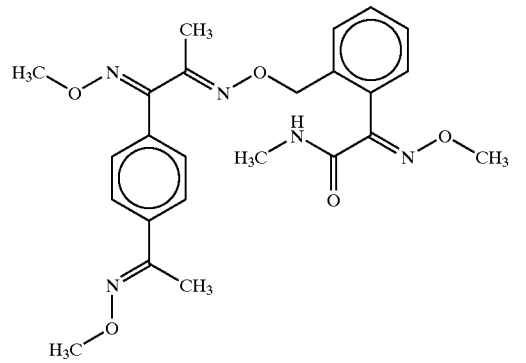

A solution of 2.0 g (4.3 mmol) of Compound 4e in 50 ml of tetrahydrofuran was treated with 3.3 g of 40% strength aqueous monomethylamine solution and stirred for 24 hours at room temperature. The resulting reaction mixture was treated with water and extracted with methyl tert-butyl ether. The organic phase was washed, dried and concentrated under reduced pressure. Purification of the residue by column chromatography on silica gel (methyl tert-butyl ether/n-hexane=1/1) gave 1.7 g (85% yield) of the title compound as a colorless oil.

$^1$H NMR ($CDCl_3$; δ in ppm): 2.10 (s, 3H); 2.22 (s, 3H); 3.87 (d, 3H); 3.90 (s, 6H); 3.99 (s, 3H); 4.92 (s, 2H); 6.67 (s, br, 1H); 7.12–7.61 (m, 8H).

Compounds I.1–I.9, I.13–I.50 and I.53-I.59, which are listed in Table 1 below, were prepared by similar methods.

The melting points (m.p.) are given in ° C., the IR bands in $cm^{-1}$ and the $^1$H NMR data in ppm relative to $CDCl_3$ as the standard.

TABLE 1

| No. | X | Y | $R^5$ | $(R^4)_n$ | M.P./IR/NMR |
| --- | --- | --- | --- | --- | --- |
| I.1. | $NOCH_3$ | O | $CH_3$ | 4-NH—$COCH_3$ | 63–66 |
| I.2. | $NOCH_3$ | NH | $CH_3$ | 4-NH—$COCH_3$ | 173–174 |
| I.3. | $NOCH_3$ | NH | $CH_3$ | 4-NH—$COC_2H_5$ | 200 |

TABLE 1-continued

| No. | X | Y | R⁵ | (R⁴)ₙ | M.P./IR/NMR |
|---|---|---|---|---|---|
| I.4. | NOCH$_3$ | O | CH$_3$ | 4-N(CH$_3$)—COC$_2$H$_5$ | 129–130 |
| I.5. | NOCH$_3$ | NH | CH$_3$ | 4-N(CH$_3$)—COC$_2$H$_5$ | 128–129 |
| I.6. | NOCH$_3$ | O | CH$_3$ | 4-NH—COC$_2$H$_5$ | 58–60 |
| I.7. | NOCH$_3$ | O | CH$_3$ | 4-N(C$_2$H$_5$)—COC$_2$H$_5$ | 138–140 |
| I.8. | NOCH$_3$ | NH | CH$_3$ | 4-N(C$_2$H$_5$)—COC$_2$H$_5$ | 93–95 |
| I.9. | NOCH$_3$ | NH | CH$_3$ | 4-NH—CO-t-C$_4$H$_9$ | 219–220 |
| I.10. | NOCH$_3$ | NH | CH$_3$ | 4-N(CH$_3$)—CO-t-C$_4$H$_9$ | 168–170 |
| I.11. | NOCH$_3$ | O | CH$_3$ | 4-NH—CO-t-C$_4$H$_9$ | 114–116 |
| I.12. | NOCH$_3$ | O | CH$_3$ | 4-N(CH$_3$)—CO-t-C$_4$H$_9$ | 111–113 |
| I.13. | CHOCH$_3$ | O | CH$_3$ | 4-NH—CO-t-C$_4$H$_9$ | 126–130 |
| I.14. | NOCH$_3$ | O | CH$_3$ | 4-N(n-C$_3$H$_7$)—CO—C$_2$H$_5$ | 123–126 |
| I.15. | NOCH$_3$ | NH | CH$_3$ | 4-N(n-C$_3$H$_7$)—CO—C$_2$H$_5$ | 125–127 |
| I.16. | CHOCH$_3$ | O | CH$_3$ | 4-NH—CO—C$_2$H$_5$ | 125–128 |
| I.17. | CHOCH$_3$ | O | CH$_3$ | 4-N(CH$_3$)—CO—C$_2$H$_5$ | 140–141 |
| I.18. | CHOCH$_3$ | O | CH$_3$ | 4-N(C$_2$H$_5$)—CO—C$_2$H$_5$ | 137–140 |
| I.19. | CHOCH$_3$ | O | CH$_3$ | 4-N(n-C$_3$H$_7$)—CO—C$_2$H$_5$ | 119–121 |
| I.20. | CHCH$_3$ | O | CH$_3$ | 4-NH—CO—C$_2$H$_5$ | 103–105 |
| I.21. | CHCH$_3$ | O | CH$_3$ | 4-N(CH$_3$)—CO—C$_2$H$_5$ | 83–86 |
| I.22. | CHCH$_3$ | O | CH$_3$ | 4-N(C$_2$H$_5$)—CO—C$_2$H$_5$ | 111–112 |
| I.23. | CHCH$_3$ | O | CH$_3$ | 4-N(n-C$_3$H$_7$)—CO—C$_2$H$_5$ | 105–107 |
| I.24. | NOCH$_3$ | NH | CH$_3$ | 4-NH—CO—OCH$_3$-3-OCH$_3$ | 143–145 |
| I.25. | NOCH$_3$ | NH | CH$_3$ | 4-N(OCH$_3$)—CO—OCH$_3$ | 1730,1677,1525,1508,1441,1337, 1305,1037,1012,978 |
| I.26. | NOCH$_3$ | NH | CH$_3$ | 4-N(C$_2$H$_5$)—CO-t-C$_4$H$_9$ | 163–164 |
| I.27. | NOCH$_3$ | NH | CH$_3$ | 4-N(n-C$_4$H$_9$)—CO-t-C$_4$H$_9$ | 77–82 |
| I.28. | NOCH$_3$ | O | CH$_3$ | 4-N(OCH$_3$)—CO—OCH$_3$ | 163–164 |
| I.29. | NOCH$_3$ | NH | CH$_3$ | 4-N(CH$_3$)—CO—CH$_3$ | 148–149 |
| I.30. | NOCH$_3$ | NH | CH$_3$ | 4-N(C$_2$H$_5$)—CO—CH$_3$ | 131–133 |
| I.31. | NOCH$_3$ | NH | CH$_3$ | 4-N(n-C$_3$H$_7$)—CO—CH$_3$ | 2936,1662,1606,1524,1508,1397, 1067,1037,1006,978 |
| I.32. | NOCH$_3$ | NH | CH$_3$ | 4-N(n-C$_3$H$_7$)—CO-t-C$_4$H$_9$ | 1675,1633,1601,1527,1508,1037, 1009,999,977,870 |
| I.33. | CHOCH$_3$ | O | CH$_3$ | 4-NH—CO—CH$_3$ | 171–174 |
| I.34. | CHOCH$_3$ | O | CH$_3$ | 4-N(CH$_3$)—CO—CH$_3$ | 135–137 |
| I.35. | CHOCH$_3$ | O | CH$_3$ | 4-N(C$_2$H$_5$)—CO—CH$_3$ | 131–133 |
| I.36. | CHOCH$_3$ | O | CH$_3$ | 4-N(n-C$_3$H$_7$)—CO—CH$_3$ | 130–131 |
| I.37. | CHOCH$_3$ | O | CH$_3$ | 4-N(CH$_3$)—CO-t-C$_4$H$_9$ | 105–106 |
| I.38. | CHOCH$_3$ | O | CH$_3$ | 4-N(C$_2$H$_5$)—CO-t-C$_4$H$_9$ | 117–118 |
| I.39. | CHCH$_3$ | O | CH$_3$ | 4-NH—CO—CH$_3$ | 124–126 |
| I.40. | CHCH$_3$ | O | CH$_3$ | 4-N(CH$_3$)—CO—CH$_3$ | 87–89 |
| I.41. | CHCH$_3$ | O | CH$_3$ | 4-N(C$_2$H$_5$)—CO—CH$_3$ | 104–106 |
| I.42. | CHCH$_3$ | O | CH$_3$ | 4-N(n-C$_3$H$_7$)—CO—CH$_3$ | 1716,1660,1507,1397,1257,1248, 1063,997,878,750 |
| I.43. | CHCH$_3$ | O | CH$_3$ | 4-NH—CO-t-C$_4$H$_9$ | 94–97 |
| I.44. | CHCH$_3$ | O | CH$_3$ | 4-N(CH$_3$)—CO-t-C$_4$H$_9$ | 1717,1640,1605,1508,1364,1353, 1253,1209,1068,1007 |
| I.45. | CHCH$_3$ | O | CH$_3$ | 4-N(C$_2$H$_5$)—CO-t-C$_4$H$_9$ | 86–88 |
| I.46. | NOCH$_3$ | O | CH$_3$ | 4-N(CH$_3$)—CO—CH$_3$ | 140–141 |
| I.47. | NOCH$_3$ | O | CH$_3$ | 4-N(C$_2$H$_5$)—CO—CH$_3$ | 99–100 |
| I.48. | NOCH$_3$ | O | CH$_3$ | 4-N(n-C$_3$H$_7$)—CO—CH$_3$ | 104–105 |
| I.49. | NOCH$_3$ | O | CH$_3$ | 4-N(C$_2$H$_5$)—CO-t-C$_4$H$_9$ | 114–115 |
| I.50. | NOCH$_3$ | O | CH$_3$ | 4-N(OCO$_2$CH$_3$)—CO—OCH$_3$ | 155 |
| I.51. | NOCH$_3$ | O | CH$_3$ | 4-C(CH$_3$)=NOCH$_3$ | 112–114 |
| I.52. | NOCH$_3$ | NH | CH$_3$ | 4-C(CH$_3$)=NOCH$_3$ | 51–54 |
| I.53. | NOCH$_3$ | O | CH$_3$ | 4-CH=NOCH$_3$ | 123–125 |
| I.54. | NOCH$_3$ | NH | CH$_3$ | 4-CH=NOCH$_3$ | 100–101 |
| I.55. | NOCH$_3$ | NH | CH$_3$ | 4-C(CH$_3$)=NOC$_2$H$_5$ | 3350,2973,2936,1676,1524,1091, 1066,1048,1005,979,895 |
| I.56. | CHOCH$_3$ | O | CH$_2$C≡CH | 4-C(CH$_3$)=NOC$_2$H$_5$ | 3280,2929,1708,1634,1285,1256, 1130,1112,1048,1004,919 |
| I.57. | CHOCH$_3$ | O | CH$_2$C≡CH | 4-C(CH$_3$)=NOCH$_3$ | 3280,2930,1708,1634,1284,1256, 1130,1112,1068,1048,1006,892, |
| I.58. | CHCH$_3$ | O | CH$_3$ | 4-CH=NOCH$_3$ | 2938,1716,1435,1253,1209,1053, 1008,922,895,760 |
| I.59. | CHOCH$_3$ | O | CH$_3$ | 4-CH=NOCH$_3$ | 2939,1709,1634,1284,1256,1130, 1112,1055,1003,921 |

USE EXAMPLES

The fungicidal activity of the compounds of the formula I is demonstrated by the following experiments:

The active ingredients are formulated as a 20% strength emulsion in a mixture of 70% by weight of cyclohexanone, 20% by weight of Nekanil® LN (Lutensol® AP6, wetting agent having emulsifier and dispersing action based on ethoxylated alkylphenols) and 10% by weight of Emulphor® EL (Emulan® EL, emulsifier based on ethoxylated fatty alcohols) and diluted with water to give the desired concentration. The experiments were evaluated visually.

The activity of the compounds of the general formula I against animal pests is demonstrated by the following experiments.

The active ingredients are formulated a) as a 0.1% strength solution in acetone or
b) as a 10% strength emulsion in a mixture of 70% by weight of cyclohexanone, 20% by weight of Nekanil® LN (Lutensol® AP6, wetting agent with emulsifier and dispersing action based on ethoxylated alkylphenols) and 10% by weight of Emulphor® EL (Emulan® EL, emulsifier based on ethoxylated fatty alcohols)

and diluted to give the desired concentration, using acetone in the case of a) and water in the case of b).

USE EXAMPLE 1

Efficacy Against Powdery Mildew of Wheat

Leaves of wheat seedlings cv. "Frühgold" in pots were sprayed with aqueous spray mixture comprising 80% of active ingredient of Table 1 and 20% of emulsifier in the dry matter and, 24 hours after the spray coating had dried on, dusted with oidia (spores) of powdery mildew of wheat (Erysiphe graminis var. tritici). The test plants were subsequently placed in a greenhouse at from 20 to 22° C. and a relative atmospheric humidity of 75 to 80%. After 7 days, the extent of mildew development was determined.

TABLE 2

| Active ingredient of Table 1 | % infection of the leaves after application of an aqueous preparation comprising 250 ppm of active ingredient |
|---|---|
| I.20 | 15 |
| I.21 | 5 |
| I.22 | 15 |
| I.23 | 15 |
| I.40 | 15 |
| I.41 | 15 |
| I.43 | 15 |
| I.45 | 15 |
| I.58 | 0 |
| Comparison substance A (No. 1433 of Table 3 in WO 95/21153) | 30 |
| No. I.13 | 0 |
| No. I.16 | 5 |
| No. I.17 | 15 |
| No. I.18 | 5 |
| No. I.19 | 5 |
| No. I.57 | 0 |
| No. I.59 | 0 |
| Comparison substance B (No. 2 of Table II in WO 95/21153) | 30 |
| Comparison substance C (No. 1433 of Table 1 in WO 95/21153) | 30 |
| No. I.12 | 5 |
| No. I.53 | 15 |
| Comparison substance D (No. 48 of Table 1 in WO 95/21153) | 30 |
| Comparison substance E (No. 1901 of Table 7 in WO 95/21153) | 60 |
| No. I.5 | 5 |
| No. I.8 | 0 |
| No. I.15 | 5 |
| No. I.25 | 5 |
| No. I.26 | 15 |
| No. I.27 | 5 |
| No. I.31 | 15 |
| No. I.32 | 15 |
| No. I.52 | 15 |
| No. I.54 | 5 |
| No. I.55 | 15 |
| Comparison substance F (No. 1898 of Table 5 in WO 95/21254) | 30 |
| Untreated | 70 |

USE EXAMPLE 2

Efficacy Against Leaf Rust of Wheat

Leaves of wheat seedlings cv. "Kanzler" in pots were dusted with leaf rust spores (Puccinia recondite). The pots were then placed for 24 hours in a chamber with high atmospheric humidity (90 to 95%) at from 20 to 22° C. During this time, the spores germinated, and the germ tubes penetrated the leaf tissue. The infected plants were subsequently sprayed to runoff point with aqueous spray mixtures comprising 80% of active ingredient of Table 1 and 20% of emulsifier in the dry matter. After the spray coating had dried on, the test plants were placed in a greenhouse at from 20 to 22° C. and a relative atmospheric humidity of 65 to 70%. After 8 days, the extent of rust development on the leaves was determined.

TABLE 3

| Active ingredient | % infection of the leaves after application of an aqueous preparation comprising ... ppm of active ingredient |
|---|---|
| | 63 ppm |
| No. I.40 | 0 |
| No. I.41 | 15 |
| No. I.43 | 5 |
| No. I.44 | 5 |
| No. I.45 | 15 |
| No. I.58 | 0 |
| Comparison substance A (No. 1433 of Table 3 in WO 95/21153) | 40 |
| No. I.13 | 15 |
| No. I.56 | 15 |
| No. I.57 | 15 |
| No. I.59 | 10 |
| Comparison substance B (No. 2 of Table II in WO 95/21153) | 60 |
| Comparison substance C (No. 1433 of Table 1 in WO 95/21153) | 40 |
| | 63 ppm |
| No. I.12 | 15 |
| Comparison substance D (No. 48 of Table I in WO 95/21153) | 70 |
| Comparison substance E (No. 1901 of Table 7 in WO 95/21153) | 40 |
| No. I.5 | 0 |
| No. I.8 | 0 |
| | 16 ppm |
| No. I.13 | 5 |
| No. I.27 | 3 |
| No. I.29 | 5 |
| No. I.30 | 15 |
| No. I.31 | 0 |
| No. I.32 | 0 |
| No. I.52 | 0 |
| No. I.54 | 0 |
| No. I.55 | 0 |
| Comparison product F (No. 1898 of Table 5 in WO 95/21154) | 60 |
| Untreated | 70 |

We claim:
1. A phenylacetic acid compound of formula I

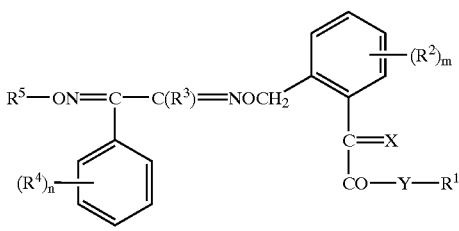

where the variables have the following meanings:
X is $NOCH_3$, $CHOCH_3$ or $CHCH_3$;
Y is O or NH;
$R^1$ is methyl;
$R^2$ is cyano, nitro, trifluoromethyl, halogen, $C_1$–$C_4$-alkyl or $C_1$–$C_4$-alkoxy;
m is 0, 1 or 2, it being possible for the radicals $R^2$ to be different if m is 2;
$R^3$ is hydrogen, cyano, $C_1$–$C_4$-alkyl, $C_1$–$C_4$-haloalkyl, $C_1$–$C_4$-alkoxy or cyclopropyl;
$R^4$ is $C_1$–$C_4$-alkylenedioxy, the alkylene groups being partially or fully halogenated, or is one of the radicals:
—C(=NO$R^a$)—$A_p$—$R^b$,
—N$R^b$—(C=O)—$A_p$—$R^a$,
—O—(C=O)—N$R^a R^b$ or
—N($R^c$)—O$R^d$, where
$R^a$, $R^b$ independently of one another are hydrogen or in each case unsubstituted or substituted alkyl, alkenyl, alkynyl, cycloalkyl, cycloalkenyl, heterocyclyl, aryl or hetaryl,
$R^c$, $R^d$ independently of one another are hydrogen or in each case unsubstituted or substituted alkyl, alkenyl, alkynyl, alkylcarbonyl, alkenylcarbonyl, alkynylcarbonyl, alkoxycarbonyl, alkenyloxycarbonyl, alkynyloxycarbonyl, cycloalkyl, cycloalkylcarbonyl, cycloalkoxycarbonyl, arylcarbonyl or hetarylcarbonyl,
p is 0 or 1 and
A is oxygen, sulfur or nitrogen, the nitrogen having attached to it hydrogen or $C_1$–$C_6$-alkyl;
n is 1 or 2, it being possible for the radicals $R^4$ to be different is n is 2;
$R^5$ is hydrogen,
$C_1$–$C_6$-alkylsulfonyl,
$C_1$–$C_6$-alkyl, $C_3$–$C_6$-alkenyl, $C_3$–$C_6$-alkynyl, it being possible for these radicals to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkoxy, heterocyclyl, heterocyclyloxy, aryl, aryloxy, arylthio, hetaryl, hetaryloxy, hetarylthio, it being possible for the cyclic groups, in turn, to be partially or fully halogenated and/or to have attached to them one to three of the following substituents:
cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylami no, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C_3$–$C_6$-alkynyloxy;
$C_3$–$C_6$-cycloalkyl, which can be partially or fully halogenated and/or, independently of each other, can have attached to it one to three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio, or a salt thereof.

2. A process for the preparation of the compound of formula I defined in claim 1, which comprises reacting a benzyl compound of formula II

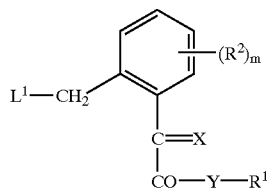

where $L^1$ is a nucleophilically exchangeably leaving group with a hydroxyimine of formula III

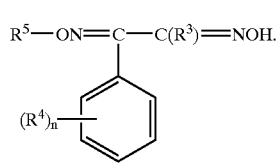

3. A process for the preparation of the compound of formula I defined in claim 1, which comprises reacting a benzyl compound of formula II

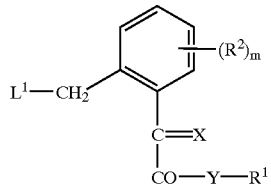

with a dihydroxyimine of formula IV

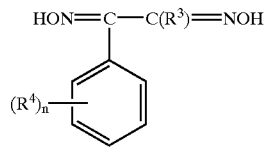

to give a compound of formula V

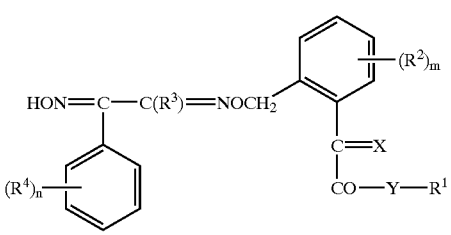

and subsequently reacting V with a compound of formula VI

where $L^2$ is a nucleophilically exchangeable leaving group to give I.

4. A process for preparing the compound of formula I defined in claim 1, which comprises reacting a benzyl compound of formula II

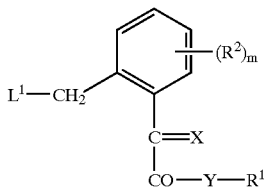

with a carbonylhydroxyimine of formula VII

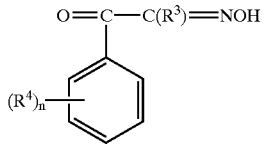

to give a compound of formula VIII

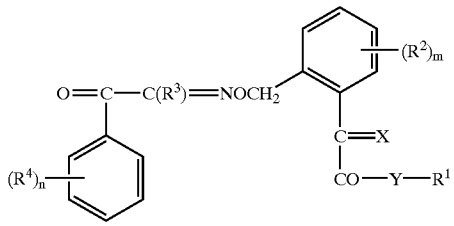

and subsequently reacting VIII a) first with hydroxylamine or a salt thereof and then with a compound of formula VI

where $L^2$ is a nucleophilically exchangeable leaving group, or b) with a hydroxylamine or a hydroxylammonium salt of formula IXa or IXb

where $Q^\ominus$ is the anion of an acid.

5. A composition against animal pests or harmful fungi, which comprises customary additives and an effective amount of the compound of formula I defined in claim 1.

6. The composition defined in claim 5 for controlling animal pests from the classes of insects, arachnids or nematodes.

7. A method of controlling animal pests or harmful fungi, which comprises treating the pests or the harmful fungi, their environment, or the plants, areas, materials or spaces to be kept free from them, with an effective amount of the compound of formula I defined in claim 1.

8. A compound of formula VIII

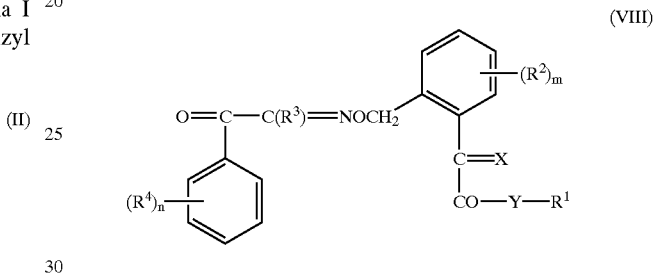

where

X is $NOCH_3$, $CHOCH_3$ or $CHCH_3$;

Y is O or NH;

$R^1$ is methyl;

$R^2$ is cyano, nitro, trifluoromethyl, halogen, $C_1$–$C_4$-alkyl or $C_1$–$C_4$-alkoxy;

m is 0, 1 or 2, it being possible for the radicals $R^2$ to be different if m is 2;

$R^3$ is hydrogen, cyano, $C_1$–$C_4$-alkyl, $C_1$–$C_4$-haloalkyl, $C_1$–$C_4$-alkoxy or cyclopropyl;

$R^4$ is $C_1$–$C_4$-alkylenedioxy, the alkylene groups being partially or fully halogenated, or is one of the radicals:

—C(=$NOR^a$)—$A_p$—$R^b$,

—$NR^b$—(C=O)—$A_p$—$R^a$,

—O—(C=O)—$NR^aR^b$ or

—N($R^c$)—$OR^d$, where $R^a$, $R^b$ independently of one another are hydrogen or in each case unsubstituted or substituted alkyl, alkenyl, alkynyl, cycloalkyl, cycloalkenyl, heterocyclyl, aryl or hetaryl, $R^c$, $R^d$ independently of one another are hydrogen or in each case unsubstituted or substituted alkyl, alkenyl, alkynyl, alkylcarbonyl, alkenylcarbonyl, alkynylcarbonyl, alkoxycarbonyl, alkenyloxycarbonyl, alkynyloxycarbonyl, cycloalkyl, cycloalkylcarbonyl, cycloalkoxycarbonyl, arylcarbonyl or hetarylcarbonyl, p is 0 or 1 and A is oxygen, sulfur or nitrogen, the nitrogen having attached to it hydrogen or $C_1$–$C_6$-alkyl;

n is 1 or 2, it being possible for the radicals $R^4$ to be different is n is 2.

9. The compound of formula I defined in claim 1, wherein $R^a$, $R^b$ independently of one another are hydrogen or in each case unsubstituted or substituted alkyl, alkenyl, alkynyl, cycloalkyl, cycloalkenyl or aryl, R$^c$, R$^d$ independently of one another are hydrogen or in each case unsubstituted or substituted alkyl, alkenyl, alkynyl, alkylcarbonyl, alkenylcarbonyl, alkynylcarbonyl, alkoxycarbonyl, alkenyloxycarbonyl, alkynyloxycarbonyl, cycloalkyl, cycloalkylcarbonyl, cycloalkoxycarbonyl or arylcarbonyl, R$^5$ is hydrogen, $C_1$–$C_6$-alkylsulfonyl, $C_1$–$C_6$-alkyl, $C_3$–$C_6$-alkenyl, $C_3$–$C_6$-alkynyl, it being possible for these radicals to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkoxy, aryl, aryloxy and arylthio, it being possible for the cyclic groups, in turn, to be partially or fully halogenated and/or to have attached to them one to three of the following substituents: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio and $C_3$–$C_6$-alkynyloxy;

$C_3$–$C_6$-cycloalkyl, which can be partially or fully halogenated and/or, independently of each other, can have attached to it one to three of the following groups: cyano, $C_1$–$C_6$-alkyl $C_1$–$C_6$-haloalkyl, $C_2$–$C_6$-alkenyl, $C_1$–$C_6$-alkoxy and $C_1$–$C_6$-alkylthio, or a salt thereof.

10. The compound of formula I defined in claim 1, wherein R$^3$ is hydrogen, cyclopropyl, methyl, ethyl, 1-methylethyl, methoxy, cyano or trifluoromethyl.

11. The compound of formula I defined in claim 1, wherein the radical R$^a$ or the radical R$^b$ is selected from the group consisting of $C_1$–$C_6$-alkyl and $C_2$–$C_6$-alkenyl.

12. The compound of formula I defined in claim 1, wherein R$^5$ is hydrogen, $C_3$–$C_6$-cycloalkyl, arylalkyl, hetarylalkyl, aryloxyalkyl or hetaryloxyalkyl.

13. The compound of formula I defined in claim 1, wherein X is NOCH$_3$.

14. A phenylacetic acid compound of formula I

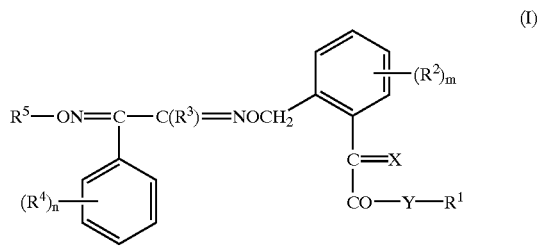

(I)

wherein

X is NOCH$_3$, CHOCH$_3$ or CHCH$_3$;

Y is O or NH;

R$^1$ is methyl;

R$^2$ is cyano, nitro, trifluoromethyl, halogen, $C_1$–$C_4$-alkyl or $C_1$–$C_4$-alkoxy;

m is 0, 1 or 2, it being possible for the radicals R$^2$ to be different if m is 2;

R$^3$ is hydrogen, cyano, $C_1$–$C_4$-alkyl, $C_1$–$C_4$-haloalkyl, $C_1$–$C_4$-alkoxy or cyclopropyl;

R$^4$ is $C_1$–$C_4$-alkylenedioxy, the alkylene groups being partially or fully halogenated, or is a radical —C(=NOR$^a$)—A$_p$—R$^b$, wherein R$^a$, R$^b$ independently of one another are hydrogen or in each case unsubstituted or substituted alkyl, alkenyl, alkynyl, cycloalkyl, cycloalkenyl, heterocyclyl, aryl or hetaryl, p is 0 or 1 and A is oxygen, sulfur or nitrogen, the nitrogen having attached to it hydrogen or $C_1$–$C_6$-alkyl;

n is 1 or 2, it being possible for the radicals R$^4$ to be different is n is 2;

R$^5$ is hydrogen, $C_1$–$C_6$-alkylsulfonyl, $C_1$–$C_6$-alkyl, $C_3$–$C_6$-alkenyl, $C_3$–$C_6$-alkynyl, it being possible for these radicals to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkoxy, heterocyclyl, heterocyclyloxy, aryl, aryloxy, arylthio, hetaryl, hetaryloxy, hetarylthio, it being possible for the cyclic groups, in turn, to be partially or fully halogenated and/or to have attached to them one to three of the following substituents: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$- alkenyloxy, benzyl, benzyloxy, aryl, aryloxy, arylthio, hetaryl, hetaryloxy, hetarylthio and $C_3-C_6$-alkynyloxy;

$C_3-C_6$-cycloalkyl, which can be partially or fully halogenated and/or, independently of each other, can have attached to it one to three of the following groups: cyano, $C_1-C_6$-alkyl, $C_1-C_6$-haloalkyl, $C_2-C_6$-alkenyl, $C_1-C_6$-alkoxy and $C_1-C_6$-alkylthio, or a salt thereof.

15. The compound of formula I defined in claim 38, wherein $R^a$, $R^b$ independently of one another are hydrogen or in each case unsubstituted or substituted alkyl, alkenyl, alkynyl, cycloalkyl, cycloalkenyl or aryl, $R^5$ is hydrogen, $C_1-C_6$-alkylsulfonyl, $C_1-C_5$-alkyl, $C_3-C_6$-alkenyl, $C_3-C_6$-alkynyl, it being possible for these radicals to be partially or fully halogenated and/or to have attached to them one to three of the following groups: cyano, nitro, hydroxyl, mercapto, amino, carboxyl, aminocarbonyl, aminothiocarbonyl, $C_1-C_6$-alkylaminocarbonyl, di-$C_1-C_6$-alkylaminocarbonyl, $C_1-C_6$-alkylaminothiocarbonyl, di-$C_1-C_6$-alkylaminothiocarbonyl, $C_1-C_6$-alkylsulfonyl, $C_1-C_6$-alkylsulfoxyl, $C_1-C_6$-alkoxy, $C_1-C_6$-haloalkoxy, $C_1-C_6$-alkoxycarbonyl, $C_1-C_6$-alkylthio, $C_1-C_6$-alkylamino, di-$C_1-C_6$-alkylamino, $C_2-C_6$-alkenyloxy, $C_3-C_6$-cycloalkyl, $C_3-C_6$-cycloalkoxy, aryl, aryloxy and arylthio, it being possible for the cyclic groups, in turn, to be partially or fully halogenated and/or to have attached to them one to three of the following substituents: cyano, nitro, hydroxyl, mercapto, amino, carboxyl, aminocarbonyl, aminothiocarbonyl, $C_1-C_6$-alkyl, $C_1-C_6$-haloalkyl, $C_1-C_6$-alkylcarbonyl, $C_1-C_6$-alkylsulfonyl, $C_1-C_6$-alkylsulfoxyl, $C_3-C_6$-cycloalkyl, $C_1-C_6$-alkoxy, $C_1-C_6$-haloalkoxy, $C_1-C_6$-alkoxycarbonyl, $C_1-C_6$-alkylthio, $C_1-C_6$-alkylamino, di-$C_1-C_6$-alkylamino, $C_1-C_6$-alkylaminocarbonyl, di-$C_1-C_6$-alkylaminocarbonyl, $C_1-C_6$-alkylaminothiocarbonyl, di-$C_1-C_6$-alkylaminothiocarbonyl, $C_2-C_6$-alkenyl, $C_2-C_6$-alkenyloxy, benzyl, benzyloxy, aryl, aryloxy, arylthio and $C_3-C_6$-alkynyloxy;

$C_3-C_6$-cycloalkyl, which can be partially or fully halogenated and/or, independently of each other, can have attached to it one to three of the following groups: cyano, $C_1-C_6$-alkyl, $C_1-C_6$-haloalkyl, $C_2-C_6$-alkenyl, $C_1-C_6$-alkoxy and $C_1-C_6$-alkylthio, or a salt thereof.

16. A composition against animal pests or harmful fungi, which comprises customary additives and an effective amount of the compound of formula I defined in claim 38.

17. A method of controlling animal pests or harmful fungi, which comprises treating the pests or the harmful fungi, their environment, or the plants, areas, materials or spaces to be kept free from them, with an effective amount of the compound of formula I defined in claim 1.

18. A compound of formula VIII

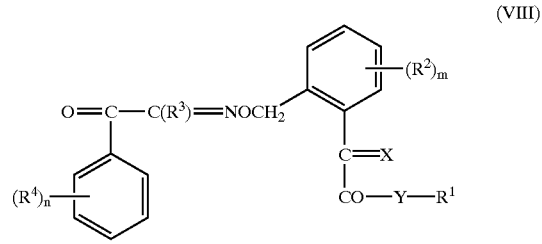

(VIII)

wherein

X is $NOCH_3$, $CHOCH_3$ or $CHCH_3$;

Y is O or NH;

$R^1$ is methyl;

$R^2$ is cyano, nitro, trifluoromethyl, halogen, $C_1-C_4$-alkyl or $C_1-C_4$-alkoxy;

m is 0, 1 or 2, it being possible for the radicals $R^2$ to be different if m is 2;

$R^3$ is hydrogen, cyano, $C_1-C_4$-alkyl, $C_1-C_4$-haloalkyl, $C_1-C_4$-alkoxy or cyclopropyl;

$R^4$ is $C_1-C_4$-alkylenedioxy, the alkylene groups being partially or fully halogenated, or is a radical —$C(=NOR^a)$—$A_p$—$R^b$, wherein $R^a$, $R^b$ independently of one another are hydrogen or in each case unsubstituted or substituted alkyl, alkenyl, alkynyl, cycloalkyl, cycloalkenyl, heterocyclyl, aryl or hetaryl, p is 0 or 1 and A is oxygen, sulfur or nitrogen, the nitrogen having attached to it hydrogen or $C_1-C_6$-alkyl;

n is 1 or 2, it being possible for the radicals $R^4$ to be different is n is 2.

* * * * *

UNITED STATES PATENT AND TRADEMARK OFFICE
CERTIFICATE OF CORRECTION

PATENT NO. : 6,509,379 B1
DATED : January 21, 2003
INVENTOR(S) : Bayer et al.

It is certified that error appears in the above-identified patent and that said Letters Patent is hereby corrected as shown below:

Column 172,
Line 7, "di-$C_1$-$C_6$-alkylami no" should be -- di-$C_1$-$C_6$-dialkylamino --.

Column 177,
Line 11, "claim 38" should be -- claim 14 --;
Line 17, "$C_1$-$C_5$-alkyl" should be -- $C_1$-$C_6$-alkyl --.

Column 178,
Line 6, "claim 38" should be -- claim 14 --.

Signed and Sealed this

Thirteenth Day of May, 2003

JAMES E. ROGAN
*Director of the United States Patent and Trademark Office*